US011905513B2

(12) United States Patent
Li et al.

(10) Patent No.: US 11,905,513 B2
(45) Date of Patent: Feb. 20, 2024

(54) ADVANCED GENOME EDITING

(71) Applicant: MBP TITAN LLC, South San Francisco, CA (US)

(72) Inventors: Xuezhi Li, Hayward, CA (US); James Kealey, Sebastopol, CA (US); Kevin Lee Dietzel, Pacifica, CA (US)

(73) Assignee: MBP TITAN, LLC, South San Francisco, CA (US)

( * ) Notice: Subject to any disclaimer, the term of this patent is extended or adjusted under 35 U.S.C. 154(b) by 132 days.

(21) Appl. No.: 16/755,513

(22) PCT Filed: Oct. 11, 2018

(86) PCT No.: PCT/US2018/055340
§ 371 (c)(1),
(2) Date: Apr. 10, 2020

(87) PCT Pub. No.: WO2019/075159
PCT Pub. Date: Apr. 18, 2019

(65) Prior Publication Data

US 2021/0317446 A1 Oct. 14, 2021

Related U.S. Application Data

(60) Provisional application No. 62/572,012, filed on Oct. 13, 2017.

(51) Int. Cl.
*C12N 15/11* (2006.01)
*C12N 1/20* (2006.01)
*C12N 9/22* (2006.01)

(52) U.S. Cl.
CPC ................ *C12N 15/11* (2013.01); *C12N 1/20* (2013.01); *C12N 9/22* (2013.01); *C12N 2310/20* (2017.05); *C12N 2800/80* (2013.01)

(58) Field of Classification Search
CPC . C12N 15/11; C12N 1/20; C12N 9/22; C12N 2310/20; C12N 2800/80; C12N 15/113; C12N 15/52; C12N 15/63; C12N 15/102; C12N 15/09
See application file for complete search history.

(56) References Cited

U.S. PATENT DOCUMENTS

2017/0247710 A1* 8/2017 Nagaraju ............. C12N 15/635

OTHER PUBLICATIONS

Whisstock et al. Quaterly Reviews of Biophysics, 2003, “Prediction of protein function from protein sequence and structure”, 36(3):307-340. (Year: 2003).*

Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*

Kisselev L., Polypeptide release factors in prokaryotes and eukaryotes: same function, different structure. Structure, 2002, vol. 10:8-9. (Year: 2002).*

Clomburg et al. Industrial biomanufacturing: The future of chemical production. Science (Epub Jan. 6, 2017), 355(38): 1-10. (Year: 2017).*

Henrad et al. Bioconversion of methane to lactate by an obligate methanotrophic bacterium. Scientific Reports (2016.), 6: 21585, internal pp. 1-9) (Year: 2016).*

Lee et al. Metabolic engineering of methanotrophs and its application to production of chemicals and biofuels from methane. Biofuels Bioproducts & Biorefining (2016), 10: 848-863. (Year: 2016).*

Nguyen et al., Metab Eng (2018), 47:323-333.

Vecherskaya et al., Environmental Microbiology Reports (2009), 1: 442-449.

* cited by examiner

*Primary Examiner* — Iqbal H Chowdhury
(74) *Attorney, Agent, or Firm* — Gene J. Yao; Barnes & Thornburg LLP

(57) ABSTRACT

Methods of genetically modifying microorganisms using advanced genome editing are disclosed. Methods of modifying the genome of these microorganisms for point mutations, deletions, and DNA insertions are also disclosed. Further, inhibiting expression of genes without manipulating the genome of the microorganism is disclosed. In some cases, the microorganism can be a methylotroph, e.g., a methanotroph.

19 Claims, 6 Drawing Sheets

Specification includes a Sequence Listing.

Cas9 only
~1000 colonies cas9+gRNA2
10 colonies cas9+gRNA5
8 colonies cas9+gRNA2+dsDNA
no colonies cPCR verification of ppdK deletion

SL540: 26/36 (72%)

SEQUENCE LISTING

<160> NUMBER OF SEQ ID NOS: 126

<210> SEQ ID NO 1
<211> LENGTH: 1713
<212> TYPE: DNA
<213> ORGANISM: Bacillus subtilis

<400> SEQUENCE: 1

```
atgaccaagg ccaccaagga acagaaaagc ctggtcaaga accgcggtgc tgaactggtt      60

gtggactgcc tcgtggaaca gggcgtgacc catgtcttcg gcatcccggg cgccaagatc     120

gacgccgtct tcgacgccct gcaggataaa ggtccggaaa tcatcgtggc acgccatgag     180

cagaacgcag ccttcatggc ccaggccgtc ggtcggctga cgggtaagcc cggcgtggtg     240

ctggtcacct ccggtccggg agcctcgaac ctggccacgg gactgctcac cgccaacacc     300

gaaggcgacc cggtggtcgc cctggccggt aatgtcatcc gggcggatcg cctgaagcgc     360

acccatcagt ccctggataa cgcggccctg ttccagccaa tcaccaaata tagtgtcgaa     420

gtgcaggatg tgaagaacat cccggaagcc gtcaccaatg cgttccgaat cgcgtccgcc     480

ggccaagcag gggcagcatt cgtgagcttc ccccaggacg tggtcaatga agtgaccaac     540

accaaaaacg tcagagccgt agccgccccg aagctgggcc ctgcagcaga tgacgccatc     600

tccgctgcca tcgcgaagat ccagaccgca aagctgccgg tcgtgctggt cggaatgaag     660

ggcggacgcc cggaggccat caaggccgtg cgtaaactgc tgaagaaggt gcagctaccg     720

ttcgtggaaa cctaccaggc cgccggcacc ctgagtcggg acttggaaga ccagtatttc     780

ggccgtatcg gcctgttccg caaccagccg ggcgacctgc tcctggaaca agccgatgtg     840

gtgctgacca tcggctacga cccgatcgaa tatgacccga agttctggaa catcaatggc     900
```

gaccgcacga tcatccatct ggacgaaatc atcgccgaca tcgaccatgc ctatcagccg 960
gacctggaac tgatcggcga catcccgagc accatcaacc acatcgaaca cgatgccgtg 1020
aaggtggaat ttgccgaacg cgaacagaag atcctgtcgg acctgaagca gtatatgcat 1080
gagggcgaac aggtgcctgc cgactggaag tcggacagag cccatccgct ggaaatcgtg 1140
aaggaactgc gtaacgccgt cgacgaccat gtcaccgtca cctgcgatat cggcagccat 1200
gccatttgga tgagccgcta cttccggagc tatgaaccgc tgaccctgat gatctccaac 1260
ggtatgcaga ccctcggcgt cgccctcccg tgggccatcg gcgcaagtct ggtgaagccg 1320
ggcgaaaaag tggtcagcgt gtccggcgac ggcggcttcc tgttctccgc tatggaactg 1380
gaaaccgcgg tccgcctgaa ggccccgatc gtgcatatcg tgtggaacga cagcacctac 1440
gacatggtcg ccttccagca gctgaaaaag tacaaccgca ccagcgccgt ggacttcggc 1500
aatatcgaca tcgtgaagta tgccgaatcc ttcggagcca ccggactgcg cgtggaatcc 1560
ccggaccagc tggcggacgt tctgcgtcag ggcatgaatg ccgaaggtcc cgtgattatc 1620
gatgtgcccg tcgactacag cgacaacatc aacctggcct cggacaaatt gccgaaggag 1680
ttcggcgaac tgatgaaaac aaaagcacta taa 1713

<210> SEQ ID NO 2
<211> LENGTH: 1719
<212> TYPE: DNA
<213> ORGANISM: Bacillus licheniformis

<400> SEQUENCE: 2
atgaataacg tcgcggccaa gaacgaaacc ctgaccgtcc ggggcgccga actcgtggtg 60
gatagcctga tccagcaggg cgtgacccat gtcttcggca tcccgggcgc caaaatcgac 120
gcggtcttcg acgtgctgaa ggataagggc cccgaactga tcgtctgccg ccatgagcag 180
aacgcggcct tcatggccgc cgccgtcggc cgcctgacgg gcaagccggg cgtctgcctg 240
gtcacctccg gcccgggcgc ctcgaatctc gcgaccggcc tggtcaccgc gaacacggaa 300
ggcgacccgg tggtcgccct ggcgggcgcc gtgaagcggg cggatcggct gaagaagacg 360
caccagtcga tggataacgc cgccctgttc cagcccatca cgaagtacag cgcggaggtg 420
gaagacgcga acaacatccc ggaggccgtg acgaacgcct tccgcgccgc ggcgtccggc 480
caggccggcg cggccttcct cagcttcccc caggatgtca ccgccggccc ggccaccgcc 540
aagccggtca aaaccatgcc cgccccgaag ctgggcgccg cgagcgatga acagatctcc 600
gccgcgatcg cgaagatcca caacgcgaat ctgccggtgg tcctcgtggg catgaagggc 660
ggccggccgg aagccatcga agccgtgcgc cgcctgctcc gcaaggtcaa gctcccgttc 720
gtggaaacct accaggcggc cggcacgctg tcgcacgatc tggaggatca gtacttcggc 780
cggatcggcc tgttccggaa ccagccgggc gacatgctcc tggaaaaggc cgacgtggtc 840
ctgaccgtgg gctacgaccc gatcgagtac gatccggtgt tctggaatgg caaaggcgaa 900
cgctcggtca tccacctcga cgaaatccag gccgatatcg atcacgacta ccagcccgag 960
atcgaactca tcggcgacat cgcggaaacc ctcaatcaca tcgagcatga ctcgctgccg 1020
gtgtccatcg acgaatcctt cgcgcccgtg ctcgactatc tcaagaaggc gctcgaagaa 1080
cagtcggagc ccccgaagga aacgaagacc gatctggtcc acccgctcca gatcgtgcgc 1140
gacctgcgcg agctgctctc cgatgacatc accgtcacct gcgacatcgg cagccacgcc 1200
atctggatgt cccgctattt ccgcacctat cgcccgcatg gcctcctgat ctccaacggc 1260
atgcagacgc tgggcgtcgc cctgccgtgg gcgatcgccg cgaccctggt gaacccgggc 1320

```
cagaaggtgg tgtcggtcag cggcgatggc ggcttcctct tctccgcgat ggaactcgaa   1380

accgccgtcc gcctcaaggc gccgatcgtg cacatcgtgt ggaacgactc cacgtacgac   1440

atggtcgcgt tccagcagga aatgaagtac aagcgcacct ccggcgtcga tttcggcggc   1500

atcgacatcg tcaagtatgc ggaatccttc ggcgccaaag gcctccgcgt gaatagcccc   1560

gatgaactgg ccgaggtcct gaaggccggc ctcgacgcgg agggcccggt ggtcatcgac   1620

atccccgtcg actactcgga taacatccac ctggccgacc agcgcttccc gaagaagttc   1680

gaggagcact tcaacaagga agcgtcgaag cagtcctga                          1719
```

<210> SEQ ID NO 3
<211> LENGTH: 1476
<212> TYPE: DNA
<213> ORGANISM: Escherichia coli

<400> SEQUENCE: 3

```
atggctaact acttcaacac cctgaacttg cgtcagcagc tggcccagct gggtaagtgc     60

cggttcatgg gccgtgatga gttcgccgat ggcgccagct acctgcaggg caaaaaggtg    120

gtgatcgtgg gctgcggagc ccagggcctg aaccagggcc tgaatatgcg cgatagcggc    180

ctggacatct cctatgctct gcgcaaggaa gcgatcgcgg aaaagcgggc atcctggcgc    240

aaggccaccg aaaacggttt caaagtgggc acctacgaag aactgatccc gcaggccgat    300

ttggtcataa acctgacccc ggacaagcag cattccgatg tggttcgcac cgtccagccg    360

ctgatgaagg acggggcagc cctgggttac tcccacggct tcaacatcgt ggaagtcggc    420

gaacagatcc gcaaggacat caccgtcgtc atggtcgcac cgaagtgtcc gggcaccgaa    480

gtccgggaag aatataagcg cggattcggc gtaccgaccc tgatcgccgt ccatcccgaa    540

aacgacccga agggcgaagg catggccatc gccaaggcct gggctgccgc caccggaggc    600

catcgcgctg gcgtgctgga aagctcgttc gtcgccgaag tgaagagcga cctgatgggc    660

gaacagacca tcctgtgcgg catgctgcag gccggtagcc tgctgtgttt cgacaagctg    720

gtcgaagaag gcaccgaccc tgcgtatgcc gaaaagctga tccagttcgg ctgggaaacc    780

atcaccgaag cgctgaaaca gggcggtatc accctgatga tggaccgcct gtcgaaccct    840

gccaagttac gtgcctatgc cctgagcgaa cagctgaagg aaatcatggc gcctctgttc    900

cagaaacata tggacgatat catcagcggc gagttcagct ccggcatgat ggcggactgg    960

gcgaatgacg acaagaagct gctgacctgg cgggaagaaa ccggcaagac ggccttcgaa   1020

accgcaccgc agtacgaagg caaaatcggc gaacaggagt acttcgacaa aggcgtcctg   1080

atgatcgcga tggtcaaggc gggagtcgaa ctggccttcg aaacaatggt cgatagcggc   1140

atcatcgagg aatccgccta ctacgaaagc ctgcatgaac tcccgctgat cgccaatacc   1200

atagcccgca agcggctgta cgaaatgaac gtcgtgatct ccgacactgc cgaatacggc   1260

aattatctct tctcctatgc ctgcgtgccg ctcctgaagc ccttcatggc cgaactgcag   1320

ccaggcgacc tggggaaggc gatccccgaa ggcgctgtcg acaacggcca gctgcgcgat   1380

gtcaacgaag ccattcgctc ccatgccatc gagcaggtcg gcaagaagct gcgtggctat   1440

atgacggaca tgaagcgcat cgcagtagcc ggataa                             1476
```

<210> SEQ ID NO 4
<211> LENGTH: 1851
<212> TYPE: DNA
<213> ORGANISM: Escherichia coli

<400> SEQUENCE: 4

```
atgccgaagt atcggtcagc caccactaca catggccgca acatggcagg cgctcgtgcc     60
ctgtggcgtg ctaccggcat gaccgatgcc gacttcggca agccgatcat cgccgtggtc    120
aactctttca cccagttcgt cccagggcac gttcatctgc gcgacctggg caagctggtg    180
gccgaacaga tcgaggccgc aggtggcgtc gcgaaagagt tcaacaccat cgccgtcgac    240
gatggcatcg ctatgggcca cggtggcatg ctgtatagcc tgccgtcccg cgaactgatc    300
gccgatagcg tcgaatatat ggtgaacgcc cattgcgccg atgctatggt gtgcatcagc    360
aactgcgaca agatcacacc ggggatgctg atggccagcc tgcggctgaa catcccggtg    420
atcttcgtga gcggtggccc gatggaagcc ggcaagacca agctgtcgga tcagatcatc    480
aagctggatc tggtcgacgc catgatccaa ggtgccgatc cgaaggtgag cgactcccag    540
tccgatcagg tggaacggag cgcctgcccg acttgcggct catgcagcgg catgttcacc    600
gccaactcca tgaattgcct gacggaagcc ctgggcctgt cccagcccgg taacgggagc    660
ctgttggcga cccatgccga ccgcaagcag ctgttcctga atgccggcaa gcgcatcgtg    720
gaactgacca agcgctatta tgaacagaac gacgaatccg ccctgccccg taatatcgcc    780
tcaaaagccg ccttcgaaaa cgccatgacc ctggacatcg ctatgggtgg cagcaccaac    840
accgtgctgc acctgctggc tgccgctcag gaagccgaga tcgacttcac catgtccgac    900
atcgacaagc tgagtcggaa ggtgccgcag ctgtgcaagg tggcaccgtc cacccagaag    960
tatcatatgg aagacgtgca tcgcgcaggc ggtgtgatcg gcatcctggg cgaactggat   1020
cgcgctggcc tgctgaatcg cgatgtgaag aacgtcctgg gcctgaccct gccgcagacc   1080
ctggaacagt acgacgttat gctgacccag gatgatgccg tcaagaatat gttccgcgca   1140
ggccctgccg gcattcgcac cacccaagcc ttcagccagg actgccggtg ggataccctg   1200
gatgacgatc gcgccaatgg ctgcatccgt agcctggaac atgcctattc caaggatggc   1260
ggtctggccg ttctgtatgg caacttcgcg gaaaacggct gcatcgtcaa gaccgctggc   1320
gtggatgatt cgatcctgaa gttcaccgga ccggccaaag tctacgaaag ccaggacgat   1380
gccgtcgaag ccatcctggg aggcaaggtc gtcgccggag atgtcgtggt gatccgctat   1440
gaaggcccga aaggcggtcc gggcatgcag gagatgctgt atccgacctc cttcttaaag   1500
agcatgggct tgggcaaagc gtgtgcgctc atcaccgatg gccgcttcag tggcggcacc   1560
agcggcctgt ccatcggcca tgtctcgccg gaagccgcca gtggcggcag catcggcctc   1620
atcgaagacg gcgatctgat cgccatcgat atcccgaatc gtggcatcca gctgcaggtg   1680
tccgacgccg aactagccgc acggagggaa gcgcaggatg cccgaggcga caaggcctgg   1740
accccgaaga accgtgaacg tcaggtgtcc ttcgcgcttc gcgcctatgc cagcctggcc   1800
accagcgccg ataagggtgc cgtgcgcgac aagagcaaac taggaggata a            1851
```

<210> SEQ ID NO 5
<211> LENGTH: 1689
<212> TYPE: DNA
<213> ORGANISM: Methylococcus capsulatus

<400> SEQUENCE: 5

```
atgaccgaca agcacccccg tccccattcg tcccaggtcg tcgacggcat ggagcgggcc     60
ccgagccgcg cgatgctgca cgccgtcggc ttcgccgatg ccgacttcgc caaaccgcag    120
atcggcatcg cttccacctg ggcgatggtg acgccgtgca acatgcacat caacaagctc    180
gccgaggacg cagcacgcgg cgtcgacggc ggcggcggca aggcagtgat cttcaacacc    240
```

```
atcaccattt ccgacggcat ctcgatgggc accgaaggaa tgaaatactc cctcgtgtcg    300

cgggaagtca tcgccgactc gatcgaaacc gtggtggcct gtcagggtta tgacggcgtg    360

gtcgccatcg gcggctgcga caagaacatg cccggctgcc tgatcgccct cgcccgcctc    420

aaccgtccgg cggtgttcgt ctatggcggc accatcctgc cgggctgcca cgacggcaag    480

aagctggacg tggtgtcggt gttcgaagcg gtcggcgccc gcgccaacca ccgcatcgac    540

gatgccgaac tgcacgccat cgaatccaat gccatccccg gtccgggctc ctgcggtggc    600

atgtataccg cgaacacgat ggcctccgcc atcgaggcat tagggatgag cctgccgggc    660

agttcggccc aggtggccat ttcccgcgcc aaggaactgg attgcgagcg ggccggcgcc    720

caggtcctca agctcctgga cctggggctc aaaccccgcg acatcatgac caagaaggcg    780

ttcgagaacg ccatcacggt ggtgatcgcc ctgggcggct ccaccaacgc cgtgctgcac    840

ctcctggcca tggccaacgc ctgcggcgtc gacctgaagc tcgacgattt cacccgcatc    900

gggcgcaaag tgccgatgct ggcggatctg aaacccagcg gcagatactc gatggccgaa    960

ctggtggaaa tcggcggcat ccagccgctg atgaagacct tgctggacgc gggactcctg   1020

cacggcgact gcatgaccgt aaccggcaag accctggaag aaaacctggc cgacgcgccc   1080

gactacccgg ccggacaaga catgatccgg tcgctggaca accccatcaa aaaggacagc   1140

catctggtga tcctcaaggg caacctggcg ccggaaggcg cggtcgccaa gatcaccggc   1200

aaggaaggac tgagcttcac cggcaccgcc cgcgtattcg actgcgagga agcggcgctc   1260

acggccatcc tcgacggcac gatcgtgaaa ggcgacgtaa tcgtcatccg ctatgaaggc   1320

cccaagggcg gccccggcat gcgcgagatg ctctcgccga cctcggcggt catgggcaag   1380

ggattgggca aggaggtcgc cctcatcacc gacggccgct ttccggcgg  cacccacggc   1440

ttcgtggtcg gccacatcac gccggaagcc tacaccggcg gccccctggc gatcgtccgg   1500

gacggcgata ccatcaccat cgacgccgaa acccgcgaat tgagcctgca cgtcaccgac   1560

gatgaaatcg gccggcgcct ggcgcagtgg actcaaccgg cgccgcgcta caccaagggc   1620

gtgctggcca aatacgccag gttggtgagc ccggcctcgg aaggcgccgt caccgacgac   1680

ggcctctga                                                           1689
```

<210> SEQ ID NO 6
<211> LENGTH: 1647
<212> TYPE: DNA
<213> ORGANISM: Carnobacterium divergens

<400> SEQUENCE: 6

```
atgtataccg tgggcgacta tctcctggag cggctctcgg aactgggcat caaagagatc     60

ttcggcgtgc cgggcgacta caacctgaag ttcctggatc acatcgtgga gcatccgaac    120

ctgaagtgga tcggcaacgc gaatgaactc aacgcggcgt atgccgccga cggctacgcc    180

cgcacgaagg gcgtctccgc gctggtgacc accttcggcg tcggcgagct ctccgccatc    240

aacggcatcg ccggctcgta tgccgagaaa gtcccggtca tccagatcgt gggcagcccc    300

acgatggcgg tgcagaatgc ccataagctg gtgcatcata ccctgggcga tggcaaattc    360

gaccacttcg agaacatgca tgagtccgtc accgaagcca tcggcagcct caccaaggag    420

aacgcggtga ccgagatcga tcgcgtgctg cgggccgccg tgctcaaacg gcgcccggtg    480

tatctgaacc tcccgatcga cgtggccgaa atggtcgtcg aaaaaccgtc gggccccctg    540

ctgcccaagc aggcgagcct gagcgcccgc gaggtcgaac tcgtgcatga gctggagaag    600
```

```
gccctgcagc aggcgaagaa cccggtggtc ctggcgggca acgagctggc gtcgttccac    660

ctcgaaacgt acctcgccga cttcatccac aagttcaacc tccccatcac gaccctcccc    720

ttcggcaagg gcgtcttcaa cgaggaagac gagcattatc tgggcgtcta tgcgggctcg    780

ccgaccgaag aaggcctgcg gaagcgcgtc gatacggcgg acctggtcgt ggcgctgggc    840

gcgaagctga cggactccgc cacctccggc ttctcgtacg acttctccga aaaacagctc    900

ttcagcctgg cgtccgacga agtcatcgtc aaagaggaac acctcgaagg catccatctg    960

ccggccgtca tgaaggcgct gacgagcatc gactaccagg gctaccaggg cgacatccag   1020

ccgatggccc ggctgaagag catcaaaccc accaaccagg tgctgaccca gcgccacttc   1080

tgggaggcca tcgaaggctt cctggaaaag ggcgacaccg ccgtcgcgga gcagggcacg   1140

agcttcttcg gcctctcgac cgtgccgctg aagagcgaaa tgtcgttcat cggccagccg   1200

ctgtggggct ccatcggcta tacgttcccg gcgatgctgg gcagccagct cgccaacccg   1260

tccagccggc acctcctgtt catcggcgac ggcagcctgc agctgacgat ccaggagctc   1320

ggcatggccc tccgcgaaaa actcaccccg atcgtgttcg tcatcaacaa taacggctat   1380

acggtcgaac gggaaatcca cggcccgaat gaaatctata acgacatccc gatgtgggac   1440

taccagaaac tcccgctcgt cttcggcggc tccgagcagt cggtcatcac ctataaagtg   1500

acgaccgaac tggaactggc gaacgcgctc aaggcggccc ggctggacaa caaccgcctg   1560

cagtggatcg aagtggtgat ggaccagacc gatgcgccgg agctcctcat gaagctgggc   1620

aagatcttcg cgaagcagaa tagctga                                       1647
```

<210> SEQ ID NO 7
<211> LENGTH: 1650
<212> TYPE: DNA
<213> ORGANISM: Methylococcus capsulatus

<400> SEQUENCE: 7

```
atgggcacgg ttgagcctgg cgctatcgga caacatctgc tcgcctgcct ttaccaggcg     60

ggcgtcgggc acatcttcgg cgttcccggc gattacgtgc tgggcttcta tgatctgatg    120

gccaaaggtc ccgtccggca tatcgggacc acgcgggagg acaccgccgc cttcgccgcc    180

gacggctatg cccgctgccg gggcatgggc gccctggcgg tgacttacgg ggtcggtgcg    240

ctcaacaccg tcaacgccgt cgccggcgcc tatgcggaat cctcgccggt ggtggtcatc    300

agcggtgcgc cgggggtgcg cgagcaaagg gaagacccgt tgatccacca ccgcttcggg    360

ccgttccggt tccagcgcga gatattcgaa cggatcacct gcgccgccgt ggtgctggac    420

gatccggtga tcgccttccg gcaggtggag cgtgcgctcg cagccgcccg tcagcactgc    480

aagccggtgt acatcgagat tcccgccgac cgggtgatgg cgccgggata tccgattcca    540

caggaaaccc cggaaacgcc ttccagcgac gattcggccc tggcggaggc ggtcgccgag    600

gccgcggagc tcctgggccg tgcggtgtcg ccggtgatcc ttgcaggcgt cgagttgcac    660

cggcgagggc tccaggacgc cctcgtcggc ctcgtcgagc aggcccgcct gccggtggcg    720

gcgaccttga ccggcaagtc ggtgttcgcc gagcgccatc ccgcctatct gggggtgtac    780

gagggtgcga tgagcacgga aaacgcccgc tacatggtcg agcagtccga cctcctgctg    840

atgctcgggg tcacgctgaa cgatgtcgac acgggcatct acacggcgcg tctcgatccg    900

cagcgcatcg tccgcgcagc ccagaacgag gtcgtgattc gccatcaccg ctatccccgc    960

gtcctgctcg cggacttcgt cacggccctg gcgcggtccg tcaaggcccg gggcgaggcg   1020

tttccgatgc cggcggggcc ggaaccgtgg gactttcccg cgccggaccg gccgatgacg   1080
```

```
atcgcccggc tggtggagcg gctcgaccgc gccctgacct ccgacatgat cgtagtgtgc   1140

gatgtcggcg actgcctgtt cgcagccacc gacctgcgcg tgcacgagcg cagcgaattt   1200

ctggcgtccg ccttctatac ctcgatgggg ttcgcggtgc ccgccgccct cggggcccag   1260

atcgcccgtc cggaccaccg ggcgctgatc ctggtcggcg acggtgcctt ccagatgacc   1320

ggaacggagc tgtcgaccca tgcccgtctc ggcctggcgc ccatcgtggt ggtgctcgac   1380

aatcgcggtt acagcaccga gcgcttcatc ctcgacggag ccttcaacga catcgccgac   1440

tggcgcttcc accggctggg cgaggtgttc ggccccctac agggctacga cgcgcccgac   1500

gaagcggcgt tcgaaaacgc gctcagcgaa gcgctggtca accgaaacat gccgagcctc   1560

atcaacgtcc gtctttcccc cggcgatgcc tcgatagcca tgaagcgtct cgccgggcat   1620

ctgcagtgcc gggtcaaggg cgagggctaa                                    1650
```

<210> SEQ ID NO 8
<211> LENGTH: 1647
<212> TYPE: DNA
<213> ORGANISM: Methylocaldum szegediense

<400> SEQUENCE: 8

```
atgggcaccg ccaaggcgga tagcatcggc cagtacctcc tgaaacgcct gtacgaggcc     60

ggcgtgaaac atatcttcgg cgtgcccggc gattacgtgc tgggcttcta cgatctgatg    120

gcgaagagcc cgatccagca cgtcggcacg acccgcgagg acaccgcggc cttcgccgcc    180

gacggctacg cccgctgtcg cggcctcggc gccctggcgg tcacctatgg cgtcggcgcc    240

ctgaacaccg tgaatgccgt cgcgggcgcc tatgccgaat cgagcccggt gatcgtcatc    300

agcggcgccc cgggcgtgcg cgaacagaag gaagacccga tgatccatca tcggttcggc    360

ccgttcacct tccagcggga aatcttcgac cggatcacct gcgccgcggt cacgctggac    420

gatcccatca tcgccttccg ccagatcgac cgggtgatcg cggcggcccg ccactcgtgc    480

aaacccgtgt atatcgaact gccccgcgac ctggtgatgg ccgaaggcca tccggtcccg    540

acggagcccc cggaagagcc cgcctccgat gaggcggccc tgagcgaagc ggtggccgaa    600

accgcggaac tgatgtccaa gtcggtgagc ccccaccgtcc tggcgggcgt cgaactgcac    660

cggcgcggcc tgcaggacgc cctggtggaa ctggtggaac gcgcccggct gccggtggcc    720

gccaccctca ccggcaagag cgtgatcgcc gaacgccacc ccgcctatct gggcgtctac    780

gaaggcgcca tgtcctcgga aaacgcccgc tacatggtgg aacagtccga tctcctgctc    840

atgctgggcg tgacgctgaa cgacatcgac accggcgtct ataccgcccg cctcgacccg    900

catcgcatcg tgcgggcggc ccagaacgag gtggtgatcc gctaccatcg ctatccgcgg    960

gtcaccctgt cggacttcgt cctgagcctg gcccgcaccg tgaaagcgaa gcatgaaacc   1020

ttccccgccc cggtcacgac ccccgaagcc acggagttcc ccatgcccga gcgcccgatg   1080

acgatcgccc gcctcatcga acgcctggac cgcgccctga cccccgacat gatcgtcgtg   1140

agcgatgtgg gcgattgcct gttcgcggcc atcgatctcc gggtctacga gcggagcgag   1200

ttcctctcgt cggccttcta caccacgatg ggcttcgccg tcccggccgc cctgggcgcc   1260

cagatcgcgc ggccggacca ccgggccctg atcctggtgg gcgatggcgc gttccagatg   1320

acgggcaccg agctcagcac gcacatccgc ttcggcctcg cgcccatcgt ggtcgtgttc   1380

aacaactgtg gctattcgac cgaacggtac atcctggacg gcccgttcaa cgacatctcg   1440

tgctggaact tcgaccggct gggcgaactg ttcggcccgc tgaacggcta tgacgcgccg   1500
```

```
gacgaggaga gcttcgagaa ggccctcgtc gaggccctgg ccaaccatgc cacgcccagc   1560

atcatcaacg tccacatcag ccgcgacgac agctccagcg cgatgcggcg gctggccgaa   1620

gtcctgaaga gccgcgtccg ggctga                                          1647


<210> SEQ ID NO 9
<211> LENGTH: 1653
<212> TYPE: DNA
<213> ORGANISM: Methylosarcina lacus

<400> SEQUENCE: 9

atgaacaccg ccaagttcga caccatcggc cagtacctgc tcaagcggct gtacgacgcg     60

ggcgtgaaac acatcttcgg cgtgccgggc gattatatcc tgggcttcta tgacctgatg    120

gtgaacagcc cggtccagca catcggcacc acgcgcgagg acaccgcggc cttcgcggcg    180

gacgcctacg cccgctgcct gggcctcggc gcgatggcgg tcacgtacgg cgtgggcgcc    240

ctgaataccg tgaatgccgt cgccggcgcg tatgccgaaa gctcgccggt gatcgtcatc    300

tccggcgccc ccggcatccg cgagcagcgg gaggacccgc tgatccatca tcggttcggc    360

ccgttcacct tccagcggga gatcttcgag cgcatcacct gcgcgaccga agtgctcaac    420

gacccggtga tcgccttccg ccagatcgat cgcgcgatcg ccaccgcccg gcggctgtgc    480

aagccggtgt acatcgagat cccgcgcgat ctggtgatgg cggaaggcta ccccatgccg    540

gacgaggccc tcgaacccct ggagagcgat gaaaccgccc tgagcgaggc gctggcggaa    600

acgatggaac tgatggcgaa aagcgtctcc ccgatgatca tcgccggcgt cgaactgcat    660

cggcggggcc tgcagagcgc cctcgtcaac ctggtggaac gcgcccatct cccggtggtc    720

gccaccctgt cgggcaaaag cgtcatggcg gaacggcacc cggcctacct gggcatctac    780

gaaggcgcga tgtcctcgga aaatgcccgg tacatggtcg aacagagcga cctcctcctc    840

atgctgggcg tcaccctcaa cgacatcgat accggcatct atacggccaa gctcgacccg    900

catcatatga tccgggcggc ccagaacgag gtggtgatct cctcgcatcg ctacccgcgg    960

gtcaccctct cggacttcct gacggcgctg gtgggcctgg tcaagacccg gagcgaaggc   1020

ttcagctcgc cgccggccgc ctacgaggcc agcgccttcc cggaaccgaa gcggccgatc   1080

accacggcgc ggatgatcgg ccggctgaac caggcgctgt cgccggaaat gatcgtggtg   1140

tgcgacgtgg gcgactgcct cttcgccgcc atcgatctgc aggtgcacga gcagtccgag   1200

ttcctcgcca gctgctacta tgccacgatg ggcttcgccg tgcccgcggc gctcggcgcc   1260

cagatcgcgc ggcccgatca ccggctgctc gtgctggtgg gcgacggcgc cttccagatg   1320

acgggcaccg aactgagcac ccatgcctat ctgggcctca acccgatcgt cgtggtgttc   1380

aacaactccg gctacggcac cgaacgcggc atcctggaag gccccttcaa cgacatcagc   1440

agctggcggt tcgaccgcct cggcgaagtg ttcggcccgc tgaagggcta tgacgccgcc   1500

accgaggagg ccttcgaagc ggcgctcatc aactccctca acaaccggac gatgccgagc   1560

atcatcaacg tccatctctc cgccgacgac gcctcctccg ccatgaagcg cctcgccgag   1620

cacctgaaga gccgcgtgaa gggcggctcg tga                                  1653


<210> SEQ ID NO 10
<211> LENGTH: 1653
<212> TYPE: DNA
<213> ORGANISM: Methylomonas denitrificans

<400> SEQUENCE: 10

atgtcgaccg cgaagttcga caccatcggc cagtatctgc tgaagcggct gtatcaggcc     60
```

```
ggcgtcaagg atatcttcgg cgtccccggc gactacgtgc tgggcttcta tgacctgatg    120

atcaagtcgc aggtgcgcca tatcggcacc acgcgggagg acagcgcggc cttcgcggcc    180

gacggctacg cccggtgtgt gggcatgggc gccctggcgg tgacgtacgg cgtcggcgcc    240

ctgaacacgg tgaacgccat cgccggcgcg tacgccgaat cgtcccccgt cgtcctcatc    300

agcggcgccc cgggcgtgtc cgagcagaag gacgatccgc tgatccatca tcgcttcggc    360

cccttcacgt tccagcgcga aatcttcgaa cggatcagct gtgcctccgt cgtcctgaat    420

gacccggtca tcgcgttccg gcagatcgac catgccatcg aggccgcccg gcgcttctgc    480

aagccggtgt atatcgaact gccgcgggac ctcgtgatgg cggagggcta ccccatgccc    540

accgagacgg tcgaaaagtt cacctccgat gaggccgcgc tgtccgaagc gatcgcggaa    600

accatgaccc tgctcagcaa ggcggtcagc ccgatgatcg tggcgggcgt ggagctgcat    660

cggcgcggcc tgcagggcgc cctggccgac ttcgtggaac ggacctgtct gcccgtggtg    720

gccaccctga cgggcaagtc ggtgatgtcg gagcgccatc ccgcctacct gggcatctac    780

gaaggcgcca tgtcctcgga agcggtgcgc gatcgggtgg agaagagcga tctgctcctg    840

atgctgggcg tgaccctcaa cgaaatcgac accggcatct acacggccaa actgaacagc    900

catagcacga tccgcgccgc gctgaacgag gtcgtgatct ccgcccaccg ctatcccggc    960

atcgcgctgg aagatttcct gggcgccctg gcctcgtcgg tgtccctcag ctcgcgcgag   1020

gtggtcagca gcccgaaacc cccggagtcg atcgccttcc cggaaccgga ccggccgatc   1080

acgacggccc gcctggtcga acggctcaac tccgccctca gcaatgacat gatcgtcgtg   1140

tgtgacgtgg gcgactgcct gttcgcggcc atcgacctcc gcgtgcatga gcagagcgag   1200

ttcctggcct ccgccttcta caccacgatg ggcttcgcgg tgcccgcggc cctcggcgcc   1260

cagatcgccc gccccgaccg gcgggcgctg atcctggtcg gcgacggcgc gttccagatg   1320

accggcaccg aactgtccac gcacgcgcgg ctgggcctga acccgatcgt cgtcgtgttc   1380

aataatggcg gctactcgac cgaacgctgc atcctggaag gcccgttcaa tgatatcaac   1440

ccctggcgct tcgaccgcct gggcgagctg ttcggccccc tggccggcta tgaggccgcc   1500

acggaagccg agttcgagga agccctgctg aacgcgctgg acaaccacgg catgccgtcc   1560

atcatcaatg tgcatctcgc cgccgacgat agctccgagg cgatgaaacg cctggccgag   1620

cacctgcaga gcaaaatcaa gcgggacgcc tga                                1653
```

<210> SEQ ID NO 11
<211> LENGTH: 1662
<212> TYPE: DNA
<213> ORGANISM: Methylomonas methanica

<400> SEQUENCE: 11

```
atgaacacgg tcaaactgga aacgatgggc cagtacctgc tgaaccgcct ctatgaggcg     60

ggcgtgaaac atgtcttcgg cgtcccgggc gactatgtcc tgggcttcta cgacctgatg    120

gagaagtccc ccatccagca tatcggcacc acccgcgaag ataccgcggc cttcgccgcc    180

gacggctacg cccgctgccg cggcctgggc gccctggccg tcacgtacgg cgtcggcgcc    240

ctcaacacgg tgaatgcggt ggcgggcgcc tacgcggagt cgtcgcccgt gatcgtcatc    300

agcggcgccc cgggcgtctg tgagcagcgc gatgacccgc tgatccacca ccgcttcggc    360

cccttcacct tccagcgcga gatcttcgaa cggatcacct gcgccaccgc ggtgctgaac    420

gacccggtga tcgcgttccg gcagatcgat cacgccatcg cctccgcccg ccattattgc    480
```

```
aagccggtct atatcgaaat cccgcgggac ctcgtgtccg tggaaggcta cccgatgccc    540

gccatcgccg cgatggagcc gtcgggctcc gacaagtccg ccctcagcga ggccgtggcg    600

gaaaccatgt cgctgctgga aaagtccgtg tccccgatgg tcatcgccgg catcgagctc    660

caccgccgcg gcctgcagaa ccgcctcctc gaactgatcg aacgcgcccg cctgcccgtg    720

acggccaccc tcaccggcaa aagcgtgatc gcggagcggc accccgcgta cctgggcatc    780

tatgagggcg cgatgtccag cgaacacgcc cgctatatgg tcgagcagtc cgacctcctc    840

ctcatgctgg gcgtgaccct gaacgaggtc gacacgggca tctacaccgc gaagctggac    900

ccccagcata ccatccgggc ggcgctgaac gaggtggtga tctcggccca ccgctatccg    960

aatatcgccc tggccgacta tctgaacgcc ctggtggacg cggtgaagcc gtcggaggcg   1020

ggcttctccg ccaaaccggg caaacccgtc gcgcgggcgt tcccggagcc cgaccgcccg   1080

atctcgatca accgcctgat cgaacgcatc aatcaggcgc tggaaccgga gacgatcgtg   1140

gtgtgcgacg tgggcgactg tctcttcgcc gccatcgatc tggaggtcca cgagcagtcg   1200

gagttcctgg cctcgggctt ctataccacg atgggcttcg ccgtgcccgc cgccctgggc   1260

gcccaggtcg cccggcccgg ccaccgcgcc ctgatcctgg tgggcgacgg cgcgttccag   1320

atgaccggca cggaactctc cacccaggcc cggctgggcc tggactcgat cgtgatcgtc   1380

ttcaacaatt cgggctattc cacggagcgg tgcatcctgg agggcccgtt caacgatatc   1440

gcccgctggc gcttcgaccg cctcggcgaa gtcttcggcc cgctgcaggg cttcgacgcg   1500

gcgaccgagg agtccttcga gtcggcgctg atccaggccc tgaacaaccg cagcatgccc   1560

agcatcatca acgtccacct cgcgagcgac gacacgagca gcgcgatgcg gcgcctggcg   1620

gaacacctga agtcgaaggt gcagggcgaa cgccccgcct ga                      1662
```

<210> SEQ ID NO 12
<211> LENGTH: 1659
<212> TYPE: DNA
<213> ORGANISM: Methylohalobius crimeensis

<400> SEQUENCE: 12

```
atggccacgc gcaactcgac gacctcgatc ggcgagtatc tcctccagcg cctgcacgag     60

gccggcgccc accacatctt cggcgtcccg ggcgattata tcctgaaatt ctatgaacag    120

atctcgcagg gcccggtccg ccacatcggc accacgcgcg aagacaccgc ggcgttcgcg    180

gcggacggct atgcccggtg ccagggcatc ggcgcgatgg ccatcaccta cggcgtgggc    240

gccctcaacg tggtgaatgc cgtcgcgggc gcgtacgccg aaagctcgcc ggtggtcgtg    300

atctcgggcg cccccggcgt gtgggaacag cgcgaggacc cgctgctgca ccaccgcttc    360

ggcccctaca cgttccagcg ggagatcttc gaccggatca cctgtgccac cacggtcctg    420

gacgatccga tcacggcgtt ccgccagatc gatcgcacga tcgccgcggc gcagcgcgaa    480

cataagccgg tctacatcga actgccgcgc gatcgggtca cggtggccgg cgtgccgctc    540

ccggccgtcg cggaggcgac gccccaggaa acgtccgacg ccgccaccct ggacgaggcc    600

gtggccgaaa cgctggccct cctcgcccag gccaagagcc ccgtgctgat cgcgggcgtg    660

gaggtccacc gctgcggcct ccaggatgcg ctcgtcgacc tggtcgtccg cgcgggcctg    720

ccggtcgcgg ccaccctgac gggcaaatcc gtcgtgggcg aacgccaccc ggcgtatatc    780

ggcgtctacg agggcgccgc gtcgtccgaa cacacccgcc agatggtgga acgcgcggac    840

gtgctcatca tgctcggcgt gacgctgaac gacgtggaca ccggcgtcta tacggcgaac    900

ctggaccccc atcgcctggt ccgcgcgtcc cagggcgagg tgaacatccg ctaccatcgg    960
```

```
tatccgcgcg tccagctgca ggacttcatc ggcgccctcg cccgccaggt cagccccgc   1020

cgcgaggccc tgccgtccca gcccttcgtc gatagcggcc ccgccttccc cgtcccgggc   1080

caggcgatga ccacggcgcg gctcatcgcc cgcctgaact gcgccctcac ccccgaaatg   1140

atcgtggtgt ccgatgtggg cgattgcctg ttcgccgcca tcgaactccg ggtctgcgaa   1200

cggagcgagt tcctggcctc cgcctactat acgacgatgg gcttcgcggt gccggccgcc   1260

ctgggcgccc aggtcgcgcg gccggatcgg cgggccctga tcctggtggg cgacggcgcc   1320

ttccagatga cgggcaccga gctgagcacc cacgcccgcc tgaacctggc gccgatcatc   1380

atcgtcttca acaacgccgg ctacagcacg gagcgcaata tcctggaggg cccgttcaat   1440

gacatcgcgg cctggcggtt cgaccgcctc ggcgaagtgt tcggccccct gcatggctac   1500

gacgccaaga cggaagatgc gttcgagacg gcgctcgccc gcgccctggc cgagacgggc   1560

tgcccgtcgc tcatcaatgt gcatctgtcc ccggacgacg cctcgccggc catgcgccgc   1620

ctgacggagc ggctgtccca tcgcgtgggc aatcagtga                          1659
```

```
<210> SEQ ID NO 13
<211> LENGTH: 1635
<212> TYPE: DNA
<213> ORGANISM: Methylobacter marinus

<400> SEQUENCE: 13

atgagcagca acccgtcgat cggccactac ctgctcacgc ggctgtacga atccggcgtg     60

caccacatct tcggcgtccc gggcgactac atcctccgct tctaccagca gctgagcgag    120

agcccggtgc agcatatcgg caccacgcgc gaagacacgg ccgccttcgc gaccgatgcg    180

tatgcccgct gtcggggcct gggcgcgatg gccgtgacct acggcgtcgg cgccctcaat    240

gtggtcaacg ccgtggcggg cgcccatgcc gagtcgagcc ccatcgtggt catctccggc    300

gcccccggca tcaaggaacg ccgggaacac cccctgctgc atcaccgctt cggcccgttc    360

cgcctgcagc gcgagatctt cgaacggatc acctgcgccg tcgcggtgct ggatgacccc    420

tataccgcct tccggcagat cgaccgggtc ctggcggcgg cgcgggagca ctgcaagccc    480

gtctacatcg agctgccgcg cgatcgcgtg gataccgagg gctatccgat cccgtcggag    540

tccctgccgg cccccgcctc cgacgccgcg agcctcaacg aagccgtgga ggaagccctg    600

cagctcctcg atgaggccgc gtcgccggtg ctggtcgccg gcgtggaact gcaccgccgg    660

ggcctccagg atcagctcct ctcgctggtg gataaaaccc atctgccggt cgccgccacg    720

ctcaccggca agtccgtcct gggcgagcgg cacccgtgtt atctgggcat ctacgagggc    780

gcgatgggct ccccccctggc gcgggaccgc gtcgagcagg ccgatttcct gctgatgctg    840

ggcgtcacgc tgaacgatgt ggacctcggc atcttcaccg cccgcctcga cgccaatcgc    900

atcatccggg cctcccagga cgaagtcatc atccaccacc accgctatcc gcaggtcctc    960

ctgcgggact tcgtgtccat gctgaacgaa cggatgaccc cgcgccccca gacgggcccg   1020

gccgtcgccg cgaagccggc cgccttcgat ttcccggtca aaggccagcc gatgaagatc   1080

atccggctga tcgcccggct gaatcggttc ctcaccccgg acatggtcgt ggtcagcgac   1140

gtgggcgatt gcctgttcag cgcgatcgac ctgcgggtgc acgaaaacag cgagttcctc   1200

gcctcggcct actacaccag catgggcttc gcggtcccgg ccgcgctggg cgcccagatc   1260

gcccgcccca cccggcgcac gctggtcctc gtgggcgacg gcgcgttcca gatgaccggc   1320

accgagctct cgaccatcgc gcacctcggc ctgaacccga tcgtgatcgt cttcaataac   1380
```

aagggctact cgaccgaacg ctatatcctg gatggcccgt tcaatgatat cccggcctgg 1440
cagttcgagc gcctgggcga actcttcggc ccgctgaccg gctatgccgc cagcaccgag 1500
gacgagttcg aagattgtct gaaccaggcc ctggcccagc ggtcgagccc ctccctcatc 1560
aacgtccacc tctccccgga cgatccgagc gccgccatgc ggggcctcgc cgaacatctg 1620
ggcaagcgcg tctga 1635

<210> SEQ ID NO 14
<211> LENGTH: 1650
<212> TYPE: DNA
<213> ORGANISM: Methylobacter luteus

<400> SEQUENCE: 14
atggaggtgc atctgatgtc ctccaacccg tccatcggcc attatctgct cgcccgcctg 60
tacgagtccg gcgtgcatca catcttcggc gtccccggcg actacatcct gcgcttctac 120
cagcagctca gcgagtcccc gatccagcac atcggcacca cgcgcgagga caccgccgcc 180
ttcgcgaccg acgcctacgc ccgctgccgg ggcctgggcg cgatggccgt gacctacggc 240
gtgggcgccc tgaacgtcgt gaacggcgtg gccggcgcgt acgcggaatc ctcgccggtc 300
gtggtgatct ccggcgcccc gggcatcaag gaacgccatg aacatccgct gctgcatcat 360
cgcttcggcc cgttccgcct gcagcatgaa atcttcgaac gcatcacctg cgcgacggcg 420
gtcctggacg atccctacat ggcgttccgg cagatcgacc gggtgctggc cgccgcccgc 480
gagcactgca agcccgtgta tatcgagctg ccgcgcgacc gggtggatgt cgaaggctat 540
ccgatgccga gcgagagcat gccggccccg gcctccgacg cggaaagcct gaacgaagcg 600
gtcgaagaaa cgctgcagct gctgggcaag gccgcgtcgc ccgtgctgat cgcgggcgtc 660
gaactgcacc gccgcggcct ccaggacaaa ctgctctccc tggtcgacaa gacccatctc 720
ccggtggccg cctcgctgac cggcaaatcg gtcctgggcg aacgccaccc gtgctatctg 780
ggcatctatg aaggcgcgat gggctcgtcc ctggcccggg actccgtgga gcagtcggac 840
ttcctcctga tgctgggcgt caccatgaac gacatcgatc tgggcatctt caccgcgaag 900
ctggacgcga accgcatcat ccgcgccacg caggatgagg tcatcatcca ccatcatcgc 960
tatccccacg tcctgctgcg ggacttcgtc accgtcctga atgagcgcat cacgccccgc 1020
ccgggcatcc gcccggccgt cgcggcggag ccggccgcct tcgacttccc ggtcaaggac 1080
cagcccatga aaatcctccg gctgatcgaa cggctcaacc gcttcctgac ccccgacatg 1140
gccgtcgtct ccgatgtcgg cgattgcctc ttcgcggcga tcgacctccg ggtgcacgag 1200
aactcggagt tcctggcgtc ggcgtattat accagcatgg gcttcgccgt gcccgcggcg 1260
ctcggcgccc agatcgcgaa cccgacccgc cgcacgctgg tgctggtcgg cgacggcgcc 1320
ttccagatga ccggcaccga actgtccacc atcgcccggt tcggcctgaa cccgatcgtg 1380
atcgtcttca ataactgtgg ctattcgacc gagcggtaca tcctggatgg ccccttcaac 1440
gatatcgcct gctggcagtt cgaacggctg agcgaggtgt tcggcccgct ctcgggctat 1500
tcggcccgga cggaggatga gttcgaaaac tgcctgaccc aggccttcgc ccagcagtcc 1560
tcgccgtccc tcatcaacgt ccacctcccc ccggatgacc cgagcgcggc catgcgcggc 1620
ctcgcggaac acctcggcaa gcgcgtctga 1650

<210> SEQ ID NO 15
<211> LENGTH: 1629
<212> TYPE: DNA
<213> ORGANISM: Lamprocystis purpurea

<400> SEQUENCE: 15

```
atgggcgact acctcctgct ccgcctgaag gaagcgggcg tcgaccactg cttcggcgtc      60
cccggcgact acgtcctgcg gttctacgat cggctctgcc ggtcggacat ccggcacatc     120
ggcaccaccc gcgaggacac cgcggccttc gcggccgacg gctacgcccg gtcccgcggc     180
ctgggcgccc tggccgtgac gtatggcgtg ggcgccctca acgtggtcaa cgcggtcgcc     240
ggcgccaacg cggagtcctc cccggtcgtc gtgatctccg gcgccccggg cgtcgcggaa     300
cagcgcgacg atccccagct gcaccatcgg ttcggcccgt tccggttcca gcgcgagatc     360
ttcgaacgca tcacctgcgc gtgtgccgtg ctcgacgacc cgtacaccgc cctgcgcgag     420
atcgaccgca cgctcgacgc ggcgcggcgg tacagccggc ccgtgtatat cgaactcccg     480
cgcgaccggg tcgacacgcc cgccttcccc atcccccacg agccggaaga ggaagccggc     540
agcgacccgg aggccctggc cgaggcggtc gccgaaaccc tggcgctcgt cggccgcgcc     600
caggcccccg tcatcctggc cggcgtggag ctgcaccgcc gcggcctgca ggacctcctg     660
gccggcttcg tgctgaaggc ccacctcccg gtggccgcga cgctgacggg caagtcggtg     720
gtcgccgagc gccagccggg ctacctgggc gtgtacgagg gcgcgatggg cccggaaggc     780
gcccgccgcg tcgtggaaga agccgacctg ctgctcctgc tgggcgtgac cccgaacgac     840
atcgacctgg gcatcaacac cgcccggctg gaccccgccc ggaccgtccg ggccggccag     900
gaagaaatct gggtccatcg gcaccgctac ccgcatgtgc acctgcggga tttcctggcc     960
gcgctgacgg atgccgtggt gccccacccc ggcccccctgc cggatgtccc cggcccggtc    1020
ggcgccccgg acttccccca gccgggccag cccatgacga tggcccgcat gatggcccgc    1080
ctgaacgact tcctgacccc cgacatgcag gtggtggccg actccggcga ctgtctgttc    1140
gcgtccgtcg acctgcgcgt ccatgcccgc agcgagttcc tggcctcggc ctattacacg    1200
acgatgggct tcgccgtccc ggccgcgctc ggcgcccagg tcgccaaccc cggccgccgc    1260
ccgctcgtgc tggtgggcga cggcgccttc cagatgaccg gcacggagct gtcgaccgcc    1320
gcccgcctgg gcctcgatcc gatcgtcatc atcggcaata atcgcggcta caccaccgaa    1380
cgcttcatcc tggaaggccc gttcaacgac atcgccgact ggcggttcca tcgcctgggc    1440
gaactgttcg gcccgctgcg gggcttctcg gcccccacgg aagacgcctt cgacgccgcc    1500
ctgggcgccg ccctggcctt ccgggacggc ccctccgtca tcgaggtggc gctgcgcccg    1560
gacgactgct ccgcggccct gacccggctc tccgaacgcc tgcgcgatgt ggtgcagcag    1620
agcgcctga                                                             1629
```

<210> SEQ ID NO 16
<211> LENGTH: 1656
<212> TYPE: DNA
<213> ORGANISM: Andreprevotia chitinilytica

<400> SEQUENCE: 16

```
atgcacatgc gggagacgga catggatacg atgggcggct acctgctgca ggccctgcat      60
cgcgagggcg tccggcatgt gttcggcgtg ccgggcgact acatcctgcg ctggtatcag     120
ctgctctcgc agagcaacct gaagcacgtc ggcacctcgc gcgaagactg cgccgcgttc     180
gccgccgacg gctacgcgcg gtgccacggc ctgggcgccc tggccgtcac ctacggcgtc     240
ggcgccctga acgtggtgaa cgcggtggcc ggcgcgaacg cggagtccag ccccgtggtg     300
gtcatcagcg gcgccccggg cgtcgcggaa cagcgccaga acccgctgct ccaccaccgc     360
```

```
ttcggcccgt tctgcttcca gcgcgaaatc ttcgaacgca tgacgtgcta cgcggcggcg    420

ctcgacgatc ccctcctggc gcggcgccag atcgaccgcg ccctggagct ggcccagctc    480

catcacaagc cggtctacct cgaactgccg cgggatctcg tggatgcgga actgccgccg    540

gccctctcgc cgcccacctc ctcggcgccc atctcggatt gggacgcgct cgaagaagcg    600

gtcgcggaaa ccctcagcct cctggcgaag gcgaaaagcg ccgcggtcct cgccggctcg    660

gagctgcacc gctaccagct gcaggacgag ctgacgcagc tcgtggaacg gggcgccctc    720

cccgtggccg ccaccctgac cggcaagtcc gtgatcgccg agcgccaccc ggcctacatg    780

ggcatctacg aaggcgcgat gggcggcgcc cgcacgcggg aactgatcga gcgggcggac    840

gtgctgctgc tgctgggcgc caccctcaat gatgtggatc tgggcatctt caccgccaag    900

ctggatgtcc agcacatggt gcaggcgacc gccgatggcg tccagatcca ccaccaccgc    960

tacaccggcg tcccccctcgg cgactatgtg cgggccctga cggcgggcat cgaacgctcg   1020

ggccgctccc tcccggtggt ggaacccccc ctggcggcca tcggcttccc gatcacctcg   1080

cagcccatga ccgtggcccg cctgatcggc cgcctcaatg ataccctgcc gcaggacatg   1140

atcgtcgtct gtgacaccgg cgactgcctc ttcgcctccc tggagctccg cgtccatgcc   1200

cgcaccgcct tcctggcctc ggcgttctac acgacgatgg gcttcgccgt gcccgcctcg   1260

ctgggcgccc agctcggctc gggccggcgc cccctggtgc tggtgggcga tggcgccttc   1320

cagatgacgg gcaccgagct ggccaccgcc gcgtggaagg gcctgaaccc catcgtcatc   1380

gtcttcaaca acgccggcta ctccaccgag cgcttcatcc tggacggccc cttcaacgac   1440

atcccgtcgt ggcagttcca tcgcctgggc gaactgttcg gcccgctggc cggcttcgat   1500

gtccacgacg aagagtcgtt cgactccgcc tggcgctcgg ccctcgccca gaccgatcgc   1560

ccgtcgctgc tgaacgtgca tctggccccc gacgacccct cgcccgcgat gcggcggctg   1620

ggcgaacatc tgggcaagcg ggtgcgggcg ggctga                              1656
```

<210> SEQ ID NO 17
<211> LENGTH: 1647
<212> TYPE: DNA
<213> ORGANISM: Lactococcus lactis

<400> SEQUENCE: 17

```
atgtacaccg taggagacta cctacttgac agactccatg agctgggcat agaggaaatc     60

ttcggagtcc cgggtgatta caacctgcag ttcctggacc agatcatcag ccacaaggac    120

atgaagtggg tgggcaacgc gaacgaactg aacgcgagct atatggcgga cggttatgcc    180

cgcaccaaga aggcagccgc gttcctcacc actttcggcg tgggcgaact cagcgccgtg    240

aacggcttgg caggcagcta tgcggaaaac ctgccggtgg tggaaatcgt cggctccccg    300

acctcgaagg tgcagaacga gggcaagttc gtgcatcata ccctggcgga cggggacttc    360

aagcatttca tgaagatgca cgaacccgtc accgctgccc gcacgctgct gaccgcggaa    420

aacgcgaccg tggagatcga ccgggtcctc tccgccctgc tgaaggaacg gaagcccgtg    480

tacatcaatc tacccgtcga cgtagcagcc gccaaggccg aaaagccctc gctcccgctg    540

aagaaggaga actcgacgag caacacgagt gaccaggaaa tcctgaacaa gatccaggag    600

tcgttaaaga acgcgaagaa gccgatcgtc atcaccggcc atgagatcat cagcttcggc    660

cttgagaaga ccgtgacaca gttcatctcc aagaccaagc tgcccatcac caccctcaac    720

ttcggcaagt ccagcgtgga cgaagccctg ccgagcttcc tgggcatcta caacggcacc    780

ctgtcggaac ccaacctgaa ggagttcgtc gaaagcgcgg acttcatcct gatgctgggc    840
```

```
gtgaagctga ccgactcctc gacgggagcc ttcacccatc acctgaacga aaacaagatg    900

atctccctca acatcgatga aggcaagatc ttcaacgagc gcatccaaaa cttcgacttc    960

gaaagcctga tctcctcgct gctggacctg tccgagatcg agtacaaggg caagtacatc   1020

gacaagaagc aggaagactt cgtgccgtcg aacgcgctgc tgtcgcagga ccgcctgtgg   1080

caggcggtcg aaaacctgac gcagtcaaac gaaaccatcg tcgccgaaca gggaacctcg   1140

ttcttcggtg cctcaagtat cttcctgaag tccaagtccc acttcatcgg ccagcccctg   1200

tggggctcga tcggctatac cttcccggca gcgctaggct cccagatcgc ggacaaggaa   1260

tcgcggcacc tgctcttcat cggcgacggc tccctgcagc tgaccgtcca ggagctgggc   1320

ctcgccatcc gggaaaagat caacccgatc tgcttcatca ttaacaacga cggctacacc   1380

gtggagcgcg agattcatgg cccgaaccag agctacaacg acatccccat gtggaactac   1440

tctaagctgc cggaatcgtt tggcgccacg gaggaccggg tggtcagcaa gatcgtccgg   1500

acggagaacg agttcgtctc ggtgatgaag gaagcgcagg cggaccccaa ccggatgtat   1560

tggatcgagc tcatcttggc caaggagggc gctccgaagg tcctgaagaa gatgggcaag   1620

ctcttcgccg aacagaacaa gtcgtaa                                        1647
```

<210> SEQ ID NO 18
<211> LENGTH: 1713
<212> TYPE: DNA
<213> ORGANISM: Lactococcus lactis

<400> SEQUENCE: 18

```
atgggctcgt cccatcatca tcaccaccat tccagcggcc tggtcccgcg cggcagccac     60

atggcctcga tgtacaccgt gggcgattac ctgctggacc ggctccacga actgggcatc    120

gaagagatct tcggcgtccc gggcgactat aacctccagt tcctggatca gatcatctcc    180

cgcgaggaca tgaaatggat cggcaatgcg aacgagctga acgcctccta tatggccgac    240

ggctatgccc gcaccaaaaa agccgccgcc ttcctgacca cgttcggcgt gggcgaactg    300

tcggccatca acggcctggc cggctcctac gccgagaacc tgcccgtggt ggaaatcgtg    360

ggctcgccga cctcgaaggt ccagaacgac ggcaagttcg tgcaccacac gctcgcggac    420

ggcgacttca agcacttcat gaagatgcac gagccggtca ccgccgcccg caccctgctg    480

acggccgaga acgcgaccta tgaaatcgac cgggtgctct cccagctcct gaaggagcgg    540

aagccggtgt acatcaacct ccccgtcgat gtggccgccg ccaaggccga gaaacccgcg    600

ctgagcctgg agaaggagtc ctccacgacc aacaccaccg aacaggtgat cctcagcaag    660

atcgaagaat ccctcaagaa cgcccagaaa cccgtggtga tcgcgggcca tgaggtgatc    720

tcgttcggcc tggagaaaac cgtcacccag ttcgtgagcg aaaccaagct ccccatcacc    780

accctcaact tcggcaagtc ggccgtggac gagtccctgc cgtccttcct gggcatctat    840

aatggcaaac tgtcggaaat cagcctgaaa aatttcgtcg aaagcgccga cttcatcctc    900

atgctgggcg tgaagctgac cgactcctcg accggcgcct tcacccacca cctcgatgaa    960

aacaagatga tctccctgaa catcgacgaa ggcatcatct tcaacaaggt ggtcgaagac   1020

ttcgacttcc gggccgtcgt gtcgagcctg tccgaactga aaggcatcga atatgaaggc   1080

cagtacatcg acaagcagta tgaagagttc atcccgtcgt cggcgccgct cagccaggat   1140

cgcctctggc aggccgtgga aagcctgacc cagtccaacg aaacgatcgt cgccgaacag   1200

ggcacctcgt tcttcggcgc cagcacgatc ttcctgaagt ccaactcccg gttcatcggc   1260
```

```
cagccgctgt ggggctcgat cggctacacg ttcccggccg cgctgggcag ccagatcgcc   1320

gacaaggaat cccgccacct cctgttcatc ggcgacggct ccctccagct gaccgtgcag   1380

gagctgggcc tgtcgatccg cgaaaagctg aatccgatct gcttcatcat caacaacgac   1440

ggctacacgg tcgaacggga gatccacggc ccgacgcagt cctacaacga catccccatg   1500

tggaactaca gcaaactccc ggaaaccttc ggcgccaccg aagaccgcgt cgtctcgaag   1560

atcgtgcgga ccgaaaacga gttcgtgtcc gtgatgaaag aggcgcaggc ggatgtgaac   1620

cggatgtact ggatcgaact ggtcctggag aaagaggacg ccccgaagct cctgaagaag   1680

atgggcaagc tcttcgccga gcagaacaaa tga                                1713
```

```
<210> SEQ ID NO 19
<211> LENGTH: 1650
<212> TYPE: DNA
<213> ORGANISM: Streptococcus didelphis

<400> SEQUENCE: 19

atgtataccg tcggcgatta tctgctggat cggctcaagg aaatcggcat cgaccatatc     60

ttcggcgtcc cgggcgacta caacctccag ttcctggatc agatcaccgc ccgcgacgac    120

ctcaaatggg tgggcaacgc caacgaactc aacgcgagct acatgtccga cggctatgcc    180

cgcaccaaga aggccgccgc cttcgtcacc accttcggcg tgggcgaact gtcggcgatc    240

aacggcctgg ccggctcgtt cgcggaaaac gtccccgtga tcgagatcgt cggctcgccg    300

acgaccaagg tgcaggaagc cggcaaactg gtgcaccata cgctcggcga cggcaacttc    360

aatcacttcc aggagatgca caaatcggtc accgtggccc aggtcaaagt cagcgccgaa    420

catgcccaga ccgacatcga ccaggtgctc ctgtccctgc tgaaggagcg gaagccggtg    480

tatatcaacc tgcccatcga tgtggcccag atgcccgccc agaagccgga atcggccctc    540

ctggtcgaga aggtcatctc cgagcaggac aagatcatcc tgcaggcgat cgagaaaggc    600

ctgaagaccg ccaagcagcc cctcatcatg gtcggccatg aagtcgccag cttcggcctg    660

gaagccacca tcaacaactt catcaaaaag aagaagtacc ccgtgacctc gctcagcctg    720

ggcaaaggca tcgtcaacga gtcgccggaa accttcctgg gcatctactc cggcgccctg    780

tccccgcagg ccctgaaaga ctacgtcgat caggcggact tcatcctcac cctcggcgtc    840

aagctgaccg actccgtgac gggcggcttc agccagggct tcgatgcgaa gcaggtgctg    900

agcctggccg ccaaccaggc gtcgctcttc ggcgaaaact accagggcta tcacttctcc    960

gacgtgatcc gcgaaatcga aaatctggac atccccagct attcgggctc ctatatcgcc   1020

aagaccaagg tcgccgattt cgaagcggag aagggccagg tcctgtccca gaagcgcttc   1080

tggcaggcga tggaatcgtt cgtccaggcc ggcgacacca tcttcgccga gcagggcacc   1140

tcgtacttcg gcgcgagcca gctcaacctg aaagagaacg tggcctacca gggccagccg   1200

ctctggggca gcatcggcta taccttcccg gccgtcttcg gcagccagct cgcgaacccc   1260

gattcgcggc atatcctgtt cgtcggcgac ggcagcctgc agctgaccgt ccaggacatc   1320

ggcctggcgc tgcgcgagca gctgaacacg atcgtgttcg tcatcaacaa cgacggctat   1380

accgtggagc gcaagatcca cggcccggaa gaggtctata atgacatccc gcagtggcag   1440

tacagccagc tccccgcctc cttcggcggc aacgactcgc aggtcctggc ccggaaagtg   1500

agcaccgaag aggagctggt cgaaatcctg gaaaaggcgc gggccgacgt gtcccggatg   1560

tattggatcg agctcatgct ccccaaaatg gacgcgccgg agtatctgga aaagctgggc   1620

aagctgttcg cccagcagaa taaagcctga                                    1650
```

<210> SEQ ID NO 20
<211> LENGTH: 1647
<212> TYPE: DNA
<213> ORGANISM: Enterococcus caccae

<400> SEQUENCE: 20
atgtacaccg tcgccgatta cctgctggat cgcctgaagg agctgggcat cgatgagctg 60
ttcggcgtgc cgggcgacta caacctgcag ttcctcgacc acatcaccgc ccgccaggac 120
ctggagtgga tcggcaacgc caacgaactg aacgccgcgt atatggccga cggctacgcc 180
cggaccaagg gcatctcggc gttcgtgacc accttcggcg tgggcgagct gtccgccatc 240
aatggcctcg ccggcagctt cgcggagaac gtcccggtcg tcgagatcgt gggctccccg 300
accaccacgg tccagaacga caagaagctg gtgcatcaca cgctgggcga cggcaatttc 360
ctgcatttcg agaagatgca tgaagaggtc accgccgcca tcgcgcacct caccgccgaa 420
aacgcgctga ccgaaatcga ccgggtgctc atcatcgcca tgatcgagaa gcgcccggtc 480
tatatcaacc tcccgatcga catcgccgag ttcaaagcca ccccgccgct cagccccctg 540
agccggtcgg ccgaaaagct gacggatgtc gaaatcgcca tcctcgacaa ggtggaaaag 600
gcgctgtcgc aggcgaagaa ccccgtcgtg atcgccggcc acgaaatcct cagctaccat 660
atcgaacatc agctggacga gttcatccag aagttcaacc tcccgatcac cacgctgccc 720
ctgggcaaac gcgcgttcaa tgaggaagac ccgcactatc tcggcaccta cagcggctcc 780
accaccgagg agccgctgaa gacccgcgtg gataccgcgg atctggtcct gctgctgggc 840
gcgaagctga cggactcggc cacctcgggc ttctccttcg gcttcaccga ccagcagatc 900
atcagcatcg gctccacgga ggtcctcttc tacggcgaaa ccttcaaagc cgtgcagctc 960
gaccgcttcg tctcggcgct caccaccctg agcttctccc ggtacgaaga tgaaatccag 1020
ccggtgaccc ggatcagcaa ccaggcgatc aaggacgaga agctgtcgca gaagcagttc 1080
tgggagatgg tcgagacgtt cctgatcccg ggcgacaccg tgatcggcga gcagggcacc 1140
tcgttcttcg gcctgaccaa cgtcgccctg aagcggaata tgcacttcat cggccagccg 1200
ctgtggggca gcatcggcta tacgttcccg tcggccctcg gctcgcagat cgccaacaag 1260
gaaagccggc atctgctgtt catcggcgat ggctccctcc agctgaccgt gcaggaactg 1320
ggcaccgccc tgcgcgagaa gctgacgccg atcgtcttcg tcatcaacaa caatggctat 1380
accgtggaac gggagatcca cggcgccacc gagcagtaca acgacatccc catgtgggat 1440
tatcagaacc tgccgctcgt gttcggcggc aacaaccaga ccgtcgccac ctacaaggtc 1500
accaccgcga tcgaactgga tgaggtcatg aaaaccgccc gcaaggacac caagcgcctg 1560
cagtggatcg aagtggtcat ggcgcaggat gacgcgccgg aactgctcaa gaaactcgcc 1620
aaaatcttcg ccaaacagaa cagctga 1647

<210> SEQ ID NO 21
<211> LENGTH: 1647
<212> TYPE: DNA
<213> ORGANISM: Enterococcus haemoperoxidus

<400> SEQUENCE: 21
atgtacacca tcagcgacta cctcctggac cggctgaagg aactcggcat cgacgaagtc 60
ttcggcgtcc cgggcgacta caacctccag ttcctcgatc atatcaccgc ccgcgaagac 120
ctgaaatgga tcggcaacgc gaatgaactc aatgccgcct acatggcgga cggctatgcc 180

```
cgcaccaagg gcatcagcgc cttcgtgacc accttcggcg tcggcgaact gagcgcggtg    240

aacggcctgg ccggctcgta cgccgagaac gtgccggtgg tcgagatcat cggcagcccc    300

accaccaccg tgcagaacaa caagaaactg gtccaccaca cgctgggcga tggcgacttc    360

ctgcggttcg aaaagatgca cgaggaagtc accgccgcga tcgcccatct gaccatcgag    420

aatgccacga gcgaaatcga ccgcgtcctg acgatcgcca tgaccgagaa gcgccccgtg    480

tatatcaacc tgccgatcga tatcgcggaa accaagacga acaagccgaa caaaccgctg    540

cagaagatga ccgagcggct cacggaagcc gaagcgacca tcctgtcgaa ggtcgagaag    600

gccctccagc aggcggagaa cccggtcatc atcgccggcc atgagatcct gtcctaccac    660

atcgagcacc agctgaatga gttcatccag aagttcaatc tccccatcac cacgctgccg    720

ctgggcaagg gcgccttcga cgaggaagac tcgcactaca tgggcacgta ttccggctcc    780

cccacggaag agcccctgaa gagccgcgtg gataacgccg atctggtcct gctgctcggc    840

gccaagctga ccgattccgc gacctccggc ttctcgttcg gcttcaccga caagcagatc    900

atcagcatcg gcgcgaccga agtcctgttc tacggcgaga aacacgaggc catccagctc    960

gatcgcttcg tgtccgccct gtccacgctc tccttctccc gcttcaccgg cgatctgctc   1020

ccggtgaaac ggatcagcaa ggtcgagttc aaggacgagc agctcaccca gaagcgcttc   1080

tggaagatgg tcgaaacgtt cctgctccag ggcgacaccg tcgtgggcga acagggcacc   1140

agcttcttcg gcctgaccaa tgtgcccctg aagaaggata tgcacttcat cggccagccg   1200

ctctggggca gcatcggcta taccttcccc agcaccctgg gctcgcagat cgccaacaag   1260

gactcccgcc acctgctgtt catcggcgat ggctcgctgc agctgaccgt gcaggagctc   1320

ggcacggcca tccgggagaa gctcacgccg atcgtcttcg tcatcaacaa caacggctac   1380

accgtggaac gcgaaatcca cggcgccacc gagcagtaca acgacatccc gatgtgggac   1440

taccagaacc tcccccctggt cttcggcggc acgagccaga ccgtggcgac gtataaagcc   1500

acgaccgaag cggagctggc cgaggtcatg aagtccgccc ggaaggatac ggagcggctg   1560

cagtggatcg aggtggtgat ggaccaggaa gacgcgcccc tgctgctgca gaagctggcc   1620

aagatcttcg ccaagcagaa ctcgtga                                        1647
```

<210> SEQ ID NO 22
<211> LENGTH: 1647
<212> TYPE: DNA
<213> ORGANISM: Enterococcus moraviensis

<400> SEQUENCE: 22

```
atgtacacgg tggcggacta tctgctggac cggctgaaag agctgggcat cgacgaagtg     60

ttcggcgtgc ccggcgacta caacctgcag ttcctcgacc acatcacggc ccggaaggac    120

ctcgaatgga tcggcaatgc caacgaactg aacgccgcct acatggccga cggctacgcc    180

cgcaccaagg gcatctccgc gctggtcacc accttcggcg tcggcgaact gtcggccatc    240

aatggcctgg ccggctcgta cgcggaaagc atcccggtga tcgaaatcgt gggctccccg    300

acgacgacgg tgcagcagaa caagaagctc gtgcatcata cgctgggcga cggcgatttc    360

ctgcggttcg agcgcatcca cgaggaggtg tcggcggcca tcgcgcacct gtccaccgag    420

aacgccccct ccgagatcga ccgcgtgctg acggtggcca tgaccgaaaa gcgcccggtc    480

tatatcaacc tcccgatcga tatcgcggag atgaaagcgt cggcccccac cacgcccctg    540

aaccacacca cggatcagct gacgaccgtc gagacggcca tcctcaccaa ggtcgaggat    600

gcgctgaagc agtccaagaa tcccgtcgtc atcgccggcc acgagatcct gagctaccac    660
```

```
atcgaaaatc agctggaaca gttcatccag aagttcaacc tgccgatcac cgtgctcccg     720

ttcggcaagg gcgccttcaa cgaagaggac gcgcattacc tgggcaccta tacgggcagc     780

acgaccgacg agtccatgaa gaatcgcgtc gaccatgcgg acctggtcct gctgctcggc     840

gccaagctca ccgactcggc cacctcgggc ttcagcttcg gcttcacgga gaagcagatg     900

atctcgatcg gctcgaccga agtgctgttc tatggcgaga agcaggagac ggtgcagctc     960

gaccgcttcg tgagcgccct gtcgaccctg tccttctccc gcttcaccga cgagatgccg    1020

agcgtgaaac gcctggccac cccgaaggtg cgcgatgaga agctgaccca gaagcagttc    1080

tggcagatgg tcgagagctt cctgctccag ggcgacaccg tcgtgggcga gcagggcacg    1140

agcttcttcg gcctgacgaa tgtgcccctg aaaaaggaca tgcacttcat cggccagccg    1200

ctgtggggca gcatcggcta tacgttcccc agcgccctgg gcagccagat cgccaacaaa    1260

gagtcccgcc acctgctgtt catcggcgac ggctcgctcc agctgacggt ccaggagctg    1320

ggcaccgcga tccgcgaaaa gctgaccccc atcgtgttcg tcatcaacaa caacggctat    1380

accgtggaac gcgagatcca cggcgcgacc gagcagtaca acgacatccc catgtgggac    1440

taccagaaac tgccgttcgt gttcggcggc accgatcaga cggtggccac ctataaggtg    1500

tccaccgaaa tcgaactcga taacgcgatg acccgggccc ggacggacgt ggaccgcctc    1560

cagtggatcg aagtcgtgat ggaccagaac gacgccccgg tcctgctgaa gaagctcgcc    1620

aagatcttcg cgaaacagaa ctcctga                                        1647
```

<210> SEQ ID NO 23
<211> LENGTH: 1647
<212> TYPE: DNA
<213> ORGANISM: Carnobacterium maltaromaticum

<400> SEQUENCE: 23

```
atgtataccg tgggcaacta cctgctggac cgcctcaccg aactgggcat ccgggatatc      60

ttcggcgtcc cgggcgatta taacctcaag ttcctggacc atgtcatgac ccataaggaa     120

ctgaattgga tcggcaacgc caacgagctg aatgcggcct atgccgccga cggctacgcg     180

cggaccaagg gcatcgcggc cctggtcacc accttcggcg tgggcgaact gagcgcggcc     240

aatggcaccg cgggctccta tgccgaaaag gtgcccgtgg tgcagatcgt gggcacgccc     300

acgacggcgg tgcagaactc ccacaaactg gtgcaccata ccctgggcga cggccgcttc     360

gatcacttcg aaaagatgca gaccgagatc aatggcgcca tcgcgcatct gaccgcggac     420

aacgccctgg cggagatcga tcgcgtgctg cggatcgccg tgaccgaacg gtgcccggtc     480

tatatcaacc tggccatcga tgtcgcggag gtggtggccg aaaaaccgct gaagcccctg     540

atggaggaat cgaagaaagt cgaggaggag acggccctcg tcctcaacaa gatcgaaaag     600

gcgctccagg actccaaaaa cccggtggtc ctgatcggca acgagatcgc cagcttccat     660

ctggaatcgg cgctggccga tttcgtcaag aagttcaacc tcccggtcac ggtgctgccc     720

ttcggcaagg gcggcttcga cgaggaggat gcgcacttca tcggcgtcta taccggcgcc     780

ccgaccgccg aaagcatcaa ggagcgggtg gaaaaggccg acctcatcct catcatcggc     840

gcgaagctga ccgatagcgc caccgcgggc ttctcctacg acttcgagga ccgccaggtc     900

atcagcgtcg gcagcgacga agtgtccttc tatggcgaga tcatgaaacc cgtggcgttc     960

gcccagttcg tgaacggcct gaactccctg aattacctgg gctacaccgg cgaaatcaag    1020

caggtggagc gggtggcgga catcgaggcg aaggcgtcga atctcaccca gaacaacttc    1080
```

```
tggaagttcg tggaaaagta cctgtcgaac ggcgacaccc tggtggccga gcagggcacc   1140

agcttcttcg gcgcctcgct cgtgccgctg aaatcgaaga tgaagttcat cggccagccg   1200

ctgtggggca gcatcggcta tacgttcccc gccatgctgg gcagccagat cgcgaatccc   1260

gcgagccggc atctgctctt catcggcgac ggctccctgc agctgaccat ccaggagctc   1320

ggcatgacct tccgggagaa actgaccccg atcgtgttcg tcatcaacaa cgatggctac   1380

accgtcgagc gggaaatcca cggcccgaac gagctctaca acgatatccc gatgtgggat   1440

tatcagaacc tcccgtacgt gttcggcggc aacaagggca acgtcgccac ctataaggtc   1500

accaccgagg aagaactggt ggccgccatg tcccaggccc ggcaggacac cacccggctg   1560

cagtggatcg aggtcgtgat gggcaaacag gattcgccgg acctcctggt ccagctgggc   1620

aaggtgttcg ccaagcagaa cagctga                                       1647
```

<210> SEQ ID NO 24
<211> LENGTH: 1647
<212> TYPE: DNA
<213> ORGANISM: Brochothrix thermosphacta

<400> SEQUENCE: 24

```
atgtatacga tcggcgacta cctcctcgac cggctgaacg agctgggcgt ggaagacatc     60

ttcggcgtgc cgggcgacta caacctgacg ttcctcgatc atatcaccgc gcatccgcag    120

ctctcctggg tcggcaatgc caacgaactc aacgccgcct acgccgccga tggctatgcg    180

cggacgaaag gcttcgccgc gctggtgacg accttcggcg tcggcgagct gtcggccatc    240

aacggcctcg ccggctcctt cgccgaacgg gtgccggtca tcgagatcgt cggcagcccg    300

gtcagcaccg tgcagaccga caagaagctg gtgcaccaca ccctgggcga cggcgacttc    360

ctgcacttcg agaagatgca tgacgccgtc acggtggcct cggcgcacct cacgatccag    420

aacgccacca gcgaaatcga ccgggtcctg acgaccgccc tctcgctgcg gcgccccggc    480

tatatcaacc tgcccatcga cgtggcggcg gccccggccg aaaaagccca gaaaaagctc    540

cagctgaaag tgaccagccc gatcgacagc acgctgctgg aaaagatcca gacggccttc    600

tcctcggcca agcagcccgt cttcatcacg ggccatgaaa tccagtccta ccacctggag    660

gataccgtgg cgaagatcgc cgcgcacacg accgtgccgg tcgcggccct ctcgctgggc    720

aagagctcca tcgatgaaac ccatccccag ttcgtcggca tctactccgg cgccctgacg    780

gcggagcccc tgaaaaccta cgtcgataac gccgatctgg tgatcctgct cggcgcccag    840

ctgaccgaca cggccacctc gggcttcagc cagtccttct cggccagcaa aatcatcgcc    900

atccacccgg aaacgaccac cgtgttcggc caggattacc cgtcgaacga tttcaaggaa    960

ctgatcgagg ccctcacgac catcgattac cgcatggaaa cctccgcggc cctgaagacg   1020

atgccgtcca ccaaggagtt catcgccacc gacacgctgc tcacccagaa tcgcttctgg   1080

gaagccatcg aaaccaactt caagcagaac gataccatcg tggcggaaca gggcacgtcg   1140

ttcttcggca tcaccaatac ccagttcaag aaagatatgc gcctgatcgg ccagcccctg   1200

tggggctcga tcggctatac gttccccgcc gccctgggct cgcagctggc cgcccgctcc   1260

aagcggcatc tgctcttcat cggcgatggc tcgctgcagc tgaccatcca ggaactgggc   1320

atggcgctcc gcgccaaact caccccccctg atcttcgtca tcaacaacaa cggctacacc   1380

gtggaacgcg agatccacgg cccgaacgaa cggtataatg acatcccgac ctgggactat   1440

gcgcagctgc cgaccgtgtt cggcggcacg gaccagaacg tggccacgta taaggtgacg   1500

accgaaaccg aactggcgga ggcgctcgtc accgccaagg cggacaccac ccgcctgcag   1560
```

```
tggatcgagg tggtgatgga ccagacggac gccccggaac tgctgaaaga gatgggccgc   1620

atcttcgcca agcagaacac ccattga                                      1647


<210> SEQ ID NO 25
<211> LENGTH: 1647
<212> TYPE: DNA
<213> ORGANISM: Carnobacterium gallinarum

<400> SEQUENCE: 25

atgtacacgg tcgccgatta cctgctcgat cggctgaagg aactgggcat caatgacatc     60

ttcggcgtcc cgggcgatta taacctcaag ttcctggacc acatcacggc ccgcgacgac    120

ctgaaatgga tcggcaacgc gaacgagctg aacgcggcgt atatggccga tggctacgcc    180

cgcaccaaag gcatggccgc gctggtcacg accttcggcg tcggcgaact ctcggccatg    240

aacggcatcg gcggctcgtt cgccgagaaa gtcccggtca tcgagatcgt gggctccccc    300

accaccgccg tccagaatgc ccagaaactg gtccatcata cgctgggcga cggccgcttc    360

aaccatttcg agaagatgca tgaggcgatc accgtgggca tcggctcgct gaccaaggag    420

aatgccatca ccgaaatcga tcgcatcctg ggcctggcgt ccgagaagcg gcagcccggc    480

tacctgaacc tgccgatcga tgtggccgaa atggaagtgg agaaaccgaa caagccgctc    540

ttcgatacca aggtcatgga aatcaaaatg gaacaggagc tcatcaagag catcgagaaa    600

gtgctcaact cggtcaagca tccggtcatc atcgccggca acgagatcgc cagcttccat    660

ctggaggcca agctggccga gttcatcgag aagttcaatc tccccgtcac cacgctgccg    720

ttcggcaagg gcgtcttcaa cgaagaagat aagcattatc tgggcgtgta tacgggcacc    780

cccacgacgg aacccctgaa gtcctacgtc gaccaggcgg atctggtcct cctgctgggc    840

gccaagctga ccgactccgc caccagcggc ttcagccagg gcttcaccga gaagcagatg    900

atctcgctgg cctcggacga ggtcatcttc cagggcgagc acctcgccgg catccagctc    960

cccaccgtcc tggatgagct gctgatgatc aactatccgg gctaccacgg cgagatccag   1020

ccgatgtcgc ggctggcgga agtgaagtcg tcctccagcc tcgtcaccca ggcgtacttc   1080

tgggaggccg tcgagtcgta cctggaagaa ggcgatacgc tcgtcgccga acagggcacc   1140

agcttcttcg gcgcctccac cgtccccatg aagaagggca tgagcttcat cggccagccg   1200

ctgtggggct ccatcggcta cacgttcccg gccatgctcg gctcgcagat cgccaagaag   1260

ggctcgcgcc atctgctgtt catcggcgac ggctcgctcc agctgaccgt ccaggaactg   1320

ggcatgacgc tccgggaaaa gctggcgccg atcgtgttca tcatcaacaa taacggctac   1380

accgtggaac gggaaatcca cggccccgaa gaaatctata acgacatccc gatgtgggac   1440

taccagaagc tcccgtccgt cttcggcggc accgccgaaa acgtggtgac ctataaggtc   1500

cagaccgagg cggagctggc caccgccatg cgcaaggccc gcctggactc gaagcggctg   1560

cagtggatcg aagtggtgat gaaccagaag gacgccccgg acctcctggt gcagatgggc   1620

aagatcttcg ccaagcagaa tagctga                                      1647


<210> SEQ ID NO 26
<211> LENGTH: 1647
<212> TYPE: DNA
<213> ORGANISM: Carnobacterium divergens

<400> SEQUENCE: 26

atgtataccg tgggcgacta tctcctggag cggctctcgg aactgggcat caaagagatc     60
```

```
ttcggcgtgc cgggcgacta caacctgaag ttcctggatc acatcgtgga gcatccgaac    120

ctgaagtgga tcggcaacgc gaatgaactc aacgcggcgt atgccgccga cggctacgcc    180

cgcacgaagg gcgtctccgc gctggtgacc accttcggcg tcggcgagct ctccgccatc    240

aacggcatcg ccggctcgta tgccgagaaa gtcccggtca tccagatcgt gggcagcccc    300

acgatggcgg tgcagaatgc ccataagctg gtgcatcata ccctgggcga tggcaaattc    360

gaccacttcg agaacatgca tgagtccgtc accgaagcca tcggcagcct caccaaggag    420

aacgcggtga ccgagatcga tcgcgtgctg cgggccgccg tgctcaaacg gcgcccggtg    480

tatctgaacc tcccgatcga cgtggccgaa atggtcgtcg aaaaaccgtc gggccccctg    540

ctgcccaagc aggcgagcct gagcgcccgc gaggtcgaac tcgtgcatga gctggagaag    600

gccctgcagc aggcgaagaa cccggtggtc ctggcgggca acgagctggc gtcgttccac    660

ctcgaaacgt acctcgccga cttcatccac aagttcaacc tccccatcac gaccctcccc    720

ttcggcaagg gcgtcttcaa cgaggaagac gagcattatc tgggcgtcta tgcgggctcg    780

ccgaccgaag aaggcctgcg gaagcgcgtc gatacggcgg acctggtcgt ggcgctgggc    840

gcgaagctga cggactccgc cacctccggc ttctcgtacg acttctccga aaaacagctc    900

ttcagcctgg cgtccgacga agtcatcgtc aaagaggaac acctcgaagg catccatctg    960

ccggccgtca tgaaggcgct gacgagcatc gactaccagg gctaccaggg cgacatccag   1020

ccgatggccc ggctgaagag catcaaaccc accaaccagg tgctgaccca gcgccacttc   1080

tgggaggcca tcgaaggctt cctggaaaag ggcgacaccg ccgtcgcgga gcagggcacg   1140

agcttcttcg gcctctcgac cgtgccgctg aagagcgaaa tgtcgttcat cggccagccg   1200

ctgtggggct ccatcggcta tacgttcccg gcgatgctgg gcagccagct cgccaacccg   1260

tccagccggc acctcctgtt catcggcgac ggcagcctgc agctgacgat ccaggagctc   1320

ggcatggccc tccgcgaaaa actcaccccg atcgtgttcg tcatcaacaa taacggctat   1380

acggtcgaac gggaaatcca cggcccgaat gaaatctata acgacatccc gatgtgggac   1440

taccagaaac tcccgctcgt cttcggcggc tccgagcagt cggtcatcac ctataaagtg   1500

acgaccgaac tggaactggc gaacgcgctc aaggcggccc ggctggacaa caaccgcctg   1560

cagtggatcg aagtggtgat ggaccagacc gatgcgccgg agctcctcat gaagctgggc   1620

aagatcttcg cgaagcagaa tagctga                                       1647
```

<210> SEQ ID NO 27
<211> LENGTH: 1104
<212> TYPE: DNA
<213> ORGANISM: Helicobacter bizzozeronii

<400> SEQUENCE: 27

```
atgcagacga cgatcggcca gtatctcctg gaccggctga agtcctacgg cgtgcagcat     60

ctcttcggcg tgcccggcga ctataacctg gccttcctcg acctgatcga agacgatccg    120

cacatccagt gggtcggcaa ctgcaacgaa ctgaatgcgt cctacgccgc cgacggctac    180

gcgcggctca agagcatggg cgccctcctg acgaccttcg gcgtcggcga gctgagcgcc    240

atcaacggca tcgccggctc gtacgcggaa tccgtgccgg tcgtgaagat cgtcggcatg    300

ccctcccgcg gcgtggtcca ttcccgcaag ctggtgcacc acaccctggg cgacggcgag    360

ttcctcaagt tctacaacat gtatgccgaa gtgagcgtcg cccagacgat cctcaacaaa    420

cagaacgccc agagcgaaat cgaccgcgtc ctgggcgaat gcttcctgca taaaaagccg    480

gtctacatcg gcctcccggt ggacgtgacg cacatcccga tcgaaacgta cgccccctcc    540
```

```
cccctggtgg ccaagagcga cccgaaaatc ctcaacgcct tcctgaagga cgcccaggag    600

ctgctgtcga agagcaaatc ccaggtggtc atggcggatt atgaagtgaa ccgctaccag    660

ttcaaccagg agctgacgcg cttcatcgaa gccgtgaacc tgcccatcgt gtcgctggcg    720

atgggcaagg gcgtcttcga tgaaacgcac ccgaacttca tcggcgtgta taacggcatc    780

ctctcggacg cccgggtgag ctcgctgatg aagcacgccg actgcgcgat cctggtgggc    840

gtgaagctga cggactcgct gacggccggc ttccactata tccgcgaaca tcacctgtcc    900

atccagatcc accccttcta ctcccagatc ggcgaaaaga cgtacgacga tatcctcatg    960

caggacgtgc tgaaagcgct cgcccagctg aagttccagg cctcgttccc gaaggagacg   1020

caccccaaaa cgccgcacct gaacggcaag ctgacccagg acaagttctt caagatcgac   1080

tcgcgcatcc tgaccccccc gtga                                          1104
```

<210> SEQ ID NO 28
<211> LENGTH: 822
<212> TYPE: DNA
<213> ORGANISM: Staphylococcus aureus

<400> SEQUENCE: 28

```
atgaaacagc gcatcggcgc ctacctgatc gatgccatcc accgcgccgg cgtggacaag     60

atcttcggcg tcccgggcga tttcaacctc gccttcctgg acgatatcat cagcaacccg    120

aacgtggatt gggtcggcaa caccaacgag ctgaacgcct cgtatgcggc cgatggctat    180

gcccgcctca acggcctggc ggccctggtc accaccttcg gcgtgggcga actgtcggcg    240

gtgaatggca tcgcgggcag ctatgccgag cgcatcccgg tgatcgccat caccggcgcc    300

cccacccgcg ccgtcgagca ggccggcaag tatgtgcatc atagcctggg cgaaggcacg    360

ttcgatgact accggaagat gttcgcccat atcaccgtgg cccagggcta catcacgccc    420

gagaatgcga cgaccgaaat cccccgcctc atcaacacgg ccatcgccga gcgccgcccg    480

gtgcatctcc acctgcccat cgatgtggcg atctcggaga tcgagatccc caccccgttc    540

gaggtgacgg cggcgaaaga cacggacgcc tcgacctata tcgagctgct ggccagcaaa    600

ctgcaccaga gcaagcagcc catcatcatc acgggccatg agatcaactc cttccatctg    660

caccaggaac tggaagattt cgtcaatcag acccagatcc ccgtggcgca gctctcgctg    720

ggcaaaggcg ccttcaacga ggaaaacccg tactatatgg gcatctacga tggcaagctg    780

cccaaaatca agtatgcgat catgtggacc acggcgatct ga                       822
```

<210> SEQ ID NO 29
<211> LENGTH: 1665
<212> TYPE: DNA
<213> ORGANISM: Fictibacillus macauensis

<400> SEQUENCE: 29

```
atgaacaacc attataccgt cggcacctat ctgctgcatc gcctgtccga gctgggcgtc     60

cgccatatgt tcggcgtgcc cggcgactat aatctgacgt tcctggacga tgtcatcgac    120

ttcgaaggca tggaatggat cggcaactgt aacgagctca acgccgccta cgcggccgac    180

ggctatgccc gcatcaacgg catggccgcc ctggtgacca ccttcggcgt cggcgagctg    240

tcggccatca acggcatcgc cggctcgtac gccgaaaaag tgccggtcgt caaaatcacg    300

ggcatgccca ccaccaacgt gatgaaccag aatctgtacg tccatcacac gctgggcgac    360

ggcaacttcc agcacttcgg caacatgttc caggaggtca ccgccgcgca gacgatgctg    420
```

```
acccaggaaa acgcggcgca ggagatcgat cgcgtgctgc tcgcctgctg gcacgaaaag    480
cgcccggtgc acatcaacct cccgatcgat gtctacaaca agccggtcaa cccccccgag    540
cattcgctcc tggaacgggg catctcgtcg aacgcgaccg cgctcgaaca gatgctgacc    600
accgtgatcc cgacgatcaa ggaggccacc tcgcccgtga tcctggcgga ttatgaggtg    660
tatcgctacc aggcccagga agccctgatg ctgctggcgg aaaagaccgg cttcccggtg    720
gccaccctga gcatgggcaa gggcgtgttc aacgaaaccc atccccagtt catcggcgtg    780
tacaacggcg acctgtcgtc cgactacgtg aagaatatgg tcgaccatgc cgactgtatc    840
ctctccatcg gcgtcaagct gaccgacagc atcacgggcg gcttcagcca tgagttcacc    900
gaggagcagg tcatcgacat ctccccgtat agcgtgagca aaaaagccct caaatgggcg    960
cccatcacga tgctggatgc gctgggcgcc atcacggatg ccctggagca gaagccgacc   1020
cccgccacca ccgcgcggct cgccgcctac tcgaacgaga gctccttcac cgcgacgaac   1080
acgacgctga cccaggagcg cttcttcgac caggtgtccc acttcctcca ggagggcgac   1140
gtgatcctgg cggaacaggg caccagcttc ttcggcgcgg ccacgatgcc gctcccgaag   1200
ggcgccacgt tcatcggcca gccgctgtgg ggcagcatcg gctacaccct gccggccctg   1260
ctgggcagcc agctggccga cgaatcccgc cgcaatctcc tgctcatcgg cgatggctcg   1320
ttccagctca ccgcccagga gctgtcgacg atgctgcgcc agcggatcgc gccgatcatc   1380
ttcctcatca acaacgacgg ctacaccgtg gaacgggcga tccacggcga gaatcaggtg   1440
tataacgaca tccagatgtg ggactattcg aagctgccgg cggtcttcgg cgcggcggac   1500
gccagcgtca cctacaaggt ccggaccgaa gaggagctgg aggcggccct gcatagcgcc   1560
cagaactcgt cccagctggt cttcatcgaa gtgatgatgg agaagaatga cacccccgaa   1620
ctgctgacgg ccctgagcaa gcgcttcgcg aatcagaaca actga                   1665
```

<210> SEQ ID NO 30
<211> LENGTH: 1083
<212> TYPE: DNA
<213> ORGANISM: Saccharomyces cerevisiae

<400> SEQUENCE: 30

```
atgagctatc ccgagaagtt cgaggggatc gccatccaga gccacgagga ctggaagaac     60
ccgaaaaaga ccaagtatga tccgaagccc ttctacgatc acgacatcga catcaagatc    120
gaggcctgcg gcgtctgcgg cagcgatatc cattgtgcgg ctggccactg gggcaacatg    180
aagatgccgt tggtcgtcgg ccacgagatc gtgggcaagg tcgtgaagtt aggcccgaaa    240
agcaacagcg gcttgaaggt gggccagcgc gtgggtgtgg gtgcgcaggt cttcagctgt    300
ctggagtgcg accgttgcaa gaacgacaac gaaccgtact gcaccaagtt cgtcaccacc    360
tactcgcagc cctacgagga cggctacgtc tcgcagggcg gttacgccaa ctatgtccga    420
gtccacgaac acttcgtggt gcccatcccg gaaaatatcc ccagccatct ggcggctccc    480
ctgctgtgcg gtggcttgac cgtctacagc cccctcgtcc gcaatggctg cggtcccggc    540
aagaaggtgg gtatcgtggg cctcggcggt ataggctcta tgggcacgct gatctcgaaa    600
gcgatgggcg cagaaacgta cgtgatctcg cgttcctcgc gcaagcgcga ggatgcgatg    660
aagatgggtg cggaccacta catcgccacg ctggaggagg gtgactgggg tgagaagtac    720
ttcgacacgt tcgacctcat cgtggtgtgc gcgagttccc tgacggacat cgacttcaat    780
atcatgccca aggcgatgaa ggtcggaggg cgcatcgtct ccatctcgat cccggagcag    840
cacgaaatgc tgtcgctgaa gccctacggc ctgaaagccg tctccattag ctactcggcg    900
```

ctcggtagta tcaaggagct caaccagctg ttgaagttgg tttccgaaaa ggacatcaag 960
atctgggtgg aaacgctccc ggtgggcgaa gccggtgtgc acgaggcctt tgagcggatg 1020
gagaaggggg atgtccgtta tcggtttaca ctcgtcggct acgataaaga gttctcggat 1080
taa 1083

<210> SEQ ID NO 31
<211> LENGTH: 1164
<212> TYPE: DNA
<213> ORGANISM: Escherichia coli

<400> SEQUENCE: 31
atgaacaact ttaatctgca caccccaacc cgcattctgt ttggtaaagg cgcaatcgct 60
ggtttacgcg aacaaattcc tcacgatgct cgcgtattga ttacctacgg cggcggcagc 120
gtgaaaaaaa ccggcgttct cgatcaagtt ctggatgccc tgaaaggcat ggacgtgctg 180
gaatttggcg gtattgagcc aaacccggct tatgaaacgc tgatgaacgc cgtgaaactg 240
gttcgcgaac agaaagtgac tttcctgctg gcggttggcg gcggttctgt actggacggc 300
accaaattta tcgccgcagc ggctaactat ccggaaaata tcgatccgtg gcacattctg 360
caaacgggcg gtaaagagat taaaagcgcc atcccgatgg gctgtgtgct gacgctgcca 420
gcaaccggtt cagaatccaa cgcaggcgcg gtgatctccc gtaaaaccac aggcgacaag 480
caggcgttcc attctgccca tgttcagccg gtatttgccg tgctcgatcc ggtttatacc 540
tacaccctgc cgccgcgtca ggtggctaac ggcgtagtgg acgcctttgt acacaccgtg 600
gaacagtatg ttaccaaacc ggttgatgcc aaaattcagg accgtttcgc agaaggcatt 660
ttgctgacgc taatcgaaga tggtccgaaa gccctgaaag agccagaaaa ctacgatgtg 720
cgcgccaacg tcatgtgggc ggcgactcag gcgctgaacg gtttgattgg cgctggcgta 780
ccgcaggact gggcaacgca tatgctgggc cacgaactga ctgcgatgca cggtctggat 840
cacgcgcaaa cactggctat cgtcctgcct gcactgtgga atgaaaaacg cgataccaag 900
cgcgctaagc tgctgcaata tgctgaacgc gtctggaaca tcactgaagg ttccgatgat 960
gagcgtattg acgccgcgat tgccgcaacc cgcaatttct ttgagcaatt aggcgtgccg 1020
acccacctct ccgactacgg tctggacggc agctccatcc cggctttgct gaaaaaactg 1080
gaagagcacg gcatgaccca actgggcgaa aatcatgaca ttacgttgga tgtcagccgc 1140
cgtatatacg aagccgcccg ctaa 1164

<210> SEQ ID NO 32
<211> LENGTH: 1149
<212> TYPE: DNA
<213> ORGANISM: Escherichia coli

<400> SEQUENCE: 32
atggcgaatc ggatgatcct caatgaaacg gcctggttcg gccgcggcgc ggtcggcgcc 60
ctcaccgatg aggtcaagcg gcggggctac cagaaggccc tgatcgtcac ggataaaacc 120
ctggtgcagt gcggcgtcgt cgccaaggtg accgacaaga tggatgcggc cggcctggcc 180
tgggcgatct acgacggcgt ggtgcccaac cccaccatca ccgtggtgaa ggaaggcctg 240
ggcgtgttcc agaactcggg cgcggattat ctcatcgcga tcggcggcgg cagcccccag 300
gacacctgca aggccatcgg catcatctcg aacaaccccg agttcgcgga cgtgcgctcc 360
ctggagggcc tgtcgccgac gaacaagccc tccgtcccga tcctcgccat cccgacgacg 420
gccggcaccg cggccgaggt gaccatcaat tacgtcatca ccgacgagga aaagcggcgc 480
aagttcgtgt gtgtggaccc ccatgacatc ccccaggtcg ccttcatcga cgccgacatg 540
atggatggca tgcccccccgc cctcaaggcc gcgacgggcg tggacgcgct gacgcatgcc 600
atcgaaggct acatcacccg gggcgcctgg gccctgacgg atgccctgca tatcaaggcc 660
atcgaaatca tcgccggcgc cctgcgcggc tccgtggccg gcgacaagga tgcgggcgag 720
gagatggcgc tgggccagta cgtggccggc atgggcttct ccaatgtggg cctgggcctg 780
gtgcatggca tggcccatcc gctcggcgcc ttctacaaca cgccgcatgg cgtcgcgaac 840
gcgatcctcc tgccgcatgt catgcgctac aatgcggact tcacgggcga gaaataccgc 900
gatatcgccc gggtcatggg cgtgaaggtc gagggcatgt cgctggaaga ggcgcggaac 960
gccgcggtcg aagccgtctt cgccctgaac cgggatgtgg gcatcccgcc gcacctgcgc 1020
gatgtcggcg tccgcaagga agacatcccc gcgctggcgc aggccgccct ggacgatgtg 1080
tgcaccggcg gcaaccccccg cgaggcgacg ctggaagaca tcgtcgaact ctaccatacc 1140
gcgtggtga 1149

<210> SEQ ID NO 33
<211> LENGTH: 1170
<212> TYPE: DNA
<213> ORGANISM: Clostridium acetobutylicum

<400> SEQUENCE: 33
atgctctcgt tcgactacag catccccacc aaggtcttct tcggcaaagg caagatcgac 60
gtgatcggcg aagagatcaa aaagtacggc tcccgcgtgc tgatcgtcta cggcggcggc 120
tcgatcaaac gcaacggcat ctatgaccgg gccacggcga tcctgaagga aaacaacatc 180
gccttctacg agctgtccgg cgtggagccc aacccgcgga tcaccacggt caagaagggc 240
atcgaaatct gtcgcgaaaa caacgtcgac ctggtgctgg ccatcggcgg cggcagcgcg 300
atcgattgct ccaaggtgat cgccgccggc gtctattatg acggcgacac ctgggacatg 360
gtcaaagacc ccagcaagat caccaaagtg ctgccgatcg cctccatcct caccctgagc 420
gcgacgggca gcgaaatgga tcagatcgcc gtgatctcga acatggagac gaacgaaaag 480
ctcggcgtgg gccacgacga tatgcggccg aagttctcgg tcctcgatcc gacgtatacc 540
ttcacggtgc cgaagaacca gaccgccgcc ggcacggcgg acatcatgtc gcataccttc 600
gaatcgtatt tcagcggcgt cgaaggcgcg tatgtccagg acggcatcgc ggaagccatc 660
ctccgcacct gcatcaagta tggcaagatc gcgatggaaa agaccgacga ctacgaggcc 720
cgcgcgaatc tgatgtgggc ctcgtccctg gccatcaatg gcctgctgag cctcggcaag 780
gatcggaaat ggtcgtgcca cccgatggag cacgagctga gcgcctatta cgacatcacc 840
cacggcgtgg gcctggccat cctgaccccc aactggatgg aatatatcct gaacgacgac 900
acgctgcata aattcgtgtc gtacggcatc aacgtctggg gcatcgataa gaacaaggac 960
aactacgaga tcgcccgcga agccatcaaa aatacgcggg agtacttcaa cagcctgggc 1020
atcccgtcga agctgcgcga ggtcggcatc ggcaaagata aactggagct gatggccaag 1080
caggcggtgc gcaactcggg cggcacgatc ggcagcctcc gccccatcaa cgcggaggat 1140
gtgctggaga tcttcaagaa gagctattga 1170

<210> SEQ ID NO 34
<211> LENGTH: 1173
<212> TYPE: DNA
<213> ORGANISM: Clostridium acetobutylicum

<400> SEQUENCE: 34
atggtcgatt tcgagtattc gatcccgacg cggatcttct tcggcaagga caaaatcaac 60
gtcctgggcc gcgaactcaa gaaatacggc agcaaagtgc tgatcgtcta cggcggcggc 120
tcgatcaagc ggaacggcat ctacgataag gccgtgtcga tcctggaaaa gaatagcatc 180
aagttctatg aactggcggg cgtcgaaccg aacccccgcg tgaccaccgt cgagaagggc 240
gtcaagatct gccgggaaaa cggcgtggaa gtcgtgctgg cgatcggcgg cggctccgcg 300
atcgactgcg ccaaggtgat cgcggcggcc tgcgagtacg acggcaatcc ctgggacatc 360
gtcctggacg gctccaagat caagcgcgtc ctcccgatcg ccagcatcct gaccatcgcc 420
gcgacgggct cggaaatgga cacctgggcc gtcatcaaca atatggatac caacgaaaag 480
ctcatcgcgg cccacccgga catggccccg aagttctcga tcctcgatcc cacctacacc 540
tacaccgtcc cgacgaacca gaccgcggcc ggcaccgccg atatcatgtc ccatatcttc 600
gaggtgtatt tctccaacac caagacggcg tacctccagg accgcatggc ggaggcgctc 660
ctccggacct gcatcaagta cggcggcatc gccctggaga agccggacga ctatgaggcc 720
cgcgccaacc tcatgtgggc gtcctccctg gcgatcaatg gcctgctgac gtacggcaaa 780
gacacgaact ggtccgtgca tctcatggag cacgagctgt cggcctatta tgatatcacc 840
cacggcgtgg gcctcgcgat cctcacgccc aactggatgg aatacatcct caacaatgat 900
acggtgtaca agttcgtcga gtacggcgtc aatgtctggg gcatcgataa ggaaaaaaat 960
cactatgaca tcgcgcatca ggcgatccag aagacgcgcg actacttcgt caacgtgctc 1020
ggcctgccct cccgcctccg cgacgtgggc atcgaagagg aaaagctgga tatcatggcc 1080
aaggagagcg tgaagctgac cggcggcacc atcggcaacc tgcgccccgt gaacgcctcc 1140
gaggtcctcc agatcttcaa aaagtcggtg tga 1173

<210> SEQ ID NO 35
<211> LENGTH: 1011
<212> TYPE: DNA
<213> ORGANISM: Escherichia coli

<400> SEQUENCE: 35
atgaaggccg cggtcgtgac caaggaccat cacgtcgatg tcacgtacaa gacgctgcgc 60
tccctgaagc atggcgaagc gctgctgaag atggagtgct gtggcgtctg ccacacggac 120
ctgcatgtga aaaacggcga cttcggcgac aagaccggcg tcatcctcgg ccacgaaggc 180
atcggcgtcg tggccgaggt gggccccggc gtcacgtccc tcaagccggg cgatcgggcc 240
tcggtggcgt ggttctatga gggctgcggc cactgcgaat attgcaactc gggcaacgaa 300
accctgtgtc ggtcggtgaa aaatgcgggc tactccgtcg acggcggcat ggcggaagaa 360
tgtatcgtgg tggccgacta cgccgtgaag gtcccggatg gcctggacag cgccgccgcc 420
tcgtcgatca cctgcgccgg cgtcaccacc tataaggcgg tgaaactgag caaaatccgc 480
ccgggccagt ggatcgccat ctacggcctg ggcggcctgg gcaacctggc cctgcagtac 540
gccaagaatg tcttcaacgc gaaggtcatc gccatcgatg tcaatgatga acagctgaag 600
ctggccacgg agatgggcgc ggacctggcg atcaacagcc acaccgaaga cgcggccaag 660
atcgtccagg agaagaccgg cggcgcccat gccgccgtgg tgaccgccgt ggccaaagcc 720
gccttcaatt ccgccgtcga cgccgtccgg gccggcggcc gggtcgtcgc ggtgggcctg 780
ccgccggagt cgatgtccct cgacatcccg cgcctggtgc tggatggcat cgaggtggtg 840

```
ggctccctgg tcggcacccg ccaggacctg accgaagcct tccagttcgc cgccgaaggc    900

aaggtcgtgc ccaaggtcgc cctgcggccc ctcgccgaca tcaacaccat cttcacggag    960

atggaggaag gcaagatccg ggccgcatg gtcatcgatt tccgccactg a             1011
```

<210> SEQ ID NO 36
<211> LENGTH: 1020
<212> TYPE: DNA
<213> ORGANISM: Escherichia coli

<400> SEQUENCE: 36

```
atgtccatga tcaaaagcta cgccgcgaaa gaggcgggcg gcgagctgga ggtgtatgag     60

tatgacccgg gcgagctgcg gccccaggac gtggaagtgc aggtcgacta ctgcggcatc    120

tgccattcgg acctctcgat gatcgataac gagtggggct tcagccagta ccccctggtg    180

gccggccacg aggtgatcgg ccgcgtggtc gccctgggct cggccgcgca ggataaaggc    240

ctgcaggtcg gccagcgcgt cggcatcggc tggacggccc gcagctgcgg ccattgcgat    300

gcctgcatca gcggcaatca gatcaattgc gaacagggcg cggtcccgac catcatgaac    360

cggggcggct tcgccgaaaa gctgcgggcc gattggcagt gggtgatccc gctgccggag    420

aacatcgata tcgagtcggc cggccccctg ctgtgcggcg gcatcaccgt cttcaagccg    480

ctcctgatgc atcatatcac ggcgaccagc cgggtcggcg tgatcggcat cggcggcctc    540

ggccacatcg cgatcaaact gctgcacgcg atgggctgcg aggtcaccgc gttctcctcg    600

aaccccgcca aggagcagga agtgctggcg atgggcgccg ataaagtcgt gaactcgcgc    660

gacccccagg ccctcaaagc cctggccggc cagttcgatc tcatcatcaa cacggtgaac    720

gtgtcgctgg actggcagcc ctacttcgaa gccctgacct atggcggcaa cttccatacc    780

gtcggcgccg tgctgacccc gctgtccgtc ccggccttca ccctgatcgc cggcgaccgc    840

agcgtgtccg gcagcgccac cggcacgccg tatgagctgc gcaagctgat gcgcttcgcc    900

gcccgcagca aggtcgcccc gaccaccgag ctgttcccca tgtccaagat caatgacgcg    960

atccagcatg tccgggacgg caaggcccgc tatcgcgtcg tcctcaaggc ggacttctga   1020
```

<210> SEQ ID NO 37
<211> LENGTH: 1149
<212> TYPE: DNA
<213> ORGANISM: Escherichia coli

<400> SEQUENCE: 37

```
atggcgaatc ggatgatcct caatgaaacg gcctggttcg gccgcggcgc ggtcggcgcc     60

ctcaccgatg aggtcaagcg gcggggctac cagaaggccc tgatcgtcac ggataaaacc    120

ctggtgcagt gcggcgtcgt cgccaaggtg accgacaaga tggatgcggc cggcctggcc    180

tgggcgatct acgacggcgt ggtgcccaac ccccaccatca ccgtggtgaa ggaaggcctg    240

ggcgtgttcc agaactcggg cgcggattat ctcatcgcga tcggcggcgg cagcccccag    300

gacacctgca aggccatcgg catcatctcg aacaaccccg agttcgcgga cgtgcgctcc    360

ctggagggcc tgtcgccgac gaacaagccc tccgtcccga tcctcgccat cccgacgacg    420

gccggcaccg cggccgaggt gaccatcaat tacgtcatca ccgacgagga aaagcggcgc    480

aagttcgtgt gtgtggaccc ccatgacatc ccccaggtcg ccttcatcga cgccgacatg    540

atggatggca tgccccccgc cctcaaggcc gcgacgggcg tggacgcgct gacgcatgcc    600

atcgaaggct acatcacccg gggcgcctgg gccctgacgg atgccctgca tatcaaggcc    660

atcgaaatca tcgccggcgc cctgcgcggc tccgtggccg gcgacaagga tgcgggcgag    720
```

```
gagatggcgc tgggccagta cgtggccggc atgggcttct ccaatgtggg cctgggcctg    780

gtgcatggca tggcccatcc gctcggcgcc ttctacaaca cgccgcatgg cgtcgcgaac    840

gcgatcctcc tgccgcatgt catgcgctac aatgcggact tcacgggcga gaaataccgc    900

gatatcgccc gggtcatggg cgtgaaggtc gagggcatgt cgctggaaga ggcgcggaac    960

gccgcggtcg aagccgtctt cgccctgaac cgggatgtgg gcatcccgcc gcacctgcgc   1020

gatgtcggcg tccgcaagga agacatcccc gcgctggcgc aggccgccct ggacgatgtg   1080

tgcaccggcg gcaacccccg cgaggcgacg ctggaagaca tcgtcgaact ctaccatacc   1140

gcgtggtga                                                           1149
```

<210> SEQ ID NO 38
<211> LENGTH: 1020
<212> TYPE: DNA
<213> ORGANISM: Escherichia coli

<400> SEQUENCE: 38

```
atgtccatga tcaaaagcta tgccgcgaag gaagccggcg gcgagctgga ggtctacgag     60

tacgaccccg gcgaactccg cccgcaggac gtggaggtgc aggtggatta ctgcggcatc    120

tgccacagcg acctgtcgat gatcgacaac gagtggggct tcagccagta cccgctggtg    180

gccggccatg aagtgatcgg ccgcgtcgtc gcgctgggct ccgccgccca ggataaaggc    240

ctgcaggtcg gccagcgcgt gggcatcggc tggaccgccc ggtcgtgcgg ccactgcgac    300

gcctgcatct cgggcaacca gatcaattgc gagcagggcg ccgtccccac catcatgaac    360

cgcggcggct tcgcggagaa gctccgcgcg gactggcagt gggtgatccc gctgccggaa    420

aatatcgata tcgaatccgc cggcccccctg ctgtgcggcg gcatcaccgt cttcaagccg    480

ctcctgatgc atcatatcac cgccacctcc cgcgtcggcg tcatcggcat cggcggcctc    540

ggccacatcg ccatcaaact cctgcatgcg atgggctgtg aagtgaccgc cttcagcagc    600

aaccccgcga aagagcagga agtgctcgcg atgggcgcgg acaaggtcgt gaacagccgc    660

gatccccagg ccctcaaagc gctggccggc cagttcgatc tcatcatcaa caccgtcaac    720

gtctcgctcg actggcagcc gtacttcgaa gcgctgacgt acggcggcaa cttccacacc    780

gtgggcgcgg tcctgacgcc cctgtcggtg ccggcgttca ccctgatcgc cggcgatcgg    840

agcgtgtcgg gctccgccac cggcaccccg tatgagctgc ggaagctgat gcggttcgcg    900

gcccgcagca aggtcgcccc gacgaccgag ctgttcccca tgagcaagat caacgacgcc    960

atccagcatg tgcgcgatgg caaagcccgg tatcgcgtgg tcctgaaagc ggatttctga   1020
```

<210> SEQ ID NO 39
<211> LENGTH: 1164
<212> TYPE: DNA
<213> ORGANISM: Escherichia coli

<400> SEQUENCE: 39

```
atgaacaatt tcaacctcca caccccgacc cgcatcctct tcggcaaggg cgccatcgcc     60

ggcctgcgcg agcagatccc gcacgacgcc cgcgtcctca tcacctatgg cggcggctcc    120

gtcaaaaaga ccggcgtgct cgatcaggtc ctggacgccc tgaagggcat ggacgtgctg    180

gagttcggcg gcatcgagcc gaacccggcc tacgagacgc tgatgaatgc ggtgaagctg    240

gtgcgcgagc agaaggtcac gttcctgctc gcggtcggcg gcggctcggt gctggacggc    300

accaagttca tcgccgccgc ggcgaattat cccgagaaca tcgatccctg gcacatcctg    360
```

```
cagacgggcg gcaaggagat caagtcggcc atcccgatgg gctgcgtcct gaccctcccc     420

gccaccggct cggagagcaa cgccggcgcc gtgatctcgc gcaaaaccac cggcgacaaa     480

caggcgttcc actccgccca tgtgcagccg gtcttcgcgg tgctggaccc cgtctacacg     540

tacaccctcc cgccgcggca ggtcgccaac ggcgtggtcg atgccttcgt gcatacggtg     600

gagcagtacg tcaccaagcc ggtggatgcc aagatccagg accgcttcgc ggagggcatc     660

ctgctgacgc tgatcgagga cggcccgaaa gccctcaagg aaccggaaaa ctacgatgtg     720

cgggcgaacg tcatgtgggc cgcgacccag gccctgaacg gcctgatcgg cgccggcgtg     780

ccccaggatt gggcgacgca catgctgggc cacgaactca ccgcgatgca cggcctcgac     840

cacgcccaga cgctcgccat cgtcctgccg gccctgtgga atgagaagcg ggacaccaag     900

cgggcgaagc tcctgcagta tgccgaacgg gtgtggaaca tcaccgaagg ctcggacgat     960

gaacgcatcg atgccgccat cgcggccacg cggaacttct tcgagcagct gggcgtcccg    1020

acccatctct ccgactacgg cctggatggc tcctccatcc ccgcgctgct gaaaaaactg    1080

gaagaacacg gcatgaccca gctgggcgaa aaccacgaca tcaccctgga tgtctcgcgc    1140

cgcatctacg aagccgcccg gtga                                          1164
```

<210> SEQ ID NO 40
<211> LENGTH: 1011
<212> TYPE: DNA
<213> ORGANISM: Geobacillus stearothermophilus

<400> SEQUENCE: 40

```
atgcgggcgg ccgtggtgac caaggaccac aaggtcagca tcgaagataa gaaactgcgg      60

gccctgaaac ccggcgaggc gctggtgcag accgaatatt gtggcgtgtg tcatacggat     120

ctccatgtca aaaacgccga tttcggcgat gtgaccggcg tgacgctcgg ccatgagggc     180

atcggcaagg tgatcgaagt cgccgaagac gtggaaagcc tcaagatcgg cgatcgcgtg     240

tccatcgcct ggatgttcga gtcgtgtggc cgctgcgagt attgcacgac cggccgggaa     300

accctgtgtc ggagcgtcaa gaatgccggc tacaccgtgg acggcgcgat ggccgaacag     360

gtcatcgtga cggccgacta tgcggtcaag gtcccggaaa agctggaccc ggccgcggcg     420

tcgtcgatca cctgcgcggg cgtcaccacc tataaggccg tcaaggtgag caatgtcaaa     480

ccgggccagt ggctgggcgt cttcggcatc ggcggcctgg gcaacctggc cctgcagtac     540

gcgaagaatg tcatgggcgc caaaatcgtg gccttcgata tcaacgatga caagctggcg     600

ttcgccaaag aactcggcgc ggatgcgatc atcaactcga aggacgtgga cccggtggcc     660

gaggtgatga aactgacgga caacaagggc ctggacgcga cggtcgtcac cagcgtcgcg     720

aagacccccct tcaatcaggc ggtcgacgtg gtcaaggcgg gcgcccgcgt ggtggccgtg     780

ggcctgccgg tcgacaaaat gaacctggat atcccgcgcc tcgtgctgga cggcatcgag     840

gtggtgggca gcctggtcgg cacccgccag gacctgcggg aggccttcga gttcgcggcc     900

gagaataaag tgacgcccaa ggtccagctc cggaagctcg aagaaatcaa cgatatcttc     960

gaggagatgg aaaacggcac gatcaccggc cggatggtca tcaagttctg a            1011
```

<210> SEQ ID NO 41
<211> LENGTH: 1020
<212> TYPE: DNA
<213> ORGANISM: Geobacillus stearothermophilus

<400> SEQUENCE: 41

```
atgaaggcgg ccgtcgtgaa cgagttcaag aaggcgctgg aaatcaagga ggtcgagcgg      60
```

```
cccaaactcg aagagggcga ggtcctggtg aagatcgagg cctgcggcgt gtgccatacc    120

gacctgcacg ccgcccacgg cgactggccg atcaagccga aactgcccct gatcccgggc    180

cacgagggcg tgggcatcgt cgtggaagtg gcgaagggcg tgaaaagcat caaagtgggc    240

gatcgcgtcg gcatcccgtg gctgtacagc gcgtgcggcg agtgcgagta ctgcctgacg    300

ggccaggaaa cgctctgccc gcatcagctg aatggcggct attccgtgga cggcggctat    360

gccgagtatt gcaaagcccc ggccgactat gtcgccaaga tcccggacaa tctggacccc    420

gtcgaggtcg cccccatcct gtgcgccggc gtgaccacct ataaggcgct gaaagtctcg    480

ggcgcccggc cgggcgagtg ggtcgcgatc tacggcatcg gcggcctggg ccacatcgcc    540

ctgcagtacg ccaaggcgat gggcctgaac gtggtcgcgg tcgacatctc cgacgagaaa    600

tcgaagctgg cgaaagatct cggcgcggac atcgccatca atggcctgaa ggaagacccg    660

gtcaaggcga tccatgacca ggtcggcggc gtccatgccg ccatctccgt cgcggtgaat    720

aagaaagcct tcgagcaggc ctatcagtcc gtcaagcgcg gcggcaccct ggtcgtggtg    780

ggcctcccga atgcggacct gccgatcccc atcttcgata cggtgctcaa cggcgtgtcg    840

gtgaagggca gcatcgtcgg cacccgcaag gacatgcagg aagccctgga tttcgccgcg    900

cggggcaagg tccgccccat cgtggaaacg gccgagctgg aggaaatcaa cgaagtgttc    960

gagcgcatgg aaaaaggcaa aatcaacggc cgcatcgtcc tgaagctgaa ggaggattga   1020
```

```
<210> SEQ ID NO 42
<211> LENGTH: 1041
<212> TYPE: DNA
<213> ORGANISM: Geobacillus themoglucosidas

<400> SEQUENCE: 42

atgaaagccc tgacctatct gggcccgggc aaaaaagaac tgatggaaaa accgaagccg     60

aagatcgaaa aagagacgga tgccatcgtc aagatgatca aaaccaccat ctgcggcacc    120

gacctccata tcctgtcggg cgacgtgccc accgtggaag agggccgcat cctgggccac    180

gagggcgtcg gcatcatcga ggaagtgggc tccgccgtca agaacttcaa gaaaggcgac    240

cgggtgctga tctcgtgcat caccagctgt ggcaagtgcg agaattgcaa gaagggcctg    300

tacgcccact gcgaggacgg cggctggatc ctgggccatc tgatcgacgg cacccaggcc    360

gagtacgtgc gcatccccca tgcggacaac agcctgtacc cgatccccga gggcgtcgac    420

gaggaagccc tggtcatgct gtcggatatc ctgcccaccg gcttcgagat cggcgtgctg    480

aacggcaagg tccagcccgg ccagaccgtg gcgatcatcg gcgccggccc ggtgggcatg    540

gccgcgctgc tgaccgccca gttctacagc ccggccgaga tcatcatggt ggacctggac    600

gataaccgcc tcgaagtggc gaagaagttc ggcgcgaccc aggtcgtcaa cagcgcggat    660

ggcaaggcgg tggagaagat catggaactc accggcggca agggcgtgga cgtggcgatg    720

gaagccgtcg gcatcccggc caccttcgat atctgccagg agatcgtgaa gccgggcggc    780

tacatcgcca acatcggcgt gcatggcaag tccgtggagt tccatatcga aaaactgtgg    840

atccgcaaca tcaccctgac gacgggcctg gtgaacacca cgagcacgcc catgctgctg    900

aagacggtgc agtcgaagaa gctcaagccc gaacagctca tcacccaccg cttcgccttc    960

agcgatatca tgaaagcgta cgaagtcttc ggcaacgccg ccaaggagaa ggcgctgaaa   1020

gtcatcatca gcaattcgtg a                                             1041

<210> SEQ ID NO 43
```

<211> LENGTH: 1023
<212> TYPE: DNA
<213> ORGANISM: Geobacillus themoglucosidas

<400> SEQUENCE: 43

```
atgaaagccg cggtggtcaa tgagttcaag cagaaactcg aaatcaagga agtcgaaaag      60
ccgaagctca actacggcga agtgctggtg aaaatcgagg cctgcggcgt ctgccacacc     120
gacctccatg cggcccacgg cgactggccc gtcaagccga agctgcccct gatcccgggc     180
catgagggcg tgggcatcgt cgtggaagtc gcggagggcg tcaagagcgt caaggtcggc     240
gaccgggtgg gcatcccctg gctgtattcc gcctgcggcg aatgcgaata ctgcctgagc     300
ggccaggaaa ccctgtgccc ccaccagctg aacggcggct atagcgcgga tggcggctat     360
gccgagtact gtaaagcccc cgccaactac gtggcgaaga tcccggaaca tctggacccc     420
gtggaagtgg cgcccatcct ctgcgcgggc gtgaccacct ataaagccct caaggtgtcc     480
aacgccaaac ccggcgagtg ggtcgccatc tacggcatcg gcggcctcgg ccatatcgcg     540
ctgcagtacg ccaaggcgat gggcctcaac gtcatcgccg tggatatcag cgacgagaaa     600
atcgaactgg cgaaacagct cggcgcggac atcgcgatca acggcctgaa agaagatccg     660
gtggaagcca tccagcagaa cgtcggcggc gcccacgccg cgatcagcgt cgccgtgacc     720
aagaaggcgt tcgaacaggc ctatcagagc gtccggcggg gcggctgcct ggtcgtggtc     780
ggcctgccca acgaggacct gcccatcccg atcttcaaca ccgtcctgaa tggcatcacc     840
gtcaagggct ccatcgtggg cacgcggaag gatatgcagg aagcgctgga tttcgcggcg     900
cggggcaagg tgcggccgat cgtcgagacg gccccgctgg agaagatcaa tgaggtcttc     960
gaacgcatgg agaagggcaa gatcaatggc cgcgtcgtgc tcaccatcgg cgtcaaccgc    1020
tga                                                                 1023
```

<210> SEQ ID NO 44
<211> LENGTH: 1023
<212> TYPE: DNA
<213> ORGANISM: Lactococcus lactis

<400> SEQUENCE: 44

```
atgaaggcgg ccgtcgtgcg gcacaacccg gacggctatg ccgatctggt ggagaaggag      60
ctccgcgcga tcaagccgaa cgaggccctc ctggacatgg agtactgcgg cgtgtgccac     120
accgacctgc acgtcgccgc cggcgatttc ggcaacaaag ccggcaccgt cctgggccat     180
gagggcatcg gcatcgtgaa ggaaatcggc accgatgtgt cgtccctcca ggtgggcgac     240
cgggtcagcg tcgcctggtt cttcgaaggc tgcggccact gcgagtactg cgtgtccggc     300
aacgagacgt tctgccggga agtcaagagc gcgggctaca gcgtcgatgg cggcatggcc     360
gaggaagcca tcgtcgtcgc cgactacgcc gtgaaggtcc cggatggcct cgatcccatc     420
gaggccagca gcatcacctg cgcgggcgtg accacctaca aggccatcaa ggtgtccggc     480
gtcaaaccgg gcgattggca ggtgatcttc ggcgccggcg gcctgggcaa cctcgcgatc     540
cagtacgcca aaaacgtctt cggcgcgaag gtcatcgcgg tggacatcaa ccaggacaag     600
ctgaacctcg cgaagaagat cggcgccgat gtcaccatca actcgggcga tgtcaacccg     660
gtcgacgaga tcaagaaaat caccggcggc ctgggcgccc agtcggccat cgtgtgcgcg     720
gtcgcccgca tcgcgttcga acaggcggtg gccagcctca aaccgatggg caaaatggtg     780
gcggtggccg tcccgaacac cgagatgacc ctgagcgtgc cgaccgtggt cttcgacggc     840
gtcgaggtcg cgggctcgct cgtcggcacc cggctggacc tcgccgaggc cttccagttc     900
```

ggcgcggagg gcaaagtcaa gccgatcgtc gcgacccgga agctggagga gatcaatgac 960
atcatcgatg agatgaaggc cggcaagatc gaaggccgga tggtcatcga tttcaccaag 1020
tga 1023

<210> SEQ ID NO 45
<211> LENGTH: 1023
<212> TYPE: DNA
<213> ORGANISM: Lactococcus lactis

<400> SEQUENCE: 45
atgaaggcgg cggtcgtgcg ccataacccg gacggctacg ccgacctggt ggaaaaggag 60
ctgcgggcca tcaagccgaa cgaggcgctg ctcgacatgg agtactgcgg cgtctgccat 120
acggacctcc acgtcgccgc cggcgactac ggcaacaagg cgggcacggt gctgggccat 180
gagggcatcg gcatcgtgaa ggaaatcggc accgacgtgt cctccctgca ggtcggcgac 240
cgggtcagcg tcgcctggtt cttcgagggc tgtggccact gcgagtattg tgtcagcggc 300
aatgaaacgt tctgtcgcga agtcaaaaac gccggctact cggtcgatgg cggcatggcg 360
gaagaagcca tcgtggtcgc ggactatgcc gtgaaggtgc cggacggcct ggaccccatc 420
gaagcgtcct cgatcacctg cgcgggcgtc acgacctaca aggcgatcaa agtgtcgggc 480
gtcaagccgg gcgactggca ggtgatcttc ggcgcgggcg gcctcggcaa cctcgccatc 540
cagtacgcca agaacgtctt cggcgccaaa gtgatcgccg tcgacatcaa tcaggacaaa 600
ctgaatctgg cgaaaaagat cggcgccgat gtcatcatca acagcggcga tgtgaacccg 660
gtggacgaga tcaaaaagat cacgggcggc ctcggcgccc agagcgcgat cgtgtgcgcc 720
gtggcccgca tcgccttcga acaggccgtc gcgtccctga agccgatggg caagatggtc 780
gccgtcgccc tcccgaacac ggaaatgacg ctgtccgtcc cgaccgtggt cttcgacggc 840
gtggaagtgg ccggctcgct ggtcggcacc cggctggacc tcgccgaggc cttccagttc 900
ggcgcggaag gcaaggtcaa gccgatcgtg gccacgcgca agctcgaaga gatcaatgat 960
atcatcgatg agatgaaggc gggcaagatc gaaggccgca tggtcatcga tttcaccaag 1020
tga 1023

<210> SEQ ID NO 46
<211> LENGTH: 1206
<212> TYPE: DNA
<213> ORGANISM: Oenococcus oeni

<400> SEQUENCE: 46
atgcgcggca gccatcatca ccatcaccac ggcagcgccg aacgggccta cgatttcctg 60
atgccctccg tcaacttctt cggcccgggc gtgatctcca agatcggcga acgggcgaaa 120
atgctcggca tgaagaagcc ggtgatcgtc accgataagt tcctggagaa tctgaaaaat 180
ggcgccgtgg cccagaccct ggccagcctc aagaagagcg gcgtcgatta cgtcgtgtat 240
aacggcgtgg agcccaaccc caaaatccac aacatcaagg aggtgaaaac cctgtacgaa 300
aaggaagacg ccgacagcat catcaccgtg ggcggcggct cggcccacga tacgggcaag 360
ggcgccggca tcatcatgac gaacggcgat gacatcacca agctggccgg catcgaaacc 420
ctgaagaatc cctccccccc cctgatcgcc gtgaatacca ccgcgggcac cggctcggaa 480
ctcacgcggc acgccgtcat cacgaacgag gaaacccatc tgaagttcgt cgtggtgtcc 540
tggcgcaaca tcccgctggt cagcttcaat gaccccaccc tgatgctgga catccccaag 600

```
ggcctcaccg cggccacggg catggacgcc ttcgtccagg cggtcgaacc gtacgtgagc    660

gtggatcaca atcccatcac cgactcccag tgtatccagg ccatcaagct gatcgaatcg    720

tcgctgcggg aggccgtggc gaacggccat aacctgcagg cccgcaccaa aatggtggaa    780

gccgaaatgc tcgcgggcat ggcgttcaat aacgccaacc tgggctacgt ccacgcgatg    840

gcccatcagc tgggcggcca gtacgacgcc ccgcatggcg tctgctgcgc cctgctcctg    900

ccgtatgcgg aggagtacaa cctgatcgcc gacccggaac gcttcgcgga actggcccgc    960

atcatgggcg agaacaccga cggcctctcg acccgcgacg cggccgaact gtccatcaag   1020

gcgatgaaac agctgtcgga ggacgtgggc atcccgcact cgatcaagga catcggcgcc   1080

aagccggagg acttcgacct gatggccgaa aatgcgctga aggacggcaa tgccttctcc   1140

aacccgcgca aaggcaccaa ggaggatatc gtcaagatct tccaggaggc ctatgacgcc   1200

aaatga                                                              1206
```

<210> SEQ ID NO 47
<211> LENGTH: 1002
<212> TYPE: DNA
<213> ORGANISM: Pectobacterium atrosepticum

<400> SEQUENCE: 47

```
atgctgaatt tcaccctcca taccccgacg aagatcctgt tcggcgaggg ccagatcgcg     60

gagctgggca aggagatccc ggccgacgcc cgcatcctca tcacctacgg cggcggctcg    120

gtcaaacaca acggcgtgct ggatcaggtg taccgggcgc tggaaggccg gaacgtgcgg    180

gagttctccg gcatcgagcc caacccgacc tacgaaacgc tcatgaaggc cgtggaggtg    240

gtccgggcgg aaaagatcga tttcctgctc gccgtgggcg gcggcagcgt cgtcgacggc    300

accaagttca tcgccgcggc ggccgactac caggccgcgc aggacccgtg gcacatcctc    360

cagaccggcg gcgccgaaat cgaccggggc gtggccctcg ccgcggtgct gaccctgccc    420

gccacgggca gcgaatccaa taacggcgcc gtcatcaccc gcaaaagcac caatgacaag    480

ctcgcgttcc ggtccccgca tacgcagccc ctcttcgccg tcctcgaccc ggtggtcacg    540

tacaccctgc cggcccggca gatcgcgaat ggcgtcgtcg acgccttcgt ccacaccgtc    600

gagcagtacc tgacctactc cgtcgacgcg aaagtccagg atcgcttcgc cgagggcctg    660

ctgctcaccc tggtcgaaga gggcccccgg gccctggccg aacccgaaaa ctacaaagtg    720

cgggcgaatg tcatgtggag cgccacgatg gcgctgaacg gcctcatcgg cgccggcgtc    780

ccccaggatt ggtcgaccca catgctgggc cacgaactca cggccctgca cggcctcgac    840

cacgcgcaga cgctggccat cgtcctgccg gccatgctgg cggcccggaa atcccagaaa    900

cgggataaac tcctgcagta cgccgagcgc gtctggaacc tccgcgacgg ctcggaagat    960

cagcggatcg acggcgccat cgccgccacg cgcgatttct ga                      1002
```

<210> SEQ ID NO 48
<211> LENGTH: 1056
<212> TYPE: DNA
<213> ORGANISM: Psychrobacter cryohalolentis

<400> SEQUENCE: 48

```
atggccaata ccaaggccta cgccgccacg gcgccggatt cgggcctggc cccgtacgcg     60

atcgaccggc gggaactgcg ggccgatgac gtggcgatcg aaatcgacta ctgtggcgtg    120

tgccatagcg atctccatac cgtggaaaac gactggggcg gctcgaagta cccggtgatc    180

ccgggccatg agatcgtcgg ccgggtgacg gcggtgggcc ccgaggtcag ccatttcaag    240
```

```
gccggcgacc tcgtgggcgt gggctgcatg gtggattcgt gtcgctcgtg cagcgcctgc    300

gacagcggcc tcgaacagta ttgcatcgag ggcagcacga tgacctacgg cagcctggac    360

cgccacgatg gctccgtcac ccacggcggc tacagcgaac gcatcgtcgt ctcggaacgg    420

ttcgtcgtgc gggtgcccga aaaactggac ccggcctcgg ccgcccccgat cctgtgcgcc    480

ggcatcacga cgtacagccc gctgaagcac ttcaaggtgg gcaagggcca taaagtcggc    540

gtcctgggca tgggcggcct gggccatatg ggcgtgaagt tcgccaaggc cctgggcgcc    600

gaggtgacga tcttcacccg gtccgaggcg aaagtggccg aagcgaagaa acagggcgcc    660

gaccatgtca tcatctcgac cgataaggag cagatgaagg ccgccgccga cagcttcgat    720

ttcctcctcg acaccatccc ggtggcgcac gacctgaatc cgtatctgaa gtgtctgaaa    780

tacgatggca cccacatcct cgtgggcctg ctgaccccca tcgaaccggc gctgcaggcc    840

ggcctcctgg tcaccaagcg gcgcgtcgtg gcgggcagcc tgatcggcgg catgcccgag    900

acgcaggaag tcctggactt ctgcgccgaa catgacatca cctgtgatat cgagatgctc    960

gacatccgca acatcaacga agcgtacgtc cgcatgaaaa agggcgatgt caagtaccgc   1020

ttcgtgatcg atatgaagac gctgaaggaa ggctga                             1056
```

<210> SEQ ID NO 49
<211> LENGTH: 1713
<212> TYPE: DNA
<213> ORGANISM: Bacillus subtilis

<400> SEQUENCE: 49

```
atgaccaagg ccaccaagga acagaaaagc ctggtcaaga accgcggtgc tgaactggtt     60

gtggactgcc tcgtggaaca gggcgtgacc catgtcttcg gcatcccggg cgccaagatc    120

gacgccgtct tcgacgccct gcaggataaa ggtccggaaa tcatcgtggc acgccatgag    180

cagaacgcag ccttcatggc ccaggccgtc ggtcggctga cgggtaagcc cggcgtggtg    240

ctggtcacct ccggtccggg agcctcgaac ctggccacgg gactgctcac cgccaacacc    300

gaaggcgacc cggtggtcgc cctggccggt aatgtcatcc gggcggatcg cctgaagcgc    360

acccatcagt ccctggataa cgcggccctg ttccagccaa tcaccaaata tagtgtcgaa    420

gtgcaggatg tgaagaacat cccggaagcc gtcaccaatg cgttccgaat cgcgtccgcc    480

ggccaagcag ggcagcattt cgtgagcttc ccccaggacg tggtcaatga agtgaccaac    540

accaaaaacg tcagagccgt agccgccccg aagctgggcc ctgcagcaga tgacgccatc    600

tccgctgcca tcgcgaagat ccagaccgca aagctgccgg tcgtgctggt cggaatgaag    660

ggcggacgcc cggaggccat caaggccgtg cgtaaactgc tgaagaaggt gcagctaccg    720

ttcgtggaaa cctaccaggc cgccggcacc ctgagtcggg acttggaaga ccagtatttc    780

ggccgtatcg gcctgttccg caaccagccg ggcgacctgc tcctggaaca agccgatgtg    840

gtgctgacca tcggctacga cccgatcgaa tatgacccga agttctggaa catcaatggc    900

gaccgcacga tcatccatct ggacgaaatc atcgccgaca tcgaccatgc ctatcagccg    960

gacctggaac tgatcggcga catcccgagc accatcaacc acatcgaaca cgatgccgtg   1020

aaggtggaat ttgccgaacg cgaacagaag atcctgtcgg acctgaagca gtatatgcat   1080

gagggcgaac aggtgcctgc cgactggaag tcggacagag cccatccgct ggaaatcgtg   1140

aaggaactgc gtaacgccgt cgacgaccat gtcaccgtca cctgcgatat cggcagccat   1200

gccatttgga tgagccgcta cttccggagc tatgaaccgc tgaccctgat gatctccaac   1260
```

ggtatgcaga ccctcggcgt cgccctcccg tgggccatcg gcgcaagtct ggtgaagccg 1320
ggcgaaaaag tggtcagcgt gtccggcgac ggcggcttcc tgttctccgc tatggaactg 1380
gaaaccgcgg tccgcctgaa ggccccgatc gtgcatatcg tgtggaacga cagcacctac 1440
gacatggtcg ccttccagca gctgaaaaag tacaaccgca ccagcgccgt ggacttcggc 1500
aatatcgaca tcgtgaagta tgccgaatcc ttcggagcca ccggactgcg cgtggaatcc 1560
ccggaccagc tggcggacgt tctgcgtcag ggcatgaatg ccgaaggtcc cgtgattatc 1620
gatgtgcccg tcgactacag cgacaacatc aacctggcct cggacaaatt gccgaaggag 1680
ttcggcgaac tgatgaaaac aaaagcacta taa 1713

<210> SEQ ID NO 50
<211> LENGTH: 1671
<212> TYPE: DNA
<213> ORGANISM: Clostridium autoethanogenum

<400> SEQUENCE: 50
atgaatcggg atatcaagaa agaggtgcag ctcaacacgg cccagatgct ggtcaagtgt 60
ctggaagccg agggcgtcaa gtatatcttc ggcatcccgg gcgaggagaa tctcgaaatc 120
atgaacgcca tctcggattc cacgatcgag ttcatcacca cccgccatga acagggcgcg 180
gccttcatgg ccgacgtgta cggccggctg accggcaagg cgggcgtgtg tctgagcacc 240
ctcggccccg gcgcgaccaa cctggtcacc ggcgtggccg acgccgactc cgacggcgcc 300
cccgtggtcg cgatcaccgg ccaggtgggc acggagcgga tgcacatcac ctcccatcag 360
ttcctcgacc tctgcaagat gttcgagccg atcaccaagc ggagcaagca gatcgtccgc 420
ccggacacgg tgtcggagat catccgcctg gtgttcaagt acgccgaaag cgaaaagccc 480
ggcgcctgtc atatcgacct gccggtcaac atcgccaaga tgcccgtcgg cgccctggag 540
aagccgctgg agaaaaaaat cccgccgaag gaacacgcgg acctgtccac catcgaggaa 600
gcggcgtccg agatcttcaa ggccaaaaac cccatcatcc tggccggcag cggcgccatc 660
cgcggcaaca gcagcaaggc ggtcaccgag ttcgccacca agctgaagat ccccgtcatc 720
aacacgatga tggccaaggg catcatcccg atggacaaca agtatagcat gtggaccatc 780
ggcatccccc agaaggacta tgtgaacaag atcatcgaag aggccgacct ggtcatcacc 840
atcggctacg acatcgtgga atatgccccg tcgaaatgga acatcaacgg cgacatcaag 900
atcgtccata tcgacgcccg cccctcgcac atcaacaaac tctaccagcc catcgtggag 960
gtggtcggcg acatcagcga cgcgctgtat aacatcctgc gccgcaccag ctcgaaagac 1020
gagccggtca aggcgctgga gatcaagtcg gaaatgctgg cggagcacga gtcctacgcg 1080
aacgacaatg cgttcccgat gaagccgcag cgcatcctca acgatgtgcg caaagtcatg 1140
ggcccgcacg acatcgtgat ctccgatgtg ggcgcccata aaatgtggat cgcccgccac 1200
tataactgct acgagccgaa tacctgcatc atctcgaacg gcttcgccac gatgggcatc 1260
ggcgtcccgg gcgcgatcgc cgccaaactc atcaacccgg ataagaaggt cctggccatc 1320
gtcggcgacg gcggcttcat gatgaataac caggaactgg agacggcgct gcgcatcaaa 1380
acgcccatcg tggtcctcat cttcaacgac tccaattacg gcctcatcaa gtggaagcag 1440
gaggagcatt atggcaaatc gtgctatgtg gacttcacca acccggactt cgtgaagctg 1500
gccgagagca tgtacgccaa aggctatcgc gtggagaaag ccgaggatct gatcccgacc 1560
ctcgaagagg ccttcaagca gaatgtcccg gcggtcatcg actgccaggt ggactatggc 1620
gagaatatca agctcaccaa gcacctcaag gaggtctatg aaaacatgtg a 1671

<210> SEQ ID NO 51
<211> LENGTH: 1719
<212> TYPE: DNA
<213> ORGANISM: Bacillus licheniformis

<400> SEQUENCE: 51

```
atgaataacg tcgcggccaa gaacgaaacc ctgaccgtcc ggggcgccga actcgtggtg     60
gatagcctga tccagcaggg cgtgacccat gtcttcggca tcccgggcgc caaaatcgac    120
gcggtcttcg acgtgctgaa ggataagggc cccgaactga tcgtctgccg ccatgagcag    180
aacgcggcct tcatggccgc cgccgtcggc cgcctgacgg gcaagccggg cgtctgcctg    240
gtcacctccg gcccgggcgc ctcgaatctc gcgaccggcc tggtcaccgc gaacacggaa    300
ggcgacccgg tggtcgccct ggcgggcgcc gtgaagcggg cggatcggct gaagaagacg    360
caccagtcga tggataacgc cgccctgttc cagcccatca cgaagtacag cgcggaggtg    420
gaagacgcga acaacatccc ggaggccgtg acgaacgcct tccgcgccgc ggcgtccggc    480
caggccggcg cggccttcct cagcttcccc caggatgtca ccgccggccc ggccaccgcc    540
aagccggtca aaaccatgcc cgccccgaag ctgggcgccg cgagcgatga acagatctcc    600
gccgcgatcg cgaagatcca caacgcgaat ctgccggtgg tcctcgtggg catgaagggc    660
ggccggccgg aagccatcga agccgtgcgc cgcctgctcc gcaaggtcaa gctcccgttc    720
gtggaaacct accaggcggc cggcacgctg tcgcacgatc tggaggatca gtacttcggc    780
cggatcggcc tgttccggaa ccagccgggc gacatgctcc tggaaaaggc cgacgtggtc    840
ctgaccgtgg gctacgaccc gatcgagtac gatccggtgt tctggaatgg caaaggcgaa    900
cgctcggtca tccacctcga cgaaatccag gccgatatcg atcacgacta ccagcccgag    960
atcgaactca tcggcgacat cgcggaaacc ctcaatcaca tcgagcatga ctcgctgccg   1020
gtgtccatcg acgaatcctt cgcgcccgtg ctcgactatc tcaagaaggc gctcgaagaa   1080
cagtcggagc cccgaagga aacgaagacc gatctggtcc acccgctcca gatcgtgcgc   1140
gacctgcgcg agctgctctc cgatgacatc accgtcacct gcgacatcgg cagccacgcc   1200
atctggatgt cccgctattt ccgcacctat cgcccgcatg gcctcctgat ctccaacggc   1260
atgcagacgc tgggcgtcgc cctgccgtgg gcgatcgccg cgaccctggt gaacccgggc   1320
cagaaggtgg tgtcggtcag cggcgatggc ggcttcctct tctccgcgat ggaactcgaa   1380
accgccgtcc gcctcaaggc gccgatcgtg cacatcgtgt ggaacgactc cacgtacgac   1440
atggtcgcgt tccagcagga aatgaagtac aagcgcacct ccggcgtcga tttcggcggc   1500
atcgacatcg tcaagtatgc ggaatccttc ggcgccaaag gcctccgcgt gaatagcccc   1560
gatgaactgg ccgaggtcct gaaggccggc ctcgacgcgg agggcccggt ggtcatcgac   1620
atccccgtcg actactcgga taacatccac ctggccgacc agcgcttccc gaagaagttc   1680
gaggagcact tcaacaagga agcgtcgaag cagtcctga                          1719
```

<210> SEQ ID NO 52
<211> LENGTH: 720
<212> TYPE: DNA
<213> ORGANISM: Clostridium autoethanogenum

<400> SEQUENCE: 52

```
atggatgatg aggtgaaagt cccgaaccac atctaccaga tgtcgaccat caatgccctg     60
gtcagcggcc tctacgacgg ctgtgtgtcg ctctcgaagc tcctgaaaaa gggcaatttc    120
```

ggcatcggca cgttcaaggg cctggatggc gagctgaccc tcctgaacgg cacgttctat 180
cgcaccaaac cggatggctc cgtgtacgtg tgcagcaaga acgtgagcgt ccccttcgcg 240
gtcgtcaccg agctggagaa ctacaatacc tataacatcc agaatcgcac ctcctatgag 300
gacatccgca aggagctgga ctcgttcatc gagtcgaaga acatcttcta tgccttctat 360
atggaaggca aattcaacta cgtcaaaacc cgcaccgtcg tgaagcagaa catgccgtac 420
aagccgatgg ccgaggtggt caaagaccag ccgatgttcg aatacaacgg cgtcgatggc 480
tacgtcgtcg gcttccggtg cccggattat gtggaaggcc tcaatgtgcc cggctaccat 540
ttccacttca tcaacaagga caaaaagttc ggcggccaca tctccgagtt ctcgatcgag 600
aacgccaaag tctacgtcca gaactgctcc tgtttccgca tggagctccc gaagaatgag 660
agcttctaca acatggaggt ccaggaccgc aacgacgaaa tcacgtccgt ggagaaatga 720

<210> SEQ ID NO 53
<211> LENGTH: 780
<212> TYPE: DNA
<213> ORGANISM: Klebsiella pneumoniae

<400> SEQUENCE: 53
atgaaccact cggccgaatg cacctgcgaa gagagcctct gcgaaaccct ccgggccttc 60
tcggcccagc acccggagag cgtcctgtac cagacgagcc tgatgtcggc gctgctgtcg 120
ggcgtgtatg aaggctcgac gaccatcgcc gacctgctga agcatggcga cttcggcctg 180
ggcaccttca atgaactgga cggcgagctc atcgccttca gctcgcaggt gtatcagctc 240
cgggccgatg gctccgcccg gaaggcccag cccgaacaga agaccccgtt cgccgtgatg 300
acctggttcc agccgcagta tcggaagacc ttcgaccacc ccgtgagccg ccagcagctc 360
cacgaggtga tcgaccagca gatcccgagc gacaacctct tctgcgccct gcgcatcgac 420
ggccatttcc gccacgcgca tacccgcacc gtcccgcggc agaccccgcc ctaccgcgcc 480
atgaccgatg tcctggatga ccagccggtc ttccggttca accagcgcga gggcgtcctg 540
gtcggcttcc gcaccccgca gcacatgcag ggcatcaacg tcgcgggcta tcatgaacac 600
ttcatcaccg atgatcgcaa gggcggcggc cacctcctcg actaccagct ggaccacggc 660
gtcctgacct tcggcgaaat ccataagctg atgatcgacc tccccgccga cagcgccttc 720
ctgcaggcga atctgcatcc ggacaacctc gatgccgcca tccgctccgt cgagtcgtga 780

<210> SEQ ID NO 54
<211> LENGTH: 1074
<212> TYPE: DNA
<213> ORGANISM: Clostridium autoethanogenum

<400> SEQUENCE: 54
atgaaggccg tcctgtggta cgacaaaaag gatgtccgcg tggaagaaat cgaggaaccg 60
aaggtgaaag aaaacgccgt gaagatcaaa gtcaagtggt gcggcatctg cggctcggac 120
ctgcatgagt atctcggcgg cccgatcttc atcccggtcg gcaccccccca cccgctgtcg 180 aagagcaccg cgcccgtcgt gctgggccac gagttctcgg gcgaagtggt ggagatcggc 240
agcaaagtga ccaagttcaa ggcgggcgac cgcgtcatcg tggaaccgat cgtcgcctgc 300
ggcaaatgcc cggcctgcct ggaaggcaag tacaatctgt gcgaggcgct gggcttccac 360
ggcctgtgcg gcagcggcgg cggcttcgcc gagtacacgg tgttcccgga agatttcgtg 420
cacaagatcc ccgacacgat ggattatgaa caggccgcgc tggtggagcc gatggcggtc 480
gcgctgcact ccctgcgggt gggcaacttc accacgggca acaccgccct ggtcctgggc 540

```
gcgggcccga tcggcctggc caccatccag tgcctcaaag cgtcgggcgc ccggatcgtc    600

atcgtcttcc agcgcaaatc ggtgcggcag gaatacgcca agaagttcgg cgcggacgtg    660

gtcctcgacc cgaatgaggt ggacgtgatc gaggaaatca aaaagctgac cggcggcgtg    720

ggcgtggaca cgagcttcga aaccaccggc gccaacgtcg gcatcaacac cgcgatccag    780

gcgctgaaat atgagggcac cgccgtcatc acctccgtct gggagaagaa cgccgagatc    840

aatccgaacg acctggtctt caccgaaaag aaggtcgtcg gcaccctcgc gtaccggcac    900

gagttcccgt cgaccatcgc cctgatgaac gacggccgca tcaagaccga tggctatatc    960

accaagcgga tcgccctgga agacatcgtc aaggagggct tcgaaaccct gaccggcccg   1020

gagaagaaaa agcacgtcaa aatcatcgtc acgcccgata aaagcctcct gtga         1074
```

```
<210> SEQ ID NO 55
<211> LENGTH: 1053
<212> TYPE: DNA
<213> ORGANISM: Bacillus subtilis

<400> SEQUENCE: 55

atgaaagccc tgctgtggca taaccagcgc gacgtgcggg tggaagaggt cccggagccc     60

gccgtccgca gcggcgcggt gaaaatcaaa gtgaaatggt gcggcatctg tggcaccgac    120

ctgcatgaat atctggccgg ccccatcttc atcccgacgg aggaacatcc gctgacgcac    180

gtcaaggccc cggtcatcct cggccatgag ttcagcggcg aggtggtgga gatcggcgaa    240

ggcgtcacca atcacaaagt cggcgatcgc gtggtcgtcg aaccgatcta ctcgtgcggc    300

aagtgtgagg cgtgcaagca cggccactat aatgtctgcg agcagctggt gttccacggc    360

ctgggcggcg acggcggcgg cttctcggag tacaccgtgg tgccggcgga tatggtccac    420

cacatcccgg atgaaatgac ctacgagcag ggcgccctgg tcgagccggc cgccgtggcg    480

gtgcacgcgg tgcgccagag caaactcaag gagggcgaag ccgtggccgt cttcggctgc    540

ggcccgatcg gcctgctggt catccaggcg gccaaagcgg cgggcgcgac ccccgtcatc    600

gcggtcgagc tgtcgaagga acgccaggag ctcgccaagc tggcgggcgc ggattatgtc    660

ctgaaccccg ccgaacagga cgtggtggcg gaaatccgga acctgaccaa cggcctgggc    720

gtcaacgtct ccttcgaggt caccggcgtg gaagtcgtcc tgcggcaggc gatcgaatcg    780

acctcgttcg agggccagac ggtcatcgtg tcggtctggg agaaggacgc caccatcacg    840

cccaataatc tggtcctgaa agagaaggaa gtggtcggca tcctcggcta ccggcatatc    900

ttcccgtccg tcatcaagct gatctcgtcg ggccagatcc aggccgagaa actcatcacc    960

aagaagatca cggtggacca ggtggtcgaa gaaggcttcg aagcgctggt caaggataag   1020

aagcaggtga agatcctcgt gtcgccgaag tga                                1053
```

```
<210> SEQ ID NO 56
<211> LENGTH: 1053
<212> TYPE: DNA
<213> ORGANISM: Paenibacillus polymyxa

<400> SEQUENCE: 56

atgcaggcgc tgcgctggca cggcatcaag gacctgcggc tggagaacat cgagcagccc     60

gccgccctcc cgggcaaggt gaagatcaag gtggaatggt gcggcatctg cggcagcgac    120

ctgcatgaat atgtcgccgg cccgatcttc atccccgaaa acgcgcagca tccgctcacg    180

ggcgagaagt cgcccatcgt gatgggccat gagttctccg gccagttctt cgacttcggc    240
```

```
gaaggcgtga cgaaaatcca ggtgggcgac cgcgaagtgg tggagccggt cttcgcgtgt    300

ggcgaatgcg atgcgtgccg gcagggcaaa tataacctgt gcgataagat gggcttcctg    360

ggcctggccg gcggcggcgg cggcttctcg gaatatgtcg ccgcggatga gcatatggtg    420

cacaaaatcc ccgagtccgt gtccttcgaa cagggcgccc tggtcgagcc gtccgccgtc    480

gccctctacg cggtccgcca gatccagctg aaggtcgatg acaaggcggt ggtcttcggc    540

gccggcccca tcggcctgct cgtcatcgaa gcgctgaacg ccagcggcgc gagcgaaatc    600

tatgcggaag agctcagcga agagcgcacc gccaaagccg aagacctggg cgccatcgtg    660

ctcgacccca acacgtacga tgtcgtcgag gaactccata agcgcacgaa tggcggcgtc    720

tacgtcccct atgaggtcac ggaagtcccg cccgtgctga cccaggccat cgagtccgcc    780

aagatctccg gcgaaatcat gatcgtcatc atcttcgaaa aggaggccct catcaagccg    840

aacaacatcg tcatgaatga acggaacctg acgggcctga tctgctacga cgatgtgttc    900

ccggccctga tctccctcat ggagaatggc tacttccccg ccgacaagct ggtcatcaaa    960

cggatcaagc tggtggatgt catcgaagcg gccttcgagt cgctcctgat cgaggagtac   1020

caggtgacca tcctcgtgtc gccgcacgcc tga                               1053
```

<210> SEQ ID NO 57
<211> LENGTH: 3696
<212> TYPE: DNA
<213> ORGANISM: Mycobacterium bovis

<400> SEQUENCE: 57

```
atggccaata tctcgtcccc gttcggccag aacgagtggc tcgtggaggc catgtatcgg     60

aagttccggg acgacccgtc cagcgtcgac ccgtcctggc acgagttcct cgtggactac    120

tcccccgagc cgaccagcca gccggcggcc gagccgaccc gggtcacgtc gccgctcgtc    180

gccgaacggg ccgccgccgc cgccccccag gcgcccccca agccggccga cacggccgcc    240

gccggcaacg gcgtggtggc ggccctggcc gccaagaccg ccgtgccgcc cccggccgaa    300

ggcgacgaag tcgccgtcct ccggggcgcg gcggcggcgg tcgtgaagaa catgagcgcg    360

tccctggagg tgccgaccgc cacgtcggtc cgggccgtcc ccgcgaaact cctcatcgac    420

aaccgcatcg tcatcaataa ccagctgaag cggacgcggg gcggcaagat ctcgttcacg    480

cacctcctcg gctacgcgct cgtgcaggcc gtcaagaagt tcccgaacat gaaccggcac    540

tacacggaag tggacggcaa acccacggcc gtcacccccg cccatacgaa cctcggcctg    600

gccatcgacc tgcagggcaa ggacggcaag cggtcgctgg tggtcgccgg catcaagcgc    660

tgcgagacga tgcgcttcgc gcagttcgtc acggcctatg aagacatcgt ccgccgggcc    720

cgggacggca agctcaccac ggaagatttc gcgggcgtca ccatctcgct caccaatccc    780

ggcacgatcg gcaccgtcca tagcgtgccg cgcctgatgc ccggccaggg cgcgatcatc    840

ggcgtcggcg cgatggaata ccccgccgag ttccagggcg cgtccgagga gcggatcgcg    900

gaactgggca tcggcaagct catcaccctc accagcacgt atgaccaccg catcatccag    960

ggcgccgagt cgggcgactt cctccggacg atccatgagc tgctgctgag cgacggcttc   1020

tgggatgagg tgttccggga actgtccatc ccgtatctgc cggtccggtg gagcacggac   1080

aaccccgata gcatcgtgga caaaaacgcc cgcgtgatga acctcatcgc cgcctaccgc   1140

aaccgcggcc acctgatggc cgacaccgat ccgctgcggc tcgacaaagc ccgcttccgg   1200

agccatcccg acctggaagt cctgacccac ggcctcaccc tgtgggatct ggatcgggtc   1260

ttcaaggtcg acggcttcgc cggcgcccag tacaagaagc tgcgcgatgt gctcggcctg   1320
```

```
ctgcgggacg cctattgccg ccacatcggc gtggagtacg cgcacatcct cgacccggaa   1380
cagaaagaat ggctggaaca gcgcgtcgaa accaagcatg tgaagcccac ggtggcgcag   1440
cagaagtaca tcctgtcgaa gctgaatgcg gccgaagcct tcgaaacctt cctgcagacc   1500
aagtacgtcg gccagaagcg cttctccctg gaaggcgccg agtccgtcat cccgatgatg   1560
gatgccgcga tcgaccagtg cgccgaacac ggcctggacg aagtcgtgat cggcatgccc   1620
catcgcggcc ggctcaacgt cctcgcgaac atcgtcggca agccgtactc gcagatcttc   1680
acggagttcg aaggcaacct gaacccctcc caggcccacg gcagcggcga cgtgaaatat   1740
cacctgggcg ccaccggcct gtatctgcag atgttcggcg acaacgacat ccaggtcagc   1800
ctgaccgcca acccctcgca tctggaagcc gtcgaccccg tcctggaagg cctggtccgc   1860
gcgaagcagg acctcctgga ccacggcagc atcgatagcg acggccagcg ggccttctcc   1920
gtggtgcccc tcatgctgca cggcgacgcc gccttcgccg gccagggcgt ggtcgccgag   1980
acgctcaacc tggcgaacct gcccggctac cgcgtcggcg gcacgatcca catcatcgtc   2040
aacaatcaga tcggcttcac caccgccccc gagtactccc gcagctcgga atactgcacc   2100
gatgtggcga aaatgatcgg cgccccgatc ttccatgtca atggcgatga tccggaagcg   2160
tgcgtgtggg tggcccgcct ggcggtggat ttccgccagc ggttcaagaa ggatgtggtg   2220
atcgacatgc tgtgctaccg ccgccggggc cataatgaag gcgacgatcc ctccatgacc   2280
aacccctaca tgtacgatgt cgtggacacg aagcgcggcg cccgcaagtc ctataccgag   2340
gccctcatcg gccggggcga tatcagcatg aaagaagccg aggatgcgct ccgcgactat   2400
cagggccagc tggaacgggt gttcaacgag gtgcgggaac tcgaaaaaca cggcgtccag   2460
ccgtccgaga gcgtggagtc cgatcagatg atcccggcgg gcctcgccac ggcggtcgat   2520
aagtccctgc tggcccggat cggcgatgcc ttcctggccc tccccaatgg cttcacggcg   2580
cacccgcggg tgcagccggt gctcgaaaaa cgccgggaaa tggcctacga aggcaagatc   2640
gactgggcct tcggcgagct gctggcgctg ggctccctgg tggccgaagg caaactggtg   2700
cgcctgtccg gccaggactc gcgccgcggc accttctccc agcgccactc ggtcctgatc   2760
gatcgccata ccggcgagga gttcaccccg ctccagctcc tggccacgaa ctccgacggc   2820
tcgcccaccg gcggcaagtt cctggtgtat gacagccccc tgagcgagta tgcggcggtc   2880
ggcttcgagt acggctacac cgtcggcaat cccgacgccg tcgtcctgtg ggaagcgcag   2940
ttcggcgact tcgtcaatgg cgcccagtcg atcatcgacg agttcatctc gtcgggcgag   3000
gccaaatggg gccagctctc gaacgtcgtg ctgctgctcc cgcacggcca cgaaggccag   3060
ggcccggatc acacctccgc ccggatcgaa cggttcctgc agctctgggc cgagggctcc   3120
atgacgatcg ccatgcccag caccccgtcc aactatttcc acctcctgcg gcgccatgcg   3180
ctcgacggca tccagcggcc cctgatcgtc ttcacgccga agagcatgct gcgccataag   3240
gccgccgtct cggagatcaa ggacttcacc gagatcaaat tccggtcggt gctggaagaa   3300
ccgacctatg aagatggcat cggcgaccgc aataaggtgt cgcgcatcct gctgacctcg   3360
ggcaagctgt actacgagct ggccgcccgc aaggccaaag acaaccggaa cgacctggcc   3420
atcgtccggc tggagcagct ggcgcccctc ccgcgccggc gcctgcgcga aaccctggat   3480
cgctatgaga acgtcaagga gttcttctgg gtgcaggagg aacccgcgaa tcagggcgcc   3540
tggccccgct tcggcctgga gctgccggag ctgctccccg acaagctggc cggcatcaag   3600
cggatcagcc gccgcgcgat gtcggccccg agctcgggct ccagcaaggt ccatgcggtc   3660
```

```
gagcagcagg agatcctgga tgaagcgttc ggctga                             3696


<210> SEQ ID NO 58
<211> LENGTH: 3696
<212> TYPE: DNA
<213> ORGANISM: Mycobacterium tuberculosis

<400> SEQUENCE: 58

atggccaaca tcagcagccc cttcggccag aatgaatggc tcgtggagga gatgtaccgg     60

aagttccggg atgatcccag ctcggtcgat ccgtcgtggc acgagttcct ggtcgactat    120

agccccgaac ccacctccca gccggcggcc gagcccacgc gggtgacctc cccgctggtc    180

gcggaacgcg ccgcggcggc ggccccccag gccccgccga aacccgccga tacggccgcc    240

gcgggcaacg gcgtcgtcgc ggccctggcc gcgaagaccg ccgtgccccc ccccgccgag    300

ggcgacgagg tggcggtgct ccggggcgcc gccgcggccg tggtcaagaa catgagcgcc    360

tccctcgaag tgccgaccgc caccagcgtc cgggcggtgc cggccaagct gctgatcgat    420

aatcggatcg tcatcaacaa tcagctgaaa cggacccgcg gcggcaagat cagcttcacc    480

catctgctcg gctatgcgct ggtccaggcc gtgaagaagt tccccaacat gaatcgccac    540

tataccgaag tcgacggcaa acccaccgcc gtgaccccgg cgcacacgaa cctcggcctg    600

gcgatcgacc tgcagggcaa ggacggcaag cggagcctcg tggtggccgg catcaaacgg    660

tgcgagacga tgcggttcgc gcagttcgtg acggcctatg aggatatcgt gcgccgcgcc    720

cgggacggca aactgaccac cgaagacttc gccggcgtca cgatctcgct gaccaacccg    780

ggcaccatcg gcacggtcca ttcggtcccg cgcctcatgc cgggccaggg cgccatcatc    840

ggcgtgggcg cgatggaata tcccgccgag ttccagggcg cctccgagga gcggatcgcc    900

gagctgggca tcggcaaact catcacgctg acctccacgt atgaccaccg catcatccag    960

ggcgcggaaa gcggcgactt cctccggacg atccatgagc tgctgctctc cgacggcttc   1020

tgggatgaag tgttccgcga gctgtcgatc ccctatctcc cggtgcgctg gagcaccgac   1080

aacccggact cgatcgtgga caaaaacgcc cgcgtcatga atctgatcgc cgcgtaccgc   1140

aatcggggcc acctcatggc ggacacggac cccctgcggc tcgataaggc ccggttccgc   1200

tcccaccccg acctcgaagt cctgacccac ggcctgaccc tgtgggacct ggatcgcgtc   1260

ttcaaggtcg atggcttcgc cggcgcccag tataagaagc tgcgcgatgt gctgggcctg   1320

ctccgcgatg cctattgccg gcatatcggc gtggagtacg cccacatcct ggaccccgag   1380

cagaaagaat ggctggaaca gcgcgtcgaa acgaagcacg tcaagcccac cgtcgcgcag   1440

cagaaataca tcctcagcaa actcaacgcc gccgaagcgt tcgaaacgtt cctccagacg   1500

aagtacgtgg gccagaaacg cttcagcctg gaaggcgcgg agagcgtcat ccccatgatg   1560

gacgccgcca tcgaccagtg cgccgaacac ggcctggatg aagtggtcat cggcatgccg   1620

caccgcggcc ggctcaacgt cctggccaat atcgtgggca agccctacag ccagatcttc   1680

accgagttcg aaggcaacct gaacccgtcg caggcgcacg gctcgggcga tgtcaagtac   1740

catctcggcg ccacgggcct gtatctgcag atgttcggcg acaacgacat ccaggtgtcc   1800

ctgacggcga accccagcca cctggaggcg gtcgatcccg tcctggaagg cctggtgcgg   1860

gccaagcagg atctcctcga ccacggctcg atcgactccg atggccagcg ggcgttcagc   1920

gtggtgcccc tcatgctgca tggcgacgcg gcgttcgcgg gccagggcgt ggtggcggaa   1980

accctcaacc tcgcgaacct cccgggctat cgggtgggcg gcaccatcca tatcatcgtg   2040

aacaaccaga tcggcttcac cacggcgccg gaatattccc ggagctcgga atattgcacg   2100
```

```
gacgtggcca agatgatcgg cgccccgatc ttccacgtca atggcgatga cccggaggcc   2160
tgtgtgtggg tcgcccggct ggccgtcgat ttccgccagc gcttcaaaaa agatgtggtc   2220
atcgacatgc tctgctaccg ccgccggggc cataatgagg gcgacgaccc ctccatgacg   2280
aacccgtacg tctacgacgt ggtcgacacc aagcgcggcg cccgcaagtc ctatacggag   2340
gcgctcatcg gccgcggcga catctcgatg aaggaagcgg aagacgcgct ccgcgactac   2400
cagggccagc tggagcgcgt cttcaacgaa gtgcgggaac tcgaaaagca tggcgtgcag   2460
ccctccgaat cggtggagag cgatcagatg atcccggccg gcctggccac cgccgtcgat   2520
aaaagcctgc tcgcccgcat cggcgacgcc ttcctggccc tgccgaacgg cttcacggcc   2580
catccccgcg tccagccggt gctggagaaa cgccgcgaaa tggcctacga gggcaagatc   2640
gattgggcct tcggcgagct gctggcgctc ggcagcctgg tggccgaagg caagctcgtg   2700
cggctctccg gccaggactc gcggcgcggc acgttctcgc agcgccattc cgtgctgatc   2760
gaccggcaca ccggcgaaga gttcaccccc ctccagctgc tggccaccaa ttcggacggc   2820
agcccgacgg gcggcaagtt cctggtctat gactccccgc tgagcgagta tgccgccgtc   2880
ggcttcgagt atggctacac cgtcggcaat ccggacgcgg tcgtgctgtg ggaagcgcag   2940
ttcggcgact tcgtgaacgg cgcccagtcg atcatcgatg agttcatctc gtcgggcgaa   3000
gccaagtggg gccagctcag caacgtggtg ctcctgctcc cgcacggcca cgagggccag   3060
ggcccggatc atacgagcgc ccgcatcgag cggttcctgc agctgtgggc cgagggctcc   3120
atgacgatcg cgatgccctc gacgccgtcc aactacttcc acctgctgcg ccggcacgcg   3180
ctggacggca tccagcgccc gctgatcgtc ttcaccccca agagcatgct ccggcacaaa   3240
gccgccgtgt ccgagatcaa ggacttcacg gagatcaaat tccggagcgt gctggaggag   3300
cccacgtacg aggacggcat cggcgaccgc aacaaggtgt cccgcatcct cctgacgagc   3360
ggcaagctgt actacgagct cgccgcccgc aaggccaagg ataaccggaa cgacctggcc   3420
atcgtgcgcc tcgaacagct ggccccgctg ccgcgccgcc ggctgcggga aaccctggac   3480
cgctacgaga acgtcaaaga gttcttctgg gtccaggaag aaccggccaa ccagggcgcg   3540
tggccgcgct tcggcctgga actgcccgag ctcctgccgg acaagctggc cggcatcaag   3600
cgcatctcgc ggcgggcgat gagcgccccg tcgagcggct cctccaaggt gcatgccgtg   3660
gagcagcagg aaatcctgga cgaggcgttc ggctga                             3696
```

<210> SEQ ID NO 59
<211> LENGTH: 3738
<212> TYPE: DNA
<213> ORGANISM: Corynebacterium terpenotabidum

<400> SEQUENCE: 59

```
atgaactcga ccaacttcgg cagcaatggc tggctggtcg accagatgca ccagcagttc     60
aaggaagatc cgcagtcggt cgacaaggaa tggcgcgact tcttcaccgc cggctcggcg    120
tccggcccgg atgccccgga aacgaccgcc ccgacgacca ccgccgccac gaccacgacc    180
gcgaccacga gcgcggcccc cgccaccgcg cagaccagcg gcgtggccgt cccgtccacc    240
gcgggcacca cccaccgggc ctcggccgcc gcgaccgtgg cctcgaacgt ggccctgagc    300
gcgaacccga tccccgaacg ggtcgccccc ccggccccga aggacgcggc cgagccgctg    360
accccgggcg aggccgccct gaaaggcgcc cagcgggcga tcgccaaaaa catggacgcc    420
agcctggata tccccaccgc gacgacggtc cgcgacatgc cggccaaact catgttcgaa    480
```

-continued

```
aaccgggcca tgatcaacaa ccatctgcgc agccagggcc ggggcaagat ctcgttcacc    540
cacatcctgg gctgggcgat ggtcaacgcc gtgaaagccc accccaccat gaataacaat    600
tacaaggtca tcgacggcaa gccgtcggtc gtgacccccg aacatatcaa tctcggcctc    660
gccatcgatc tggtcagcaa aaacggctcg cggaacctgg tcgtggccgc catccgcgcg    720
tgcgaaacct tcgacttcga gggcttcgtg gacgcctacg aggacatcgt ggtccgcgcc    780
cggaagggca aactgacgat ggacgacttc agcggcgtca ccatccagct gaccaacccg    840
ggcggcatcg gcacccgcca ctccgtcccg cgcctgacgc acggccaggg cgcgatcatc    900
ggcgtgggcg cgatggacta cccggcggag ttcgccggcg cctcggaaga ccgcctcgcg    960
gacctgggcg tgggcaaact ggtgaccatc acgagcacgt atgaccaccg gatcatccag   1020
ggcgccgagt cgggcgagtt cctgcgcgac atgagccgcc agctcatcga cgatggcttc   1080
tgggacggca tctacgccag cctgaaagtc ccgtatgcgc ccgtgcggtg gtcgcaggac   1140
gtgcccaaca ccggcgtcga caagagcacc cgcgtcatgc agctcatcga ggcgtaccgc   1200
tcccgcggcc acctgatcgc cgacatcgac ccgctgcatt ggacccagcc cggcctgccg   1260
gtgccggacc atagcgacct ggacatcgaa tcccacggcc tgaccctgtg ggacttcgac   1320
cggcgcttcc acgtcggcgg cttcgccggc cgcgaatcga tgaccctgcg ggaagtgctg   1380
gccacgctgc ggaaggcgta tacgctgaag gtcggctccg aatataccca tatcctcgac   1440
aaggacgaac gcctctggct ccaggagcac atcgaggccg gccagcagaa gctcagcaac   1500
cccgaacaga agtatctgct gcagacgctg aactccgccg aggcgttcga aaacttcctg   1560
cagaccaaat atatcggcca gaagcgcttc agcctggaag gcgccgaagc cctgatcccg   1620
ctgctcgatg ccgccgcgga tcaggccgcc gaacagggcc tcgaagaggt ggtgatcggc   1680
atgccgcatc gcggccggct gaatgtcctc gcgaacatcg tcggcaaacc gtacagcacc   1740
atcttcggcg agttcgaggg caacatcgag ccggccgccg cgggcggctc cggcgatgtc   1800
aaataccatc tgggcgccga gggcgtgtat acgcagatgt tcggcgacaa cgacatcaag   1860
gtgacgctga ccgccaaccc ctcccacctg gaagcggtca atcccgtcat ggagggcctc   1920
gcgcgggcgc atcaggatat ctcgccccgg gcggaggatc ggccgatcat gccgatcctg   1980
atgcacggcg acgccgcctt caccggcctg ggcatcgtcc cggaaacgat caacatggcc   2040
cagctgcggg gctactccgt gggcggcacg gtgcatgtgg tggtcaacaa ccagatcggc   2100
ttcaccacga cgccggatcg cggccggtcc acgcactacg cgacggacat cgcgaagggc   2160
ttcgattgcc ccgtcttcca cgtcaacggc gacgatccgg aggccgtcgt ctgggtcgcc   2220
cggctcgccg tggaataccg gcgccgcttc ggcaaagacg tgttcatcga cctggtgtgt   2280
tatcggcgcc gcggccataa tgaagccgat gaccccagca tgacccagcc cgaactgtac   2340
agcatcatcg agagccggcc gacggtccgg agcctgtatc atgacacgct ggtcggccgg   2400
ggcgacatca cggcggaaga cgcccagcgg gccgccgacg acttccacgg ccagctggaa   2460
agcgtcttca accaggtcaa ggaaggcgtg aagggcgtga ccccggcggc ccagaccggc   2520
atcgccggcg gccaggacct gtccaccggc ctcgacacca gcatcaccgc ggatgtgatc   2580
gccgagatcg gcgattccta taccgtggat gcccccgaag acttcaatgt ccaccagcgc   2640
gtgaagcccg tggtcaaacg gcggcaccag atgtcgcgcc agggcaagat cgattgggcg   2700
ttcggcgaac tcctcgcgtt cggctcgctg gcccgggaag gccggctggt ccggctcgcc   2760
ggcgaggact cgcagcgggg caccttcacc cagcggcacg ccatcctgtt cgacagcacc   2820
accaacaagc ccttcagccc cctggaaatg gtcgcgcgga actccggcaa cggcggctcg   2880
```

```
ttccgggcct tcaattcccc gctgacggaa tatgcgggca tgggcttcga gtatggctac   2940

tcggtgggca acctggatgc cgtggtggcc tgggaggcgc agttcggcga cttcgcggac   3000

ggcgcccaga cgatcatcga cgagtacatc tcctccggcg aggccaaatg gggccagctg   3060

tcgagcgtga tcctgctgct cccgcacggc tacgagggcc agggcccgga ccactcctcc   3120

gcccgcatcg aacgctacct gcagatggcc gccgaaggct cgatgaccat cgcgcagccg   3180

tcgacgcccg ccaaccactt ccacctgctc cgccgccacg ccctgggcac catgcggcgc   3240

ccgctggtcg tcttcacccc gaagtccatg ctgcgcaaca aggcggccgt ctcctcggtc   3300

gaagacttca cggaagtcac caagttccgg agcgtcctgg atgacccccg gttcgcggat   3360

ggcaccgccg accggagcgg cgtcaagacg gtgctgatgt gttccggcaa gatctactat   3420

gatctggaga agaagcgggc ggaagacggc cgcgacgata tcgccatcgt ccgcgtcgaa   3480

atgctgcatc ccatcccgca taaccgcatc cgcgaaacgg tcgtggaggg ctaccccggc   3540

gcggaggtgc gctgggtgca ggacgagccc gccaaccagg gcgcctggcc gttcctggcc   3600

ctcaacctcc ccgagcgcat ccccggcttc accatgaagc gcgtcagccg ccgggcccag   3660

agcagcaccg ccacgggcgt ggccaaggtc caccatctgg agcaggagac gctgctgacc   3720

gaagccttcg ccacctga                                                 3738
```

<210> SEQ ID NO 60
<211> LENGTH: 3777
<212> TYPE: DNA
<213> ORGANISM: Rhodococcus jostii

<400> SEQUENCE: 60

```
atgagctcgt cctcgacctc ccagttcggc cagaaccagt ggctcgtgga tgaaatgtac     60

cagcgcttcc aggatgatcc gtcgtccgtg gacgcctcct ggcatgagtt cctgacggac    120

tatagccccg acgccgccgc caaggcgggc gcggcgaacg gccacggcac caacggcacc    180

accacggcgg cgccggcggc ggcgccgtcc gccaaagccg cgaccccccc ggtccccgag    240

agcgagacgg ccccgaaacc ccagaccaag acggcgaacg gcgcggcgcc gaaagccgcg    300

cccaacggcg cggcgccgaa ggccgcggcc cccaagaccg aggcccccaa gaaggccgcc    360

cccgcgaagg aaacggccgc gacggacgcg aaagcctcgg ccccggcccc cgccgtggag    420

gaatccaagg tgctgcgggg cgccgccgcc gccgtcgcca agaatatgtc cgcgtcgctc    480

gccatcccga ccgccacctc cgtccgggcc atcccggcga agctgatgtt cgacaaccgc    540

atcgtcatca acaaccacct ggcgcggacc cggggcggca agatctcgtt cacccatctg    600

ctgggctacg cgatcgtgca ggccgtgaaa gcgttcccca acatgaaccg ccacttcgcg    660

gagatcgatg gcaagcccaa tgcggtgacc cccgcccata ccaatctggg cctcgcgatc    720

gatctgccgg gcaaagatgg cagccgctcg ctggtcgtcg cggccatcaa gaacaccgat    780

acgcacaatt tcacccagtt ctatagcgcc tacgaggata tcgtgcgccg ggcgcgggac    840

ggcaaactga ccgccgaaga cttcagcggc gtcacgatct cgctgaccaa cccgggcggc    900

atcggcaccg tccattccgt cccgcgcctg atgaacggcc agggcgccat catcggcgcg    960

ggcgcgatgg agtacccggc cgagttccag ggcgcctcgg acgagcggct ggccgaaatc   1020

ggcgtcggca agctgatgac cctcacgagc acctacgatc atcggatcat ccagggcgcc   1080

gaatccggcg acttcctccg gacgatccat aatctgctca tcagcgacga gttctacgac   1140

gaaatcttcc atgccctgca tatcccctat gaacccgtcc ggtggcgcaa agacgtgccc   1200
```

gaaggcgccg tggataagaa cacccgggtc ctggagctca tcgccgccta ccggaaccgc 1260
ggccacctga tggcggacac cgacccgctg cagttcgtga aggacaagtt ccggtcgcac 1320
ccggacctcg acgtgcgcac ccatgatctg acgctctggg acctggatcg ggagttcaaa 1380
gtgggcggct tccacggcca ggagaagatg aagctgcgcg atgtcctgtc ggtgctgcgc 1440
gatgcgtatt gtcgccatgt cggcgtggag tatacccaca tcctggagcc ggagcagcag 1500
cagtggctgc aggatcgcgt cgaggcccac cacgtcaaac cgacggtcgc ccagcagaag 1560
tatatcctgt ccaaactgaa cgccgccgag gccttcgaga cgttcctgca gacgaagtat 1620
gtcggccaga aacgcttctc gctggagggc gcggagagcg tgatccccat gatggacgcc 1680
gtcatcgacc aggccgccga gcatcagctg gacgaggtgg tgatcggcat gccgcatcgg 1740
ggccgcctga atgtcctggc gaacatcgtg ggcaagccgt attccaagat cttcaccgag 1800
ttcgagggca acatgaaccc ggcggcggcc cacggcagcg gcgacgtgaa gtatcacctg 1860
ggcgccgaag gcacgtatat ccagatgttc ggcgataacg acatcaccgt ctcgctcacc 1920
gcgaacccga gccatctgga agccgtggac ccggtgctgg agggcctggt ccgggccaag 1980
caggacatcc tcgacaaggg cgaagacggc ttcacggtgc tcccccctcat gctccacggc 2040
gacgcggcct tcgccggcca gggcgtggtc gccgagacgc tcaacctcgc cctgctgcgc 2100
ggctaccgga ccggcggcac cgtgcacatc gtggtgaaca accaggtcgg cttcacgacc 2160
gcccccgagt atagccgctc cagcgagtac tgcacggatg tggcgaagat gatcggcgcc 2220
cccatcttcc acgtcaacgg cgatgacccc gaggcgtgcg tgtgggtggc ccagctggcg 2280
gtggacttcc gcgagaagtt ccagaaggac gtggtcatcg acatgatctg ttatcggcgg 2340
cggggccata atgagggcga cgatccgagc atgacccagc ccgcgatgta cgacgtgatc 2400
gacacgaaac gctccgtccg caaatcctat accgagtcgc tgatcggccg cggcgacatc 2460
tcgctgaagg aagcggagga cgccctgcgc gactatcagg gccagctgga acgggtcttc 2520
aatgaggtgc gcgagctgga gaagtacacg cccgaaccga gcgagagcgt cgagctggac 2580
caggtcctgc ccacgaagct gaaaacctcc gtcgatgaat cggtgctgga gcgcatcggc 2640
gatgccttcg tgaacgtccc ggagggcttc acggtccatc cgcgggtgaa gccggtgatc 2700
gaaaagcgcc gcgagatgag ccgcgaaggc aagatcgact gggccttcgc cgagctgctg 2760
gccttcggct ccctggtgga tcagggcaag atggtgcgcc tctccggcca ggacagcaag 2820
cgcggcacgt tcacccagcg ccactcggtc ctcatcgacc gcaaaaccgg cgccgaatat 2880
acccccctcc agaacctggg cagcgaaaac ccgggcaagt tcctggtcta cgattccgcg 2940
ctgagcgagt tcgcggcggt cggcttcgag tacggctata gcgtcggcaa ccccgacgcg 3000
ctggtgctgt gggaagccca gttcggcgat ttcgtgaatg gcgcccagag catcatcgac 3060
gagttcatct cgtcgggcga agccaaatgg ggccagctga gcgacgtggt cctgctgctg 3120
ccccacggcc acgaaggcca gggcccggac catacgtccg gccgcatcga acggttcctc 3180
cagctgtgtg ccgaaggctc catgaccgtg gcggtcccca gcacgccggc ctcgtacttc 3240
cacctgctgc gccggcatag cctcgacggc atccgccggc cgctcgtcgt gttcaccccc 3300
aaaagcatgc tgcgcaacaa agccgccgtg agcgacgtgg aagacttcac gaccggcaag 3360
ttccggagcg tcttcgagga gcccacctac gagacgggcg atgccgagcg ggacaaggtg 3420
cgccgggtcc tcctggtgtc gggcaagctg tactgggagc tgctggccaa gaagcagaag 3480
gataaccgcg aggacatcgc catcgtgcgc atcgaacagc tgtaccccgt cccctcgcgg 3540
cggctccgcg agacgctgga ccgctacccc aacgccaccg agttccgctg ggtgcaggag 3600
gagcccgcca accagggcgc ctggcccttc ttcggcctcg cgctgcccga actgctgccc 3660
gacaaactgt cgggcatcaa gcgcatcagc cgccggtcca tgtcggcccc gtcctccggc 3720
tcgtccaagg tgcacgcggt cgaacagcag gaaatcatcg acgaggcctt cggctga 3777

<210> SEQ ID NO 61
<211> LENGTH: 1116
<212> TYPE: DNA
<213> ORGANISM: Porphyromonas gingivalis

<400> SEQUENCE: 61
atgcagctgt tcaaactcaa aagcgtgacg caccacttcg atacgttcgc ggagttcgcc 60
aaggagttct gcctcggcga gcgggacctg gtcatcacca atgagttcat ctacgagccc 120
tatatgaagg cgtgccagct cccgtgccac ttcgtcatgc aggaaaagta cggccagggc 180
gaaccgtcgg atgagatgat gaacaacatc ctggcggata tccggaacat ccagttcgac 240
cgggtcatcg gcatcggcgg cggcaccgtc atcgacatct ccaaactgtt cgtcctgaaa 300
ggcctcaacg acgtgctgga cgccttcgac cgcaaaatcc cgctcatcaa ggagaaggag 360
ctcatcatcg tgcccacgac ctgcggcacc ggctcggaag tgaccaacat ctcgatcgcc 420
gagatcaagt cgcgccacac caagatgggc ctggcggatg acgcgatcgt ggccgaccat 480
gccatcatca tccccgagct gctgaagagc ctgccgttcc acttctatgc gtgctccgcc 540
atcgatgccc tgatccacgc catcgagagc tacgtctcgc cgaaggcctc cccgtacagc 600
cggctgttca gcgaggcggc ctgggacatc atcctggaag tcttcaagaa gatcgccgag 660
cacggccccg aatatcggtt cgaaaagctc ggcgagatga tcatggccag caattacgcc 720
ggcatcgcct tcggcaacgc cggcgtcggc gccgtccacg ccctgtcgta cccgctgggc 780
ggcaattatc atgtgccgca tggcgaagcg aattaccagt tcttcaccga ggtgttcaag 840
gtctatcaga agaaaaaccc gttcggctac atcgtcgagc tgaactggaa gctgtcgaag 900
atcctgaact gccagccgga gtatgtgtat cccaagctgg atgaactcct gggctgcctg 960
ctgaccaaaa agccgctgca tgaatatggc atgaaggacg aagaggtgcg gggcttcgcc 1020
gaatcggtgc tgaagaccca gcagcgcctg ctcgccaaca actacgtgga gctgaccgtc 1080
gacgaaatcg aaggcatcta ccgccggctg tactga 1116

<210> SEQ ID NO 62
<211> LENGTH: 1116
<212> TYPE: DNA
<213> ORGANISM: Clostridium kluyveri

<400> SEQUENCE: 62
atgaagctcc tgaagctggc cccggatgtg tacaaattcg ataccgccga ggagttcatg 60
aagtatttca aggtcggcaa gggcgacttc atcctgacga acgagttcct ctataaaccc 120
ttcctggaaa agttcaatga tggcgccgac gccgtgttcc aggaaaagta cggcctgggc 180
gagccgtccg acgaaatgat caacaacatc atcaaggata tcggcgacaa acagtacaat 240
cggatcatcg cggtgggcgg cggcagcgtc atcgatatcg ccaaaatcct gtcgctgaaa 300
tacacggacg attccctgga cctgttcgaa ggcaaggtcc cgctggtgaa gaataaagag 360
ctcatcatcg tcccgaccac ctgcggcacc ggctcggaag tgacgaatgt ctcggtcgcc 420
gaactgaagc ggcgccatac gaagaaaggc atcgcctccg acgaactcta tgcgacgtac 480
gcggtcctgg tgcccgagtt catcaaaggc ctgccctata agttcttcgt gacgagctcc 540

```
gtcgacgccc tcatccatgc gaccgaggcc tacgtgtcgc cgaacgccaa cccctacacc    600

gacatgttct cggtcaaggc gatggaactg atcctgaacg gctacatgca gatggtggag    660

aagggcaacg attatcgcgt ggaaatcatc gaggatttcg tgatcggctc caactacgcg    720

ggcatcgcgt tcggcaacgc gggcgtcggc gcggtccatg ccctcagcta ccccatcggc    780

ggcaactacc atgtcccgca tggcgaagcc aactacctct tcttcacgga gatcttcaag    840

acctactacg agaagaaccc gaatggcaag atcaaggacg tgaataagct cctggcgggc    900

atcctcaagt gcgatgagtc cgaggcgtac gattcgctct cgcagctgct ggacaaactg    960

ctctcgcgca agccgctgcg cgagtacggc atgaaggagg aagagatcga aaccttcgcc   1020

gacagcgtga tcgaaggcca gcagcggctg ctggtcaaca actacgagcc cttcagccgc   1080

gaggatatcg tcaacaccta caaaaagctc tactga                             1116
```

<210> SEQ ID NO 63
<211> LENGTH: 1296
<212> TYPE: DNA
<213> ORGANISM: Porphyromonas gingivalis

<400> SEQUENCE: 63

```
atgaaggacg tgctggccga gtacgcctcg cgcatcgtct cggcggaaga agcggtcaag     60

cacatcaaga acggcgagcg cgtcgcgctc tcgcatgccg ccggcgtccc gcagtcctgc    120

gtcgatgccc tggtccagca ggccgatctc ttccagaatg tcgaaatcta ccatatgctc    180

tgcctgggcg agggcaagta catggccccc gagatggcgc cgcatttccg ccatatcacg    240

aatttcgtcg gcggcaactc gcggaaagcc gtggaggaga accgggccga cttcatcccc    300

gtgttcttct acgaggtccc cagcatgatc cgcaaagata tcctccacat cgacgtggcg    360

atcgtgcagc tgagcatgcc ggatgagaac ggctactgca gcttcggcgt gagctgtgac    420

tacagcaagc cggccgccga atccgcccac ctcgtcatcg gcgagatcaa ccggcagatg    480

ccgtacgtcc acggcgacaa cctgatccac atcagcaagc tggactacat cgtcatggcc    540

gactatccga tctatagcct ggcgaaaccc aagatcggcg aggtcgagga ggccatcggc    600

cggaactgcg ccgagctgat cgaagacggc gccaccctcc agctgggcat cggcgccatc    660

ccggacgccg ccctgctctt cctgaaagac aagaaagacc tgggcatcca caccgaaatg    720

ttcagcgacg gcgtcgtcga actggtccgg agcggcgtca tcaccggcaa gaaaaaaacc    780

ctgcacccgg gcaaaatggt cgcgacgttc ctgatgggct ccgaagatgt ctatcatttc    840

atcgacaaga accccgacgt ggagctctac ccggtggact atgtgaacga cccgcgcgtc    900

atcgcccaga acgacaacat ggtcagcatc aactcctgta tcgagatcga cctcatgggc    960

caggtcgtga gcgaatgtat cggctccaag cagttctcgg gcacgggcgg ccaggtggac   1020

tacgtccgcg gcgcggcgtg gtcgaagaac ggcaagtcga tcatggccat cccctccacc   1080

gccaagaacg gcaccgcctc gcgcatcgtg ccgatcatcg cggagggcgc cgcggtgacg   1140

accctgcgga acgaagtgga ttacgtggtc acggagtatg gcatcgccca gctgaagggc   1200

aagtcgctcc gccagcgggc ggaagcgctg atcgcgatcg cgcacccgga cttccgggag   1260

gagctgacca aacacctgcg gaaacggttc ggctga                             1296
```

<210> SEQ ID NO 64
<211> LENGTH: 1296
<212> TYPE: DNA
<213> ORGANISM: Porphyromonas gingivalis

<400> SEQUENCE: 64
atgcagtggc aggaactcta ccggcagcgc gtgtgctccg cggatgaagc cgtcgtggat 60
agcctgaagc ccggcaccaa ggtggtcttc ggccatgccg ccgccgcgcc cgtgcggttc 120
tcgcaggcca tgtatcgcca gcgcgaaaag ctcgaaaaca tcaccgtgtt ccatatgctc 180
tatttcggcg atgcccccca cctggccccc gaaatgcgct cccatgtcca cccgacgctc 240
aacttcctgg aaggcaatag ccgcccgcg tcgcgggatc ggcgcgtgga tttcatcccc 300
tgccacttcc acgaagtgcc cgagctgttc cgccagggct tcttcccccct cgacgtggcg 360 gtggtgcagg tgtcgacccc gaacgaggag ggctattgta gcttcggcgt ctcgtgtgac 420
tatacgaagg ccgcggccga atgtgccccg gtcgtggtgg ccgaggtgaa caagcagatg 480
ccgttcatcg gcggcgagaa cctgatccat atctccaagc tgacccatat catcgaagtg 540
gatgagccga tcgccgaggt gctgccccccc gcgatcagcg acctggagct gcgcatcggc 600
cagaactgcg cgtccctcat caaggacggc gatacgctcc agctgggcat cggcggcatc 660
ccggacgcgg tgctgcgggc cctggaaggc cataaagacc tcggcatcca cacggagatg 720
ttcaccgacg gcgtgatgcg gatgatccgg aagggcatca tcaacggcaa gaaaaagacc 780
ctgcacccgg aaaaagtggt gaccagcctg atcttcggca gcaaagaact gtacgacttc 840
gtcaacaaca acccggtgat cgagtgctat ccggtcgatt atatcaacaa tccggatgtc 900
atcggcaaga acgaccgcat ggtgagcatc aactcctgcc tggaaatgga cctgatgggc 960
caggccgcga gcgaaagcat cggctacgaa cagttctccg gctcgggcgg ccaggtggat 1020
ttcctgcggg gcgcgaagcg gtccaaaggc ggcatcagca tcatggcctt cccctccacg 1080
gccaagaagg gcacggagtc ccgcatcgtg cccatcctga aggagggcgc gtgcgtcacg 1140
accggccgca atgaggtgga ttacgtcgtc accgagtacg gcgtcgcccg cctccggggc 1200
gccaccctcc ggcagcgggc cgaggccctg acggccatcg cccatcccga cttccgcccc 1260
gccctggagg aagagatccg ccggcgcttc gagtga 1296

<210> SEQ ID NO 65
<211> LENGTH: 1317
<212> TYPE: DNA
<213> ORGANISM: Clostridium aminobutyricum

<400> SEQUENCE: 65
atggattgga aaaagatcta cgaagatcgc acctgcaccg ccgatgaagc cgtcaagtcc 60
atcaagtccg gcgaccgcgt cctgttcgcc cactgtgtcg ccgaaccccc ggtgctggtc 120
gaagcgatgg tggccaacgc cgcggcgtac aagaacgtca ccgtgagcca tatggtgacc 180
ctgggcaagg gcgaatatag caagcccgag tacaaggaga acttcacgtt cgagggctgg 240
ttcacctccc cgtcgacgcg gggctcgatc gcggagggcc acggccagtt cgtgcccgtg 300
ttcttccatg aggtgccgtc cctgatccgc aaggatatct tccacgtcga cgtgttcatg 360
gtcatggtgt ccccgcccga tcataacggc ttctgctgtg tcggcgtcag cagcgactac 420
acgatgcagg ccatcaagtc ggccaagatc gtgctggcgg aagtcaacga ccaggtgccc 480
gtggtgtatg gcgatacgtt cgtgcatgtc tcgaacatcg ataagttcgt ggaaacctcg 540
catccgctcc cggaaatcgg cctgccgaaa atcggcgagg tggaagcggc catcggcaaa 600
cactgtgcct ccctgatcga agacggctcg acgctgcagc tgggcatcgg cgccatcccc 660
gacgccgtgc tcagccagct gaaagacaag aagcacctgg gcatccactc ggagatgatc 720
tccgacggcg tcgtggacct gtatgaggcg ggcgtgatcg actgctccca gaagtcgatc 780
gacaagggca aaatggcgat caccttcctg atgggcacca agcgcctgta cgacttcgcg 840
gcgaacaatc cgaaggtgga gctgaaaacg gtggactaca tcaaccatcc gtcggtggtg 900
gcccagtgct ccaagatggt gtgcatcaac gcctgcctgc aggtggattt catgggccag 960
atcgtgagcg acagcatcgg caccaagcgc ttctcgggcg tgggcggcca ggtcgacttc 1020
gtgcggggcg cctccatgag catcgacggc aagggcaagg cgatcatcgc catgccgtcg 1080
gtcgccaaga agaaggacgg cagcatgatc tcgaaaatcg tccccttcat cgatcacggc 1140
gccgccgtga ccacctcgcg gaacgacgcc gattatgtgg tcacggagta cggcatcgcc 1200
gagatgaaag gcaagtccct ccaggaccgg gcccgggcgc tcatcaacat cgcgcacccg 1260
gatttcaagg atgagctgaa ggcggagttc gagaagcggt tcaacgcggc gttctga 1317

<210> SEQ ID NO 66
<211> LENGTH: 2577
<212> TYPE: DNA
<213> ORGANISM: Clostridium aminobutyricum

<400> SEQUENCE: 66
atgaaggtga ccaaccagaa agaactgaag cagaaactga acgaactgcg ggaggcgcag 60
aaaaagttcg ccacctatac ccaggagcag gtggacaaaa tcttcaagca gtgtgcgatc 120
gccgccgcca aagaacggat caacctggcg aaactcgccg tcgaagaaac cggcatcggc 180
ctcgtggagg acaagatcat caaaaatcac ttcgccgccg aatatatcta taacaaatac 240
aagaacgaga agacctgcgg catcatcgac catgacgact cgctgggcat caccaaagtc 300
gccgagccca tcggcatcgt ggccgcgatc gtgcccacca ccaacccgac gagcaccgcc 360
atcttcaagt cgctgatctc cctgaagacg cgcaatgcga tcttcttcag cccccatccg 420
cgggccaaaa agtcgacgat cgcggcggcc aaactgatcc tggacgccgc ggtcaaggcc 480
ggcgccccga aaaatatcat cggctggatc gacgaaccgt ccatcgagct gtcccaggac 540
ctcatgtccg aagccgacat catcctggcg accggcggcc cgagcatggt gaaggccgcc 600
tattccagcg gcaaaccggc catcggcgtc ggcgccggca acacccccgc gatcatcgac 660
gagtccgccg acatcgacat ggccgtctcc tcgatcatcc tgagcaagac ctacgataac 720
ggcgtcatct gcgcgtcgga acagagcatc ctggtcatga actccatcta tgaaaaggtc 780
aaggaagagt tcgtgaagcg cggctcgtat atcctgaacc agaatgaaat cgcgaagatc 840
aaggagacga tgttcaagaa cggcgccatc aacgccgaca tcgtcggcaa gagcgcctat 900
atcatcgcga agatggccgg catcgaagtg ccgcagacca ccaagatcct gatcggcgaa 960
gtccagtccg tcgaaaagtc cgaactgttc tcccacgaaa agctgagccc ggtgctcgcc 1020
atgtacaaag tcaaagactt cgacgaggcc ctcaaaaagg cgcagcggct catcgaactg 1080
ggcggcagcg gccatacctc gtcgctgtac atcgatagcc agaacaacaa ggacaaagtc 1140
aaagagttcg gcctggcgat gaagacgagc cgcaccttca tcaacatgcc gagcagccag 1200
ggcgcgtccg gcgacctgta caacttcgcc atcgccccga gcttcacgct cggctgcggc 1260
acctggggcg gcaattcggt gtcgcagaac gtggaaccga aacatctgct gaacatcaaa 1320
tccgtcgcgg agcgccgcga aaatatgctc tggttcaagg tcccgcagaa gatctatttc 1380
aaatatggct gcctgcgctt cgccctcaaa gaactgaaag acatgaataa gaaacgcgcc 1440
ttcatcgtca ccgataaaga tctgttcaag ctgggctacg tgaacaaaat cacgaaggtc 1500
ctggatgaga tcgatatcaa gtacagcatc ttcaccgaca tcaagtccga tcccaccatc 1560
gactccgtca agaagggcgc caaagagatg ctcaacttcg aaccggacac catcatcagc 1620

```
atcggcggcg gctcgccgat ggacgcggcc aaggtcatgc atctgctcta tgaatatccg   1680
gaggccgaga tcgaaaacct ggccatcaac ttcatggaca tccggaaacg catctgcaac   1740
ttcccgaagc tcggcacgaa agccatcagc gtggccatcc ccacgaccgc gggcaccggc   1800
tcggaagcca cgccgttcgc ggtcatcacg aatgacgaaa ccggcatgaa atacccccctg   1860
acctcctacg agctcacccc caatatggcc atcatcgaca cggagctcat gctcaacatg   1920
ccgcggaagc tcaccgccgc caccggcatc gatgccctgg tgcacgccat cgaagcctac   1980
gtgagcgtga tggcgaccga ctataccgat gagctggccc tccgggccat caagatgatc   2040
ttcaagtatc tgccgcgggc ctacaaaaac ggcacgaatg acatcgaggc ccgcgaaaag   2100
atggcgcatg cgagcaacat cgcgggcatg gccttcgcga acgccttcct gggcgtgtgc   2160
catagcatgg cgcacaaact gggcgcgatg catcacgtcc cgcatggcat cgcctgtgcc   2220
gtcctgatcg aggaggtcat caagtacaac gccacggatt gtccgaccaa acagaccgcc   2280
ttcccgcagt acaagtcccc gaacgcgaag cggaaatacg cggagatcgc ggagtacctg   2340
aatctgaaag gcaccagcga caccgaaaaa gtcacggccc tcatcgaagc catctcgaaa   2400
ctgaaaatcg atctgagcat cccccagaac atctccgcgg ccggcatcaa taagaaggat   2460
ttctataaca cgctggacaa gatgagcgag ctggcgttcg atgaccagtg cacgaccgcc   2520
aacccccggt atccgctgat ctccgaactc aaggacatct acatcaagtc cttctga      2577
```

<210> SEQ ID NO 67
<211> LENGTH: 2676
<212> TYPE: DNA
<213> ORGANISM: Escherichia coli

<400> SEQUENCE: 67

```
atggcggtga cgaacgtcgc cgaactgaac gccctcgtcg aacgggtgaa aaaggcgcag     60
cgggagtacg cctcgttcac gcaggagcag gtggataaaa tcttccgcgc cgccgccctg    120
gccgcggccg acgcccgcat cccgctcgcc aaaatggcgg tggccgagtc cggcatgggc    180
atcgtggagg acaaggtcat caagaaccat ttcgcctccg agtacatcta caacgcctac    240
aaggacgaga agacctgcgg cgtcctgtcg gaggacgata ccttcggcac catcacgatc    300
gccgagccca tcggcatcat ctgcggcatc gtcccgacca ccaatcccac ctccaccgcc    360
atcttcaaaa gcctcatctc cctgaaaacc cgcaatgcga tcatcttcag cccccatccc    420
cgcgccaaag acgccacgaa caaggcggcc gacatcgtcc tccaggccgc catcgcggcc    480
ggcgcccccca aagacctgat cggctggatc gaccagccgt cggtggagct gtccaacgcc    540
ctcatgcatc acccggacat caatctcatc ctggccacgg gcggcccggg catggtgaag    600
gccgcctact ccagcggcaa gccggcgatc ggcgtgggcg cgggcaacac gcccgtggtc    660
atcgacgaaa cggccgatat caaacgcgcc gtcgcctccg tgctcatgag caagaccttc    720
gacaacggcg tgatctgcgc gtcggaacag tcggtcgtgg tcgtcgactc cgtgtacgac    780
gcggtgcgcg agcgcttcgc cacgcatggc ggctacctgc tgcagggcaa ggagctgaaa    840
gccgtgcagg acgtgatcct caaaaacggc gccctgaacg ccgccatcgt cggccagccc    900
gcgtataaga tcgcggagct ggccggcttc tcggtcccgg agaacacgaa gatcctgatc    960
ggcgaggtca cggtcgtcga cgagagcgaa cccttcgccc acgagaagct gtccccgacc   1020
ctggcgatgt accgggcgaa agacttcgaa gacgcggtcg agaaggccga gaaactggtg   1080
gcgatgggcg gcatcggcca tacgagctgt ctgtacaccg accaggacaa tcagcccgcc   1140
```

```
cgcgtgtcct acttcggcca gaaaatgaag accgcccgca tcctcatcaa tacgcccgcg   1200

agccagggcg gcatcggcga tctctacaat ttcaagctcg cgccgtcgct gaccctcggc   1260

tgcggctcct ggggcggcaa ctccatctcc gagaacgtgg gcccgaaaca cctcatcaac   1320

aagaagaccg tggccaagcg ggcggagaac atgctgtggc ataagctgcc caagtcgatc   1380

tacttccgcc ggggctcgct gcccatcgcg ctggacgaag tcatcacgga cggccacaag   1440

cgggcgctga tcgtgacgga ccgcttcctg ttcaataacg gctacgccga ccagatcacc   1500

tccgtcctga aggccgcggg cgtcgaaacg gaagtcttct tcgaagtcga agccgacccg   1560

accctctcca tcgtccggaa gggcgccgag ctggccaatt ccttcaagcc ggatgtcatc   1620

atcgcgctgg gcggcggctc gccgatggac gccgccaaaa tcatgtgggt gatgtacgag   1680

caccccgaaa cgcacttcga agaactggcg ctgcgcttca tggatatccg caagcggatc   1740

tacaaattcc cgaaaatggg cgtgaaagcg aagatgatcg cggtgacgac caccagcggc   1800

acgggctccg aggtgacgcc gttcgcggtc gtcaccgatg atgccaccgg ccagaaatac   1860

cccctggccg actacgccct gacccccgac atggccatcg tggacgccaa tctcgtgatg   1920

gacatgccga agagcctctg cgccttcggc ggcctggatg ccgtgacgca tgcgatggag   1980

gcgtatgtca gcgtgctggc gtccgagttc tcggacggcc aggcgctgca ggccctgaag   2040

ctgctgaagg agtacctgcc ggcctcctac cacgagggct ccaaaaaccc ggtggcccgg   2100

gagcgggtcc actcggcggc caccatcgcg ggcatcgcct tcgcgaacgc cttcctcggc   2160

gtgtgccatt cgatggccca caagctgggc tcccagttcc atatccccca cggcctggcg   2220

aacgcgctgc tgatctgtaa cgtcatccgg tacaacgcga acgataaccc gaccaaacag   2280

accgccttct cccagtatga ccgcccccag gcccggcgcc gctatgcgga aatcgccgac   2340

catctcggcc tgtcggcccc gggcgaccgc accgccgcca agatcgagaa gctgctggcc   2400

tggctcgaaa cgctgaaggc cgaactgggc atcccgaagt cgatccgcga agccggcgtc   2460

caggaagcgg acttcctggc gaatgtggat aaactgagcg aggacgcctt cgatgaccag   2520

tgcacgggcg ccaacccgcg ctacccgctc atcagcgagc tgaaacagat cctgctcgac   2580

acctattatg gccgcgatta cgtcgagggc gaaaccgccg cgaagaagga ggccgccccg   2640

gccaaagccg aaaagaaggc caagaaaagc gcctga                             2676
```

<210> SEQ ID NO 68
<211> LENGTH: 1164
<212> TYPE: DNA
<213> ORGANISM: Escherichia coli

<400> SEQUENCE: 68

```
atgaacaact ttaatctgca caccccaacc cgcattctgt ttggtaaagg cgcaatcgct     60

ggtttacgcg aacaaattcc tcacgatgct cgcgtattga ttacctacgg cggcggcagc    120

gtgaaaaaaa ccggcgttct cgatcaagtt ctggatgccc tgaaaggcat ggacgtgctg    180

gaatttggcg gtattgagcc aaacccggct tatgaaacgc tgatgaacgc cgtgaaactg    240

gttcgcgaac agaaagtgac tttcctgctg gcggttggcg gcggttctgt actggacggc    300

accaaattta tcgccgcagc ggctaactat ccggaaaata tcgatccgtg gcacattctg    360

caaacgggcg gtaaagagat taaaagcgcc atcccgatgg gctgtgtgct gacgctgcca    420

gcaaccggtt cagaatccaa cgcaggcgcg gtgatctccc gtaaaaccac aggcgacaag    480

caggcgttcc attctgccca tgttcagccg gtatttgccg tgctcgatcc ggtttatacc    540

tacaccctgc cgccgcgtca ggtggctaac ggcgtagtgg acgcctttgt acacaccgtg    600
```

gaacagtatg ttaccaaacc ggttgatgcc aaaattcagg accgtttcgc agaaggcatt 660
ttgctgacgc taatcgaaga tggtccgaaa gccctgaaag agccagaaaa ctacgatgtg 720
cgcgccaacg tcatgtgggc ggcgactcag gcgctgaacg gtttgattgg cgctggcgta 780
ccgcaggact gggcaacgca tatgctgggc cacgaactga ctgcgatgca cggtctggat 840
cacgcgcaaa cactggctat cgtcctgcct gcactgtgga atgaaaaacg cgataccaag 900
cgcgctaagc tgctgcaata tgctgaacgc gtctggaaca tcactgaagg ttccgatgat 960
gagcgtattg acgccgcgat tgccgcaacc cgcaatttct ttgagcaatt aggcgtgccg 1020
acccacctct ccgactacgg tctggacggc agctccatcc cggctttgct gaaaaaactg 1080
gaagagcacg gcatgaccca actgggcgaa aatcatgaca ttacgttgga tgtcagccgc 1140
cgtatatacg aagccgcccg ctaa 1164

<210> SEQ ID NO 69
<211> LENGTH: 1149
<212> TYPE: DNA
<213> ORGANISM: Escherichia coli

<400> SEQUENCE: 69
atggcgaatc ggatgatcct caatgaaacg gcctggttcg gccgcggcgc ggtcggcgcc 60
ctcaccgatg aggtcaagcg gcggggctac cagaaggccc tgatcgtcac ggataaaacc 120
ctggtgcagt gcggcgtcgt cgccaaggtg accgacaaga tggatgcggc cggcctggcc 180
tgggcgatct acgacggcgt ggtgcccaac cccaccatca ccgtggtgaa ggaaggcctg 240
ggcgtgttcc agaactcggg cgcggattat ctcatcgcga tcggcggcgg cagcccccag 300
gacacctgca aggccatcgg catcatctcg aacaaccccg agttcgcgga cgtgcgctcc 360
ctggagggcc tgtcgccgac gaacaagccc tccgtcccga tcctcgccat cccgacgacg 420
gccggcaccg cggccgaggt gaccatcaat tacgtcatca ccgacgagga aaagcggcgc 480
aagttcgtgt gtgtggaccc ccatgacatc ccccaggtcg ccttcatcga cgccgacatg 540
atggatggca tgcccccgc cctcaaggcc gcgacgggcg tggacgcgct gacgcatgcc 600
atcgaaggct acatcacccg gggcgcctgg gccctgacgg atgccctgca tatcaaggcc 660
atcgaaatca tcgccggcgc cctgcgcggc tccgtggccg gcgacaagga tgcgggcgag 720
gagatggcgc tgggccagta cgtggccggc atgggcttct ccaatgtggg cctgggcctg 780
gtgcatggca tggcccatcc gctcggcgcc ttctacaaca cgccgcatgg cgtcgcgaac 840
gcgatcctcc tgccgcatgt catgcgctac aatgcggact tcacgggcga gaaataccgc 900
gatatcgccc gggtcatggg cgtgaaggtc gagggcatgt cgctggaaga ggcgcggaac 960
gccgcggtcg aagccgtctt cgccctgaac cgggatgtgg gcatcccgcc gcacctgcgc 1020
gatgtcggcg tccgcaagga agacatcccc gcgctggcgc aggccgccct ggacgatgtg 1080
tgcaccggcg gcaacccccg cgaggcgacg ctggaagaca tcgtcgaact ctaccatacc 1140
gcgtggtga 1149

<210> SEQ ID NO 70
<211> LENGTH: 1407
<212> TYPE: DNA
<213> ORGANISM: Clostridium beijerinckii

<400> SEQUENCE: 70
atgaacaagg acacgctgat ccccaccacg aaagacctca aggtgaagac caacggcgag 60

```
aacatcaacc tgaaaaacta caaggacaac agcagctgct tcggcgtgtt cgaaaacgtc    120
gaaaacgcca tcagctcggc ggtgcatgcc cagaaaatcc tcagcctgca ctatacgaag    180
gaacagcgcg aaaagatcat caccgaaatc cgcaaggccg cgctccagaa caaagaggtg    240
ctggccacga tgatcctgga ggaaacccat atgggccgct acgaagataa aatcctgaag    300
cacgagctgg tggcgaaata cacgcccggc accgaagacc tgacgaccac cgcctggagc    360
ggcgataacg gcctgacggt ggtggagatg tcgccgtatg gcgtgatcgg cgcgatcacc    420
ccgtccacca acccgaccga aacggtcatc tgtaactcga tcggcatgat cgcggccggc    480
aacgcggtcg tgttcaatgg ccacccgtgc gccaagaagt gcgtcgcctt cgccgtcgag    540
atgatcaaca aggccatcat ctcctgcggc ggcccggaga acctcgtgac gacgatcaaa    600
aacccgacga tggagtccct ggatgccatc atcaagcacc cgtccatcaa gctgctctgc    660
ggcaccggcg gcccgggcat ggtcaaaacg ctgctgaact ccggcaaaaa agccatcggc    720
gcgggcgcgg gcaacccccc cgtcatcgtg gatgacaccg ccgacatcga gaaagccggc    780
cggtcgatca tcgaaggctg ctccttcgac aataacctcc cgtgcatcgc cgagaaagag    840
gtcttcgtct tcgagaacgt cgcggacgat ctgatctcca acatgctgaa gaacaacgcc    900
gtcatcatca acgaagacca ggtgtccaag ctgatcgacc tcgtgctgca gaagaacaat    960
gaaacccagg agtacttcat caacaagaag tgggtcggca aggacgcgaa gctgttcctg   1020
gacgaaatcg atgtggagtc ccgagcaat gtgaagtgca tcatctgcga ggtcaacgcg   1080
aaccacccct tcgtcatgac cgagctcatg atgccgatcc tgccgatcgt gcgggtgaag   1140
gatatcgacg aagccatcaa gtacgcgaaa atcgcggaac agaatcggaa gcattcggcc   1200
tatatctaca gcaagaacat cgataacctc aaccgcttcg aacgggagat cgacaccacc   1260
atcttcgtca agaacgccaa atccttcgcc ggcgtgggct atgaggcgga aggcttcacc   1320
accttcacga tcgccggctc caccggcgag ggcatcacct ccgcccggaa cttcacccgc   1380
cagcgccgct gcgtgctggc gggctga                                         1407
```

<210> SEQ ID NO 71
<211> LENGTH: 1083
<212> TYPE: DNA
<213> ORGANISM: Saccharomyces cerevisiae

<400> SEQUENCE: 71

```
atgagctatc ccgagaagtt cgaggggatc gccatccaga gccacgagga ctggaagaac     60
ccgaaaaaga ccaagtatga tccgaagccc ttctacgatc acgacatcga catcaagatc    120
gaggcctgcg gcgtctgcgg cagcgatatc cattgtgcgg ctggccactg gggcaacatg    180
aagatgccgt tggtcgtcgg ccacgagatc gtgggcaagg tcgtgaagtt aggcccgaaa    240
agcaacagcg gcttgaaggt gggccagcgc gtgggtgtgg gtgcgcaggt cttcagctgt    300
ctggagtgcg accgttgcaa gaacgacaac gaaccgtact gcaccaagtt cgtcaccacc    360
tactcgcagc cctacgagga cggctacgtc tcgcagggcg gttacgccaa ctatgtccga    420
gtccacgaac acttcgtggt gcccatcccg gaaaatatcc ccagccatct ggcggctccc    480
ctgctgtgcg gtggcttgac cgtctacagc cccctcgtcc gcaatggctg cggtcccggc    540
aagaaggtgg gtatcgtggg cctcggcggt ataggctcta tgggcacgct gatctcgaaa    600
gcgatgggcg cagaaacgta cgtgatctcg cgttcctcgc gcaagcgcga ggatgcgatg    660
aagatgggtg cggaccacta catcgccacg ctggaggagg gtgactgggg tgagaagtac    720
ttcgacacgt tcgacctcat cgtggtgtgc gcgagttccc tgacggacat cgacttcaat    780
```

```
atcatgccca aggcgatgaa ggtcggaggg cgcatcgtct ccatctcgat cccggagcag    840

cacgaaatgc tgtcgctgaa gccctacggc ctgaaagccg tctccattag ctactcggcg    900

ctcggtagta tcaaggagct caaccagctg ttgaagttgg tttccgaaaa ggacatcaag    960

atctgggtgg aaacgctccc ggtgggcgaa gccggtgtgc acgaggcctt tgagcggatg   1020

gagaaggggg atgtccgtta tcggtttaca ctcgtcggct acgataaaga gttctcggat   1080

taa                                                                 1083
```

<210> SEQ ID NO 72
<211> LENGTH: 1023
<212> TYPE: DNA
<213> ORGANISM: Acinetobacter baylyi

<400> SEQUENCE: 72

```
atgacgacca acgtcatcca tgcctatgcg gccatgcagg ccggcgaggc gctggtgccg     60

tatagcttcg acgcgggcga gctccagccg catcaggtcg aggtgaaggt ggaatactgc    120

ggcctgtgtc attccgatgt gtcggtcctg aataacgaat ggcactcctc cgtctatccg    180

gtggtcgccg gccacgaggt catcggcacg atcacccagc tgggcagcga agccaagggc    240

ctgaagatcg gccagcgcgt cggcatcggc tggacggccg agagctgcca ggcctgcgat    300

cagtgcatct ccggccagca ggtgctgtgc accggcgaga acaccgccac catcatcggc    360

catgccggcg gcttcgcgga taaagtgcgg gccggctggc agtgggtgat cccgctcccg    420

gatgagctcg atcccacgag cgccggcccg ctgctgtgtg gcggcatcac cgtgttcgac    480

ccgatcctga agcaccagat ccaggccatc caccatgtcg ccgtgatcgg catcggcggc    540

ctgggccaca tggcgatcaa gctgctcaag gcctggggct gtgaaatcac cgccttcagc    600

agcaatccca acaagaccga cgaactgaag gcgatgggcg ccgaccatgt ggtcaactcc    660

cgcgatgacg cggaaatcaa gagccagcag ggcaagttcg acctgctgct gtcgacggtg    720

aatgtccccc tcaactggaa cgcctacctg aataccctgg ccccgaacgg cacgttccac    780

ttcctgggcg tcgtcatgga gccgatcccg gtgccggtgg gcgccctcct gggcggcgcg    840

aaaagcctga ccgcctcgcc cacgggcagc cccgccgccc tccgcaagct gctggagttc    900

gccgcccgca agaacatcgc gccccagatc gaaatgtatc ccatgagcga gctgaacgaa    960

gccatcgagc gcctgcatag cggccaggcc cgctatcgga tcgtgctcaa agcggacttc   1020

tga                                                                 1023
```

<210> SEQ ID NO 73
<211> LENGTH: 1020
<212> TYPE: DNA
<213> ORGANISM: Escherichia coli

<400> SEQUENCE: 73

```
atgtccatga tcaaaagcta cgccgcgaaa gaggcgggcg gcgagctgga ggtgtatgag     60

tatgacccgg gcgagctgcg gccccaggac gtggaagtgc aggtcgacta ctgcggcatc    120

tgccattcgg acctctcgat gatcgataac gagtggggct tcagccagta ccccctggtg    180

gccggccacg aggtgatcgg ccgcgtggtc gccctgggct cggccgcgca ggataaaggc    240

ctgcaggtcg gccagcgcgt cggcatcggc tggacggccc gcagctgcgg ccattgcgat    300

gcctgcatca gcggcaatca gatcaattgc gaacagggcg cggtcccgac catcatgaac    360

cggggcggct tcgccgaaaa gctgcgggcc gattggcagt gggtgatccc gctgccggag    420
```

aacatcgata tcgagtcggc cggccccctg ctgtgcggcg gcatcaccgt cttcaagccg 480
ctcctgatgc atcatatcac ggcgaccagc cgggtcggcg tgatcggcat cggcggcctc 540
ggccacatcg cgatcaaact gctgcacgcg atgggctgcg aggtcaccgc gttctcctcg 600
aaccccgcca aggagcagga agtgctggcg atgggcgccg ataaagtcgt gaactcgcgc 660
gacccccagg ccctcaaagc cctggccggc cagttcgatc tcatcatcaa cacggtgaac 720
gtgtcgctgg actggcagcc ctacttcgaa gccctgacct atggcggcaa cttccatacc 780
gtcggcgccg tgctgacccc gctgtccgtc ccggccttca ccctgatcgc cggcgaccgc 840
agcgtgtccg gcagcgccac cggcacgccg tatgagctgc gcaagctgat gcgcttcgcc 900
gcccgcagca aggtcgcccc gaccaccgag ctgttcccca tgtccaagat caatgacgcg 960
atccagcatg tccgggacgg caaggcccgc tatcgcgtcg tcctcaaggc ggacttctga 1020

<210> SEQ ID NO 74
<211> LENGTH: 1167
<212> TYPE: DNA
<213> ORGANISM: Escherichia coli

<400> SEQUENCE: 74
atgaacctgc atgaatatca ggccaagcag ctgttcgcgc ggtatggcct cccggcgccg 60
gtcggctacg cctgtacgac cccgcgggaa gcggaggagg ccgcctccaa gatcggcgcc 120
ggcccgtggg tggtcaaatg ccaggtgcat gcgggcggcc ggggcaaggc gggcggcgtg 180
aaggtcgtca actccaagga ggacatccgc gccttcgccg agaactggct gggcaagcgg 240
ctggtgacct atcagacgga cgccaatggc cagcccgtca atcagatcct ggtcgaggcg 300
gccacggaca tcgcgaaaga actgtacctc ggcgccgtcg tggaccggag cagccggcgg 360
gtggtgttca tggcgtccac cgagggcggc gtggaaatcg aaaaagtggc cgaggaaacc 420
ccgcacctga tccataaagt cgcgctggac ccgctgaccg gccccatgcc gtatcagggc 480
cgggaactcg cgttcaagct cggcctggag ggcaagctgg tgcagcagtt cacgaaaatc 540
ttcatgggcc tggcgaccat cttcctggag cgcgacctgg ccctgatcga aatcaacccg 600
ctggtcatca cgaagcaggg cgacctgatc tgcctggacg gcaagctcgg cgccgacggc 660
aacgccctgt tccgccagcc ggacctgcgg gaaatgcgcg atcagtcgca ggaggacccc 720
cgggaggccc aggcggccca gtgggagctg aattatgtgg cgctcgatgg caatatcggc 780
tgcatggtca atggcgcggg cctggcgatg ggcacgatgg acatcgtgaa gctgcatggc 840
ggcgagcccg ccaacttcct ggacgtgggc ggcggcgcga ccaaagagcg ggtgacggaa 900
gcgttcaaga tcatcctgag cgacgataaa gtcaaggccg tgctggtcaa catcttcggc 960
ggcatcgtcc gctgcgacct gatcgccgac ggcatcatcg gcgcggtggc ggaggtcggc 1020
gtcaatgtgc cggtcgtggt ccgcctggag ggcaacaacg ccgaactggg cgccaagaag 1080
ctggccgatt ccggcctgaa catcatcgcg gcgaagggcc tgaccgatgc cgcgcagcag 1140
gtcgtggccg ccgtcgaggg caagtga 1167

<210> SEQ ID NO 75
<211> LENGTH: 870
<212> TYPE: DNA
<213> ORGANISM: Escherichia coli

<400> SEQUENCE: 75
atgtccatcc tcatcgacaa gaacaccaag gtgatctgcc agggcttcac cggctcccag 60
ggcaccttcc acagcgagca ggcgatcgcc tacggcacca agatggtggg cggcgtcacc 120
cccggcaagg gcggcaccac ccatctcggc ctcccggtgt tcaatacggt gcgggaagcc 180
gtggcggcca ccggcgcgac cgccagcgtc atctatgtgc ccgcgccgtt ctgcaaggac 240
tccatcctgg aagccatcga cgccggcatc aagctcatca tcaccatcac cgagggcatc 300
cccaccctcg acatgctgac ggtgaaagtc aagctggacg aggcgggcgt ccggatgatc 360
ggccccaact gcccgggcgt catcaccccc ggcgagtgca aaatcggcat ccagccgggc 420
cacatccaca aaccgggcaa ggtgggcatc gtctcgcgct ccggcaccct cacctatgaa 480
gccgtcaagc agaccaccga ctatggcttc ggccagtcga cctgcgtcgg catcggcggc 540
gaccccatcc cgggctcgaa cttcatcgac atcctggaga tgttcgagaa agacccccag 600
accgaggcca tcgtgatgat cggcgagatc ggcggctcgg cggaggagga ggcggcggcg 660
tacatcaaag agcatgtgac caagccggtc gtgggctata tcgcgggcgt gacggcgccc 720
aagggcaagc gcatgggcca tgcgggcgcc atcatcgcgg gcggcaaagg caccgcggat 780
gagaagttcg ccgccctgga ggccgccggc gtcaagaccg tccgcagcct cgccgatatc 840
ggcgaagccc tgaagaccgt gctcaagtga 870

<210> SEQ ID NO 76
<211> LENGTH: 1362
<212> TYPE: DNA
<213> ORGANISM: Clostridium kluyveri

<400> SEQUENCE: 76
atgtcgaatg aagtctcgat caaggaactg atcgaaaagg cgaaggtggc ccagaagaaa 60
ctggaagcct actcgcagga gcaggtggat gtcctggtca aggccctggg caaggtcgtg 120
tatgataacg cggagatgtt cgccaaagaa gcggtggaag aaacggaaat gggcgtgtac 180
gaggacaagg tggcgaagtg ccacctgaaa tccggcgcca tctggaacca tatcaaggac 240
aagaaaaccg tgggcatcat caaggaagag ccggagcggg ccctggtcta cgtcgccaag 300
cccaagggcg tggtggccgc caccacgccc atcaccaacc ccgtcgtcac gccgatgtgt 360
aatgcgatgg ccgcgatcaa gggccgcaat acgatcatcg tggccccgca ccccaaagcg 420
aaaaaggtgt ccgcccacac cgtcgagctg atgaacgccg agctgaagaa gctgggcgcc 480
ccggagaaca tcatccagat cgtggaagcg ccctcgcggg aggcggcgaa ggaactcatg 540
gagagcgccg acgtggtcat cgccaccggc ggcgcgggcc gggtgaaggc cgcctactcg 600
tccggccgcc ccgcgtacgg cgtcggcccg ggcaactcgc aggtcatcgt cgacaagggc 660
tatgactaca acaaggccgc gcaggacatc atcaccggcc gcaagtatga caacggcatc 720
atctgctcct ccgagcagag cgtgatcgcg cccgccgaag actatgacaa ggtgatcgcc 780
gccttcgtcg agaatggcgc gttctacgtg gaggatgaag aaaccgtgga aaagttccgc 840
tccaccctgt tcaaagacgg caagatcaat tccaagatca tcggcaagag cgtccagatc 900
atcgccgacc tggcgggcgt caaggtcccc gagggcacga aggtcatcgt gctgaagggc 960
aagggcgcgg gcgagaagga tgtcctgtgc aaggaaaaga tgtgcccggt gctggtggcc 1020
ctgaagtacg acaccttcga agaggccgtc gaaatcgcga tggccaacta tatgtatgaa 1080
ggcgccggcc acaccgccgg catccattcg gacaacgacg agaacatccg ctacgcgggc 1140
accgtgctcc ccatcagccg cctcgtggtg aaccagccgg ccaccaccgc cggcggcagc 1200
ttcaataacg gcttcaaccc caccaccacc ctgggctgcg gcagctgggg ccgcaacagc 1260
atctcggaaa acctcacgta cgaacatctc atcaacgtct cccgcatcgg ctatttcaac 1320
aaggaagcga aggtgccctc ctatgaagag atctggggct ga 1362

<210> SEQ ID NO 77
<211> LENGTH: 1356
<212> TYPE: DNA
<213> ORGANISM: Porphyromonas gingivalis

<400> SEQUENCE: 77
atggagatca aggaaatggt gtccctggcc cgcaaggccc agaaggagta ccaggccacc 60
cataatcagg aagccgtgga caacatctgc cgcgccgcgg cgaaagtcat ctacgaaaat 120
gccgccatcc tcgcccgcga ggcggtcgat gaaaccggca tgggcgtgta cgaacacaag 180
gtggccaaga atcagggcaa aagcaagggc gtgtggtaca acctgcataa caagaaaagc 240
atcggcatcc tgaacatcga cgagcgcacc ggcatgatcg agatcgccaa gcccatcggc 300
gtcgtcggcg cggtcacgcc gaccaccaat cccatcgtca ccccgatgtc caacatcatc 360
ttcgcgctga aaacctgcaa cgcgatcatc atcgcccccc acccgcgcag caaaaaatgc 420
tcggcccacg ccgtgcggct catcaaggaa gccatcgcgc cgttcaacgt gccggagggc 480
atggtgcaga tcatcgaaga gccgtcgatc gagaagaccc aggaactgat gggcgccgtc 540
gacgtggtgg tggccaccgg cggcatgggc atggtgaagt cggcgtatag ctcgggcaag 600
ccgagcttcg gcgtgggcgc cggcaacgtg caggtcatcg tcgattcgaa catcgatttc 660
gaagccgccg cggaaaagat catcacgggc cgcgcgttcg ataacggcat catctgctcc 720
ggcgaacaga gcatcatcta caacgaggcg gataaggagg ccgtcttcac ggccttccgg 780
aaccacggcg cgtacttctg cgatgaagcc gaaggcgatc gcgcccgggc ggcgatcttc 840
gaaaacggcg ccatcgccaa agacgtggtg ggccagagcg tggcgttcat cgccaagaaa 900
gcgaacatca atatccccga aggcacgcgc atcctggtgg tggaagcccg cggcgtcggc 960
gcggaagatg tgatctgcaa ggaaaagatg tgccccgtga tgtgcgccct gtcctacaaa 1020
cacttcgaag agggcgtcga gatcgcccgc accaacctcg cgaacgaggg caacggccac 1080
acctgcgcca tccattcgaa taatcaggcc cacatcatcc tggccggcag cgagctcacc 1140
gtcagccgca tcgtggtcaa cgcgccctcc gccaccaccg ccggcggcca tatccagaac 1200
ggcctggccg tgacgaacac cctgggctgc ggctcgtggg gcaacaacag catctcggaa 1260
aacttcacct ataagcatct gctcaatatc agccgcatcg ccccgctgaa cagcagcatc 1320
catatcccgg acgacaaaga gatctgggaa ctctga 1356

<210> SEQ ID NO 78
<211> LENGTH: 287
<212> TYPE: DNA
<213> ORGANISM: Artificial Sequence
<220> FEATURE:
<223> OTHER INFORMATION: Variant of mxaF promoter

<400> SEQUENCE: 78
gaggttcagg cgaaaccgca gactcaaggg cgcttgctcc cgggaaagat cgtattagtt 60
tgcctcgatc ggcggtcctt gtgacaggga gatattcccg acggatccgg ggcattcgag 120
cggaaccgcc cgccgtggga gtttttccag cgagcattcg agagtttttc aaggcggctt 180
cgaggggtta ttccgtaacg ccgccgacat gatctgtccc ggaatctccg ccgctgttcg 240
tagagcgccg atgcagggtc ggcatcaatc attcttggag gagacac 287

<210> SEQ ID NO 79
<211> LENGTH: 4107

<212> TYPE: DNA
<213> ORGANISM: Artificial Sequence
<220> FEATURE:
<223> OTHER INFORMATION: Cas9 sequence used in Expression Vector

<400> SEQUENCE: 79
atggacaaga agtattcgat cggcctggac atcggcacca acagcgtcgg ctgggcggtc 60
atcacggatg agtacaaggt gccgtcgaag aagttcaagg tgctgggcaa taccgaccgc 120
catagcatca agaagaatct catcggcgca ctgctgttcg actccggcga aaccgccgaa 180
gcgacccgcc tcaagcgcac ggcccggcgg cgctatacgc gccggaagaa ccgcatctgc 240
tacctccagg aaatcttctc caacgagatg gccaaggtgg atgactcctt cttccatcgc 300
ctggaagaat ccttcctggt cgaagaagat aagaaacatg agcgccaccc catcttcggc 360
aatatcgtgg acgaggtggc gtatcacgag aaatacccga ccatctatca cctgcggaaa 420
aagctggtgg actcgacgga caaagccgac ctgcgcctca tctatctggc cctggcccac 480
atgatcaagt tccggggcca tttcctgatc gaaggcgacc tgaaccccga taacagcgac 540
gtggacaagc tcttcatcca gctcgtccag acctataacc agctgttcga ggagaacccc 600
atcaacgcct cgggcgtgga cgccaaggcc atcctgagcg cacggctctc caagtcgcgc 660
cgcctggaaa acctgatcgc gcagctgccg ggcgaaaaga aaaacggcct gttcggcaac 720
ctgatcgccc tgtccctcgg cctcaccccg aacttcaagt ccaacttcga cctggccgag 780
gacgcgaagc tccagctgtc gaaagacacc tacgatgacg acctggacaa cctcctggcg 840
cagatcggcg accagtacgc cgacctcttc ctcgcggcca agaatctgtc ggacgccatc 900
ctgctgtcgg atatcctgcg ggtgaatacg gagatcacga aggcccccct ctcggcctcg 960
atgatcaagc gctacgacga gcaccatcag gacctgacgc tgctcaaggc cctcgtccgg 1020
cagcagctgc cggagaagta taaagagatc ttcttcgacc agtccaagaa cggctacgcg 1080
ggctacatcg acggcggcgc gtcgcaggag gagttctata aattcatcaa gccgatcctg 1140
gagaaaatgg acggcaccga agaactcctc gtcaagctga accgggagga tctgctccgc 1200
aagcagcgca ccttcgacaa tggctccatc ccgcaccaga tccatctcgg cgagctgcac 1260
gccatcctgc gccgccagga ggacttctac cccttcctca aagacaaccg ggagaaaatc 1320
gagaagatcc tgacgttccg catcccctac tacgtgggcc ccctcgcccg cggcaactcg 1380
cggttcgcgt ggatgacccg gaagagcgag gagacgatca ccccgtggaa tttcgaggag 1440
gtcgtcgata aaggcgcgtc ggcgcagtcg ttcatcgagc gcatgaccaa cttcgataaa 1500
aatctgccga acgaaaaagt cctgcccaag catagcctgc tgtacgagta cttcacggtc 1560
tacaacgagc tgacgaaagt gaaatatgtc acggagggca tgcgcaaacc ggccttcctg 1620
tccggcgagc agaaaaaggc catcgtggat ctgctgttca agacgaaccg gaaggtcacc 1680
gtgaaacagc tgaaggaaga ttacttcaag aaaatcgagt gcttcgattc cgtcgaaatc 1740
agcggcgtgg aggaccgctt caatgcctcg ctgggcacct atcacgatct cctcaagatc 1800
atcaaggaca aggacttcct ggacaacgaa gagaacgagg acatcctgga agacatcgtc 1860
ctcaccctga ccctgttcga ggaccgcgaa atgatcgaag agcgcctgaa gacctacgcc 1920
cacctgttcg acgacaaggt catgaagcag ctcaagcgcc gccggtacac cggctggggc 1980
cgcctgtccc ggaagctgat caacggcatc cgcgataagc agagcggcaa gacgatcctg 2040
gacttcctca agagcgacgg cttcgccaat cggaatttca tgcagctcat ccacgacgat 2100
agcctgacct tcaaagagga tatccagaag gcgcaggtgt ccggccaggg cgacagcctg 2160

```
cacgaacata tcgccaacct ggcgggctcc cccgcgatca agaaaggcat cctccagacg   2220

gtcaaagtcg tggacgagct ggtcaaggtg atgggccgcc acaaaccgga gaatatcgtc   2280

atcgagatgg cacgcgagaa ccagaccacg cagaagggcc agaagaacag ccgggaacgc   2340

atgaaacgga tcgaagaggg catcaaggaa ctgggctcgc agatcctgaa ggagcacccc   2400

gtcgaaaaca cgcagctcca gaacgagaag ctgtatctgt actatctcca gaacggccgg   2460

gacatgtatg tcgatcagga actggatatc aaccgcctct ccgattacga tgtggaccac   2520

atcgtgccgc agagcttcct gaaagacgac tcgatcgaca acaaggtcct gacccggtcg   2580

gacaagaacc gcggcaagtc ggataacgtg ccgtcggaag aagtcgtgaa aaagatgaag   2640

aactactggc ggcagctcct gaacgcgaag ctcatcacgc agcgcaagtt cgacaatctg   2700

accaaggccg agcgcggcgg cctctcggaa ctcgacaagg cgggcttcat caaacggcag   2760

ctcgtcgaga cgcgccagat caccaaacac gtggcccaga tcctggacag ccggatgaac   2820

accaaatacg acgaaaacga caagctgatc cgcgaagtca aggtcatcac gctgaagagc   2880

aagctggtgt cggatttccg caaggatttc cagttctaca aggtgcgcga gatcaacaat   2940

taccatcacg cgcacgatgc ctatctcaat gcggtcgtgg gcaccgccct gatcaaaaag   3000

tacccgaaac tggagtccga gttcgtctac ggcgactata aggtctatga tgtccgcaag   3060

atgatcgcca aatcggagca ggagatcggc aaggcgaccg cgaaatattt cttctactcg   3120

aacatcatga atttcttcaa gaccgagatc acgctggcga acggcgaaat ccgcaagcgg   3180

cccctgatcg aaaccaatgg cgagaccggc gagatcgtgt gggacaaagg ccgggatttc   3240

gccaccgtcc gcaaggtcct ctcgatgccg caggtgaaca tcgtcaagaa gacggaggtc   3300

cagaccggcg gcttcagcaa agaaagcatc ctccccaagc ggaatagcga caaactgatc   3360

gcccggaaga aggactggga cccgaagaag tatggcggct tcgatagccc caccgtcgcc   3420

tattccgtcc tggtggtggc gaaggtggag aaaggcaaaa gcaagaaact gaagagcgtg   3480

aaggagctgc tgggcatcac catcatggaa cgcagcagct tcgagaagaa cccgatcgac   3540

ttcctggaag ccaaaggcta taaggaagtg aagaaggacc tcatcatcaa actcccgaag   3600

tattcgctgt tcgagctgga aaatggccgc aaacggatgc tcgcctccgc gggcgaactc   3660

cagaagggca acgaactggc gctgccgtcc aaatacgtca acttcctcta tctggccagc   3720

cattacgaaa agctgaaggg ctcgcccgaa gataacgagc agaaacagct gttcgtcgag   3780

cagcacaagc actacctcga cgagatcatc gagcagatca gcgagttctc caagcgggtg   3840

atcctcgcgg acgccaacct ggacaaggtg ctgtcggcgt acaacaaaca tcgggataag   3900

ccgatccgcg agcaggccga aaatatcatc cacctgttca ccctgacgaa cctcggcgcc   3960

cccgccgcct tcaagtattt cgataccacc atcgaccgga agcgctatac ctccaccaaa   4020

gaggtcctgg atgccaccct catccaccag tccatcacgg gcctgtacga gacccgcatc   4080

gacctgtcgc agctgggcgg cgactaa                                        4107
```

<210> SEQ ID NO 80
<211> LENGTH: 35
<212> TYPE: DNA
<213> ORGANISM: Artificial Sequence
<220> FEATURE:
<223> OTHER INFORMATION: J23111 Promoter-gRNA sequence

<400> SEQUENCE: 80

```
ttgacggcta gctcagtcct aggtatagtg ctagc                                 35
```

<210> SEQ ID NO 81
<211> LENGTH: 83
<212> TYPE: DNA
<213> ORGANISM: Artificial Sequence
<220> FEATURE:
<223> OTHER INFORMATION: Cas9 handle and terminator region

<400> SEQUENCE: 81
gttttagagc tagaaatagc aagttaaaat aaggctagtc cgttatcaac ttgaaaaagt 60
ggcaccgagt cggtgctttt ttt 83

<210> SEQ ID NO 82
<211> LENGTH: 20
<212> TYPE: DNA
<213> ORGANISM: Artificial Sequence
<220> FEATURE:
<223> OTHER INFORMATION: pSL148 - Targeting Sequence

<400> SEQUENCE: 82
gctcgaagcc cattaccacg 20

<210> SEQ ID NO 83
<211> LENGTH: 138
<212> TYPE: DNA
<213> ORGANISM: Artificial Sequence
<220> FEATURE:
<223> OTHER INFORMATION: pSL148 - Full sgRNA sequence

<400> SEQUENCE: 83
ttgacggcta gctcagtcct aggtatagtg ctagcgctcg aagcccatta ccacggtttt 60
agagctagaa atagcaagtt aaaataaggc tagtccgtta tcaacttgaa aaagtggcac 120
cgagtcggtg cttttttt 138

<210> SEQ ID NO 84
<211> LENGTH: 201
<212> TYPE: DNA
<213> ORGANISM: Artificial Sequence
<220> FEATURE:
<223> OTHER INFORMATION: pSL148 - Donor Sequence

<400> SEQUENCE: 84
gttcgacgcc gaattcgaag ccatcaagca ccaggccggg gtcgccgccg acatcggcct 60
gagcgccgtc catctcgccg acatcggcga acgtttcctc gccgtcgtac gccgccatac 120
cggcaagcct ttccccgagg acgtctacga gcagctcgag atcgcgatcc gggcggtatt 180
cgactcctgg atgggaaacg c 201

<210> SEQ ID NO 85
<211> LENGTH: 20
<212> TYPE: DNA
<213> ORGANISM: Artificial Sequence
<220> FEATURE:
<223> OTHER INFORMATION: pSL150 - Targeting Sequence

<400> SEQUENCE: 85
tcaaccacga tacactccag 20

<210> SEQ ID NO 86
<211> LENGTH: 138
<212> TYPE: DNA
<213> ORGANISM: Artificial Sequence
<220> FEATURE:
<223> OTHER INFORMATION: pSL150 - Full sgRNA sequence

<400> SEQUENCE: 86

```
ttgacggcta gctcagtcct aggtatagtg ctagctcaac cacgatacac tccaggtttt     60

agagctagaa atagcaagtt aaaataaggc tagtccgtta tcaacttgaa aaagtggcac    120

cgagtcggtg ctttttt                                                   138
```

<210> SEQ ID NO 87
<211> LENGTH: 199
<212> TYPE: DNA
<213> ORGANISM: Artificial Sequence
<220> FEATURE:
<223> OTHER INFORMATION: pSL150 - Donor Sequence

<400> SEQUENCE: 87

```
gtgaccgagc ctatctggaa ttgctcaagg ccctggccca gttgcgcctg ctggaacggc     60

tgaatgctcg aaaaatgggc cggaaccggc tctgatcctg cagtgacaag cggcgaacgc    120

gacagttcga ggagaccatc atgacgatga aaaagcgtgt ctacgccttc tccgaaggcg    180

acggcaagaa caaacgcct                                                 199
```

<210> SEQ ID NO 88
<211> LENGTH: 20
<212> TYPE: DNA
<213> ORGANISM: Artificial Sequence
<220> FEATURE:
<223> OTHER INFORMATION: pSL128 - Targeting Sequence

<400> SEQUENCE: 88

```
ggaccagaac aatccgttgt                                                 20
```

<210> SEQ ID NO 89
<211> LENGTH: 138
<212> TYPE: DNA
<213> ORGANISM: Artificial Sequence
<220> FEATURE:
<223> OTHER INFORMATION: pSL128 - Full sgRNA sequence

<400> SEQUENCE: 89

```
ttgacggcta gctcagtcct aggtatagtg ctagcggacc agaacaatcc gttgtgtttt     60

agagctagaa atagcaagtt aaaataaggc tagtccgtta tcaacttgaa aaagtggcac    120

cgagtcggtg ctttttt                                                   138
```

<210> SEQ ID NO 90
<211> LENGTH: 1044
<212> TYPE: DNA
<213> ORGANISM: Artificial Sequence
<220> FEATURE:
<223> OTHER INFORMATION: pSL128 - Donor Sequence

<400> SEQUENCE: 90

```
taccatgcgc atcgatctga ccgagacgca gctggatgcc ctggtggaaa tctaccggat     60

gatgcggccg ggcgaaccgc cgaccaagga ggccgcccag accctgttcg aaaatctgtt    120

tttctcggcc gaacgctatg atctgtcggc tgtcggccgg atgaagttca accggcgcct    180

ggggcggacc gatcctaccg gccccggcgt gctggaaaac gatgacatca tcgcggtgct    240

gaaggaactg atcaacatcc gtaacggggg gggcacggtc gacgacatcg accatctggg    300

taaccgccgc gtccggtccg tgggggagat ggtggagaat cagttcaggc tcgggctggt    360

ccgggtcgaa cgggccgtga aggagcgtct gtcgctgccc gacgccgatg gtctgatgcc    420

acaggagatc atcaacgcca aaccggtggc cgcttccatc aaggaattct tcggttcgag    480
```

ccagctttcg cggttcatgg accagaataa cccattatct gaggtcactc acaagcgccg 540
tgtctcggct ctggggccgg gggggctggc gcgtgagcgc gccggcttcg aagtgcgcga 600
cgtgcatacc acccactacg gccgtgtctg tccgatcgaa acgcccgaag gtccgaacat 660
cggcctgatc aactcgctcg cggtctactc gcgcaccaac gaatacggct ttctggagac 720
gccgtatcga aaggtgatcg acggccgggt gaccgatcag atcgagtacc tgtcggctat 780
cgaggagggc cagtactaca ttgctcaggc cagcgcctcg gtcgatgaaa acggcatgct 840
caaggatgaa ctggtgtcgt gtcgccacaa ggatgaattc accctggcgt cgcgggaaaa 900
catcaactac atggatgtgt cgtccaaaca gatcgtgtcg gtcgcggcct cgctgatccc 960
cttcctcgaa cacgatgatg ccaaccgcgc cctgatgggc tcgaacatgc agcggcaggc 1020
cgtcccgacg ctgcgtacgg agaa 1044

<210> SEQ ID NO 91
<211> LENGTH: 20
<212> TYPE: DNA
<213> ORGANISM: Artificial Sequence
<220> FEATURE:
<223> OTHER INFORMATION: gap gRNA5 - Targeting Sequence

<400> SEQUENCE: 91
cgtcgtgcat gagtgcaccg 20

<210> SEQ ID NO 92
<211> LENGTH: 138
<212> TYPE: DNA
<213> ORGANISM: Artificial Sequence
<220> FEATURE:
<223> OTHER INFORMATION: gap gRNA5 - Full sgRNA sequence

<400> SEQUENCE: 92
ttgacggcta gctcagtcct aggtatagtg ctagccgtcg tgcatgagtg caccggtttt 60
agagctagaa atagcaagtt aaaataaggc tagtccgtta tcaacttgaa aaagtggcac 120
cgagtcggtg cttttttt 138

<210> SEQ ID NO 93
<211> LENGTH: 1307
<212> TYPE: DNA
<213> ORGANISM: Artificial Sequence
<220> FEATURE:
<223> OTHER INFORMATION: gap gRNA5 - Donor Sequence

<400> SEQUENCE: 93
ccgggacgga acgcttgcca ggccatctgg atgtggcggg gaccggcgcc gtcgacgaac 60
acgatctcga ggtcgtcggc caccgccaga tagagcatgt tgcgaatggg gacgaacagt 120
gggtcggggc gccggcggcc gagcagtacc cggctgaggt tgtaggttgc ggcgccgagc 180
aggcgtgcct cgcgtcggag ttcgcgcgaa cgatggaagg tttcctgcat gtggatggcg 240
tcgcttgctg ggtcccggtt taagctatca gccttggtgc gcgaagggca agaactggac 300
gctcggcgcg gcgctttgct atattggcca cgctttgtat tgacagattc cccggagaat 360
gcccgattct ccctcgccga aggcccgcag gcgtccggcc gggacggcct cgactgctct 420
ccccacccca ctccgccggt cgccaagggt gcgagggctc tcgcgcatga ccccatcctc 480
actttatttc agcatttctg gagcagggca atgacgatta agattgcaat caatggatat 540
gggcgcatcg gccgcaacat cctgcgggcg atttacgaaa ccgggcgcaa ggatgtggag 600

```
atcgtcgcca tcaatgacct gggggatgcc cagatcaacg cccatctcac ccgccatgac    660

accgtgcacg ggccgttccg ggggaccgtg gaggtcggcg agggcgaaat catcgtcaac    720

ggcgaccgca tcagggtttt ttccgagaag gatccttcca agctgccctg gggggctttg    780

ggcgtggacg tcgtgcatga gtgatagcac ctgttccgca ccaaggccaa atgccagccg    840

catctcgatg ccggcgccaa gaaggtgatc atttcggccc cggccgacaa gaacgagtgc    900

gacgcgacca tcgtctacgg ggtcaatgag catacgctga aagccgccca caccgtcatc    960

tcgaatgcat cctgcaccac caactgcctg gcgccgctgg tcaagccgct gctgggaaaa   1020

atcgggatcg tgtccggcct catgaccacc gtgcattcct acaccaacga ccaggtgctc   1080

accgacgttt atcacaagga tctgtaccgg gcacgggcgg cggcgctgaa catgatcccg   1140

accaagaccg gcgcggcgca ggccgtgggg ctggtgctgc cggagctgga cggcaaactg   1200

tccggtttcg ccatccgggt gccgaccgcc aatgtatcgg tcgtggacct gaccttcatc   1260

gcggcccggg aaaccgacaa ggacgagatc aacgccatcc tcaaggc                 1307
```

```
<210> SEQ ID NO 94
<211> LENGTH: 20
<212> TYPE: DNA
<213> ORGANISM: Artificial Sequence
<220> FEATURE:
<223> OTHER INFORMATION: pIK11 - Targeting Sequence

<400> SEQUENCE: 94

cccatcacct atcagcacaa                                                 20
```

```
<210> SEQ ID NO 95
<211> LENGTH: 138
<212> TYPE: DNA
<213> ORGANISM: Artificial Sequence
<220> FEATURE:
<223> OTHER INFORMATION: pIK11 - Full sgRNA sequence

<400> SEQUENCE: 95

ttgacggcta gctcagtcct aggtatagtg ctagccccat cacctatcag cacaagtttt     60

agagctagaa atagcaagtt aaaataaggc tagtccgtta tcaacttgaa aaagtggcac    120

cgagtcggtg ctttttttt                                                138
```

```
<210> SEQ ID NO 96
<211> LENGTH: 1149
<212> TYPE: DNA
<213> ORGANISM: Artificial Sequence
<220> FEATURE:
<223> OTHER INFORMATION: pIK11 - Donor Sequence

<400> SEQUENCE: 96

aagatcgatg acaccgtcaa ctgggtgaaa aaggtcgatc tgaagaccgg cctgccgatc     60

cgcgatccgg agtacagcac ccgcatggac cacaatgcca aaggcatctg tccctcggcc    120

atgggctatc acaaccaggg catcgagtcc tacgatccgg acaagaagct gttcttcatg    180

ggcgtgaacc acatctgcat ggactgggag ccgttcatgc tgccctaccg cgccggccag    240

ttctttgtgg gggcgaccct caacatgtat ccgggaccca aggggatgct gggtcaggtc    300

aaggcgatga acgcggtcac cggcaagatg gaatgggaag tgccggagaa gtttgcggtc    360

tggggtggca ccttggcgac cgccggcgac ctcgtgttct acggtaccct cgacggcttc    420

atcaaggccc gcgacacccg taccggcgag ctgaagtggc agttccagtt gccctccggc    480

gtgatcggcc atcccatcac gtaccaacat aacggcaagc aatacattgc catctactcc    540
```

```
ggcgtcggcg gctggccagg agtagggctg gtattcgacc tgaaggaccc gaccgcaggt    600

ctgggagctg tgggtgcgtt cagggaactg gcgcattaca cccagatggg tggatcggtg    660

ttcgtgttct cgctttgagt cgaaggggtg gaggcgctcc tgggggagcg cccctatccc    720

atgctgtcga aaggatgaat catgcgaatg aaccgtattg cagccgcggg gttggccgcc    780

tccctcgcgg tcgtgggatg cgtgcaggca gcgacgagcg tcgaaccgct caaggtctgc    840

tccgcggaaa acgagatgcc gtattcggac aaggccggag agggtttcga aaataagttg    900

gctgagctcc ttggaaaggg attgggacgg ccagtcgaga acgtgtggtg gaccgatgcc    960

cgctatttcg tccgggatta tctggacagg ggtttgtgcg atgtggtcat cggcgtcgat   1020

accggcgacc cgcggatgct caccagcagt ccttattacc ggtccggcta cgtattcgtc   1080

taccgcaagg acacgggact gagcatccaa gattggaaca gcgcggcact gaagaccgtg   1140

aagcggatc                                                           1149
```

<210> SEQ ID NO 97
<211> LENGTH: 20
<212> TYPE: DNA
<213> ORGANISM: Artificial Sequence
<220> FEATURE:
<223> OTHER INFORMATION: pSL178 - Targeting Sequence

<400> SEQUENCE: 97

```
tcaaccacga tacactccag                                                 20
```

<210> SEQ ID NO 98
<211> LENGTH: 138
<212> TYPE: DNA
<213> ORGANISM: Artificial Sequence
<220> FEATURE:
<223> OTHER INFORMATION: pSL178 - Full sgRNA sequence

<400> SEQUENCE: 98

```
ttgacggcta gctcagtcct aggtatagtg ctagctcaac cacgatacac tccaggtttt     60

agagctagaa atagcaagtt aaaataaggc tagtccgtta tcaacttgaa aaagtggcac    120

cgagtcggtg cttttttt                                                  138
```

<210> SEQ ID NO 99
<211> LENGTH: 322
<212> TYPE: DNA
<213> ORGANISM: Artificial Sequence
<220> FEATURE:
<223> OTHER INFORMATION: pSL178 - Donor Sequence

<400> SEQUENCE: 99

```
gtgttccctg gaacacgcca tcaatttcga tctcgtgctc aacaccgacc atctgccagc     60

cggtaacgct ctgccgaccg tactcatggc ggtacggcag ttcggcttcg aaatcttcga    120

tctcggtcag cgggaagcct cgtgagcccg gcggtgggac agaccgcatc ccgtctgcta    180

acggtcgaga tcgtcgacgt ctgccgggag atattttccg ggcgttgtag ccgggtggtc    240

gcgccagcgg cagacggtga ggtcggcgtt ctgccccgtc atacgccgtt cctgacccgg    300

ctccggcccg gcgagataag gc                                             322
```

<210> SEQ ID NO 100
<211> LENGTH: 20
<212> TYPE: DNA
<213> ORGANISM: Artificial Sequence
<220> FEATURE:

<223> OTHER INFORMATION: pSL179 - Targeting Sequence

<400> SEQUENCE: 100
tcaaccacga tacactccag 20

<210> SEQ ID NO 101
<211> LENGTH: 138
<212> TYPE: DNA
<213> ORGANISM: Artificial Sequence
<220> FEATURE:
<223> OTHER INFORMATION: pSL179 - Full sgRNA sequence

<400> SEQUENCE: 101
ttgacggcta gctcagtcct aggtatagtg ctagctcaac cacgatacac tccaggtttt 60
agagctagaa atagcaagtt aaaataaggc tagtccgtta tcaacttgaa aaagtggcac 120
cgagtcggtg cttttttt 138

<210> SEQ ID NO 102
<211> LENGTH: 2028
<212> TYPE: DNA
<213> ORGANISM: Artificial Sequence
<220> FEATURE:
<223> OTHER INFORMATION: pSL179 - Donor sequence

<400> SEQUENCE: 102
gtgttccctg gaacacgcca tcaatttcga tctcgtgctc aacaccgacc atctgccagc 60
cggtaacgct ctgccgaccg tactcatggc ggtacggcag ttcggcttcg aaatcttcga 120
tctcggtcag cgggaagcct cgtgagcccg gcggtgggac agaccgcatc ccgtctgcta 180
acggtcgaga tcgtcgacgt ctgccgggag atattttccg ggcgttgtag ccgggtggtc 240
gcgccagcgg cagacggtga ggtcggcgtt ctgccccgtc atacgccgtt cctgacccgg 300
ctccggcccg gcgagataag gctcaggacc gaggcaggcg aagaccagta tttctacctc 360
tccgggggct acatggaggt gcagcgctgg gaggtcagca tcctggccga ccaggtgctc 420
cgctcccaag agatcgaccg ggaagcggcc ctggcggcca agcgcaacgc agagcggatg 480
ctccgcgaga accggattcc cggcgagcgt gaccgagcct atctggaatt gctcaaggcc 540
ctggcccagt tgcgcctgct ggaacggctg aatgctcgaa aaatgggccg gaaccggctc 600
tgatcctgca gtgacaagcg gcgaacgcga cagttcgagg agaccatcat gacgatgaaa 660
aagcgtgtct acgccttctc cgaaggcgac ggcaagaaca aacgcctgct cggcggcaag 720
ggcgccaacc tctgcgaaat gacgcagatc gggctcaacg tgccgccggg tttcgttatt 780
accacggaag cctgcctcga atacctggca gacaagaagc tgccggccgg cttgatggac 840
gaagtccggg agcacatggc ccggctcgaa cgggctaccg gcaagcgctt cggcgatccc 900
gccaatccac tcttggtttc ggtgcgttcc ggttcggccc tgtccatgcc gggcatgatg 960
gataccattc tcaacctcgg cctcaaccac gatacactct ttcctcgccg tcgtacgccg 1020
ccataccggc aagcctttcc ccgaggacgt ctacgagcag ctcgagatcg cgatccgggc 1080
ggtattcgac tcctggatgg gaaagcgcgc ggtggattac cgccgcgaat tccacatcac 1140
gcccgaccag gccaacggca cggcggtgaa cgtggtgacc atggtgttcg gcaacatggg 1200
cgacgactcc gccaccggtg tcggcttcac ccgcaatccg ggtaccggtg agaacgagat 1260
gttcggcgag tatctggtca acgcccaggg tgaggatgtg gtagccggaa tccgcacgcc 1320
caagcccgtg cacgagatgg caaccgaaat gccggcgctt tacgcccaac tggtggaact 1380
gcgcgacaag ctcgaagccc attaccacga ggtgcaggac ttcgagtaca ccatcgagaa 1440
gggggtcttg tactgtctgc agacgcgcaa cggcaagatg aacgcccagg cgatggtgcg 1500
cacctcggtc gagatgtgcc gggaaggact gatcacgcgg gatcaggccc tcttgcgggt 1560
caaccccgcc catctggaac agttactcca tccctgcctc gacacctcgc acaaccccac 1620
gccgctggcg caggggctgc ctgcctcgcc cggcgccgcc agcggccgtt gcgtgttcga 1680
tgcggatcag gccgaactgt tgggacgggc cggtgaaaag gtcatcctgg tgcgtgagga 1740
gaccaagccg gaagacatcc acggcttctt cgcggcccag ggaatcctca ccagtcgcgg 1800
cggcaagacc tcgcatgccg ccgtggtcgc ccgcggcatg ggcaaggcct gcgtggccgg 1860
ggccgaaggc atcagggtgg acagccgggc gcggctggca acggtgggag aggtcacgtt 1920
gcacgaaggt gacatcatca ccatcgacgg cagcaccggc cgtgtctatc tcggcgcgat 1980
cccgacgatc gcgccgacct tctccgaaca cctcaggaca ctgctgtc 2028

<210> SEQ ID NO 103
<211> LENGTH: 20
<212> TYPE: DNA
<213> ORGANISM: Artificial Sequence
<220> FEATURE:
<223> OTHER INFORMATION: pSL162 - Targeting Sequence

<400> SEQUENCE: 103
tcaaccacga tacactccag 20

<210> SEQ ID NO 104
<211> LENGTH: 138
<212> TYPE: DNA
<213> ORGANISM: Artificial Sequence
<220> FEATURE:
<223> OTHER INFORMATION: pSL162 - Full sgRNA sequence

<400> SEQUENCE: 104
ttgacggcta gctcagtcct aggtatagtg ctagctcaac cacgatacac tccaggtttt 60
agagctagaa atagcaagtt aaaataaggc tagtccgtta tcaacttgaa aaagtggcac 120
cgagtcggtg cttttttt 138

<210> SEQ ID NO 105
<211> LENGTH: 199
<212> TYPE: DNA
<213> ORGANISM: Artificial Sequence
<220> FEATURE:
<223> OTHER INFORMATION: pSL162 - Donor Sequence

<400> SEQUENCE: 105
gtgaccgagc ctatctggaa ttgctcaagg ccctggccca gttgcgcctg ctggaacggc 60
tgaatgctcg aaaaatgggc cggaaccggc tctgatcctg cagtgacaag cggcgaacgc 120
gacagttcga ggagaccatc atgacgatga aaaagcgtgt ctacgccttc tccgaaggcg 180
acggcaagaa caaacgcct 199

<210> SEQ ID NO 106
<211> LENGTH: 20
<212> TYPE: DNA
<213> ORGANISM: Artificial Sequence
<220> FEATURE:
<223> OTHER INFORMATION: pSL154 - Targeting Sequence

<400> SEQUENCE: 106
tcaaccacga tacactccag 20

```
<210> SEQ ID NO 107
<211> LENGTH: 138
<212> TYPE: DNA
<213> ORGANISM: Artificial Sequence
<220> FEATURE:
<223> OTHER INFORMATION: pSL154 - Full sgRNA sequence

<400> SEQUENCE: 107

ttgacggcta gctcagtcct aggtatagtg ctagctcaac cacgatacac tccaggtttt     60

agagctagaa atagcaagtt aaaataaggc tagtccgtta tcaacttgaa aaagtggcac    120

cgagtcggtg ctttttt                                                   138


<210> SEQ ID NO 108
<211> LENGTH: 1075
<212> TYPE: DNA
<213> ORGANISM: Artificial Sequence
<220> FEATURE:
<223> OTHER INFORMATION: pSL154  - Donor Sequence

<400> SEQUENCE: 108

gtgaccgagc ctatctggaa ttgctcaagg ccctggccca gttgcgcctg ctggaacggc     60

tgaatgctcg aaaaatgggc cggaaccggc tctgatcctg cagtgacaag cggcgaacgc    120

gacagttcga ggagaccatc atgacgatga aaaagcgtgt ctacgccttc tccgaaggcg    180

acggcaagaa caaacgcctg ctcggcggca agggcgccaa cctctgcgaa atgacgcaga    240

tcgggctcaa cgtgccgccg ggtttcgtta ttaccacgga agcctgcctc gaatacctgg    300

cagacaagaa gctgccggcc ggcttgatgg acgaagtccg ggagcacatg gcccggctcg    360

aacgggctac cggcaagcgc ttcggcgatc ccgccaatcc actcttggtt tcggtgcgtt    420

ccggttcggc cctgtccatg ccgggcatga tggataccat tctcaacctc ggcctcaacc    480

acgatacact ctaagtgcca gggcgtgccc ttgggctccc cgggcgcggg gttgatccgg    540

cagaccggca acgagcgctt cggtcacgat gcctaccggc ggttcatcca gttgttcggc    600

aaggttgccc tcggtgttcc cgacgagctg ttcgacgccg aattcgaagc catcaagcac    660

caggccgggg tcgccgccga catcggcctg agcgccgtcc atctcgccga catcggcgaa    720

cgtttcctcg ccgtcgtacg ccgccatacc ggcaagcctt tccccgagga cgtctacgag    780

cagctcgaga tcgcgatccg ggcggtattc gactcctgga tgggaaagcg cgcggtggat    840

taccgccgcg aattccacat cacgcccgac caggccaacg gcacggcggt gaacgtggtg    900

accatggtgt tcggcaacat gggcgacgac tccgccaccg gtgtcggctt cacccgcaat    960

ccgggtaccg gtgagaacga gatgttcggc gagtatctgg tcaacgccca gggtgaggat   1020

gtggtagccg gaatccgcac gcccaagccc gtgcacgaga tggcaaccga aatgc        1075


<210> SEQ ID NO 109
<211> LENGTH: 20
<212> TYPE: DNA
<213> ORGANISM: Artificial Sequence
<220> FEATURE:
<223> OTHER INFORMATION: pSL175 - Targeting Sequence

<400> SEQUENCE: 109

tactacggag caagttcccg                                                 20


<210> SEQ ID NO 110
<211> LENGTH: 138
<212> TYPE: DNA
<213> ORGANISM: Artificial Sequence
```

<220> FEATURE:
<223> OTHER INFORMATION: pSL175 - Full sgRNA sequence

<400> SEQUENCE: 110

```
ttgacggcta gctcagtcct aggtatagtg ctagctacta cggagcaagt tcccggtttt     60

agagctagaa atagcaagtt aaaataaggc tagtccgtta tcaacttgaa aaagtggcac    120

cgagtcggtg ctttttt                                                   138
```

<210> SEQ ID NO 111
<211> LENGTH: 1045
<212> TYPE: DNA
<213> ORGANISM: Artificial Sequence
<220> FEATURE:
<223> OTHER INFORMATION: pSL175 - Donor Sequence

<400> SEQUENCE: 111

```
gccaggacag aaatgcctcg acttcgctgc tgcccaaggt tgccgggtga cgcacaccgt     60

ggaaacggat gaaggcacga acccagttga cataagcctg ttcggttcgt aaactgtaat    120

gcaagtagcg tatgcgctca cgcaactggt ccagaacctt gaccgaacgc agcggtggta    180

acggcgcagt ggcggttttc atggcttgtt atgactgttt ttttgtacag tctatgcctc    240

gggcatccaa gcagcaagcg cgttacgccg tgggtcgatg tttgatgtta tggagcagca    300

acgatgttac gcagcagcaa cgatgttacg cagcagggca gtcgccctaa aacaaagtta    360

ggtggctcaa gtatgggcat cattcgcaca tgtaggctcg gccctgacca agtcaaatcc    420

atgcgggctg ctcttgatct tttcggtcgt gagttcggag acgtagccac ctactcccaa    480

catcagccgg actccgatta gctcccccaa ctgagagaac tcaaaggtta ccccagttgg    540

ggcgggtaac ttgctccgta gtaagacatt catcgcgctt gctgccttcg accaagaagc    600

ggttgttggc gctctcgcgg cttacgttct gcccaggttt gagcagccgc gtagtgagat    660

ctatatctat gatctcgcag tctccggcga gcaccggagg cagggcattg ccaccgcgct    720

catcaatctc ctcaagcatg aggccaacgc gcttggtgct tatgtgatct acgtgcaagc    780

agattacggt gacgatcccg cagtggctct ctatacaaag ttgggcatac gggaagaagt    840

gatgcacttt gatatcgacc caagtaccgc cacctaacaa ttcgttcaag ccgagatcgg    900

cttcataact tcgtatagca tacattatac gaagttattg gcagagcatt acgctgactt    960

gaccagaggc tgcatttcca ccgctgattg cgattcggaa ggtgcaggcc ggagggtccg   1020

gaccgccgct ccacccgttg ttttc                                         1045
```

<210> SEQ ID NO 112
<211> LENGTH: 20
<212> TYPE: DNA
<213> ORGANISM: Artificial Sequence
<220> FEATURE:
<223> OTHER INFORMATION: pSL163 - Targeting Sequence

<400> SEQUENCE: 112

```
tcaaccacga tacactccag                                                 20
```

<210> SEQ ID NO 113
<211> LENGTH: 138
<212> TYPE: DNA
<213> ORGANISM: Artificial Sequence
<220> FEATURE:
<223> OTHER INFORMATION: pSL163 - Full sgRNA sequence

<400> SEQUENCE: 113

```
ttgacggcta gctcagtcct aggtatagtg ctagctcaac cacgatacac tccaggtttt     60

agagctagaa atagcaagtt aaaataaggc tagtccgtta tcaacttgaa aaagtggcac    120

cgagtcggtg cttttttt                                                  138


<210> SEQ ID NO 114
<211> LENGTH: 1785
<212> TYPE: DNA
<213> ORGANISM: Artificial Sequence
<220> FEATURE:
<223> OTHER INFORMATION: pSL163 - Donor Sequence

<400> SEQUENCE: 114

gtgaccgagc ctatctggaa ttgctcaagg ccctggccca gttgcgcctg ctggaacggc     60

tgaatgctcg aaaaatgggc cggaaccggc tctgatcctg cagtgacaag cggcgaacgc    120

gacagttcga ggagaccatc atgacgatga aaaagcgtgt ctacgccttc tccgaaggcg    180

acggcaagaa caaacgcctg ctcggcggca agggcgccaa cctctgcgaa atgacgcaga    240

tcgggctcaa cgtgccgccg ggtttcgtta ttaccacgga agcctgcctc gaatacctgg    300

cagacaagaa gctgccggcc ggcttgatgg acgaagtccg ggagcacatg gcccggctcg    360

aacgggctac cggcaagcgc ttcggcgatc ccgccaatcc actcttggtt tcggtgcgtt    420

ccggttcggc cctgtccatg ccgggcatga tggataccat tctcaacctc ggcctcaacc    480

acgatacact ctaattgacg gctagctcag tcctaggtat agtgctagca aaaagctcaa    540

cgagaggaag ttccatggcc atcatcaagg agttcatgcg cttcaaggtg cacatggagg    600

gctccgtgaa cggccacgag ttcgagatcg agggcgaggg cgagggccgc ccctacgagg    660

gcacccagac cgccaagctg aaggtgacca agggtggccc cctgcccttc gcctgggaca    720

tcctgtcccc tcagttcatg tacggctcca aggcctacgt gaagcacccc gccgacatcc    780

ccgactactt gaagctgtcc ttccccgagg gcttcaagtg ggagcgcgtg atgaacttcg    840

aggacggcgg cgtggtgacc gtgacccagg actcctccct ccaggacggc gagttcatct    900

acaaggtgaa gctgcgcggc accaacttcc cctccgacgg ccccgtaatg cagaagaaga    960

ccatgggctg ggaggcctcc tccgagcgga tgtaccccga ggacggcgcc ctgaagggcg   1020

agatcaagca gaggctgaag ctgaaggacg gcggccacta cgacgctgag gtcaagacca   1080

cctacaaggc caagaagccc gtgcagctgc ccggcgccta caacgtcaac atcaagttgg   1140

acatcacctc ccacaacgag gactacacca tcgtggaaca gtacgaacgc gccgagggcc   1200

gccactccac cggcggcatg gacgagctgt acaagtaagg gttgatccgg cagaccggca   1260

acgagcgctt cggtcacgat gcctaccggc ggttcatcca gttgttcggc aaggttgccc   1320

tcggtgttcc cgacgagctg ttcgacgccg aattcgaagc catcaagcac caggccgggg   1380

tcgccgccga catcggcctg agcgccgtcc atctcgccga catcggcgaa cgtttcctcg   1440

ccgtcgtacg ccgccatacc ggcaagcctt tccccgagga cgtctacgag cagctcgaga   1500

tcgcgatccg ggcggtattc gactcctgga tgggaaagcg cgcggtggat taccgccgcg   1560

aattccacat cacgcccgac caggccaacg gcacggcggt gaacgtggtg accatggtgt   1620

tcggcaacat gggcgacgac tccgccaccg gtgtcggctt cacccgcaat ccgggtaccg   1680

gtgagaacga gatgttcggc gagtatctgg tcaacgccca gggtgaggat gtggtagccg   1740

gaatccgcac gcccaagccc gtgcacgaga tggcaaccga aatgc                   1785


<210> SEQ ID NO 115
<211> LENGTH: 20
```

<212> TYPE: DNA
<213> ORGANISM: Artificial Sequence
<220> FEATURE:
<223> OTHER INFORMATION: pSL165 - Targeting Sequence

<400> SEQUENCE: 115
tcaaccacga tacactccag 20

<210> SEQ ID NO 116
<211> LENGTH: 138
<212> TYPE: DNA
<213> ORGANISM: Artificial Sequence
<220> FEATURE:
<223> OTHER INFORMATION: pSL165 - Full sgRNA sequence

<400> SEQUENCE: 116
ttgacggcta gctcagtcct aggtatagtg ctagctcaac cacgatacac tccaggtttt 60
agagctagaa atagcaagtt aaaataaggc tagtccgtta tcaacttgaa aaagtggcac 120
cgagtcggtg cttttttt 138

<210> SEQ ID NO 117
<211> LENGTH: 2184
<212> TYPE: DNA
<213> ORGANISM: Artificial Sequence
<220> FEATURE:
<223> OTHER INFORMATION: pSL165 - Donor sequence

<400> SEQUENCE: 117
gtgaccgagc ctatctggaa ttgctcaagg ccctggccca gttgcgcctg ctggaacggc 60
tgaatgctcg aaaaatgggc cggaaccggc tctgatcctg cagtgacaag cggcgaacgc 120
gacagttcga ggagaccatc atgacgatga aaaagcgtgt ctacgccttc tccgaaggcg 180
acggcaagaa caaacgcctg ctcggcggca agggcgccaa cctctgcgaa atgacgcaga 240
tcgggctcaa cgtgccgccg ggtttcgtta ttaccacgga agcctgcctc gaatacctgg 300
cagacaagaa gctgccggcc ggcttgatgg acgaagtccg ggagcacatg gcccggctcg 360
aacgggctac cggcaagcgc ttcggcgatc ccgccaatcc actcttggtt tcggtgcgtt 420
ccggttcggc cctgtccatg ccgggcatga tggataccat tctcaacctc ggcctcaacc 480
acgatacact ctaattgacg gctagctcag tcctaggtat agtgctagca aaaagctcaa 540
cgagaggaag ttccatgagc tatcccgaga agttcgaggg gatcgccatc cagagccacg 600
aggactggaa gaacccgaaa aagaccaagt atgatccgaa gcccttctac gatcacgaca 660
tcgacatcaa gatcgaggcc tgcggcgtct gcggcagcga tatccattgt gcggctggcc 720
actggggcaa catgaagatg ccgttggtcg tcggccacga gatcgtgggc aaggtcgtga 780
agttaggccc gaaaagcaac agcggcttga aggtgggcca gcgcgtgggt gtgggtgcgc 840
aggtcttcag ctgtctggag tgcgaccgtt gcaagaacga caacgaaccg tactgcacca 900
agttcgtcac cacctactcg cagccctacg aggacggcta cgtctcgcag ggcggttacg 960
ccaactatgt ccgagtccac gaacacttcg tggtgcccat cccggaaaat atccccagcc 1020
atctggcggc tcccctgctg tgcggtggct tgaccgtcta cagcccccctc gtccgcaatg 1080 gctgcggtcc cggcaagaag gtgggtatcg tgggcctcgg cggtataggc tctatgggca 1140
cgctgatctc gaaagcgatg ggcgcagaaa cgtacgtgat ctcgcgttcc tcgcgcaagc 1200
gcgaggatgc gatgaagatg ggtgcggacc actacatcgc cacgctggag gagggtgact 1260
ggggtgagaa gtacttcgac acgttcgacc tcatcgtggt gtgcgcgagt tccctgacgg 1320

```
acatcgactt caatatcatg cccaaggcga tgaaggtcgg agggcgcatc gtctccatct   1380

cgatcccgga gcagcacgaa atgctgtcgc tgaagcccta cggcctgaaa gccgtctcca   1440

ttagctactc ggcgctcggt agtatcaagg agctcaacca gctgttgaag ttggtttccg   1500

aaaaggacat caagatctgg gtggaaacgc tcccggtggg cgaagccggt gtgcacgagg   1560

cctttgagcg gatggagaag gggatgtcc gttatcggtt tacactcgtc ggctacgata    1620

aagagttctc ggattaaggg ttgatccggc agaccggcaa cgagcgcttc ggtcacgatg   1680

cctaccggcg gttcatccag ttgttcggca aggttgccct cggtgttccc gacgagctgt   1740

tcgacgccga attcgaagcc atcaagcacc aggccggggt cgccgccgac atcggcctga   1800

gcgccgtcca tctcgccgac atcggcgaac gtttcctcgc cgtcgtacgc cgccataccg   1860

gcaagccttt ccccgaggac gtctacgagc agctcgagat cgcgatccgg gcggtattcg   1920

actcctggat gggaaagcgc gcggtggatt accgccgcga attccacatc acgcccgacc   1980

aggccaacgg cacggcggtg aacgtggtga ccatggtgtt cggcaacatg ggcgacgact   2040

ccgccaccgg tgtcggcttc acccgcaatc cgggtaccgg tgagaacgag atgttcggcg   2100

agtatctggt caacgcccag ggtgaggatg tggtagccgg aatccgcacg cccaagcccg   2160

tgcacgagat ggcaaccgaa atgc                                          2184
```

<210> SEQ ID NO 118
<211> LENGTH: 4107
<212> TYPE: DNA
<213> ORGANISM: Artificial Sequence
<220> FEATURE:
<223> OTHER INFORMATION: dCas9

<400> SEQUENCE: 118

```
atggacaaga agtattcgat cggcctggcc atcggcacca acagcgtcgg ctgggcggtc     60

atcacggatg agtacaaggt gccgtcgaag aagttcaagg tgctgggcaa taccgaccgc    120

catagcatca agaagaatct catcggcgca ctgctgttcg actccggcga aaccgccgaa    180

gcgacccgcc tcaagcgcac ggcccggcgg cgctatacgc gccggaagaa ccgcatctgc    240

tacctccagg aaatcttctc caacgagatg gccaaggtgg atgactcctt cttccatcgc    300

ctggaagaat ccttcctggt cgaagaagat aagaaacatg agcgccaccc catcttcggc    360

aatatcgtgg acgaggtggc gtatcacgag aaatacccga ccatctatca cctgcggaaa    420

aagctggtgg actcgacgga caaagccgac ctgcgcctca tctatctggc cctggcccac    480

atgatcaagt tccggggcca tttcctgatc gaaggcgacc tgaaccccga taacagcgac    540

gtggacaagc tcttcatcca gctcgtccag acctataacc agctgttcga ggagaacccc    600

atcaacgcct cgggcgtgga cgccaaggcc atcctgagcg cacggctctc caagtcgcgc    660

cgcctggaaa acctgatcgc gcagctgccg ggcgaaaaga aaaacggcct gttcggcaac    720

ctgatcgccc tgtccctcgg cctcaccccg aacttcaagt ccaacttcga cctggccgag    780

gacgcgaagc tccagctgtc gaaagacacc tacgatgacg acctggacaa cctcctggcg    840

cagatcggcg accagtacgc cgacctcttc ctcgcggcca agaatctgtc ggacgccatc    900

ctgctgtcgg atatcctgcg ggtgaatacg gagatcacga aggcccccct ctcggcctcg    960

atgatcaagc gctacgacga gcaccatcag gacctgacgc tgctcaaggc cctcgtccgg   1020

cagcagctgc cggagaagta taaagagatc ttcttcgacc agtccaagaa cggctacgcg   1080

ggctacatcg acggcggcgc gtcgcaggag gagttctata aattcatcaa gccgatcctg   1140

gagaaaatgg acggcaccga agaactcctc gtcaagctga accgggagga tctgctccgc   1200
```

```
aagcagcgca ccttcgacaa tggctccatc ccgcaccaga tccatctcgg cgagctgcac   1260

gccatcctgc gccgccagga ggacttctac cccttcctca aagacaaccg ggagaaaatc   1320

gagaagatcc tgacgttccg catcccctac tacgtgggcc ccctcgcccg cggcaactcg   1380

cggttcgcgt ggatgacccg gaagagcgag gagacgatca ccccgtggaa tttcgaggag   1440

gtcgtcgata aaggcgcgtc ggcgcagtcg ttcatcgagc gcatgaccaa cttcgataaa   1500

aatctgccga acgaaaaagt cctgcccaag catagcctgc tgtacgagta cttcacggtc   1560

tacaacgagc tgacgaaagt gaaatatgtc acggagggca tgcgcaaacc ggccttcctg   1620

tccggcgagc agaaaaaggc catcgtggat ctgctgttca agacgaaccg gaaggtcacc   1680

gtgaaacagc tgaaggaaga ttacttcaag aaaatcgagt gcttcgattc cgtcgaaatc   1740

agcggcgtgg aggaccgctt caatgcctcg ctgggcacct atcacgatct cctcaagatc   1800

atcaaggaca aggacttcct ggacaacgaa gagaacgagg acatcctgga agacatcgtc   1860

ctcaccctga ccctgttcga ggaccgcgaa atgatcgaag agcgcctgaa gacctacgcc   1920

cacctgttcg acgacaaggt catgaagcag ctcaagcgcc gccggtacac cggctggggc   1980

cgcctgtccc ggaagctgat caacggcatc cgcgataagc agagcggcaa gacgatcctg   2040

gacttcctca agagcgacgg cttcgccaat cggaatttca tgcagctcat ccacgacgat   2100

agcctgacct tcaaagagga tatccagaag gcgcaggtgt ccggccaggg cgacagcctg   2160

cacgaacata tcgccaacct ggcgggctcc cccgcgatca agaaaggcat cctccagacg   2220

gtcaaagtcg tggacgagct ggtcaaggtg atgggccgcc acaaaccgga gaatatcgtc   2280

atcgagatgg cacgcgagaa ccagaccacg cagaagggcc agaagaacag ccgggaacgc   2340

atgaaacgga tcgaagaggg catcaaggaa ctgggctcgc agatcctgaa ggagcacccc   2400

gtcgaaaaca cgcagctcca gaacgagaag ctgtatctgt actatctcca gaacggccgg   2460

gacatgtatg tcgatcagga actggatatc aaccgcctct ccgattacga tgtggacgcc   2520

atcgtgccgc agagcttcct gaaagacgac tcgatcgaca acaaggtcct gacccggtcg   2580

gacaagaacc gcggcaagtc ggataacgtg ccgtcggaag aagtcgtgaa aaagatgaag   2640

aactactggc ggcagctcct gaacgcgaag ctcatcacgc agcgcaagtt cgacaatctg   2700

accaaggccg agcgcggcgg cctctcggaa ctcgacaagg cgggcttcat caaacggcag   2760

ctcgtcgaga cgcgccagat caccaaacac gtggcccaga tcctggacag ccggatgaac   2820

accaaatacg acgaaaacga caagctgatc cgcgaagtca aggtcatcac gctgaagagc   2880

aagctggtgt cggatttccg caaggatttc cagttctaca aggtgcgcga gatcaacaat   2940

taccatcacg cgcacgatgc ctatctcaat gcggtcgtgg gcaccgccct gatcaaaaag   3000

tacccgaaac tggagtccga gttcgtctac ggcgactata aggtctatga tgtccgcaag   3060

atgatcgcca aatcggagca ggagatcggc aaggcgaccg cgaaatattt cttctactcg   3120

aacatcatga atttcttcaa gaccgagatc acgctggcga acggcgaaat ccgcaagcgg   3180

cccctgatcg aaaccaatgg cgagaccggc gagatcgtgt gggacaaagg ccgggatttc   3240

gccaccgtcc gcaaggtcct ctcgatgccg caggtgaaca tcgtcaagaa gacggaggtc   3300

cagaccggcg gcttcagcaa agaaagcatc ctccccaagc ggaatagcga caaactgatc   3360

gcccggaaga aggactggga cccgaagaag tatggcggct tcgatagccc caccgtcgcc   3420

tattccgtcc tggtggtggc gaaggtggag aaaggcaaaa gcaagaaact gaagagcgtg   3480

aaggagctgc tgggcatcac catcatggaa cgcagcagct tcgagaagaa cccgatcgac   3540
```

ttcctggaag ccaaaggcta taaggaagtg aagaaggacc tcatcatcaa actcccgaag 3600
tattcgctgt tcgagctgga aaatggccgc aaacggatgc tcgcctccgc gggcgaactc 3660
cagaagggca acgaactggc gctgccgtcc aaatacgtca acttcctcta tctggccagc 3720
cattacgaaa agctgaaggg ctcgcccgaa gataacgagc agaaacagct gttcgtcgag 3780
cagcacaagc actacctcga cgagatcatc gagcagatca gcgagttctc caagcgggtg 3840
atcctcgcgg acgccaacct ggacaaggtg ctgtcggcgt acaacaaaca tcgggataag 3900
ccgatccgcg agcaggccga aaatatcatc cacctgttca ccctgacgaa cctcggcgcc 3960
cccgccgcct tcaagtattt cgataccacc atcgaccgga agcgctatac ctccaccaaa 4020
gaggtcctgg atgccaccct catccaccag tccatcacgg gcctgtacga gacccgcatc 4080
gacctgtcgc agctgggcgg cgactaa 4107

<210> SEQ ID NO 119
<211> LENGTH: 20
<212> TYPE: DNA
<213> ORGANISM: Artificial Sequence
<220> FEATURE:
<223> OTHER INFORMATION: oriV_dcas9_gRNA3 - Targeting Sequence

<400> SEQUENCE: 119
ataatgtgtg gaattgtgag 20

<210> SEQ ID NO 120
<211> LENGTH: 138
<212> TYPE: DNA
<213> ORGANISM: Artificial Sequence
<220> FEATURE:
<223> OTHER INFORMATION: oriV_dcas9_gRNA3 - Full sgRNA sequence

<400> SEQUENCE: 120
tttatagcta gctcagccct tggtacaatg ctagcataat gtgtggaatt gtgaggtttt 60
agagctagaa atagcaagtt aaaataaggc tagtccgtta tcaacttgaa aaagtggcac 120
cgagtcggtg cttttttt 138

<210> SEQ ID NO 121
<211> LENGTH: 72
<212> TYPE: DNA
<213> ORGANISM: Artificial Sequence
<220> FEATURE:
<223> OTHER INFORMATION: Ptrc_laxZ - Promoter

<400> SEQUENCE: 121
ttgacaatta atcatccggc tcgtataatg tgtggaattg tgagcggata acaattaacg 60
agaggaagtt cc 72

<210> SEQ ID NO 122
<211> LENGTH: 3075
<212> TYPE: DNA
<213> ORGANISM: Artificial Sequence
<220> FEATURE:
<223> OTHER INFORMATION: Ptrc_laxZ - LacZ sequence used in Vector

<400> SEQUENCE: 122
atgaccatga ttacggattc actggccgtc gttttacaac gtcgtgactg ggaaaaccct 60
ggcgttaccc aacttaatcg ccttgcagca catccccctt tcgccagctg gcgtaatagc 120
gaagaggccc gcaccgatcg cccttcccaa cagttgcgca gcctgaatgg cgaatggcgc 180
tttgcctggt ttccggcacc agaagcggtg ccggaaagct ggctggagtg cgatcttcct 240

```
gaggccgata ctgtcgtcgt cccctcaaac tggcagatgc acggttacga tgcgcccatc    300
tacaccaacg tgacctatcc cattacggtc aatccgccgt ttgttcccac ggagaatccg    360
acgggttgtt actcgctcac atttaatgtt gatgaaagct ggctacagga aggccagacg    420
cgaattattt ttgatggcgt taactcggcg tttcatctgt ggtgcaacgg gcgctgggtc    480
ggttacggcc aggacagtcg tttgccgtct gaatttgacc tgagcgcatt tttacgcgcc    540
ggagaaaacc gcctcgcggt gatggtgctg cgctggagtg acggcagtta tctggaagat    600
caggatatgt ggcggatgag cggcattttc cgtgacgtct cgttgctgca taaaccgact    660
acacaaatca gcgatttcca tgttgccact cgctttaatg atgatttcag ccgcgctgta    720
ctggaggctg aagttcagat gtgcggcgag ttgcgtgact acctacgggt aacagtttct    780
ttatggcagg gtgaaacgca ggtcgccagc ggcaccgcgc ctttcggcgg tgaaattatc    840
gatgagcgtg gtggttatgc cgatcgcgtc acactacgtc tgaacgtcga aaacccgaaa    900
ctgtggagcg ccgaaatccc gaatctctat cgtgcggtgg ttgaactgca caccgccgac    960
ggcacgctga ttgaagcaga agcctgcgat gtcggtttcc gcgaggtgcg gattgaaaat   1020
ggtctgctgc tgctgaacgg caagccgttg ctgattcgag gcgttaaccg tcacgagcat   1080
catcctctgc atggtcaggt catggatgag cagacgatgg tgcaggatat cctgctgatg   1140
aagcagaaca actttaacgc cgtgcgctgt tcgcattatc cgaaccatcc gctgtggtac   1200
acgctgtgcg accgctacgg cctgtatgtg gtggatgaag ccaatattga aacccacggc   1260
atggtgccaa tgaatcgtct gaccgatgat ccgcgctggc taccggcgat gagcgaacgc   1320
gtaacgcgaa tggtgcagcg cgatcgtaat cacccgagtg tgatcatctg gtcgctgggg   1380
aatgaatcag gccacggcgc taatcacgac gcgctgtatc gctggatcaa atctgtcgat   1440
ccttcccgcc cggtgcagta tgaaggcggc ggagccgaca ccacggccac cgatattatt   1500
tgcccgatgt acgcccgcgt ggatgaagac cagcccttcc cggctgtgcc gaaatggtcc   1560
atcaaaaaat ggctttcgct acctggagag acgcgcccgc tgatcctttg cgaatacgcc   1620
cacgcgatgg gtaacagtct tggcggtttc gctaaatact ggcaggcgtt tcgtcagtat   1680
ccccgtttac agggcggctt cgtctgggac tgggtggatc agtcgctgat taaatatgat   1740
gaaaacggca acccgtggtc ggcttacggc ggtgattttg gcgatacgcc gaacgatcgc   1800
cagttctgta tgaacggtct ggtctttgcc gaccgcacgc cgcatccagc gctgacggaa   1860
gcaaaacacc agcagcagtt tttccagttc cgtttatccg ggcaaaccat cgaagtgacc   1920
agcgaatacc tgttccgtca tagcgataac gagctcctgc actggatggt ggcgctggat   1980
ggtaagccgc tggcaagcgg tgaagtgcct ctggatgtcg ctccacaagg taaacagttg   2040
attgaactgc ctgaactacc gcagccggag agcgccgggc aactctggct cacagtacgc   2100
gtagtgcaac cgaacgcgac cgcatggtca gaagccgggc acatcagcgc ctggcagcag   2160
tggcgtctgg cggaaaacct cagtgtgacg ctccccgccg cgtcccacgc catcccgcat   2220
ctgaccacca gcgaaatgga tttttgcatc gagctgggta ataagcgttg gcaatttaac   2280
cgccagtcag gctttctttc acagatgtgg attggcgata aaaaacaact gctgacgccg   2340
ctgcgcgatc agttcacccg tgcaccgctg gataacgaca ttggcgtaag tgaagcgacc   2400
cgcattgacc ctaacgcctg ggtcgaacgc tggaaggcgg cgggccatta ccaggccgaa   2460
gcagcgttgt tgcagtgcac ggcagataca cttgctgatg cggtgctgat tacgaccgct   2520
cacgcgtggc agcatcaggg gaaaacctta tttatcagcc ggaaaaccta ccggattgat   2580
```

ggtagtggtc aaatggcgat taccgttgat gttgaagtgg cgagcgatac accgcatccg 2640
gcgcggattg gcctgaactg ccagctggcg caggtagcag agcgggtaaa ctggctcgga 2700
ttagggccgc aagaaaacta tcccgaccgc cttactgccg cctgttttga ccgctgggat 2760
ctgccattgt cagacatgta taccccgtac gtcttcccga gcgaaaacgg tctgcgctgc 2820
gggacgcgcg aattgaatta tggcccacac cagtggcgcg gcgacttcca gttcaacatc 2880
agccgctaca gtcaacagca actgatggaa accagccatc gccatctgct gcacgcggaa 2940
gaaggcacat ggctgaatat cgacggtttc catatgggga ttggtggcga cgactcctgg 3000
agcccgtcag tatcggcgga attccagctg agcgccggtc gctaccatta ccagttggtc 3060
tggtgtcaaa aataa 3075

<210> SEQ ID NO 123
<211> LENGTH: 4077
<212> TYPE: DNA
<213> ORGANISM: Methylococcus capsulatus

<400> SEQUENCE: 123
atggcttact cgtttaccga gaaaaaacga attcgcaaga gtttcggaaa gcgtcaggac 60
gtgctggagg tcccctatct tctggcgaca caggttgact cgtaccggcg gtttttgcaa 120
ctcgacaagc agcccgccgc ccggagcgac gaaggtctgc atgcggcgtt gaagtcggtt 180
ttcccgatca agagccattc cggcaacatc gtactcgaat atgtgagtta ccggctgggc 240
gacccggtgt tcgacgtcaa ggaatgccag cagcgtggaa ccacctacgc cgccccgctg 300
cgcgtgctcg tccgtctggt ggtctacgac aaggatgcgc cggtgggcgc caaggtcgtc 360
agagacatca aggagcagga gatctacatg ggcgaaattc cgctcatgac cgacaacggc 420
acgttcgtca tcaacggtac cgagcgggtg atcgtttccc aactgcaccg ttcgcccggc 480
gtatttttcg accatgatcg gggaaagacc cattcttcgg gaaagctgct gttcaatgcc 540
agaatcatcc cctaccgcgg gtcctggctg gacttcgaat tcgaccacaa ggactgcgtt 600
tacgtccgta tcgacaggcg tcgcaagctg cccgccacgg tgttgctgcg agccctgggc 660
tatgacaacg agcagatcat cgccgagttt ttcgacacca accgtttcct gctctcatcc 720
gccggcattc agctggaact gatacccgag cggctgcgcg gcgatatcgc cagcttcgac 780
attcggcttg gcgatcagat cgtggtcgag aaggaccacc ggatcacggc gcgtcacatc 840
cggatgctgc aaaaggagaa cgtgaacctc ctcgacgtcc ccaaggacta cctgtacggc 900
aagattcttg cccacaacgt cgtggatact tcgacgggcg aactgatcgc caaggtgaat 960
caggagatca cggaggatgt ctatgcgcgt ctcgtggctg cggccatccc cgagatccgt 1020
acgctctatg tgaacgatct cgaccgcggt ccgtacattt ccaataccat gcgcatcgat 1080
ctgaccgaga cgcagctgga tgccctggtg gaaatctacc ggatgatgcg gccgggcgaa 1140
ccgccgacca aggaggccgc ccagaccctg ttcgaaaatc tgtttttctc ggccgaacgc 1200
tatgatctgt cggctgtcgg ccggatgaag ttcaaccggc gcctggggcg gaccgatcct 1260
accggccccg gcgtgctgga aaacgatgac atcatcgcgg tgctgaagga actgatcaac 1320
atccgtaacg gggggggcac ggtcgacgac atcgaccatc tgggtaaccg ccgcgtccgg 1380
tccgtggggg agatggtgga gaatcagttc aggctcgggc tggtccgggt cgaacgggcc 1440
gtgaaggagc gtctgtcgct gcccgacgcc gatggtctga tgccacagga gatcatcaac 1500
gccaaaccgg tggccgcttc catcaaggaa ttcttcggtt cgagccagct ttcgcagttc 1560
atggaccaga acaatccgtt gtcggaggtc actcacaagc gccgtgtctc ggctctgggg 1620

-continued

```
ccgggggggc tggcgcgtga gcgcgccggc ttcgaagtgc gcgacgtgca taccacccac   1680
tacggccgtg tctgtccgat cgaaacgccc gaaggtccga acatcggcct gatcaactcg   1740
ctcgcggtct actcgcgcac caacgaatac ggctttctgg agacgccgta tcgaaaggtg   1800
atcgacggcc gggtgaccga tcagatcgag tacctgtcgg ctatcgagga gggccagtac   1860
tacattgctc aggccagcgc ctcggtcgat gaaaacggca tgctcaagga tgaactggtg   1920
tcgtgtcgcc acaaggatga attcaccctg gcgtcgcggg aaaacatcaa ctacatggat   1980
gtgtcgtcca aacagatcgt gtcggtcgcg gcctcgctga tccccttcct cgaacacgat   2040
gatgccaacc gcgccctgat gggctcgaac atgcagcggc aggccgtccc gacgctgcgt   2100
acggagaagc ctctggtggg cacgggcatg gaacgcatcg tcgcccgcga ttccggcgtg   2160
gcggtcgtcg ccaagcgcgg tggcacggtc gagttcgtgg acgccagccg catcgtggtc   2220
cgggtgaacg acgaggagac cgaggcgggg gttccgggtg tggatatcta caacctgacc   2280
aaatacaccc gttccaacca gaacacctgt attaaccaga ggccgttggt taagccgggc   2340
gacgtcgtgg cccgcaacga cgtgctggcg gatggtcctt cgaccgacat gggcgaactg   2400
gcgctgggcc agaatctgct ggtcgcgttc atgccctgga acggttacaa cttcgaagac   2460
tcgatcctga tttcggaacg cgtggtgcag gacgaccgtt tcacgaccat ccacatcgag   2520
gagaagacct gcgtcgctcg agacaccaaa ctggggcccg aggaaatcac cgccgacatt   2580
ccgaacgttg ggaggccgc gctgtccaag ctggacgagt cgggtatcgt ctacatcggc   2640
gccgaggtca aggccggcga catcctggtg ggcaaggtga cgcccaaggg cgaaacccag   2700
ctcaccccgg aggagaagct gctgcgagcg atcttcggtg agaaggcctc ggatgtgaag   2760
gacacttcgc tgcgcgtgcc ttcgggtatg gacggcacgg tcatagacgt gcaggtcttc   2820
acccgcgacg gcgtgaagaa ggatgaacgc gcccgtcaga tcgaggaagc cgagattgag   2880
agggttcgca aggatctgaa cgatcagctc cgtatcatcg agaaggactt ttaccagcgg   2940
gccgagcaga tggttctggg caaggtcgcc gacatggggc cgggcggtct gaagcgcggc   3000
gccaccatca cccgggaata cctggattcg atcaagcccg cccagtggct ggagatccgg   3060
ttgcaggacg aagacgtcaa tcttcagatc gaagcgatcg ccgagcagat cgcccagcag   3120
cgcgaggaaa tcgcgaagcg gctcgaagag aagcgccgca agatcaccat gggtgacgac   3180
ctcgctccgg gtgtgctcaa gatggtaaag gtgtacctgg ccgtcaagcg ccgtattcag   3240
ccgggcgaca agatggccgg ccgccacggg aacaaaggtg tgatttcccg catcgtaccg   3300
gtggaagaca tgccgtattc ggctgacggt acgccggtcg acatcgtgtt gaacccactg   3360
ggcgtgcctt cgcgcatgaa cgtaggccag gtgctcgaga cccatctcgg ctgggcggcc   3420
aagggtgtgg gcctgaagat cggcggatg ctggaggcca aggccaagat cgaggagatc   3480
cggtctttcc tcactcaggt gtacaacgtg agtggccgcc aggaggacat cgccagtctg   3540
agcgacgccg aggtgctgga gctcgccggt aatctgcagg acggcgtgcc gatggcgact   3600
cccgtgttcg atggagccac cgaggaagac atcaaggcca tgctgcggct ggccgatctt   3660
cccgaaagcg gccaggcaac tttgttcgac ggacgtaccg gcgacgtgtt cgaccgtccg   3720
gtgaccgtcg gttacatgta catgctcaaa ctcaatcatc tggtcgacga caagatgcac   3780
gcacggtcca ccggtccgta cagtctggtg acccagcagc cgctgggcgg caaggcgcaa   3840
ttcggtggac agcgtttcgg cgaaatggag gtgtgggcgt tggaggccta cggtgccgcc   3900
tatactctgc aggagatgct gacggtgaaa tctgacgacg tgaacggcag gaccaagatg   3960
```

tacaagaaca tcgtcgacgg tgatcaccgt atggaagccg ccatgcccga gtcgttcaac 4020
gtcctgatca aagagatccg ctcgctcgga atcaacatcg agctcgagca ggactga 4077

<210> SEQ ID NO 124
<211> LENGTH: 20
<212> TYPE: DNA
<213> ORGANISM: Artificial Sequence
<220> FEATURE:
<223> OTHER INFORMATION: RPOB gRNA targeting sequence

<400> SEQUENCE: 124
ggaccagaac aatccgttgt 20

<210> SEQ ID NO 125
<211> LENGTH: 103
<212> TYPE: DNA
<213> ORGANISM: Artificial Sequence
<220> FEATURE:
<223> OTHER INFORMATION: RPOB gRNA with Handle and Terminator

<400> SEQUENCE: 125
ggaccagaac aatccgttgt gttttagagc tagaaatagc aagttaaaat aaggctagtc 60
cgttatcaac ttgaaaaagt ggcaccgagt cggtgctttt ttt 103

<210> SEQ ID NO 126
<211> LENGTH: 1044
<212> TYPE: DNA
<213> ORGANISM: Artificial Sequence
<220> FEATURE:
<223> OTHER INFORMATION: RpoB Donor DNA

<400> SEQUENCE: 126
taccatgcgc atcgatctga ccgagacgca gctggatgcc ctggtggaaa tctaccggat 60
gatgcggccg ggcgaaccgc cgaccaagga ggccgcccag accctgttcg aaaatctgtt 120
tttctcggcc gaacgctatg atctgtcggc tgtcggccgg atgaagttca accggcgcct 180
ggggcggacc gatcctaccg gccccggcgt gctggaaaac gatgacatca tcgcggtgct 240
gaaggaactg atcaacatcc gtaacggggg gggcacggtc gacgacatcg accatctggg 300
taaccgccgc gtccggtccg tgggggagat ggtggagaat cagttcaggc tcgggctggt 360
ccgggtcgaa cgggccgtga aggagcgtct gtcgctgccc gacgccgatg gtctgatgcc 420
acaggagatc atcaacgcca aaccggtggc cgcttccatc aaggaattct tcggttcgag 480
ccagctttcg cggttcatgg accagaataa cccattatct gaggtcactc acaagcgccg 540
tgtctcggct ctggggccgg gggggctggc gcgtgagcgc gccggcttcg aagtgcgcga 600
cgtgcatacc acccactacg gccgtgtctg tccgatcgaa acgcccgaag gtccgaacat 660
cggcctgatc aactcgctcg cggtctactc gcgcaccaac gaatacggct ttctggagac 720
gccgtatcga aaggtgatcg acggccgggt gaccgatcag atcgagtacc tgtcggctat 780
cgaggagggc cagtactaca ttgctcaggc cagcgcctcg gtcgatgaaa acggcatgct 840
caaggatgaa ctggtgtcgt gtcgccacaa ggatgaattc accctggcgt cgcgggaaaa 900
catcaactac atggatgtgt cgtccaaaca gatcgtgtcg gtcgcggcct cgctgatccc 960
cttcctcgaa cacgatgatg ccaaccgcgc cctgatgggc tcgaacatgc agcggcaggc 1020
cgtcccgacg ctgcgtacgg agaa 1044

ADVANCED GENOME EDITING

This application is the National Stage of International Application No. PCT/2018/055340, filed Oct. 11, 2018, and claims benefit to U.S. Provisional Application No. 62/572,012, filed Oct. 13, 2017, which is incorporated herein in its entirety.

SEQUENCE LISTING

This application contains a Sequence Listing, which has been submitted electronically in ASCII format and is hereby incorporated by reference in its entirety. The ASCII copy was created on Oct. 11, 2018, is named INX00399_SL.txt and is 208,080 bytes in size.

BACKGROUND OF THE INVENTION

Genomic editing is the key to molecular biology. Genome editing uses specific nucleases to create site-specific double-strand breaks (DSBs) at desired locations within the genome of a cell in order to insert, delete, or replace one or more nucleotides. The DSBs are then repaired, which result in the desired modifications.

Currently there are four families of engineered nucleases that are used for genome edits, including meganucleases, zinc finger nucleases (ZFN), transcription activator-like effector-based nucleases (TALEN), and clustered regularly interspaced short palindromic repeats (CRISPR)-Cas systems.

In general, the meganucleases method of gene editing is the least efficient of the methods mentioned above. Due to the nature of its DNA-binding element and the cleaving element, it is limited to recognizing one potential target every 1,000 nucleotides. Boglioli, E., Richard, M, "Rewriting the book of life: a new era in precision genome editing". Boston Consulting Group, September 2015. ZFN was developed to overcome the limitations of meganucleases. The number of possible targets ZFN can recognize was increased to one in every 140 nucleotides. Boglioli, E., 2015. However, both methods are unpredictable due to the ability of their DNA-binding elements affecting each other. As a result, high degrees of expertise and lengthy and costly validation processes are required.

TALE nucleases are the most precise and specific method and yield a higher efficiency than the previous two methods using meganucleases and ZFN. TALEN achieves higher efficiency because the DNA-binding element contains an array of TALE subunits, each of them having the capability of recognizing a specific DNA nucleotide chain independent from others, resulting in a higher number of target sites with high precision. New TALEN take about one week and a few hundred dollars to create, with specific expertise in molecular biology and protein engineering. Boglioli, E., 2015.

CRISPR nucleases are slightly less precise compared to TALENs. However, the CRISPR method has been shown to be the quickest and cheapest method. CRISPR also requires the least amount of expertise in molecular biology as the design lays in the guide RNA instead of the proteins. One major advantage that CRISPR has over the ZFN and TALEN methods is that it can be directed to target different DNA sequences using its ~80 nt CRISPR single guide ribonucleic acids (sgRNAs), while both ZFN and TALEN methods required construction and testing of the proteins created for targeting each DNA sequence. Barrangou, R., and Doudna, J. A., "Applications of CRISPR technologies in research and beyond". *Nature Biotechnology.* 34:933-941, 2016.

The subject matter of the present invention relates to microorganisms, such as methanotrophs, and methods to genomically edit their DNA.

Incorporation by Reference

All publications, patents, and patent applications cited herein are hereby incorporated by reference in their entireties to the same extent as if each individual publication, patent, or patent application was specifically and individually indicated to be incorporated by reference in its entirety. In the event of a conflict between a term herein and a term in an incorporated reference, the term herein controls.

SUMMARY

Disclosed herein is a method of genetic engineering comprising: (a) contacting a microorganism capable of converting a $C_1$ carbon to a multicarbon product with a polynucleotide encoding for a Cas enzyme and a guide ribonucleic acid (gRNA); and (b) growing the microorganism until genetic modification occurs.

In some cases, the microorganism capable of converting a $C_1$ carbon to a multicarbon product is a methylotroph. For example, the methylotroph can be a methanotroph. If the microorganism is a methanotroph, it can be from the genera *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis*, or *Methyloacidophilum*. Particular methanotrophs that can be used are methanotrophs from the genus *Methylococcus*, such as *Methylococcus capsulatus.*

In some cases, the $C_1$ carbon is carbon monoxide (CO), carbon dioxide ($CO_2$), methane ($CH_4$), or any combination thereof. For example, the $C_1$ carbon used can be $CH_4$.

In some cases, the Cas enzyme is Cas1, Cas1B, Cas2, Cas3, Cas4, Cas5, Cas5d, Cas5t, Cas5h, Cas5a, Cas6, Cas7, Cas8, Cas9, Cas10, Csy1, Csy2, Csy3, Csy4, Cse1, Cse2, Cse3, Cse4, Cse5e, Csc1, Csc2, Csa5, Csn1, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Csd1, Csd2, Cst1, Cst2, Csh1, Csh2, Csa1, Csa2, Csa3, Csa4, Csa5, C2c1, C2c2, C2c3, Cpf1, CARF, DinG, homologues thereof, or modified versions thereof. For example, the Cas enzyme use can be Cas9.

In some cases, the polynucleotide encoding for a gRNA used can be at least partially homologous to a promoter, intron, or coding sequence of an RNA polymerase beta-subunit (rpoB) gene or a gene within the 2,3-butanediol (2,3-BDO), 1,4-butanediol (1,4-BDO), isobutyraldehyde, or isobutanol pathway. For example, the polynucleotide encoding for a gRNA can be at least partially homologous to a promoter, intron, or coding sequence of rpoB. Additionally, the polynucleotide encoding for a gRNA can be directed to a promoter, intron, or coding sequence of gene within the 2,3-BDO pathway. If targeting the promoter, intron, or coding sequence of a gene within the 2,3-BDO pathway, the promoter, intron or coding sequence can be from the genes encoding an acetoin reductase, alpha-acetolactate decarboxylase, or acetolactate synthase.

In some cases the polynucleotide encoding for a gRNA can be directed to a promoter, intron, or coding sequence of a gene within the 1,4-BDO pathway. If targeting the promoter, intron, or coding sequence of a gene within the 1,4-BDO pathway, the promoter, intron or coding sequence can be from the genes encoding a pyruvate dehydrogenase (aceEF), citrate synthase (gltA), aconitate hydratase 1 (acnA), isocitrate dehydrogenase (icdA), citrate synthase (gltA), succinyl-CoA synthetase (SucC), CoA-dependent succinate semialdehyde dehydrogenase (SucD), 4-hyrobutyrate dehydrogenase (4hbD), 4-hydroxybutyryl-CoA transferase (Cat2), aldehyde dehydrogenase (Ald), alcohol dehydrogenase (Adh), or α-ketoglutarate decarboxylase (kgd).

In some cases, the polynucleotide encoding for a gRNA can be directed to a promoter, intron, or coding sequence of a gene within the isobutyraldehyde pathway. If targeting the promoter, intron, or coding sequence of a gene within the isobutyraldehyde pathway, the promoter, intron or coding sequence can be from the genes encoding an acetolactate synthase (AlsS), ketol-acid reductoisomerase (IlvC), dihydroxy-acid dehydratase (IlvD), and 2-keto acid decarboxylase (KDC).

In some cases, the polynucleotide encoding for a gRNA can be directed to a promoter, intron, or coding sequence of a gene within the isobutanol pathway. If targeting the promoter, intron, or coding sequence of a gene within the isobutanol pathway, the promoter, intron or coding sequence can be from the genes encoding an AlsS, IlvC, IlvD, KDC, or Adh.

In some cases, the microorganism used has a lower transformation efficiency compared to an *E. coli* bacterium. The transformation efficiency of the microorganism is increased prior to trying to transform the microorganism with any nucleic acids.

In some cases, the polynucleotide encoding for the gRNA can be transformed prior to the polynucleotide encoding for a Cas enzyme. Additionally, the method can further comprise contacting the microorganism with a donor polynucleotide. In some cases, the microorganism is contacted with the donor polynucleotide prior to being contacted with a polynucleotide encoding for a Cas enzyme. In some cases, the microorganism is contacted concurrently with the donor polynucleotide and the polynucleotide encoding for a gRNA. In some cases, the donor polynucleotide and the polynucleotide encoding for a gRNA are on a single plasmid. The donor polynucleotides used in the methods can be less than 1000 bases. For example, the donor polynucleotide can be less than 600 bases. In some cases, the donor polynucleotide can be less than 100 bases.

In some cases, the polynucleotide encoding for a Cas enzyme can be within a plasmid. The plasmid in some cases does not comprise a strong promoter. In some cases, the plasmid can comprise a mutated promoter. In some cases, the promoter can be a pMxaF promoter.

Also disclosed is a genetically modified microorganism capable of converting a $C_1$ carbon to a multicarbon product comprising a nucleic acid encoding a heterologous Cas enzyme. The genetically modified microorganism can be a methylotroph, such as a methanotroph or any of the genus and/or species described throughout. The $C_1$ carbon is carbon monoxide (CO), carbon dioxide ($CO_2$), methane ($CH_4$), any combination thereof, or any $C_1$ described throughout.

In some cases, the genetically modified microorganism comprises a heterologous Cas enzyme. Any of the Cas enzymes described throughout can be used. The Cas enzymes can be expressed in a plasmid. The plasmids can also include a stronger, mutated, and/or pMxaF promoter.

In some cases, the genetically modified microorganism can further comprise a polynucleotide encoding for a gRNA. In some cases, the genetically modified microorganism can comprise a polynucleotide encoding for a gRNA that is at least partially homologous to a portion of a promoter, intron, or coding sequence of an rpoB gene or a gene within the 2,3-BDO, 1,4-BDO, isobutyraldehyde, or isobutanol pathway. For example, the polynucleotide encoding for a gRNA can be at least partially homologous to a promoter, intron, or coding sequence of rpoB.

In some cases, the genetically modified microorganism can have a lower transformation efficiency compared to an *E. coli* bacteria. However, before transformation with nucleic acids, the transformation efficiency of the microorganism can be increased.

In some cases, the microorganism can comprise a point mutation compared to a wild-type microorganism of the same species. For example, the point mutation can be within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, the microorganism can comprise a deletion of one or more nucleotides compared to a wild-type microorganism of the same species. For example, the deletion of one or more nucleotides can be within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, the microorganism can comprise an addition of one or more nucleotides compared to a wild-type microorganism of the same species. For example, the addition of one or more nucleotides can be within a promoter, intron, or coding sequence of an rpoB gene or a gene within the 2,3-butanediol (2,3-BDO), 1,4-butanediol (1,4-BDO), isobutyraldehyde, or isobutanol pathway.

Also disclosed herein is a method of replacing a single nucleotide within the genome of a microorganism that is capable of converting a $C_1$ carbon to a multicarbon product comprising: (a) contacting the microorganism with a polynucleotide encoding for i) a Cas enzyme and ii) a polynucleotide encoding for a gRNA; and (b) growing the microorganism until a single nucleotide is replaced within the genome of the microorganism.

In some cases, the microorganism can be a methylotroph, such as a methanotroph or any microorganism described throughout. In some cases, the $C_1$ carbon can be any $C_1$ carbon described throughout. In some cases, the Cas enzyme can be any described throughout, such as a Cas9 enzyme. The Cas enzymes can be expressed in a plasmid. The plasmids can also include a stronger, mutated, and/or pMxaF promoter. In some cases, the polynucleotide encoding for a gRNA is at least partially complementary to a polynucleotide that is within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, the polynucleotide encoding for a gRNA is transformed prior to the polynucleotide encoding for a Cas enzyme. In some instances, the method can further comprise contacting the microorganism with a donor polynucleotide. For example, the microorganism can be contacted with the donor polynucleotide prior to being contacted with a polynucleotide encoding for a Cas enzyme. In some cases, the microorganism can be contacted concurrently with the donor polynucleotide and polynucleotide encoding for a gRNA. In some cases, the donor polynucleotide and polynucleotide encoding for a gRNA are contained on a single plasmid. In some cases, the donor polynucleotide can be less than 1000 bases. For example, the donor polynucleotide can be less than 600 bases. In some cases, the donor polynucleotide is can be less than 100 bases.

In some cases, the replacement of a single nucleotide can result in a different nucleotide. In some cases, the replacement occurs at a single nucleotide within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, as a result of the single nucleotide replacement, the expression of one or more genes can be changed. Additionally, in some cases, the replacement can change the activity of one or more enzymes.

Also disclosed herein is a method of removing one or more nucleotides from the genome of a genetically modified microorganism that is capable of converting a $C_1$ carbon to a multicarbon product comprising: (a) contacting the microorganism with a polynucleotide encoding for i) a Cas enzyme and ii) a polynucleotide encoding for a gRNA; and (b) growing the microorganism until one or more nucleotides within the genome of the microorganism is removed.

In some cases, the microorganism can be a methylotroph, such as a methanotroph or any microorganism described throughout. In some cases, the $C_1$ carbon can be any $C_1$ carbon described throughout. In some cases, the Cas enzyme can be any described throughout, such as a Cas9 enzyme. The Cas enzymes can be expressed in a plasmid. The plasmids can also include a stronger, mutated, and/or pMxaF promoter. In some cases, the polynucleotide encoding for a gRNA is at least partially complementary to a polynucleotide that is within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, two or more nucleotides are removed from the targeted nucleic acid. For example, the removal of two or more nucleotides can occur within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, the polynucleotide encoding for a gRNA is transformed prior to the polynucleotide encoding for a Cas enzyme. In some instances, the method can further comprise contacting the microorganism with a donor polynucleotide. For example, the microorganism can be contacted with the donor polynucleotide prior to being contacted with a polynucleotide encoding for a Cas enzyme. In some cases, the microorganism can be contacted concurrently with the donor polynucleotide and polynucleotide encoding for a gRNA. In some cases, the donor polynucleotide and polynucleotide encoding for a gRNA are contained on a single plasmid. In some cases, the donor polynucleotide can be less than 1500 bases. In some cases, the donor polynucleotide can be less than 1000 bases. For example, the donor polynucleotide can be less than 600 bases. In some cases, the donor polynucleotide is can be less than 100 bases.

In some cases, the removal of one or more nucleotides can change the expression of one or more genes. In some cases, the removal of one or more nucleotides can change the activity of one or more enzymes.

Disclosed herein is a method of adding one or more nucleotides to the genome of a microorganism capable of converting a $C_1$ carbon to a multicarbon product comprising: (a) contacting the microorganism with a polynucleotide encoding for i) a Cas enzyme and ii) a polynucleotide encoding for a gRNA; and (b) growing the microorganism until one or more nucleotides is added to the genome of the microorganism.

In some cases, the microorganism can be a methylotroph, such as a methanotroph or any microorganism described throughout. In some cases, the $C_1$ carbon can be any $C_1$ carbon described throughout. In some cases, the Cas enzyme can be any described throughout, such as a Cas9 enzyme. The Cas enzymes can be expressed in a plasmid. The plasmids can also include a stronger, mutated, and/or pMxaF promoter. In some cases, the polynucleotide encoding for a gRNA is at least partially complementary to a polynucleotide that is within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, two or more nucleotides can be added to a target nucleic acid. For example, the addition of one or more nucleotides can occur within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, the polynucleotide encoding for a gRNA is transformed prior to the polynucleotide encoding for a Cas enzyme. In some instances, the method can further comprise contacting the microorganism with a donor polynucleotide. For example, the microorganism can be contacted with the donor polynucleotide prior to being contacted with a polynucleotide encoding for a Cas enzyme. In some cases, the microorganism can be contacted concurrently with the donor polynucleotide and polynucleotide encoding for a gRNA. In some cases, the donor polynucleotide and polynucleotide encoding for a gRNA are contained on a single plasmid. In some cases, the donor polynucleotide can be less than 1500 bases. In some cases, the donor polynucleotide can be less than 1000 bases. For example, the donor polynucleotide can be less than 600 bases. In some cases, the donor polynucleotide is can be less than 100 bases.

In some cases, the addition of one or more nucleotides can change the expression of one or more genes. In some cases, the addition of one or more nucleotides can change the activity of one or more enzymes.

Also disclosed herein is a method of inhibiting expression of a gene within a methylotroph comprising contacting the methylotroph with a polynucleotide encoding for i) a modified Cas enzyme and ii) a polynucleotide encoding for a gRNA, where the modified Cas enzyme does not cleave nucleic acids.

In some cases, the microorganism can be a methylotroph, such as a methanotroph or any microorganism described throughout. In some cases, the modified Cas enzyme can be any described throughout, such as a modified Cas9 enzyme. In some cases, the Cas enzyme can be expressed within a plasmid. In some cases, the polynucleotide encoding for a gRNA is at least partially complementary to a polynucleotide that is within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, the inhibition of gene expression is greater than 10% compared to a wild-type microorganism of the same species. For example, the inhibition of gene expression is greater than 50% compared to a wild-type microorganism of the same species.

Also disclosed herein is a vector comprising a polynucleotide encoding for a Cas9 enzyme, where the Cas9 enzyme is capable of being expressed in a methylotroph, such as a methanotroph (e.g., a methanotroph from the genus *Methylococcus*).

Further disclosed herein is a method of screening for genome editing in a methylotroph comprising contacting the methylotroph with a first polynucleotide encoding for a gRNA, and subsequently with a second polynucleotide encoding a Cas9 enzyme, where the first polynucleotide encoding for a gRNA is at least partially complementary to a polynucleotide that is within a promoter, intron, or coding sequence of an rpoB gene. In some cases, the methylotroph can be a methanotroph, for example from the genus *Methylococcus*.

In some cases, the Cas enzyme can be any Cas enzyme disclosure throughout, such as a Cas9 enzyme. In some cases, the Cas enzyme can be expressed within a plasmid.

The method used herein can produce colonies when plated. These can be referred to as colony forming units (CFU). In some cases, the method described herein can produce CFU that are decreased by at least 1.1 fold. In some cases, the CFU can be decreased by at least 2 fold. In some cases, the CFU can be decreased by at least 3 fold. In some cases, the CFU can be decreased by at least 4 fold.

DETAILED DESCRIPTION OF THE INVENTION

Figure 1:
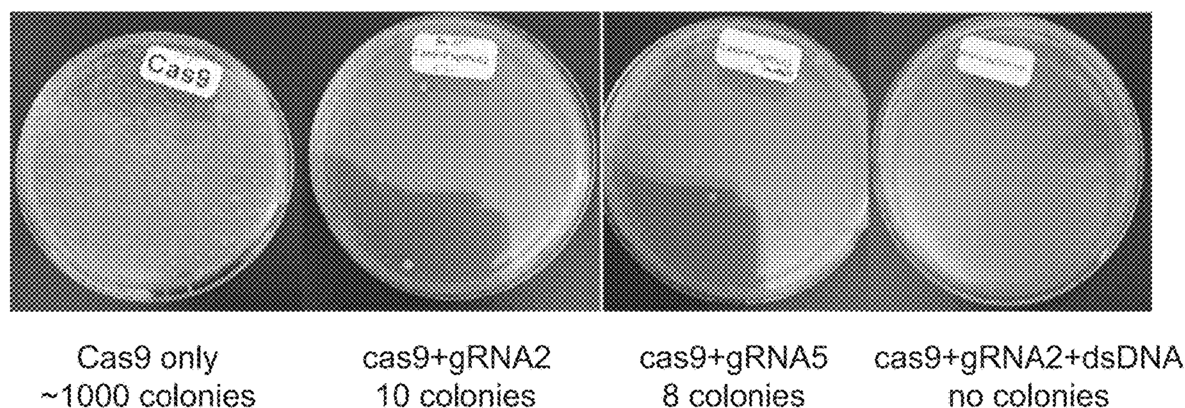
FIG. 1 depicts plates of *Methylococcus capsulatus* colonies. *Methylococcus capsulatus* were transformed with a plasmid expressing: 1) Cas9 only; 2) Cas9+gRNA2; 3) Cas9+gRNA5; or 4) Cas9+gRNA2+double stranded DNA (dsDNA). *Methylococcus capsulatus* that were transformed with all three (i.e., group 4) did not produce any colonies, indicating a lack of gene editing. The other groups, which are negative controls, grew colonies indicating an off target effect.

As summarized above, aspects of the invention include genetically modified microorganisms that are produced using advanced genomic editing tools. The genetically modified microorganisms include methylotrophs, such as methanotrophs, which are capable of using a $C_1$ carbon source, such as methane, as the primary carbon source for the organism. Additionally, as summarized above, advanced genome editing tools can be used to inhibit the expression of a gene.

Advanced genome editing can be used in many ways to alter the genome of a microorganism. For example, advanced genome editing can be used to generate a point mutation at any sequence within the genome. Additionally, advanced genome editing can be used to add one or more nucleotides to any sequence within a genome.

The precision, accuracy, and efficacy of the advanced genome editing is very high compared to that of traditional methods of genetic engineering.

Before the present invention is described in greater detail, it is to be understood that this invention is not limited to particular cases described, as such can, of course, vary. It is also to be understood that the terminology used herein is for the purpose of describing particular cases only, and is not intended to be limiting, since the scope of the present invention will be limited only by the appended claims.

I. Definitions

The term "about" in relation to a reference numerical value and its grammatical equivalents as used herein can include the numerical value itself and a range of values plus or minus 10% from that numerical value. For example, the amount "about 10" includes 10 and any amounts from 9 to 11. For example, the term "about" in relation to a reference numerical value can also include a range of values plus or minus 10%, 9%, 8%, 7%, 6%, 5%, 4%, 3%, 2%, or 1% from that value. In some cases, the numerical disclosed throughout can be "about" that numerical value even without specifically mentioning the term "about."

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The phrases "recombinant host cell," "genetically engineered host cell," "engineered host cell," "genetically modified host cell," and their grammatical equivalents as used herein may be used interchangeably and can refer to host cells that have been genetically modified to: (a) express one or more exogenous polynucleic acids; (b) over-express one or more endogenous and/or one or more exogenous polynucleic acids, such as those included in a vector, or which have an alteration in expression of an endogenous gene; or (c) knock-out or down-regulate an endogenous gene. In addition, certain genes may be physically removed from the genome (e.g., knock-outs) or they may be engineered to have reduced, altered or enhanced activity. The phrases "recombinant host cell," "genetically engineered host cell," "engineered host cell," and "genetically modified host cell" refer not only to the particular subject host cell, but to the progeny or potential progeny of such a cell. Because certain modifications may occur in succeeding generations due to either mutation or environmental influences, such progeny may not, in fact, be identical to the parent cell, but are still included within the scope of the term(s) as used herein.

The terms "engineer," "genetically engineer," "modify," "genetically modify," and their grammatical equivalents as used herein can refer to any manipulation of a microorganism that results in a detectable change in the microorganism, where the manipulation includes, but is not limited to, introducing non-native metabolic functionality via heterologous (exogenous) polynucleic acids or removing native-functionality via polynucleic acid deletions, mutations or knock-outs. The term "metabolically engineered" generally involves rational pathway design and assembly of biosynthetic genes (or open reading frames), genes associated with operons, and control elements of such polynucleic acids, for the production of a desired metabolite. "Metabolically engineered" may further include optimization of metabolic flux by regulation and optimization of transcription, translation, protein stability and protein functionality using genetic engineering and appropriate culture condition including the reduction of, disruption, or knocking out of, a competing metabolic pathway that competes with an intermediate leading to a desired pathway.

As used herein, the terms "genetic modification," "genetically modified" and their grammatical equivalents can refer to any modification of a polynucleic acid and/or polypeptide that results in an altered nucleic acid or polypeptide (i.e., relative to the wild-type nucleic acid or polypeptide sequence). Genetic modification includes, for example, point mutations, substitutions, deletions, or insertions of single or multiple residues in a polynucleic acid (or the encoded polypeptide), which includes alterations arising within a protein-encoding region of a gene as well as alterations in regions outside of a protein-encoding sequence, such as, but not limited to, regulatory or promoter sequences. A genetic modification may be an alteration of any type. For instance, the modification may be a deletion, insertion, mutation, rearrangement, or any combination thereof. In certain cases, a portion of a genetically modified microorganism's genome may be replaced with one or more heterologous (exogenous) polynucleic acids. In some cases, the modification is naturally-occurring. In other cases, the modification is the result of artificial selection pressure. In still other cases, the modification is the result of genetic engineering. One form of genetic modification is disruption, such as by knockout. As used herein, the term "introducing," as used in phrases such as "introducing into the host cell" at least one polynucleic acid includes methods known in the art for introducing polynucleic acids into a cell, including, but not limited to transformation (e.g., calcium chloride, electroporation), transduction, transfection, conjugation and the like.

The term "genetic modification" or "genetically modified" and their grammatical equivalents as used herein can refer to one or more alterations of a nucleic acid, e.g., the nucleic acid within a microorganism's genome. For example, genetic modification can refer to alterations, additions, and/or deletion of nucleic acid (e.g., whole genes or fragments of genes).

The term "disrupting" and its grammatical equivalents as used herein can refer to a process of altering a gene, e.g., by deletion, insertion, mutation, rearrangement, or any combination thereof. For example, a gene can be disrupted by knockout. Disrupting a gene can be partially reducing or completely suppressing expression (e.g., mRNA and/or protein expression) of the gene. Disrupting can also include inhibitory technology, such as shRNA, siRNA, microRNA, dominant negative, or any other means to inhibit functionality or expression of a gene or protein.

The term "gene editing" and its grammatical equivalents as used herein can refer to genetic engineering in which one or more nucleotides are inserted, replaced, or removed from a genome. For example, gene editing can be performed using a nuclease (e.g., a natural-existing nuclease or an artificially engineered nuclease).

As used herein, the term "endogenous," and its grammatical equivalents when used in reference to polynucleic acids (and the polypeptides encoded therein), can refer to polynucleic acids and polypeptides that are expressed in the organism in which they originated (i.e., they are innate to the organism). In contrast, the terms "heterologous" and "exogenous" are used interchangeably, and as defined herein with reference to polynucleic acids (and the polypeptides encoded therein), indicates polynucleic acids and polypeptides that are expressed in an organism other than the organism from which they (i.e., the polynucleic acid or polypeptide sequences) originated or where derived.

As used herein, the term "homolog" and its grammatical equivalents, as used with respect to an original protein, polypeptide, gene, or polynucleic acid (or ORF encoding the same) of a first family or species, can refer to distinct proteins, genes, or polynucleic acids of a second family or species that correspond (structurally, functionally, and/or genomically) to the original protein, gene, or polynucleic acid of the first family or species. Most often, "homologs" will have functional, structural or genomic similarities. Techniques are known by which homologs of a protein, gene or polynucleic acid can readily be cloned using genetic probes and PCR. Identity of cloned sequences as "homologs" can be confirmed using functional assays and/or by genomic mapping of the genes.

As used herein, the term "strong promoter" and its grammatical equivalents as used herein can refer to a promoter that has the ability to increase the transcription at a high level. For example, pMxaF, J2311, J12100, and J23102 each can be considered a strong promoter. As used herein, the term "weak promoter" and its grammatical equivalents as used herein can refer to a promoter that has the ability to increase the transcription, but at a low level. For example, pBAD, J23110, lacO, J23116, J23106, J23105, J23108, J23107, J23115, and J23114 can each be considered a weak promoter. Additionally, the term "medium strength promoter" and its grammatical equivalents, as used herein can refer to a promoter that has the ability to increase the transcription at a level that is less than what is considered high but higher than what is considered low. For example, J23118, J23104, J23101, J23119, and uMCA3034, can each be considered a medium strength promoter. In some cases, medium strength promoters can be used in lieu of strong or weak promoters.

The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C."

As used herein, the term "substantially similar" and its grammatical equivalents, when used in reference to the similarity between a sequence and a reference sequence, means that the sequences are at least 50% (but not 100%) identical. In some cases, the sequences are 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.9%, 99.99%, 99.999%, or 99.9999% identical. In some cases, the term substantially similar refers to a sequence that is at least 50% identical. In some instances, the term substantially similar refers to a sequence that is 55% identical. In some instances, the term substantially similar refers to a sequence that is 60% identical. In some instances, the term substantially similar refers to a sequence that is 65% identical. In some instances, the term substantially similar refers to a sequence that is 70% identical. In some instances, the term substantially similar refers to a sequence that is 75% identical. In some instances, the term substantially similar refers to a sequence that is 80% identical. In other instances, the term substantially similar refers to a sequence that is 81% identical. In other instances, the term substantially similar refers to a sequence that is 82% identical. In other instances, the term substantially similar refers to a sequence that is 83% identical. In other instances, the term substantially similar refers to a sequence that is 84% identical. In other instances, the term substantially similar refers to a sequence that is 85% identical. In other instances, the term substantially similar refers to a sequence that is 86% identical. In other instances, the term substantially similar refers to a sequence that is 87% identical. In other instances, the term substantially similar refers to a sequence that is 88% identical. In other instances, the term substantially similar refers to a sequence that is 89% identical. In some instances, the term substantially similar refers to a sequence that is 90% identical. In some instances, the term substantially similar refers to a sequence that is 91% identical. In some instances, the term substantially similar refers to a sequence that is 92% identical. In some instances, the term substantially similar refers to a sequence that is 93% identical. In some instances, the term substantially similar refers to a sequence that is 94% identical. In some instances, the term substantially similar refers to a sequence that is 95% identical. In some instances, the term substantially similar refers to a sequence that is 96% identical. In some instances, the term substantially similar refers to a sequence that is 97% identical. In some instances, the term substantially similar refers to a sequence that is 98% identical. In some instances, the term substantially similar refers to a sequence that is 99% identical. In some instances, the term substantially similar refers to a sequence that is 99.9% identical. In some instances, the term substantially similar refers to a sequence that is 99.99% identical. In some instances, the term substantially similar refers to a sequence that is 99.999% identical. In some instances, the term substantially similar refers to a sequence that is 99.9999% identical. To determine the percentage of identity between two sequences, the two sequences are aligned, using, for example, the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids/nucleotides is determined between the two sequences. Methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Molec. Biol., 1990:215:403). A particularly preferred method for determining the percentage identity between two polypeptides involves the Clustal W algorithm (Thompson, J D, Higgines, D G and Gibson T J, 1994, Nucleic Acid Res 22(22): 4673-4680 together with the BLOSUM 62 scoring matrix (Henikoff S & Henikoff, J G, 1992, Proc. Natl. Acad. Sci. USA 89: 10915-10919) using a gap opening penalty of 10 and a gap extension penalty of 0.1, so that the highest order match obtained between two sequences where at least 50% of the total length of one of the two sequences is involved in the alignment.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

As will be apparent to those of skill in the art upon reading this disclosure, each of the individual cases described and illustrated herein has discrete components and features which may be readily separated from or combined with the features of any of the other several cases without departing from the scope or spirit of the present invention. Any recited method can be carried out in the order of events recited or in any other order which is logically possible.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

II. Genetically Modified Microorganisms and Methods of Making the Same

The present disclosure is directed, in part, to genetically modified microorganisms that have been modified using advanced genome editing techniques.

Microorganisms

In some cases, the microorganisms can use $C_1$ carbon substrates, such as CO, $CO_2$, and $CH_4$, to synthesize a desired end product. This, however, does not mean that these microorganisms use solely $C_1$ carbons. Some of the microorganisms can be made to utilize additional carbon substrates, including carbon substrates that the microorganism naturally uses. For example, if the microorganism naturally uses sugar for carbon substrates, this microorganism can be made to utilize a different carbon source such as a $C_1$ carbon.

The microorganisms can be a prokaryote or a eukaryote. In some cases, for example, the microorganisms can be bacteria, yeast, or algae.

Microorganisms that can convert $C_1$ carbon substrates into desired products include those capable of using natural gas as a carbon substrate. For example, the microorganism can use methane contained within the natural gas as a carbon source to make such desired products. Such microorganisms can include methanotrophs. Methanotrophs that can be particularly useful include those from the genera *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis, Methyloacidophilum*, or any combinations thereof. In some cases, the methanotroph is from the genus *Methylococcus*. In one instance, the methanotroph can be a methanotroph from the species *Methylococcus capsulatus*. In some cases, the methanotroph can be an obligate methanotroph. In other cases, the methanotroph can be a facultative methanotroph.

Some microorganisms are capable of using $CO_2$ as a substrate. Such microorganisms include methanogens.

Microorganisms that are capable of using $CO_2$ as a substrate can contain chlorophyll. Examples thereof include algae and cyanobacteria.

Some microorganisms are capable of using CO as a substrate. Examples include anaerobic microorganisms such as *Clostridium*. These microorganism can be genetically modified so as to make substantial amounts of 2,3-BDO.

In some cases, the microorganism used in the methods described throughout can be one that does not naturally express any Cas enzymes. In this case, any Cas enzymes that are present within the microorganism are heterologous to that microorganism.

In some cases, the heterologous Cas enzyme that is present within the microorganism can be expressed within a plasmid. The plasmids expressing the heterologous Cas enzyme can comprise a promoter, including but not limited to such promoters as a pMxaF or pBAD promoter. In some cases however, the plasmid does not comprise a strong promoter, for example a weak promoter. In some cases, the plasmid can comprise a mutated promoter. For example, the promoter can be a mutated promoter, such as a mutated pMxaF promoter. In some cases, the mutation contained in the promoter can make the promoter weaker.

Nucleic Acids Encoding for Enzymes

Certain enzymes can be used to generate useful chemical products. Some useful chemical products can include, but are not limited to, isobutanol, isobutyraldehyde, 2,3-butanediol (2,3-BDO), and 1,4-butanediol (1,4-BDO). In some cases, certain proteins, such as RNA polymerase beta-subunits (EC:2.7.7.6) (encoded by such genes as rpoB or rpoB2) can confer to a microorganism resistance to some antibiotics, such as rifampin. In some cases, the polynucleotide of the promoters or introns of these enzymes can be altered by using the techniques described throughout.

Isobutanol

In some cases, polynucleotides encoding for enzymes of the isobutanol pathway can be used. For example, the microorganism can contain (either endogenously or heterologous) one or more polynucleotides encoding for an acetolactate synthase (AlsS); ketol-acid reductoisomerase (KARI); dihydroxy-acid dehydratase (DHAD); 2-keto acid decarboxylase (KDC); and alcohol dehydrogenase (ADH). One or more of the polynucleotides can be native to the microorganism. In some cases, one or more of the polynucleotides can be heterologous to the microorganism.

In some cases, the acetolactate synthase (AlsS) can be encoded by a polynucleotide that is substantially similar to a gram positive bacterium AlsS gene. In some cases, the AlsS can be encoded by a polynucleotide that is substantially similar to SEQ ID NO: 1. In some other cases, the AlsS can be encoded by a polynucleotide that is substantially similar to SEQ ID NO: 2.

In some cases, the ketol-acid reductoisomerase can be encoded by a polynucleotide that is substantially similar to a gram negative bacterium ketol-acid reductoisomerase gene. In some cases, the ketol-acid reductoisomerase can be encoded by a polynucleotide that is substantially similar to SEQ ID NO: 3.

In some cases, the dihydroxy-acid dehydratase can be encoded by a polynucleotide that is substantially similar to a gram negative bacterium dihydroxy-acid dehydratase gene. In some cases, the dihydroxy-acid dehydratase can be encoded by a polynucleotide that is substantially similar to SEQ ID NO: 4. In some cases, the dihydroxy-acid dehydratase can be encoded by a polynucleotide that is substantially similar to SEQ ID NO: 5.

In some cases, the 2-keto acid decarboxylase (KDC) can be encoded by a polynucleotide that is substantially similar to a gram positive bacterium KDC gene. In some cases, the KDC can be encoded by a polynucleotide that is substantially similar to any one of SEQ ID NOs: 6 to 29.

In some cases, the alcohol dehydrogenase (ADH) can be encoded by a polynucleotide that is substantially similar to a gram positive or gram negative bacterium ADH gene. In some cases, the ADH can be encoded by a polynucleotide that is substantially similar to any one of SEQ ID NOs: 30 to 48.

In some cases, the promoters and/or the introns of the isobutanol pathway genes can be altered using the advance genome editing tools described herein. This alteration may enhance the expression of the genes that are controlled by the promoters and/or introns. In some cases, the alternation may inhibit the expression of the genes that are controlled by the promoters and/or introns.

In some cases, the codons can be optimized based on the microorganism in which the genes will be provided or the enzymes will be expressed.

Isobutyraldehyde

In some instances, polynucleotides encoding enzymes of the isobutyraldehyde pathway can be used. For example, the microorganism can contain (either endogenously or heterologous) one or more polynucleotides encoding for an acetolactate synthase (AlsS); ketol-acid reductoisomerase; dihydroxy-acid dehydratase; and 2-keto acid decarboxylase (KDC). One or more of the polynucleotides can be native to the microorganism. In some cases, one or more of the polynucleotides can be heterologous to the microorganism.

In some cases, the acetolactate synthase (AlsS) can be encoded by a polynucleotide that is substantially similar to a gram positive bacterium AlsS gene. In some cases, the AlsS can be encoded by a polynucleotide that is substantially similar to SEQ ID NO: 1. In some other cases, the AlsS can be encoded by a polynucleotide that is substantially similar to SEQ ID NO: 2.

In some cases, the ketol-acid reductoisomerase can be encoded by a polynucleotide that is substantially similar to a gram negative bacterium ketol-acid reductoisomerase gene. In some cases, the ketol-acid reductoisomerase can be encoded by a polynucleotide that is substantially similar to SEQ ID NO: 3.

In some cases, the dihydroxy-acid dehydratase can be encoded by a polynucleotide that is substantially similar to a gram negative bacterium dihydroxy-acid dehydratase gene. In some cases, the dihydroxy-acid dehydratase can be encoded by a polynucleotide that is substantially similar to SEQ ID NO: 4. In some cases, the dihydroxy-acid dehydratase can be encoded by a polynucleotide that is substantially similar to SEQ ID NO: 5.

In some cases, the 2-keto acid decarboxylase (KDC) can be encoded by a polynucleotide that is substantially similar to a gram positive bacterium KDC gene. In some cases, the KDC can be encoded by a polynucleotide that is substantially similar to any one of SEQ ID NOs: 6 to 29.

In some cases, the promoters and/or the introns of the isobutyraldehyde pathway genes can be altered using the advance genome editing tools described herein. This alteration may enhance the expression of the genes that are controlled by the promoters and/or introns. In some cases, the alternation may inhibit the expression of the genes that are controlled by the promoters and/or introns.

In some cases, the codons can be optimized based on the microorganism in which the genes will be provided or the enzymes will be expressed.

2,3-BDO

In some instances, polynucleotides encoding enzymes of the 2,3-BDO pathway can be used. For example, the microorganism can contain (either endogenously or heterologous) one or more polynucleotides encoding for an acetolactate synthase (AlsS), alpha-acetolactate decarboxylase (budA), and/or acetoin reductase. One or more of the polynucleotides can be native to the microorganism. In some cases, one or more of the polynucleotides can be heterologous to the microorganism.

In some cases, the acetolactate synthase can be encoded by a polynucleotide that is substantially similar to any one of SEQ ID NOs: 49 to 51.

In some cases, the alpha-acetolactate decarboxylase can be encoded by a polynucleotide that is substantially similar to SEQ ID NO: 52 or 53.

In some cases, the acetoin reductase can be encoded by a polynucleotide that is substantially similar to any one of SEQ ID NOs: 54 to 56. In some cases, the acetoin reductase can be NADPH-dependent. In some cases, the acetoin reductase can be NADH-dependent.

In some cases, the promoters and/or the introns of the 2,3-BDO pathway genes can be altered using the advance genome editing tools described herein.

In some cases, the codons can be optimized based on the microorganism in which the genes will be provided or the enzymes will be expressed.

1,4-BDO

In some instances, polynucleotides encoding enzymes of the 1,4-BDO pathway can be used. For example, the microorganism can contain (either endogenously or heterologous) one or more polynucleotides encoding for a pyruvate dehydrogenase (aceEF), citrate synthase (gltA), aconitate hydratase 1 (acnA), isocitrate dehydrogenase (icdA), α-ketoglutarate decarboxylase (kgd), succinyl-CoA synthetase (sucC), CoA-dependent succinate semialdehyde dehydrogenase (sucD), 4-hyrobutyrate dehydrogenase (4hbD), 4-hydroxybutyryl-CoA transferase (cat2), aldehyde dehydrogenase (ald), and/or alcohol dehydrogenase (adh).

In some cases, the α-ketoglutarate decarboxylase (kgd) can be encoded by a polynucleotide that is substantially similar to any one of SEQ ID NOs: 57 to 60.

In some cases, the 4-hydroxybutyrate dehydrogenase (4hbD) can be encoded by a polynucleotide that is substantially similar to SEQ ID NO. 61 or 62.

In some cases, the 4-hydroxybutyrate CoA transferase (Cat2) can be encoded by a polynucleotide that is substantially similar to any one of SEQ ID NOs: 63 to 65.

In some cases, the aldehyde dehydrogenase gene and/or alcohol dehydrogenase can be encoded by a polynucleotide that is substantially similar to any one of SEQ ID NOs: 66 to 73.

In some cases, the succinyl CoA synthease beta subunit (sucC) can be encoded by a polynucleotide that is substantially similar to SEQ ID NO: 74.

In some cases, the succinyl CoA synthease alpha subunit (sucD) can be encoded by a polynucleotide that is substantially similar to any one of SEQ ID NOs: 75 to 77.

In some cases, the promoters and/or the introns of the 1,4-BDO pathway genes can be altered using the advance genome editing tools described herein.

In some cases, the codons can be optimized based on the microorganism in which the genes will be provided or the enzymes will be expressed.

RNA Polymerase Beta-Subunits

In some cases, polynucleotides encoding for RNA polymerase beta-subunits can be used. RNA polymerase beta-subunits (e.g., those with an EC:2.7.7.6) can be used to confer onto a microorganism resistance to some antibiotics, such as rifampin. In some cases, RNA polymerase beta-subunits can be expressed endogenously by a microorganism. Repression or knocking out of the genes encoding RNA polymerase beta-subunits (including but not limited to RNA polymerase beta-subunits encoded by such genes as rpoB or rpoB2) can lead to the loss of resistance to such antibiotics, such as rifampin. In these cases, repressing or knocking out of the genes encoding RNA polymerase beta-subunits can lead to cell death.

The microorganism can contain (either endogenously or heterologous) one or more polynucleotides encoding for RNA polymerase beta-subunits. One or more of the polynucleotides can be native to the microorganism. In some cases, one or more of the polynucleotides can be heterologous to the microorganism.

In some cases, the RNA polymerase beta-subunits can be encoded by a polynucleotide that is substantially similar to SEQ ID NO: 123 or 126. In some cases, the gRNA used can be substantially similar to SEQ ID NO: 124 or 125.

In some cases, the donor DNA can be substantially similar to SEQ ID NO: 126.

In some cases, the promoters and/or the introns of the RNA polymerase beta-subunits gene(s) can be altered using the advance genome editing tools described herein. This alteration may enhance the expression of the genes that are controlled by the promoters and/or introns. In some cases, the alternation may inhibit the expression of the genes that are controlled by the promoters and/or introns.

In some cases, the codons can be optimized based on the microorganism in which the genes will be provided or the enzymes will be expressed.

Vectors

Since Cas enzymes are not native to some microorganisms, expression vectors can be used to express Cas enzymes within most microorganisms and cells. Methylotrophs such as methanotrophs do not naturally express Cas enzymes. Therefore, in some cases, the Cas enzymes can be expressed using certain expression vectors. Vector constructs prepared for introduction into the host microorganisms described throughout may typically, but not always, comprise a replication system (i.e. vector) recognized by the host. In some cases, the vector includes the intended polynucleotide fragment encoding the desired polypeptide and, optionally, transcription and translational initiation regulatory sequences operably linked to the polypeptide-encoding segment. Expression vectors may include, for example, an origin of replication or autonomously replicating sequence (ARS), expression control sequences, a promoter, an enhancer and necessary processing information sites, such as ribosome-binding sites, RNA splice sites, polyadenylation sites, transcriptional terminator sequences, mRNA stabilizing sequences, polynucleotides homologous to host chromosomal DNA, and/or a multiple cloning site. Signal peptides may also be included where appropriate, preferably from secreted polypeptides of the same or related species, which allow the protein to cross and/or lodge in cell membranes or be secreted from the cell.

The vectors can be constructed using standard methods (see, e.g., Sambrook et al., Molecular Biology: A Laboratory Manual, Cold Spring Harbor, N.Y. 1989; and Ausubel, et al., Current Protocols in Molecular Biology, Greene Publishing, Co. N.Y, 1995).

Manipulation of polynucleotides that encode the enzymes disclosed throughout is typically carried out in recombinant vectors. Vectors which may be employed include bacterial plasmids, bacteriophage, artificial chromosomes, episomal vectors and gene expression vectors. Vectors may be selected to accommodate a polynucleotide encoding a protein of a desired size. Following production of a selected vector, a suitable host cell (e.g., the microorganisms described herein) is transfected or transformed with the vector. Each vector contains various functional components, which generally include a cloning site, an origin of replication and at least one selectable marker gene. A vector may additionally possess one or more of the following elements: an enhancer, promoter, a transcription termination sequence and/or other signal sequences. Such sequence elements may be optimized for the selected host species. Such sequence elements may be positioned in the vicinity of the cloning site, such that they are operatively linked to the gene encoding a preselected enzyme.

Vectors, including cloning and expression vectors, may contain polynucleotides that enable the vector to replicate in one or more selected microorganisms. For example, the sequence may be one that enables the vector to replicate independently of the host chromosomal DNA and may include origins of replication or autonomously replicating sequences. Such sequences are well known for a variety of bacteria, yeast and viruses. For example, the origin of replication from the plasmid pBR322 is suitable for most gram-negative bacteria, the origin of replication for 2 micron plasmid is suitable for yeast, and various viral origins of replication (e.g. SV40, adenovirus) are useful for cloning vectors.

A cloning or expression vector may contain a selection gene, also referred to as a selectable marker. This gene encodes a protein necessary for the survival or growth of transformed microorganisms in a selective culture medium. Microorganisms not transformed with the vector containing the selection gene will therefore not survive in the culture medium. Typical selection genes encode proteins that confer resistance to antibiotics and other toxins, e.g. ampicillin, neomycin, methotrexate, hygromycin, thiostrepton, apramycin or tetracycline, complement auxotrophic deficiencies, or supply critical nutrients not available in the growth media.

The replication of vectors may be performed in *E. coli*. An example of a *E. coli*-selectable marker is the β-lactamase gene, which confers resistance to the antibiotic ampicillin. These selectable markers can be obtained from *E. coli* plasmids, such as pBR322 or a pUC plasmid such as pUC18 or pUC19, or pUC119.

The vectors of the present invention can comprise one or more switches, such as an inducible or repressible switch, e.g., an arabinose or lanthanum switch. The vectors can also comprise one or more different/same promoters.

Promoters

Vectors may contain a promoter that is recognized by the host microorganism. The promoter may be operably linked to a coding sequence of interest. Such a promoter may be inducible or constitutive. Polynucleotides are operably linked when the polynucleotides are in a relationship permitting them to function in their intended manner.

Different promoters can be used to drive the expression of the genes. For example, if temporary gene expression (i.e., non-constitutively expressed) is desired, expression can be driven by inducible promoters.

In some cases, the desired gene is expressed temporarily. In other words, the desired gene is not constitutively expressed. The expression of the desired gene can be driven by inducible or repressible promoters. Examples of inducible or repressible promoters include, but are not limited to, those promoters inducible or repressible by: (a) sugars such as arabinose and lactose (or non-metabolizable analogs, e.g., isopropyl β-D-1-thiogalactopyranoside (IPTG)); (b) metals such as rare earth metals (e.g., lanthanum or cerium), copper, and calcium; (c) temperature; (d) nitrogen-source; (e) oxygen; (f) cell state (growth or stationary); (g) metabolites such as phosphate; (h) CRISPRi; (i) jun; (j) fos; (k) metallothionein; and/or (l) heat shock. These promoters can be used in a methanotroph system. An example of an inducible promoter that can be used within methanotrophs is a pBAD promoter.

Inducible or repressible promoters that can be particularly useful are sugar and rare earth metal switches. For example, promoters that are sensitive to the sugar arabinose can be used as an inducible switch. In some cases, arabinose switches can be used to drive expression of one or more genes. For example, in the presence arabinose, a desired vector or expression of a gene set can be "turned-on." The arabinose switch can turn on the expression of a desired gene.

Other particularly useful switches can be rare earth metal switches, such as lanthanum switches. In some cases, the lanthanum switch can be a repressible switch that can be used to repress expression of one or more genes, until the repressor is removed, after which the genes are "turned-on". For example, in the presence the metal lanthanum, the desired gene set or vector can be "turned-off." The lanthanum switch can turned off (and expression of the genes induced) by either removing the lanthanum from the media or diluting the lanthanum in the media to levels where its repressible effects are reduced, minimized, or eliminated.

Constitutively expressed promoters can also be used in the vector systems herein. For example, the expression of one or more desired genes can be controlled by constitutively active promoters. Examples of such promoters include but are not limited to pMxaF and p.Bba.J23111.

Promoters suitable for use with prokaryotic hosts may include, for example, the α-lactamase and lactose promoter systems, alkaline phosphatase, the tryptophan (trp) promoter system, the erythromycin promoter, apramycin promoter, hygromycin promoter, methylenomycin promoter and hybrid promoters such as the tac promoter. Promoters for use in bacterial systems will also generally contain a Shine-Dalgarno sequence operably linked to the coding sequence.

Generally, a strong promoter may be employed to provide for high level transcription and expression of the desired product. For example, promoters that can be used include but are not limited to a pMxaF promoter. In some cases, a mutation can increase the strength of the promoter and therefore result in elevated levels of expression.

In some cases however, a weaker promoter is desired. For example, this is the case where too much expression of a certain gene results in a detrimental effect (e.g., the killing of cells). A weak promoter can be used, for example, a pBAD promoter. However, in some cases, a weaker promoter can be made by mutation. For example, the pMxaF promoters can be mutated to be weaker.

One or more promoters of a transcription unit can be an inducible promoter. For example, a green fluorescent protein (GFP) can be expressed from a constitutive promoter while an inducible promoter is used to drive transcription of a gene coding for one or more enzymes as disclosed herein and/or the amplifiable selectable marker.

Some vectors may contain prokaryotic sequences that facilitate the propagation of the vector in bacteria. Thus, the vectors may have other components such as an origin of replication (e.g., a polynucleotide that enables the vector to replicate in one or more selected microorganisms), antibiotic resistance genes for selection in bacteria, and/or an amber stop codon which can permit translation to read through the codon. Additional selectable gene(s) may also be incorporated. Generally, in cloning vectors, the origin of replication is one that enables the vector to replicate independently of the host chromosomal DNA, and includes origins of replication or autonomously replicating sequences. Such sequences can include the ColEl origin of replication in bacteria or other known sequences.

Genes

The genes described throughout all have a promoter driving their expression. The methods described herein, e.g., genome editing and expression inhibition using Cas, can be used to edit the polynucleotide of the promoters or used to inhibit the effectiveness of the promoters. Inhibition can be done by blocking the transcription machinery (e.g., transcription factors) from binding to the promoter or by altering the promoter in such a way that the transcription machinery no longer recognizing the promoter sequence.

The vectors described throughout can also comprise a polynucleotide encoding for one or more of the genes within the 2,3-butanediol (2,3-BDO), 1,4-butanediol (1,4-BDO), isobutyraldehyde, or isobutanol pathway. The vectors described throughout can also comprise a polynucleotide encoding for an RNA polymerase beta-subunit. These vectors can also contain one or more regulatory elements (inducible and/or repressible promoters) that control the expression of the genes within the vectors. In some cases, the switches that can be used include, but are not limited to, inducible or repressible switches, e.g., an arabinose or lanthanum switches. These genes can be heterologous to the microorganism in which the vector is contacted with (and eventually transformed with).

The genes used in the vectors can be any genes described throughout the application. For example, the genes of the 2,3-BDO, 1,4-BDO, isobutanol, and/or isobutyraldehyde pathways. These enzymes can be encoded by a polynucleotide that is at least 60%, 65%, 70%, 75%, 80%, 85%, 90%, 91%, 92%, 93%, 94%, 95%, 96%, 97%, 98%, 99%, 99.9%, 99.99%, 99.999%, or 99.9999% identical to any one of SEQ ID NOs: 1 to 77. In some cases, the RNA polymerase beta-subunit genes can be used in the vectors. This enzyme can be encoded by a polynucleotide that is at least 60%, 65%, 70%, 75%, 80%, 85%, 90%, 91%, 92%, 93%, 94%, 95%, 96%, 97%, 98%, 99%, 99.9%, 99.99%, 99.999%, or 99.9999% identical to SEQ ID NOs: 123 or 126.

The genes that are inserted into a microorganism can be heterologous to the microorganism itself. For example, if the microorganism is a methanotroph, the inserted genes can, for example, be from yeast, a bacterium, or a different species of methanotroph. Further, the genes can be endogenously part of the genome of the microorganism.

III. Techniques for Genetic Modification

The microorganisms disclosed herein may be genetically engineered by using classic microbiological techniques. These classical techniques can be in addition to the advanced genome editing techniques. Some of such classical techniques are generally disclosed, for example, in Sambrook et al., 1989, Molecular Cloning: A Laboratory Manual, Cold Spring Harbor Labs Press.

The genetically modified microorganisms disclosed herein may include a polynucleotide that has been inserted, deleted or modified (i.e., mutated; e.g., by insertion, deletion, substitution, and/or inversion of nucleotides), in such a manner that such modifications provide the desired effect of expression (e.g., over-expression or decreased expression) of one or more enzymes as provided herein within the microorganism. Genetic modifications which result in an increase in gene expression or function can be referred to as amplification, overproduction, overexpression, activation, enhancement, addition, or up-regulation of a gene. Addition of a gene to increase expression can include maintaining the gene(s) on replicating plasmids or integrating the cloned gene(s) into the genome of the production microorganism. Furthermore, increasing the expression of desired genes can include operatively linking the cloned gene(s) to native or heterologous transcriptional control elements. Additionally, increasing expression of a desired gene can also include modifying the promoter region of the gene. Genetic modifications which result in a decrease in gene expression or function can be referred to as reduction, repression, underproduction, deactivation, deletion, or down-regulation of a gene. In some cases, the genetic modification which results in a decrease in gene expression or function can be complete elimination of gene expression (knockout) or partial elimination of gene expression (knockdown—e.g., via RNAi).

Where desired, the expression of one or more of the enzymes provided herein is under the control of a regulatory sequence that controls directly or indirectly the enzyme expression in a time-dependent fashion during the fermentation. Inducible promoters can be used to achieve this. As discussed throughout, the methods described herein can be used to alter the polynucleotide of the promoters.

In some cases, a microorganism is transformed or transfected with a genetic vehicle, such as an expression vector comprising a heterologous polynucleotide encoding for the enzymes as provided herein. In some cases, the heterologous polynucleotide encoding for the enzymes throughout can be altered using the techniques described throughout, before or after, the heterologous enzyme is placed within the microorganism.

To facilitate insertion and expression of different genes coding for the enzymes as disclosed herein from the constructs and expression vectors, the constructs may be designed with at least one cloning site for insertion of any gene coding for any enzyme disclosed herein. The cloning site may be a multiple cloning site, e.g., containing multiple restriction sites.

Transfection

Standard transfection techniques can be used to insert genes into a microorganism. As used herein, the term "transfection" or "transformation" can refer to the insertion of an exogenous nucleic acid or polynucleotide into a host cell. The exogenous nucleic acid or polynucleotide may be maintained as a non-integrated vector, for example, a plasmid, or alternatively, may be integrated into the host cell genome. The term transfecting or transfection is intended to encompass all conventional techniques for introducing nucleic acid or polynucleotide into microorganisms. Examples of transfection techniques include, but are not limited to, calcium phosphate precipitation, DEAE-dextran-mediated transfection, lipofection, electroporation, microinjection, rubidium chloride or polycation mediated transfection, protoplast fusion, and sonication. The transfection method that provides optimal transfection frequency and expression of the construct in the particular host cell line and type is favored. For stable transfectants, the constructs are integrated so as to be stably maintained within the host chromosome. In some cases, the preferred transfection is a stable transfection.

Transformation

Expression vectors or other nucleic acids may be introduced to selected microorganisms by any of a number of suitable methods. For example, vector constructs may be introduced to appropriate cells by any of a number of transformation methods for plasmid vectors. Standard calcium-chloride-mediated bacterial transformation is still commonly used to introduce naked DNA to bacteria (see, e.g., Sambrook et al., 1989, Molecular Cloning, A Laboratory Manual, Cold Spring Harbor Laboratory Press, Cold Spring Harbor, N.Y.), but electroporation and conjugation may also be used (see, e.g., Ausubel et al., 1988, Current Protocols in Molecular Biology, John Wiley & Sons, Inc., NY, N.Y.).

For the introduction of vector constructs to yeast or other fungal cells, chemical transformation methods may be used (e.g., Rose et al., 1990, Methods in Yeast Genetics, Cold Spring Harbor Laboratory Press, Cold Spring Harbor, N.Y.). Transformed cells may be isolated on selective media appropriate to the selectable marker used. Alternatively, or in addition, plates or filters lifted from plates may be scanned for GFP fluorescence to identify transformed clones.

For the introduction of vectors comprising differentially expressed sequences to certain types of cells, the method used may depend on the form of the vector. Plasmid vectors may be introduced by any of a number of transfection methods, including, for example, lipid-mediated transfection ("lipofection"), DEAE-dextran-mediated transfection, electroporation or calcium phosphate precipitation (see, e.g., Ausubel et al., 1988, Current Protocols in Molecular Biology, John Wiley & Sons, Inc., NY, N.Y.).

Lipofection reagents and methods suitable for transient transfection of a wide variety of transformed and non-transformed or primary cells are widely available, making lipofection an attractive method of introducing constructs to eukaryotic, and particularly mammalian cells in culture. Many companies offer kits and ways for this type of transfection.

The host cell may be capable of expressing the construct encoding the desired protein, processing the protein and transporting a secreted protein to the cell surface for secretion. Processing includes co- and post-translational modification such as leader peptide cleavage, GPI attachment, glycosylation, ubiquitination, and disulfide bond formation.

Microorganisms can be transformed or transfected with the above-described expression vectors or polynucleotides coding for one or more enzymes as disclosed herein and cultured in nutrient media modified as appropriate for the specific microorganism, inducing promoters, selecting transformants, or amplifying the genes encoding the desired sequences. In some cases, electroporation methods can be used to deliver an expression vector.

Expression of a vector (and the gene contained in the vector) can be verified by an expression assay, for example, qPCR or by measuring levels of RNA. Expression level can be indicative also of copy number. For example, if expression levels are extremely high, this can indicate that more than one copy of a gene was integrated in a genome. Alternatively, high expression can indicate that a gene was integrated in a highly transcribed area, for example, near a highly expressed promoter. Expression can also be verified by measuring protein levels, such as through Western blotting.

CRISPR/Cas

The methods disclosed throughout can involve pinpoint nucleotide replacement, pinpoint insertion of one or more nucleotides (e.g., addition of genes or parts of genes) or the pinpoint deletion of one or more nucleotide (e.g., deletion of genes or parts of genes). Methods described herein can use a CRISPR/cas system. For example, double-strand breaks (DSBs) can be generated using a CRISPR/cas system, e.g., a type II CRISPR/cas system. A Cas enzyme used in the methods disclosed herein can be Cas9, which catalyzes DNA cleavage. Enzymatic action by Cas9 from *Streptococcus pyogenes* or any closely related Cas9 can generate double stranded breaks at target site sequences which hybridize to 20 nucleotides of a guide sequence and have a protospacer-adjacent motif (PAM) following the 20 nucleotides of the target sequence.

A vector can also encode a Cas enzyme. Cas enzymes that can be used include class 1 and class 2. Non-limiting examples of Cas enzymes include Cas1, Cas1B, Cas2, Cas3, Cas4, Cas5, Cas5d, Cas5t, Cas5h, Cas5a, Cas6, Cas7, Cas8, Cas9 (also known as Csn1 or Csx12), Cas10, Csy1, Csy2, Csy3, Csy4, Cse1, Cse2, Cse3, Cse4, Cse5e, Csc1, Csc2, Csa5, Csn1, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Csd1, Csd2, Cst1, Cst2, Csh1, Csh2, Csa1, Csa2, Csa3, Csa4, Csa5, C2c1, C2c2, C2c3, Cpf1, CARF, DinG, homologues thereof, or modified versions thereof. An unmodified Cas enzyme can have DNA cleavage activity. A Cas enzyme can direct cleavage of one or both strands at a target sequence, such as within a target sequence and/or within a complement of a target sequence. For example, a Cas enzyme can direct cleavage of one or both strands within 1, 2, 3, 4, 5, 6, 7, 8, 9, 10, 15, 20, 25, 30, 35, 40, 45, 50, 60, 70, 80, 90, 100, 125, 150, 175, 200, 300, 400, 500, or more base pairs from the first or last nucleotide of a target sequence. A vector that encodes a Cas enzyme that is mutated with respect to a corresponding wild-type enzyme such that the mutated Cas enzyme lacks the ability to cleave one or both strands of a target polynucleotide containing a target sequence can be used. Additionally, a modified Cas enzyme that lacks the ability to cleave but has the ability to block binding of the transcriptional machinery can be used.

A vector that encodes a Cas enzyme comprising one or more nuclear localization sequences (NLSs) can be used. For example, there can be 1, 2, 3, 4, 5, 6, 7, 8, 9, 10 NLSs used. A Cas enzyme can comprise the NLSs at or near the ammo-terminus (e.g., 1, 2, 3, 4, 5, 6, 7, 8, 9, 10 NLSs), or at or near the carboxy-terminus (e.g., 1, 2, 3, 4, 5, 6, 7, 8, 9, 10 NLSs), or any combination of these (e.g., one or more NLS at the ammo-terminus and one or more NLS at the carboxy terminus). When more than one NLS is present, each can be selected independently of others, such that a single NLS can be present in more than one copy and/or in combination with one or more other NLSs present in one or more copies.

Cas enzyme used in the methods can comprise at most 6 NLSs. An NLS is considered near the N- or C-terminus when the nearest amino acid to the NLS is within 50 amino acids along a polypeptide chain from the N- or C-terminus, e.g., within 1, 2, 3, 4, 5, 10, 15, 20, 25, 30, 40, or 50 amino acids.

Guide RNA

As used herein, the term "guide RNA" (gRNA) and its grammatical equivalents can refer to an RNA which can be specific for a target DNA and can form a complex with Cas enzyme. An RNA/Cas complex can assist in "guiding" Cas enzyme to a target DNA.

A method disclosed herein also can comprise introducing into a microorganism at least one guide RNA or other nucleic acid, e.g., DNA encoding at least one guide RNA. A guide RNA can interact with a RNA-guided endonuclease to direct the endonuclease to a specific target site, at which site the 5' end of the guide RNA base pairs with a specific protospacer sequence in a chromosomal sequence.

A guide RNA can comprise two RNAs, e.g., CRISPR RNA (crRNA) and transactivating crRNA (tracrRNA). A guide RNA can sometimes comprise a single-chain RNA, or single guide RNA (sgRNA) formed by fusion of a portion (e.g., a functional portion) of crRNA and tracrRNA. A guide RNA can also be a dualRNA comprising a crRNA and a tracrRNA. Furthermore, a crRNA can hybridize with a target DNA.

As discussed above, a guide RNA can be an expression product. For example, a DNA that encodes a guide RNA can be a vector comprising a sequence coding for the guide RNA. A guide RNA can be transferred into a microorganism by transfecting the microorganism with an isolated guide RNA or plasmid DNA comprising a sequence encoding for the guide RNA and a promoter. A guide RNA can also be transferred into a microorganism in other ways, such as using virus-mediated gene delivery.

A guide RNA can be isolated. For example, a guide RNA can be transfected in the form of an isolated RNA into a microorganism. A guide RNA can be prepared by in vitro transcription using any in vitro transcription system. A guide RNA can be transferred to a microorganism in the form of isolated RNA rather than in the form of plasmid comprising encoding sequence for a guide RNA.

A guide RNA can comprise three regions: a first region at the 5' end that can be complementary to a target site in a chromosomal sequence; a second internal region that can form a stem loop structure; and a third 3' region that can be single-stranded. A first region of each guide RNA can also be different such that each guide RNA guides a fusion protein to a specific target site. Further, second and third regions of each guide RNA can be identical in all guide RNAs.

A first region of a guide RNA can be complementary to sequence at a target site in a chromosomal sequence such that the first region of the guide RNA can base pair with the target site. In some cases, a first region of a guide RNA can comprise from 10 nucleotides to 25 nucleotides (i.e., from 10 nts to 25 nts; or 10 nts to 25 nts; or from 10 nts to 25 nts; or from 10 nts to 25 nts) or more. For example, a region of base pairing between a first region of a guide RNA and a target site in a chromosomal sequence can be 10, 11, 12, 13, 14, 15, 16, 17, 18, 19, 20, 22, 23, 24, 25, or more nucleotides in length. Sometimes, a first region of a guide RNA can be 19, 20, or 21 nucleotides in length.

A guide RNA can also comprises a second region that forms a secondary structure. For example, a secondary structure formed by a guide RNA can comprise a stem (or hairpin) and a loop. A length of a loop and a stem can vary. For example, a loop can range from 3 to 10 nucleotides in length, and a stem can range from 6 to 20 base pairs in length. A stem can comprise one or more bulges of 1 to 10 nucleotides. The overall length of a second region can range from 16 to 60 nucleotides in length. For example, a loop can be 4 nucleotides in length and a stem can be 12 base pairs.

A guide RNA can also comprise a third region at the 3' end that can be essentially single-stranded. For example, a third region is sometimes not complementarity to any chromosomal sequence in a cell of interest and is sometimes not complementarity to the rest of a guide RNA. Further, the length of a third region can vary. A third region can be more than 4 nucleotides in length. For example, the length of a third region can range from 5 to 60 nucleotides in length.

A guide RNA can be introduced into a microorganism as an RNA molecule. For example, a RNA molecule can be transcribed in vitro and/or can be chemically synthesized. An RNA can be transcribed from a synthetic DNA molecule, e.g., a gBlocks® gene fragment. A guide RNA can then be introduced into a microorganism as an RNA molecule. A guide RNA can also be introduced into a microorganism in the form of a non-RNA nucleic acid molecule, e.g., DNA molecule. For example, a DNA encoding a guide RNA can be operably linked to promoter control sequence for expression of the guide RNA in a microorganism of interest. A RNA coding sequence can be operably linked to a promoter sequence that is recognized by an RNA polymerase. Plasmid vectors that can be used to express guide RNA include, but are not limited to, px330 vectors and px333 vectors. In some cases, a plasmid vector (e.g., px333 vector) can comprise two guide RNA-encoding DNA sequences.

A DNA sequence encoding a guide RNA can also be part of a vector. Further, a vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. A DNA molecule encoding a guide RNA can also be linear. A DNA molecule encoding a guide RNA can also be circular.

When DNA sequences encoding an RNA-guided endonuclease and a guide RNA are introduced into a cell, each DNA sequence can be part of a separate molecule (e.g., one vector containing an RNA-guided endonuclease coding sequence and a second vector containing a guide RNA coding sequence) or both can be part of a same molecule (e.g., one vector containing coding (and regulatory) sequence for both an RNA-guided endonuclease and a guide RNA).

Donor DNA

As used herein, the term “donor DNA” and its grammatical equivalents can refer to a polynucleotide that provides a template for “repair” during the insertion of one or more nucleotides during genome editing. For example, the Cas9 enzyme can provide specific double stranded DNA breaks using a guide RNA. Should one or more nucleotides be desired to be inserted into this double stranded break, the donor DNA can be used. The donor DNA can be inserted into the double stranded break site. Further, a single strand of DNA can be provided at the break site and a microorganism’s repair mechanisms can be used to complete the full insertion of a double stranded DNA.

Timing of Transformation

The timing of the expression of the specific components used in genome editing can be important in its efficacy. For example, for some microorganisms, transformation of plasmids expressing a Cas protein, guide RNA, and/or donor DNA can be simultaneously introduced into the microorganism and effectively be used to insert or delete one or more nucleotides.

However, for certain microorganisms that are capable of converting a $C_1$ carbon into a product, e.g., methanotrophs, the order in which a Cas protein, guide RNA, and/or donor DNA are transformed into the microorganism makes a significant difference in the effectiveness of genome editing as well as survival of the microorganism. For example, the transformation of Cas proteins prior to the transformation of the guide RNA and/or donor DNA results in an increased amount of cell death and decreased editing efficiency. To increase editing efficiency and to reduce unwanted cell death, the microorganisms can be transformed with a guide RNA and/or donor DNA prior to the transformation of a Cas protein.

In some cases, the guide RNA, donor DNA, and/or Cas enzyme, are found on separate plasmids/vectors. In some cases, the guide RNA and donor DNA are on a single plasmid/vector, while the Cas enzyme is expressed from a separate plasmid/vector. In some cases, the guide RNA is expressed on a single plasmid/vector, while the donor DNA and Cas enzyme are expressed on a separate plasmid/vector. In some cases, the donor DNA is expressed on a single plasmid/vector, while the guide RNA and Cas enzyme are expressed on a separate plasmid/vector.

In some cases, the guide RNA and Cas enzyme can be controlled by different promoters. For example, in some cases, the guide RNA can be controlled by a constitutively expressed promoter while the expression of the Cas enzyme is controlled by an inducible promoter. In some cases, should a donor DNA be required, it can be expressed under the control of either a constitutively expressed promoter or an inducible promoter. This, in some cases, can allow for transformation of a microorganism with guide RNA and Cas enzyme (and optionally donor DNA) at the same time.

Site-Specific Insertion

Insertion of the one or more nucleotides (e.g., genes) can be site-specific. For example, one or more nucleotides (e.g., genes) can be inserted adjacent to a promoter.

Modification of a targeted locus of a microorganism can be produced by introducing DNA into microorganisms, where the DNA has homology to the target locus. DNA can include a marker gene, allowing for selection of cells comprising the integrated construct. Homologous DNA in a target vector can recombine with DNA at a target locus. A marker gene can be flanked on both sides by homologous DNA sequences, a 3' recombination arm, and a 5' recombination arm.

A variety of enzymes can catalyze insertion of foreign DNA into a microorganism genome. For example, site-specific recombinases can be clustered into two protein families with distinct biochemical properties, namely tyrosine recombinases (in which DNA is covalently attached to a tyrosine residue) and serine recombinases (where covalent attachment occurs at a serine residue). In some cases, recombinases can comprise Cre, fC31 integrase (a serine recombinase derived from *Streptomyces* phage fC31), or bacteriophage derived site-specific recombinases (including Flp, lambda integrase, bacteriophage HK022 recombinase, bacteriophage R4 integrase and phage TP901-1 integrase).

The CRISPR/Cas system can be used to perform site specific insertion. For example, a nick on an insertion site in the genome can be made by CRISPR/Cas to facilitate the insertion of a transgene at the insertion site.

The techniques which can be used to allow a DNA or RNA construct entry into a host microorganism in the methods described herein include, but are not limited to, calcium phosphate/DNA coprecipitation, microinjection of DNA into a nucleus, electroporation, bacterial protoplast fusion with intact cells, transfection, lipofection, infection, particle bombardment, sperm mediated gene transfer, or any other technique.

Certain aspects disclosed herein can utilize vectors (including the ones described above). Any plasmids and vectors can be used as long as they are replicable and viable in a selected host microorganism. Vectors known in the art and those commercially available (and variants or derivatives thereof) can be engineered to include one or more recombination sites for use in the methods herein. Vectors that can be used include, but are not limited to, expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), pXT1, pSG5, pPbac, pMbac, pMClneo, and pOG44 (Stratagene, Inc.), and pYES2, pAC360, pBlueBa-cHis A, B, and C, pVL1392, pBlueBac111, pCDM8, pcDNA1, pZeoSV, pcDNA3, pREP4, pCEP4, and pEBVHis (Invitrogen, Corp.), and variants or derivatives thereof.

These vectors can be used to express a gene or portion of a gene of interest. A gene or a portion of a gene can be inserted by using known methods, such as restriction enzyme-based techniques.

IV. Methods of Altering Nucleic Acids

The nucleic acids contained within the microorganism disclosed throughout can be altered in specific ways. Depending on the type of modification desired, guide RNAs can be made and targeted to specific sequences. For example, the nucleic acids described throughout can be within the microorganism described herein. Then if specific modifications are desired, the modifications can be made within the microorganism without going through an entire process of genetically engineering the microorganism from the beginning.

In some cases, wild-type, unmodified microorganisms can be altered by the methods described. For example, wild-type methylotrophs, such as methanotrophs, e.g. *Methylococcus capsulatus*, can be genetically altered. In some cases, previously genetically modified microorganisms can be altered by the methods described. For example, the genetically modified microorganism described herein, such as those that produce 2,3-BDO, 1,4-BDO, isobutanol and/or isobutyraldehyde, can be further genetically modified using the methods described throughout. The nucleic acids within the microorganism (both heterologous or native) can be introduced with point mutations, addition of one or more nucleic acids, and/or deletion of one or more nucleic acids.

General Methods

Generally described throughout are methods of genetic engineering. In one example, described herein is a method of genetic engineering comprising: (a) contacting a microorganism that is capable of converting a $C_1$ carbon to a multicarbon product with a polynucleotide encoding for a Cas enzyme and a guide ribonucleic acid (gRNA); and (b) growing the microorganism until a genetic modification occurs.

In some cases, the microorganism is a microorganism as described throughout, such as a methylotroph. For example, the methylotroph can be a methanotroph, such as from the genera *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis*, or *Methyloacidophilum*. In some cases, the methanotroph can be from the genus *Methylococcus*, such as a *Methylococcus capsulatus.*

In some cases, the $C_1$ carbon can be any $C_1$ carbon disclosed throughout. For example, in some cases the $C_1$ carbon is carbon monoxide (CO), carbon dioxide ($CO_2$), methane ($CH_4$), or any combination thereof. In some cases, the $C_1$ carbon is $CH_4$.

The Cas enzymes that can be used for any of the methods described throughout include but are not limited to Cas1, Cas1B, Cas2, Cas3, Cas4, Cas5, Cas5d, Cas5t, Cas5h, Cas5a, Cas6, Cas7, Cas8, Cas9 (also known as Csn1 or Csx12), Cas10, Csy1, Csy2, Csy3, Csy4, Cse1, Cse2, Cse3, Cse4, Cse5e, Csc1, Csc2, Csa5, Csn1, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Csd1, Csd2, Cst1, Cst2, Csh1, Csh2, Csa1, Csa2, Csa3, Csa4, Csa5, C2c1, C2c2, C2c3, Cpf1, CARF, DinG, homologues thereof, or modified versions thereof. In some cases, the Cas enzyme is a Cas9 enzyme.

In some cases, the gRNA can be at least partially or fully homologous to any one of the genes or promoters described throughout. In some instances, the gRNA is at least partially homologous or fully homologous to a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, the term "at least partially homologous" can refer to having at least two or more nucleotides identical in a sequence. In most cases, the term at least partially homologous refers to a polynucleotide that is identical in at least a 10 nucleotide stretch. Thus, at least 10 or more nucleotides from the gRNA can bind to the polynucleotide that is being pinpointed and/or altered.

In some cases, the gRNA is directed to a promoter, intron, or coding sequence of gene within the 2,3-BDO pathway. The gene within the 2,3-BDO can be an acetoin reductase, alpha-acetolactate decarboxylase, and/or acetolactate synthase gene.

In other cases, the gRNA is directed to a promoter, intron, or coding sequence of a gene within the 1,4-BDO pathway. The gene can be within the 1,4-BDO pathway can be a pyruvate dehydrogenase (aceEF), citrate synthase (gltA), aconitate hydratase 1 (acnA), isocitrate dehydrogenase (icdA), citrate synthase (gltA), succinyl-CoA synthetase (SucC), CoA-dependent succinate semialdehyde dehydrogenase (SucD), 4-hyrobutyrate dehydrogenase (4hbD), 4-hydroxybutyryl-CoA transferase (Cat2), aldehyde dehydrogenase (Ald), alcohol dehydrogenase (Adh), and/or α-ketoglutarate decarboxylase (kgd) gene.

In some cases, the gRNA is directed to a promoter, intron, or coding sequence of a gene within the isobutyraldehyde pathway. The gene within the isobutyraldehyde pathway can be an acetolactate synthase (AlsS), ketol-acid reductoisomerase (IlvC), dihydroxy-acid dehydratase (IlvD), and/or 2-keto acid decarboxylase (KDC) gene.

In other cases, the gRNA is directed to a gene within the isobutanol pathway. The gene within the isobutanol pathway can be an AlsS, IlvC, IlvD, KDC, and/or ADH gene.

In some cases, the gRNA is transformed prior to a polynucleotide encoding for a Cas enzyme.

In some cases, the microorganism is also contacted with a donor polynucleotide. In some cases, the donor polynucleotide is contacted with the microorganism prior to being contacted with a polynucleotide encoding for a Cas enzyme. In some cases, the microorganism is contacted concurrently with a donor polynucleotide and a guide RNA. In some cases, the donor polynucleotide and guide RNA are on a single plasmid.

If a donor polynucleotide is used, the donor polynucleotide can be less than 10,000 bases. For example, the donor polynucleotide can be less than 5,000 bases. In some cases, the donor polynucleotide is less than 4,000 bases. In some cases, the donor polynucleotide is less than 3,000 bases. In some cases, the donor polynucleotide is less than 2,000 bases. In some cases, the donor polynucleotide is less than 1,000 bases. In some cases, the donor polynucleotide is less than 950 bases. In some cases, the donor polynucleotide is less than 900 bases. In some cases, the donor polynucleotide is less than 850 bases. In some cases, the donor polynucleotide is less than 800 bases. In some cases, the donor polynucleotide is less than 750 bases. In some cases, the donor polynucleotide is less than 700 bases. In some cases, the donor polynucleotide is less than 650 bases. In some cases, the donor polynucleotide is less than 600 bases. In some cases, the donor polynucleotide is less than 550 bases. In some cases, the donor polynucleotide is less than 500 bases. In some cases, the donor polynucleotide is less than 450 bases. In some cases, the donor polynucleotide is less than 400 bases. In some cases, the donor polynucleotide is less than 350 bases. In some cases, the donor polynucleotide is less than 300 bases. In some cases, the donor polynucleotide is less than 250 bases. In some cases, the donor polynucleotide is less than 200 bases. In some cases, the donor polynucleotide is less than 150 bases. In some cases, the donor polynucleotide is less than 100 bases. In some cases, the donor polynucleotide is less than 95 bases. In some cases, the donor polynucleotide is less than 90 bases. In some cases, the donor polynucleotide is less than 85 bases. In some cases, the donor polynucleotide is less than 80 bases. In some cases, the donor polynucleotide is less than 75 bases. In some cases, the donor polynucleotide is less than 70 bases. In some cases, the donor polynucleotide is less than 65 bases. In some cases, the donor polynucleotide is less than 60 bases. In some cases, the donor polynucleotide is less than 55 bases. In some cases, the donor polynucleotide is less than 50 bases. In some cases, the donor polynucleotide is less than 45 bases. In some cases, the donor polynucleotide is less than 40 bases. In some cases, the donor polynucleotide is less than 35 bases. In some cases, the donor polynucleotide is less than 30 bases. In some cases, the donor polynucleotide is less than 25 bases. In some cases, the donor polynucleotide is less than 20 bases. In some cases, the donor polynucleotide is less than 15 bases. In some cases, the donor polynucleotide is less than 10 bases. In some cases, the donor polynucleotide is less than 5 bases.

If a donor polynucleotide is used, the donor polynucleotide can be from 10,000 bases to 1 base. For example, the donor polynucleotide can be from 5,000 to 5 bases. In some cases, the donor polynucleotide can be from 2,500 to 10 bases. In some cases, the donor polynucleotide can be from 2,000 to 15 bases. In some cases, the donor polynucleotide can be from 1,500 to 25 bases. In some cases, the donor polynucleotide can be from 1,000 to 100 bases. In some cases, the donor polynucleotide can be from 750 to 125 bases. In some cases, the donor polynucleotide can be from 500 to 250 bases. In some cases, the donor polynucleotide can be from 1,000 bases to 1 base. In some cases, the donor polynucleotide can be from 900 to 5 bases. In some cases, the donor polynucleotide can be from 750 to 10 bases. In some cases, the donor polynucleotide can be from 650 to 5 bases. In some cases, the donor polynucleotide can be from 700 to 10 bases. In some cases, the donor polynucleotide can be from 600 to 10 bases. In some cases, the donor polynucleotide can be from 500 to 5 bases.

In some cases, the polynucleotide encoding for a Cas enzyme is within a plasmid.

In some cases, the plasmids used do not comprise a strong promoter. For example, the plasmid can comprise a mutated promoter. In some cases, the mutation can lead to a decrease in activity. In some cases, the promoter is a pMxaF promoter.

In some cases, the microorganism that is being used does not efficiently take up nucleic compared to an *E. coli* bacteria. Transformation efficiency can refer to the number of viable transformants obtained based on a predetermined amount of a compound to be transformed, which is often measured as colony forming units (CFU) per μg compound used. For example, transfection/transformation efficiency of highly competent *E. coli* cells can reach approximately $2\times10^{10}$-$4\times10^{10}$ cfu/μg of nucleic acid used for the transformations. In some cases, the microorganisms used throughout have very low transformation efficiency. In some cases, the transformation efficiency of the microorganisms used herein is lower than $2\times10^{10}$ cfu/μg. For example, the transformation efficiency of the microorganism used herein can be 0 cfu/μg. In some cases, the transformation efficiency can be 0 to $1\times10^{2}$ cfu/μg; $1\times10^{2}$ cfu/μg to $1\times10^{3}$ cfu/μg; $1\times10^{3}$ cfu/μg to $1\times10^{4}$ cfu/μg; $1\times10^{4}$ cfu/μg to $1\times10^{5}$ cfu/μg; $1\times10^{5}$ cfu/μg to $1\times10^{6}$ cfu/μg; $1\times10^{6}$ cfu/μg to $1\times10^{7}$ cfu/μg; $1\times10^{7}$ cfu/μg to $1\times10^{8}$ cfu/μg; $1\times10^{8}$ cfu/μg to $1\times10^{9}$ cfu/μg; $1\times10^{9}$ cfu/μg to $1\times10^{10}$ cfu/μg; or $1\times10^{10}$ cfu/μg to $1.9999\times10^{10}$ cfu/μg. In some cases, the transformation efficiency can be 0 cfu/μg to less than 1 cfu/μg; 1 cfu/μg to 5 cfu/μg; 5 cfu/μg to 10 cfu/μg; 10 cfu/μg to 20 cfu/μg; 20 cfu/μg to 30 cfu/μg; 30 cfu/μg to 40 cfu/μg; 40 cfu/μg to 50 cfu/μg; 50 cfu/μg to 100 cfu/μg; 100 cfu/μg to 150 cfu/μg; 150 cfu/μg to 200 cfu/μg; 200 cfu/μg to 250 cfu/μg; 250 cfu/μg to 500 cfu/μg; 500 cfu/μg to 1000 cfu/μg; 1000 cfu/μg to 1500 cfu/μg; 1500 cfu/μg to 2000 cfu/μg; or 2000 cfu/μg to 5000 cfu/μg.

In some cases, the microorganism is made electroporation competent prior to transformation. In some cases, some chemical is made to make the microorganism electroporation competent prior to transformation. In some cases, a microorganism can be made to take up nucleic acids more efficiently compared to a non-modified microorganism.

Point Mutations

Described herein is a method of replacing a single nucleotide within the genome of a microorganism comprising: (a) contacting the microorganism with a polynucleotide encoding for i) a Cas enzyme and ii) a gRNA; and (b) growing the microorganism until a single nucleotide is replaced within the genome of the microorganism.

As described above, the microorganism used can be a microorganism that is capable of converting a $C_1$ carbon to a multicarbon product, for example, a methylotroph or any other microorganism described throughout the disclosure.

Further, as described throughout, the $C_1$ carbon can be carbon monoxide (CO), carbon dioxide ($CO_2$), methane ($CH_4$), or any combination thereof.

Additionally, as described through, the Cas enzyme can be any described throughout, including but not limited to Cas9.

As described throughout, the gRNA can target particular pathway genes. For example, as described throughout, the gRNA can be at least partially complementary to a polynucleotide that is within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, the gRNA is transformed prior to a polynucleotide encoding for a Cas enzyme.

In some cases, the polynucleotide encoding for a Cas enzyme is within a plasmid.

In some cases, the plasmids used do not comprise a strong promoter. For example, the plasmid can comprise a mutated promoter. In some cases, the mutation can lead to a decrease in activity. In some cases, the promoter is a pMxaF promoter.

In some cases, when the replacement method is used, the replacement results in a different nucleotide. For example, should a nucleotide within a specific genetic sequence be desired, this method can change the desired nucleotide, e.g., from A to T, C, or G; from T to A, C, or G; from C to A, T, or G; or from G to A, T, or C.

In some cases, the replacement occurs at a single nucleotide within a promoter, intron, or coding sequence of an rpoB gene or a gene within the 2,3-butanediol (2,3-BDO), 1,4-butanediol (1,4-BDO), isobutyraldehyde, or isobutanol pathway. The replacement can in some cases result in a change of expression of one or more genes. The replacement in some cases can also result in a change of activity of one or more enzymes.

Adding Nucleotides

Described herein is a method of adding one or more nucleotides to the genome of a microorganism comprising: (a) contacting the microorganism with a polynucleotide encoding for i) a Cas enzyme and ii) a gRNA; and (b) growing the microorganism until one or more nucleotides is added to the genome of the microorganism.

As described above, the microorganism used can be a microorganism that is capable of converting a $C_1$ carbon to a multi-carbon product, for example, a methylotroph or any other microorganism described throughout the disclosure.

Further, as described throughout, the $C_1$ carbon can be carbon monoxide (CO), carbon dioxide ($CO_2$), methane ($CH_4$), or any combination thereof.

Additionally, as described through, the Cas enzyme can be any described throughout, including but not limited to Cas9.

As described throughout, the gRNA can target particular pathway genes to insert one or more nucleotides. For example, as described throughout, the gRNA can be at least partially complementary to a polynucleotide that is within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, the gRNA is transformed prior to a polynucleotide encoding for a Cas enzyme.

In some cases, the polynucleotide encoding for a Cas enzyme is within a plasmid.

In some cases, the plasmids used do not comprise a strong promoter. For example, the plasmid can comprise a mutated promoter. In some cases, the mutation can lead to a decrease in activity. In some cases, the promoter is a pMxaF promoter.

In some cases, the microorganism is also contacted with a donor polynucleotide. In some cases, the donor polynucleotide is contacted with the microorganism prior to being contacted with a polynucleotide encoding for a Cas enzyme. In some cases, the microorganism is contacted concurrently with a donor polynucleotide and a guide RNA. In some cases, the donor polynucleotide and guide RNA are on a single plasmid.

If a donor polynucleotide is used, the donor polynucleotide can be less than 10,000 bases. For example, the donor polynucleotide can be less than 5,000 bases. In some cases, the donor polynucleotide is less than 4,000 bases. In some cases, the donor polynucleotide is less than 3,000 bases. In some cases, the donor polynucleotide is less than 2,000 bases. In some cases, the donor polynucleotide is less than 1,000 bases. In some cases, the donor polynucleotide is less than 950 bases. In some cases, the donor polynucleotide is less than 900 bases. In some cases, the donor polynucleotide is less than 850 bases. In some cases, the donor polynucleotide is less than 800 bases. In some cases, the donor polynucleotide is less than 750 bases. In some cases, the donor polynucleotide is less than 700 bases. In some cases, the donor polynucleotide is less than 650 bases. In some cases, the donor polynucleotide is less than 600 bases. In some cases, the donor polynucleotide is less than 550 bases. In some cases, the donor polynucleotide is less than 500 bases. In some cases, the donor polynucleotide is less than 450 bases. In some cases, the donor polynucleotide is less than 400 bases. In some cases, the donor polynucleotide is less than 350 bases. In some cases, the donor polynucleotide is less than 300 bases. In some cases, the donor polynucleotide is less than 250 bases. In some cases, the donor polynucleotide is less than 200 bases. In some cases, the donor polynucleotide is less than 150 bases. In some cases, the donor polynucleotide is less than 100 bases. In some cases, the donor polynucleotide is less than 95 bases. In some cases, the donor polynucleotide is less than 90 bases. In some cases, the donor polynucleotide is less than 85 bases. In some cases, the donor polynucleotide is less than 80 bases. In some cases, the donor polynucleotide is less than 75 bases. In some cases, the donor polynucleotide is less than 70 bases. In some cases, the donor polynucleotide is less than 65 bases. In some cases, the donor polynucleotide is less than 60 bases. In some cases, the donor polynucleotide is less than 55 bases. In some cases, the donor polynucleotide is less than 50 bases. In some cases, the donor polynucleotide is less than 45 bases. In some cases, the donor polynucleotide is less than 40 bases. In some cases, the donor polynucleotide is less than 35 bases. In some cases, the donor polynucleotide is less than 30 bases. In some cases, the donor polynucleotide is less than 25 bases. In some cases, the donor polynucleotide is less than 20 bases. In some cases, the donor polynucleotide is less than 15 bases. In some cases, the donor polynucleotide is less than 10 bases. In some cases, the donor polynucleotide is less than 5 bases.

If a donor polynucleotide is used, the donor polynucleotide can be from 10,000 bases to 1 base. For example, the donor polynucleotide can be from 5,000 to 5 bases. In some cases, the donor polynucleotide can be from 2,500 to 10 bases. In some cases, the donor polynucleotide can be from 2,000 to 15 bases. In some cases, the donor polynucleotide can be from 1,500 to 25 bases. In some cases, the donor polynucleotide can be from 1,000 to 100 bases. In some cases, the donor polynucleotide can be from 750 to 125 bases. In some cases, the donor polynucleotide can be from 500 to 250 bases. In some cases, the donor polynucleotide can be from 1,000 bases to 1 base. In some cases, the donor polynucleotide can be from 900 to 5 bases. In some cases, the donor polynucleotide can be from 750 to 10 bases. In some cases, the donor polynucleotide can be from 650 to 5 bases. In some cases, the donor polynucleotide can be from 700 to 10 bases. In some cases, the donor polynucleotide can be from 600 to 10 bases. In some cases, the donor polynucleotide can be from 500 to 5 bases.

The method described herein can result in a polynucleotide where two or more nucleotides are added. In some cases, the number of nucleotides added can be up to 10 kb. In some cases, however, the efficiency of gene editing efficiency can be increased by inserting less than 1000 base pairs. In some cases, the efficiency of gene editing can be significantly increased by inserting 500 nucleotides or less. In some cases, the efficiency of gene editing can be even more significantly increased by inserting 100 nucleotides or less.

The amount of nucleotides that can be inserted using the techniques described herein can potentially be endless. In some cases, the number of nucleotides inserted can be from 1 to 5, 4 to 10, 9 to 15, 14 to 20, 19 to 25, 24 to 30, 29 to 35, 34 to 40, 39 to 45, 44 to 50, 49 to 55, 54 to 60, 59 to 65, 64 to 70, 69 to 75, 74 to 80, 79 to 85, 84 to 90, 89 to 95, or 94 to 100. In some cases, the number of nucleotides that can be inserted can be under 5000 kb, for example, from 99 to 500, 499 to 1000, 999 to 1500, 1499 to 2000, 1999 to 2500, 2499 to 3000, 2999 to 3500, 3499 to 4000, 3999 to 4500, or 4499 to 4999.

As described throughout, the gRNA can target particular pathway genes. For example, as described throughout, the gRNA can be at least partially complementary to a polynucleotide that is within a promoter, intron, or coding sequence of an rpoB gene or a gene within the 2,3-butanediol (2,3-BDO), 1,4-butanediol (1,4-BDO), isobutyraldehyde, or isobutanol pathway. Targeting these sequences can add additional nucleotides within the promoter, intron, or coding sequence. This addition can affect the expression of their respective genes. This addition can also affect the activity of the gene product, e.g., an enzyme of the pathway.

Deleting Nucleotides

Described herein is a method of removing one or more nucleotides from the genome of a genetically modified microorganism comprising: (a) contacting the microorganism with a polynucleotide encoding for i) a Cas enzyme and ii) a gRNA; and (b) growing the microorganism until one or more nucleotides within the genome of the microorganism is removed.

As described above, the microorganism used can be a microorganism that is capable of converting a $C_1$ carbon to a multicarbon product, for example, a methylotroph or any other microorganism described throughout the disclosure.

Further, as described throughout, the $C_1$ carbon can be carbon monoxide (CO), carbon dioxide ($CO_2$), methane ($CH_4$), or any combination thereof.

Additionally, the Cas enzyme can be any described throughout, including but not limited to Cas9.

In some cases, the polynucleotide encoding for a Cas enzyme is within a plasmid.

In some cases, the plasmids used do not comprise a strong promoter. For example, the plasmid can comprise a mutated promoter. In some cases, the mutation can lead to a decrease in activity. In some cases, the promoter is a pMxaF promoter.

In some cases, the gRNA is transformed prior to a polynucleotide encoding for a Cas enzyme.

As described throughout, the gRNA can target particular pathway genes to delete one or more nucleotides. For example, as described throughout, the gRNA can be at least partially complementary to a polynucleotide that is within a promoter, intron, or coding sequence of an rpoB gene or a gene within the 2,3-butanediol (2,3-BDO), 1,4-butanediol (1,4-BDO), isobutyraldehyde, or isobutanol pathway.

The method described herein can result in a polynucleotide where one or more nucleotides are deleted. The amount of nucleotides that can be deleted using the techniques described herein can potentially be endless. In some cases, the number of nucleotides deleted can be from 1 to 5, 4 to 10, 9 to 15, 14 to 20, 19 to 25, 24 to 30, 29 to 35, 34 to 40, 39 to 45, 44 to 50, 49 to 55, 54 to 60, 59 to 65, 64 to 70, 69 to 75, 74 to 80, 79 to 85, 84 to 90, 89 to 95, or 94 to 100. In some cases, the number of nucleotides that can be deleted can be under 5000 kb, for example, from 99 to 500, 499 to 1000, 999 to 1500, 1499 to 2000, 1999 to 2500, 2499 to 3000, 2999 to 3500, 3499 to 4000, 3999 to 4500, or 4499 to 4999. In some cases, the number of nucleotides that are deleted can be up to 10 kb or more.

As described throughout, the gRNA can target particular pathway genes. For example, as described throughout, the gRNA can be at least partially complementary to a polynucleotide that is within a promoter, intron, or coding sequence of an rpoB gene or a gene within the 2,3-butanediol (2,3-BDO), 1,4-butanediol (1,4-BDO), isobutyraldehyde, or isobutanol pathway. Targeting these sequences can delete nucleotides within the promoter, intron, or coding sequence. This deletion can affect the expression of their respective genes. This deletion can also affect the activity of the gene product, e.g., an enzyme of the pathway.

IV. Methods of Inhibiting Gene Expression

Modified Cas Enzyme

The Cas enzymes can be genetically altered (by the methods described throughout or any other method) so that it is catalytically inactive. For example, one or more nucleotides encoding an amino acid sequence that is a part of the catalytic domain of the Cas enzyme can be altered. In other words, one or more nucleotides that encode for the catalytic domain of the Cas enzyme can be deleted, added, or substituted. The resulting sequence can encode for a Cas enzyme that is catalytically inhibited and/or inactive.

The catalytically inactive enzyme can be used to inhibit expression of one or more genes. For example, a specific gRNA can be used to target the promoter, intron, and/or coding sequence of a particular gene. The specific gRNA and inactive Cas enzyme can be expressed within a microorganism. Once this happens, gene expression can be reduced or inhibited.

The binding of the catalytically inactive Cas enzyme can result in steric hindrance of the transcription mechanism. For example, the inactive Cas enzyme that is bound to the gRNA can interrupt transcript initiation or elongation by RNA polymerase.

In some cases, the binding of this blocking complex can be permanent. In some cases the binding of this blocking complex can be temporary. Further, the inactive Cas enzyme can be expressed within a microorganism and be under the control of an inducible or repressible promoter. Additionally, in some cases the gRNA can be expressed within a vector and also be controlled by an inducible and/or repressible promoter. This way, the induction or repression of the desired gene can be specifically controlled at any time by the addition or removal of the inducing/repressing agent.

Targeting Specific Genes

The expression of any number of genes can be inhibited by the methods described throughout. For example, an rpoB gene or any of the genes described within the 2,3-BDO, 1,4-BDO, isobutanol, and/or isobutyraldehyde pathways can be targeted by the gRNA and thus by the inactive Cas enzyme. Any of the gRNA described throughout can be used herein. The gRNA can be substantially similar to the genes described throughout.

Inhibiting Gene Expression

Described herein is a method of inhibiting the expression of a gene within a microorganism comprising contacting the microorganism with a polynucleotide encoding for i) a modified Cas enzyme and ii) a gRNA, where the modified Cas enzyme does not cleave nucleic acids. Also described herein is a method of inhibiting the expression of a gene within a microorganism comprising contacting the microorganism with i) a gRNA and ii) a polynucleotide encoding for a modified Cas enzyme, where the modified Cas enzyme does not cleave nucleic acids.

In some cases, the microorganism used can be a microorganism that is capable of converting a $C_1$ carbon to a multicarbon product. For example, the microorganism can be a microorganism as described throughout, such as a methylotroph. For example, the methylotroph can be a methanotroph, such as from the genera *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis*, or *Methyloacidophilum*. In some cases, the methanotroph can be from the genus *Methylococcus*, such as a *Methylococcus capsulatus*.

In some cases, the $C_1$ carbon can be any $C_1$ carbon disclosed throughout. For example, in some cases the $C_1$ carbon is carbon monoxide (CO), carbon dioxide ($CO_2$), methane ($CH_4$), or any combination thereof. In some cases, the $C_1$ carbon is $CH_4$.

The modified Cas enzymes that can be used for any of the methods described throughout include but are not limited to Cas1, Cas1B, Cas2, Cas3, Cas4, Cas5, Cas5d, Cas5t, Cas5h, Cas5a, Cas6, Cas7, Cas8, Cas9 (also known as Csn1 or Csx12), Cas10, Csy1, Csy2, Csy3, Csy4, Cse1, Cse2, Cse3, Cse4, Cse5e, Csc1, Csc2, Csa5, Csn1, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Csd1, Csd2, Cst1, Cst2, Csh1, Csh2, Csa1, Csa2, Csa3, Csa4, Csa5, C2c1, C2c2, C2c3, Cpf1, CARF, DinG, or homologues thereof. In some cases, the Cas enzyme is a modified Cas9 enzyme. As described above, the modification can be a modified that renders the Cas enzyme partially inactive. The partial inactivity can mean that the Cas enzyme has the ability to bind to its targeted sequence, but does not have the ability to cleave the nucleic acids. In some cases, the polynucleotide encoding for a Cas enzyme or a modified Cas enzyme is within a plasmid.

In some cases, the gRNA can be at least partially or fully homologous to any one of the genes or promoters described throughout. In some instances, the gRNA is at least partially homologous or fully homologous to a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, the gRNA is directed to a promoter, intron, or coding sequence of gene within the 2,3-BDO pathway. The gene within the 2,3-BDO can be an acetoin reductase, alpha-acetolactate decarboxylase, and/or acetolactate synthase gene.

In other cases, the gRNA is directed to a promoter, intron, or coding sequence of a gene within the 1,4-BDO pathway. The gene can be within the 1,4-BDO pathway can be a pyruvate dehydrogenase (aceEF), citrate synthase (gltA), aconitate hydratase 1 (acnA), isocitrate dehydrogenase (icdA), citrate synthase (gltA), succinyl-CoA synthetase (SucC), CoA-dependent succinate semialdehyde dehydrogenase (SucD), 4-hyrobutyrate dehydrogenase (4hbD), 4-hydroxybutyryl-CoA transferase (Cat2), aldehyde dehydrogenase (Ald), alcohol dehydrogenase (Adh), and/or α-ketoglutarate decarboxylase (kgd) gene.

In some cases, the gRNA is directed to a promoter, intron, or coding sequence of a gene within the isobutyraldehyde pathway. The gene within the isobutyraldehyde pathway can be an acetolactate synthase (AlsS); ketol-acid reductoisomerase (IlvC); dihydroxy-acid dehydratase (IlvD); and/or 2-keto acid decarboxylase (KDC) gene.

In other cases, the gRNA is directed to a gene within the isobutanol pathway. The gene within the isobutanol pathway can be an AlsS, IlvC, IlvD, KDC, and/or ADH gene.

In some cases, the plasmids used do not comprise a strong promoter. For example, the plasmid can comprise a mutated promoter. In some cases, the mutation can lead to a decrease in activity. In some cases, the promoter is a pMxaF promoter.

In some cases, the gRNA is transformed prior to a polynucleotide encoding for a Cas enzyme.

In some cases, the microorganism that is being used does not efficiently take up nucleic acid compared to an *E. coli* bacteria. Transformation efficiency can refer to the number of viable transformants obtained based on a predetermined amount of a compound to be transformed, which is often measured as colony forming units (CFU) per μg compound used. For example, transfection/transformation efficiency of highly competent *E. coli* cells can reach approximately $2\times10^{10}$-4×10 cfu/μg of nucleic acid used for the transformations. In some cases, the microorganisms used throughout have very low transformations efficiency. In some cases, the transformation efficiency of the microorganisms used herein is lower than $2\times10^{10}$ cfu/μg. For example, the transformation efficiency of the microorganism used herein can be 0 cfu/μg. In some cases, the transformation efficiency can be 0 to $1\times10^2$ cfu/μg; $1\times10^2$ cfu/μg to $1\times10^3$ cfu/μg; $1\times10^3$ cfu/μg to $1\times10^4$ cfu/μg; $1\times10^4$ cfu/μg to $1\times10^5$ cfu/μg; $1\times10^5$ cfu/μg to $1\times10^6$ cfu/μg; $1\times10^6$ cfu/μg to $1\times10^7$ cfu/μg; $1\times10^7$ cfu/μg to $1\times10^8$ cfu/μg; $1\times10^8$ cfu/μg to $1\times10^9$ cfu/μg; $1\times10^9$ cfu/μg to $1\times10^{10}$ cfu/μg; or $1\times10^{10}$ cfu/μg to $1.9999\times10^{10}$ cfu/μg. In some cases, the transformation efficiency can be 0 cfu/μg to less than 1 cfu/μg; 1 cfu/μg to 5 cfu/μg; 5 cfu/μg to 10 cfu/μg; 10 cfu/μg to 20 cfu/μg; 20 cfu/μg to 30 cfu/μg; 30 cfu/μg to 40 cfu/μg; 40 cfu/μg to 50 cfu/μg; 50 cfu/μg to 100 cfu/μg; 100 cfu/μg to 150 cfu/μg; 150 cfu/μg to 200 cfu/μg; 200 cfu/μg to 250 cfu/μg; 250 cfu/μg to 500 cfu/μg; 500 cfu/μg to 1000 cfu/μg; 1000 cfu/μg to 1500 cfu/μg; 1500 cfu/μg to 2000 cfu/μg; or 2000 cfu/μg to 5000 cfu/μg.

In some cases, the microorganism is made electroporation competent prior to transformation. In some cases, some chemical is made to make the microorganism electroporation competent prior to transformation.

In some cases, the inhibition of gene expression is greater than 10%, 20%, 30%, 40%, 50%, 60%, 70%, 80%, or 90%, compared to a wild-type microorganism of the same species. In some cases, the inhibition of gene expression is greater than 5%, 15%, 25%, 35%, 45%, 55%, 65%, 75%, 85%, or 95% compared to a wild-type microorganism of the same species. In some cases, the inhibition of gene expression is greater than 10% compared to a wild-type microorganism of the same species. In some cases, the inhibition of gene expression is greater than 50% compared to a wild-type microorganism of the same species. In some cases, the inhibition of gene expression is 100% compared to a wild-type microorganism of the same species.

EXAMPLES

Example 1

Single Plasmid

The *Streptococcus pyogenes* Cas9 gene was codon optimized for expression in *Methylococcus capsulatus*. The codon optimized Cas9 gene was expressed using a pMxaF promoter. A single guide RNA (gRNA) targeting multiple sites along a gene of interest were expressed driven by a Pmmo2 or J23115 promoter. Double stranded DNA having a 1.5 kb homologous region were created. Two gRNA constructs were tested initially.

Initial tests proved to be ineffective at gene editing. As seen in FIG. 1, no colonies were seen when Cas9, gRNA, and double stranded donor DNA were transfected into a *Methylococcus capsulatus*. Later tests showed that pMxaF driving the expression of Cas9 is toxic to *Methylococcus capsulatus*.

Four (4) different promoters were used to drive Cas9 expression: pMxaF_Cas9; pMxaF*_Cas9; pBAD_Cas9; PJ23115_gRNA. pMxaF*_Cas9 was found to be the most efficient and least toxic.

Example 2

Two Plasmid System

Figure 2:
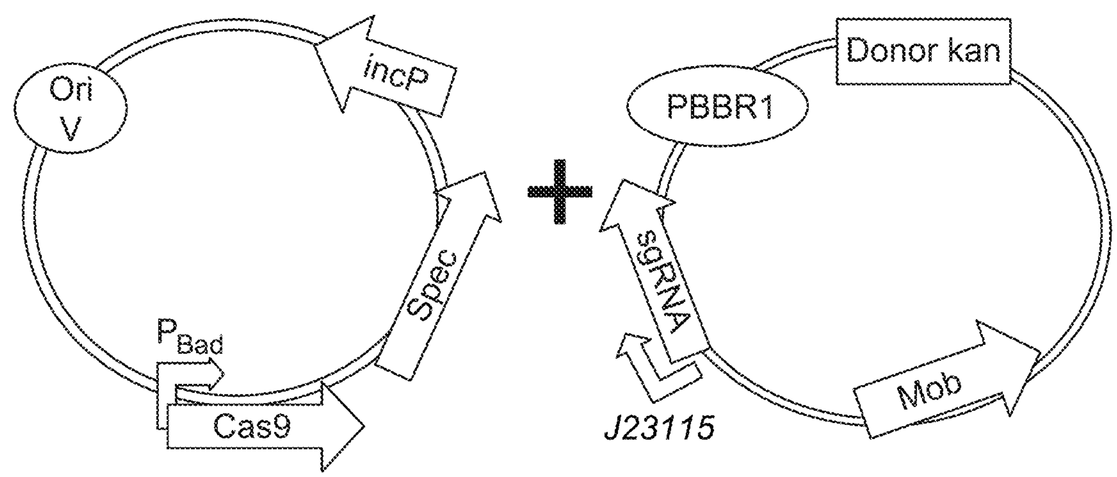
FIG. 2 depicts a two plasmid approach for advanced genome editing (AGE). In one plasmid, Cas9 is expressed with a promoter, such as a weak promoter. In the second plasmid, a gRNA and a donor dsDNA are expressed.

In order to mitigate the toxic effects of Cas9, a two plasmid system was designed. See FIG. 2. In one plasmid, the Cas9 was driven by either pBAD or a mutant pMxaF (a "weak" promoter), whereas the sgRNA was driven by a J23115 promoter.

It was found that pBAD or mutant pMxaF produces enough Cas9 expression to cleave the dsDNA without much off-target effects. However, it was still found that in the presence of gRNA, very few colonies were observed. Of those few colonies, no correct gene editing was observed.

Example 3

Rifamycin Testing

Figure 3:
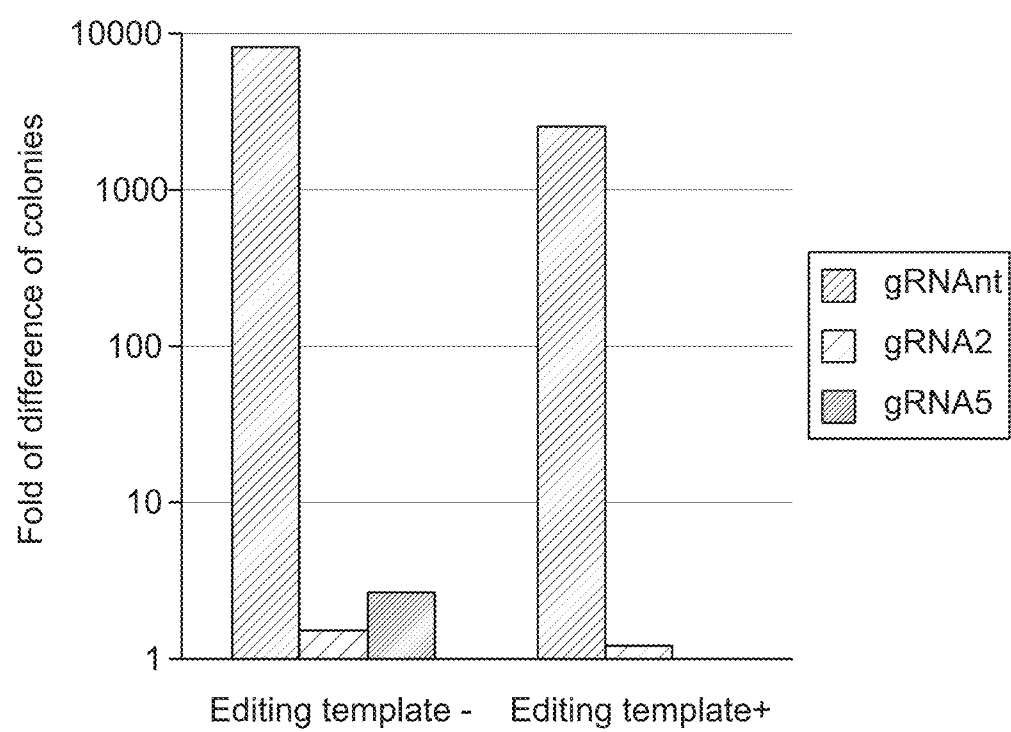
FIG. 3 depicts the number of colony forming units (CFU) for gene editing of the gene rpoB. As shown, the targeting of the rpoB gene resulted in four orders of magnitude drop of CFUs.
Figure 4:
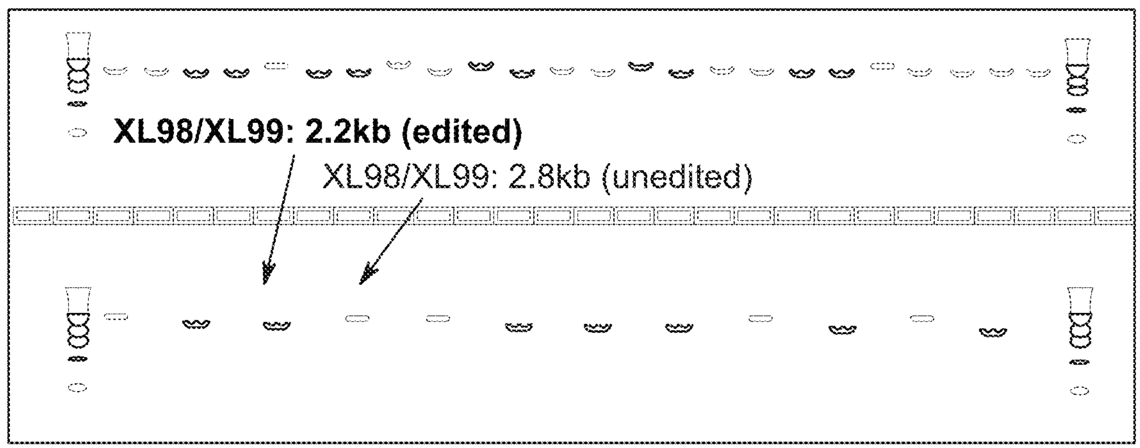
FIG. 4 depicts a colony polymerase chain reaction (cPCR) verification of a ppdK deletion of about 600 bases. As shown in the gel, approximately 72% of the clones were successfully edited.
Figure 5:
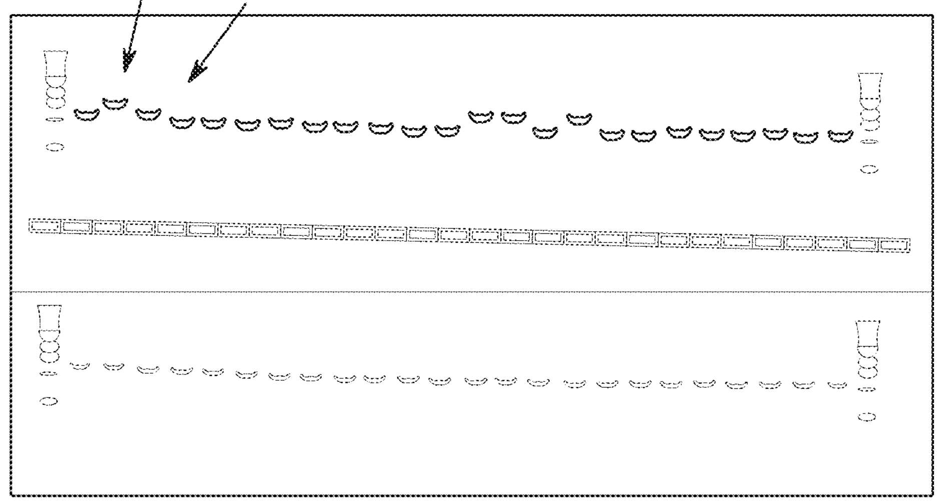
FIG. 5 depicts a cPCR verification of a ppdK addition of about 400 bases. As shown in the gel, several clones were successfully edited.
Figure 6:
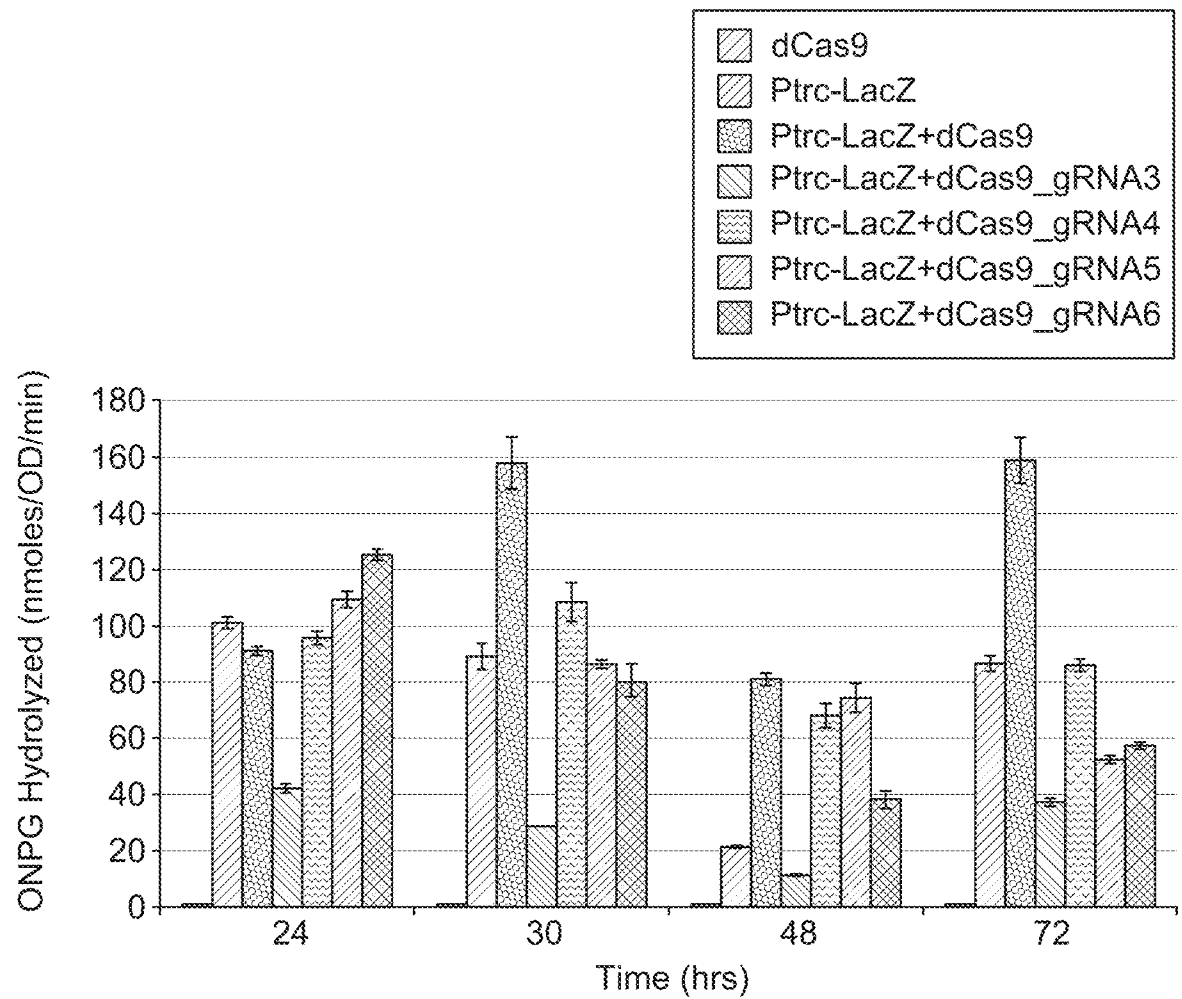
FIG. 6 shows that the expression of LacZ was successfully inhibited by the introduction of dCas9 in combination of a LacZ specific gRNA after 24, 30, 48, and 72 hours. The inhibition of LacZ in some strains was up to 8-fold (30 hours–Ptrc=LacZ+dCas9_gRNA3).

In order to quickly and efficiently troubleshoot the issues with genome editing within *Methylococcus capsulatus*, gene editing targeting the rpoB was used. In *Methylococcus capsulatus* the rpoB gene confers resistance to the antibiotic rifamycin. Therefore, in the presence of rifamycin, *Methylococcus capsulatus* having an active rpoB gene will form many colonies, while the *Methylococcus capsulatus* that were edited will be killed. A 1 kb long rpoB dsDNA was designed and used as the editing template in this experiment. As shown in FIG. 3, the gRNA targeting rpoB was effective and resulted in four orders of magnitude drop of colony forming units (CFU). However, verification revealed that the efficiency of gene editing was only approximately 0.5 to 1%.

Even though the use of a mutant pMxaF gave low background, editing efficiency was still low. In order to improve the efficiency of genome editing, the number of unedited clones needed to be reduced. Therefore, additional testing focused on "killing" efficiency.

Example 4

Promoters and Transformation Order

It was found that promoter strength of Cas9/gRNA affects the activity of CRISPR-Cas9 system. A stronger promoter that drives gRNA expression works better than a weaker promoter. On the other hand, Cas9 expression by a strong promoter is lethal to the microorganism.

The best "killing" rate was observed when the gRNA was present first then Cas9 encoding plasmid was subsequently transformed. However, even though the kill rate went up, increased editing efficiency did not improve.

A new approach was taken. The gRNA and donor DNA, contained on the same plasmid, were first transformed into a *Methylococcus capsulatus*. After this plasmid containing both the gRNA and donor DNA was inserted, a plasmid expression Cas9 was then transformed. Editing efficiency was achieved at about 70%, using rpoB as a target.

Other systems were tested, including a Red promoter driving Cas9 expression. However, this promoter did not result in high editing efficiency. Additionally, Cas9 was first transformed and then gRNA and donor DNA was later transformed. This procedure resulted in very low editing. It was found that high rates of transformation and recombination was required for advance genome editing.

Example 5

Cas9 Expression in Methanotrophs

The *Streptococcus pyogenes* Cas9 gene was codon optimized for expression in *Methylococcus capsulatus*. The codon optimized Cas9 gene was expressed using a variant pMxaF promoter referred to as pMxaF*. The pMxaF*-Cas9 DNA cassette was then cloned into an OriV-based plasmid. The final construct was named pSL95. The pMxaF* and Cas9 sequences used are displayed in Table 1.

TABLE 1

| SEQ ID NO. | NAME | SEQUENCE |
|---|---|---|
| 78 | pMxaF* | GAGGTTCAGGCGAAACCGCAGACTCAAGGGCGCTTGCTCCCGGGAA<br>AGATCGTATTAGTTTGCCTCGATCGGCGGTCCTTGTGACAGGGAGAT<br>ATTCCCGACGGATCCGGGGCATTCGAGCGGAACCGCCCGCCGTGGG<br>AGTTTTTCCAGCGAGCATTCGAGAGTTTTTCAAGGCGGCTTCGAGGG<br>GTTATTCCGTAACGCCGCCGACATGATCTGTCCCGGAATCTCCGCCG<br>CTGTTCGTAGAGCGCCGATGCAGGGTCGGCATCAATCATTCTTGGAG<br>GAGACAC |
| 79 | Cas9 | ATGGACAAGAAGTATTCGATCGGCCTGGACATCGGCACCAACAGCG<br>TCGGCTGGGCGGTCATCACGGATGAGTACAAGGTGCCGTCGAAGAA<br>GTTCAAGGTGCTGGGCAATACCGACCGCCATAGCATCAAGAAGAAT<br>CTCATCGGCGCACTGCTGTTCGACTCCGGCGAAACCGCCGAAGCGAC<br>CCGCCTCAAGCGCACGGCCCGGCGGCGCTATACGCGCCGGAAGAAC<br>CGCATCTGCTACCTCCAGGAAATCTTCTCCAACGAGATGGCCAAGGTG<br>GATGACTCCTTCTTCCATCGCCTGGAAGAATCCTTCCTGGTCGAAGAA<br>GATAAGAAACATGAGCGCCACCCCATCTTCGGCAATATCGTGGACGA<br>GGTGGCGTATCACGAGAAATACCCGACCATCTATCACCTGCGGAAAA<br>AGCTGGTGGACTCGACGGACAAAGCCGACCTGCGCCTCATCTATCTGG<br>CCCTGGCCCACATGATCAAGTTCCGGGGCCATTTCCTGATCGAAGGCG<br>ACCTGAACCCCGATAACAGCGACGTGGACAAGCTCTTCATCCAGCTCG<br>TCCAGACCTATAACCAGCTGTTCGAGGAGAACCCCATCAACGCCTCGG<br>GCGTGGACGCCAAGGCCATCCTGAGCGCACGGCTCTCCAAGTCGCGCC<br>GCCTGGAAAACCTGATCGCGCAGCTGCCGGGCGAAAAGAAAAACGGC<br>CTGTTCGGCAACCTGATCGCCCTGTCCCTCGGCCTCACCCCGAACTTCA<br>AGTCCAACTTCGACCTGGCCGAGGACGCGAAGCTCCAGCTGTCGAAAG<br>ACACCTACGATGACGACCTGGACAACCTCCTGGCGCAGATCGGCGACC<br>AGTACGCCGACCTCTTCCTCGCGGCCAAGAATCTGTCGGACGCCATCCT<br>GCTGTCGGATATCCTGCGGGTGAATACGGAGATCACGAAGGCCCCCCT<br>CTCGGCCTCGATGATCAAGCGCTACGACGAGCACCATCAGGACCTGAC<br>GCTGCTCAAGGCCCTCGTCCGGCAGCAGCTGCCGGAGAAGTATAAAGA<br>GATCTTCTTCGACCAGTCCAAGAACGGCTACGCGGGCTACATCGACGG<br>CGGCGCGTCGCAGGAGGAGTTCTATAAATTCATCAAGCCGATCCTGGA<br>GAAAATGGACGGCACCGAAGAACTCCTCGTCAAGCTGAACCGGGAGGA<br>TCTGCTCCGCAAGCAGCGCACCTTCGACAATGGCTCCATCCCGCACCAG<br>ATCCATCTCGGCGAGCTGCACGCCATCCTGCGCCGCCAGGAGGACTTCT<br>ACCCCTTCCTCAAAGACAACCGGGAGAAAATCGAGAAGATCCTGACGTT<br>CCGCATCCCCTACTACGTGGGCCCCCTCGCCCGCGGCAACTCGCGGTTCG<br>CGTGGATGACCCGGAAGAGCGAGGAGACGATCACCCCGTGGAATTTCGA<br>GGAGGTCGTCGATAAAGGCGCGTCGGCGCAGTCGTTCATCGAGCGCATG<br>ACCAACTTCGATAAAAATCTGCCGAACGAAAAAGTCCTGCCCAAGCATA<br>GCCTGCTGTACGAGTACTTCACGGTCTACAACGAGCTGACGAAAGTGAA<br>ATATGTCACGGAGGGCATGCGCAAACCGGCCTTCCTGTCCGGCGAGCAG<br>AAAAAGGCCATCGTGGATCTGCTGTTCAAGACGAACCGGAAGGTCACCG<br>TGAAACAGCTGAAGGAAGATTACTTCAAGAAAATCGAGTGCTTCGATTC<br>CGTCGAAATCAGCGGCGTGGAGGACCGCTTCAATGCCTCGCTGGGCACC<br>TATCACGATCTCCTCAAGATCATCAAGGACAAGGACTTCCTGGACAACG<br>AAGAGAACGAGGACATCCTGGAAGACATCGTCCTCACCCTGACCCTGTT<br>CGAGGACCGCGAAATGATCGAAGAGCGCCTGAAGACCTACGCCCACCTG<br>TTCGACGACAAGGTCATGAAGCAGCTCAAGCGCCGCCGGTACACCGGCT<br>GGGGCCGCCTGTCCCGGAAGCTGATCAACGGCATCCGCGATAAGCAGAG<br>CGGCAAGACGATCCTGGACTTCCTCAAGAGCGACGGCTTCGCCAATCGGA<br>ATTTCATGCAGCTCATCCACGACGATAGCCTGACCTTCAAAGAGGATATC<br>CAGAAGGCGCAGGTGTCCGGCCAGGGCGACAGCCTGCACGAACATATCG<br>CCAACCTGGCGGGCTCCCCCGCGATCAAGAAAGGCATCCTCCAGACGGTC<br>AAAGTCGTGGACGAGCTGGTCAAGGTGATGGGCCGCCACAAACCGGAGA<br>ATATCGTCATCGAGATGGCACGCGAGAACCAGACCACGCAGAAGGGCCA<br>GAAGAACAGCCGGGAACGCATGAAACGGATCGAAGAGGGCATCAAGGA<br>ACTGGGCTCGCAGATCCTGAAGGAGCACCCCGTCGAAAACACGCAGCTC<br>CAGAACGAGAAGCTGTATCTGTACTATCTCCAGAACGGCCGGGACATGTA<br>TGTCGATCAGGAACTGGATATCAACCGCCTCTCCGATTACGATGTGGACC<br>ACATCGTGCCGCAGAGCTTCCTGAAAGACGACTCGATCGACAACAAGGTC<br>CTGACCCGGTCGGACAAGAACCGCGGCAAGTCGGATAACGTGCCGTCGG<br>AAGAAGTCGTGAAAAAGATGAAGAACTACTGGCGGCAGCTCCTGAACGC<br>GAAGCTCATCACGCAGCGCAAGTTCGACAATCTGACCAAGGCCGAGCGC<br>GGCGGCCTCTCGGAACTCGACAAGGCGGGCTTCATCAAACGGCAGCTCG<br>TCGAGACGCGCCAGATCACCAAACACGTGGCCCAGATCCTGGACAGCCG<br>GATGAACACCAAATACGACGAAAACGACAAGCTGATCCGCGAAGTCAAG<br>GTCATCACGCTGAAGAGCAAGCTGGTGTCGGATTTCCGCAAGGATTTCCA<br>GTTCTACAAGGTGCGCGAGATCAACAATTACCATCACGCGCACGATGCCT<br>ATCTCAATGCGGTCGTGGGCACCGCCCTGATCAAAAAGTACCCGAAACTG<br>GAGTCCGAGTTCGTCTACGGCGACTATAAGGTCTATGATGTCCGCAAGAT<br>GATCGCCAAATCGGAGCAGGAGATCGGCAAGGCGACCGCGAAATATTTC<br>TTCTACTCGAACATCATGAATTTCTTCAAGACCGAGATCACGCTGGCGAA<br>CGGCGAAATCCGCAAGCGGCCCCTGATCGAAACCAATGGCGAGACCGGC<br>GAGATCGTGTGGGACAAAGGCCGGGATTTCGCCACCGTCCGCAAGGTCCT<br>CTCGATGCCGCAGGTGAACATCGTCAAGAAGACGGAGGTCCAGACCGGC<br>GGCTTCAGCAAAGAAAGCATCCTCCCCAAGCGGAATAGCGACAAACTGA<br>TCGCCCGGAAGAAGGACTGGGACCCGAAGAAGTATGGCGGCTTCGATAG |

TABLE 1-continued

| SEQ ID NO. | NAME | SEQUENCE |
|---|---|---|
| | | CCCCACCGTCGCCTATTCCGTCCTGGTGGTGGCGAAGGTGGAGAAAGGCA AAAGCAAGAAACTGAAGAGCGTGAAGGAGCTGCTGGGCATCACCATCAT GGAACGCAGCAGCTTCGAGAAGAACCCGATCGACTTCCTGGAAGCCAAA GGCTATAAGGAAGTGAAGAAGGACCTCATCATCAAACTCCCGAAGTATT CGCTGTTCGAGCTGGAAAATGGCCGCAAACGGATGCTCGCCTCCGCGGG CGAACTCCAGAAGGGCAACGAACTGGCGCTGCCGTCCAAATACGTCAAC TTCCTCTATCTGGCCAGCCATTACGAAAAGCTGAAGGGCTCGCCCGAAGA TAACGAGCAGAAACAGCTGTTCGTCGAGCAGCACAAGCACTACCTCGAC GAGATCATCGAGCAGATCAGCGAGTTCTCCAAGCGGGTGATCCTCGCGG ACGCCAACCTGGACAAGGTGCTGTCGGCGTACAACAAACATCGGGATAA GCCGATCCGCGAGCAGGCCGAAAATATCATCCACCTGTTCACCCTGACGA ACCTCGGCGCCCCCGCCGCCTTCAAGTATTTCGATACCACCATCGACCGGA AGCGCTATACCTCCACCAAAGAGGTCCTGGATGCCACCCTCATCCACCAG TCCATCACGGGCCTGTACGAGACCCGCATCGACCTGTCGCAGCTGGGCGG CGACTAA |

Example 6

Synthetic gRNA Expression

Synthetic gRNA were made which contained a 20 bp target region and a 83 bp Cas9 handle and terminator region. This synthetic gRNA was made to be driven by a constitutively expressed J23111 promoter. This J23111 promoter-gRNA sequence was cloned into a pBBR1-based plasmid (pSL90). Other J series promoters such as J23115 were also tested resulting in high editing efficiency (>50%). Additionally, a donor sequence was cloned in the same pBBR1-based plasmid containing the gRNA. The J23111 and Cas9 sequences used are shown in Table 2.

TABLE 2

| SEQ ID NO. | NAME | SEQUENCE |
|---|---|---|
| 80 | J23111 | TTGACGGCTAGCTCAGTCCTAGGTATAGTGCTAGC |
| 81 | Cas9 handle and terminator region | GTTTTAGAGCTAGAAATAGCAAGTTAAAATAAGGCTAGT CCGTTATCAACTTGAAAAAGTGGCACCGAGTCGGTGCTT TTTTT |

Example 7

Preparation for Genome Editing

A two-step two-plasmid system was employed in order to achieve high editing efficiency via CRISPR-Cas9 genome editing in *Methylococcus capsulatus*.

A "base" strain was created by transforming a pBBR1_gRNA_donor plasmid into *Methylococcus capsulatus* through electroporation. The base strains were frozen as a stock for future editing.

To perform gene editing, the base strain was pre-cultured by thawing out frozen stock vial of the base strain. The pre-cultures were grown to saturation (Optical Density (OD) at 600 nm of approximately 1-1.5). Once saturation was reached, a 1:100 dilution was made. The diluted cells were allowed to grow to an appropriate cell density (OD of 0.4-0.8). The cells were then prepared for electroporation.

The cells were washed three times in a solution comprising 2.5% sucrose and concentrated. The concentrated cells were then re-suspend in the solution comprising 2.5% sucrose to achieve an OD between 40-90. 300 ng of genetic materials to be electroporated, for example pSL95 (from example 1), were used for electroporation per 50 ul electrocompetent cells. The cells were cultured in IM5 media supplemented with 2.5% sucrose for at least 4 hours up to overnight. Then cells were plated on agar plates containing spectinomycin and kanamycin. The plates were placed in incubators containing 95% methane and 5% $CO_2$ until the appearance of colonies.

Editing efficiency was measured by confirming the proper nucleotide sequence using PCR and sequencing. First, a pair of primers were designed so that they anneal to the outside of donor region. PCR reactions were performed on several colonies (e.g., 8-12 colonies (colony PCR)), using the aforementioned primers for the amplification reaction. DNA sequencing of the amplified DNA products was used to determine the number of isolates that display correct editing (editing efficiency).

Example 8

Incorporating Point Mutations Using AGE

Point mutations were incorporating using AGE within the ppdK locus.

Two gRNAs were designed to knock out ppdK function through introducing stop codons and frame shift mutations. The gRNA and donor sequences are listed in Table 3A.

TABLE 3A

| Plasmid | gRNA1 | Targeting Sequence | Full sgRNA sequence | Donor sequence | Editing efficiency |
|---|---|---|---|---|---|
| pSL148 | gRNA1 | GCTCGAAG CCCATTAC CACG (SEQ ID NO. 82) | TTGACGGCTAGCTCAGTCC TAGGTATAGTGCTAGCGCT CGAAGCCCATTACCACGGT TTTAGAGCTAGAAATAGCA AGTTAAAATAAGGCTAGTC CGTTATCAACTTGAAAAAG TGGCACCGAGTCGGTGCTT TTTTT (SEQ ID NO. 83) | GTTCGACGCCGAATTCGAAGCC ATCAAGCACCAGGCCGGGGTCG CCGCCGACATCGGCCTGAGCGC CGTCCATCTCGCCGACATCGGCG AACGTTTCCTCGCCGTCGTACGC CGCCATACCGGCAAGCCTTTCCC CGAGGACGTCTACGAGCAGCTC GAGATCGCGATCCGGGCGGTAT TCGACTCCTGGATGGGAAACGC (SEQ ID NO. 84) | 83% |
| pSL150 | gRNA2 | TCAACCAC GATACACT CCAG (SEQ ID NO. 85) | TTGACGGCTAGCTCAGTCC TAGGTATAGTGCTAGCTCA ACCACGATACACTCCAGGT TTTAGAGCTAGAAATAGCA AGTTAAAATAAGGCTAGTC CGTTATCAACTTGAAAAAG TGGCACCGAGTCGGTGCTT TTTTT (SEQ ID NO. 86) | GTGACCGAGCCTATCTGGAATTG CTCAAGGCCCTGGCCCAGTTGCG CCTGCTGGAACGGCTGAATGCTC GAAAAATGGGCCGGAACCGGCT CTGATCCTGCAGTGACAAGCGG CGAACGCGACAGTTCGAGGAGA CCATCATGACGATGAAAAAGCG TGTCTACGCCTTCTCCGAAGGCG ACGGCAAGAACAAACGCCT (SEQ ID NO. 87) | 100% |

Additional targets were chosen for point mutations. For example, the genes rpoB, MCA2598, and MDH were targeted for point mutation editing. Editing efficiency for these genes ranged from 88% to 96%. The gRNA and donor sequences are listed in Table 3B.

TABLE 3B

| Plasmid | Gene Target | Targeting Sequence | Full sgRNA sequence | Donor sequence | Editing efficiency |
|---|---|---|---|---|---|
| pSL128 | rpoB | GGACCAGA ACAATCCG TTGT (SEQ ID NO. 88) | TTGACGGC TAGCTCAG TCCTAGGT ATAGTGCT AGCGGACC AGAACAAT CCGTTGTG TTTTAGAG CTAGAAAT AGCAAGTT AAAATAAG GCTAGTCC GTTATCAA CTTGAAAA AGTGGCAC CGAGTCGG TGCTTTTTT T (SEQ ID NO. 89) | TACCATGCGCATCGATCTGACCGAGACGCAGCTGGATGCCCTG GTGGAAATCTACCGGATGATGCGGCCGGGCGAACCGCCGACC AAGGAGGCCGCCCAGACCCTGTTCGAAAATCTGTTTTTCTCGG CCGAACGCTATGATCTGTCGGCTGTCGGCCGGATGAAGTTCAA CCGGCGCCTGGGGCGGACCGATCCTACCGGCCCCGGCGTGCT GGAAAACGATGACATCATCGCGGTGCTGAAGGAACTGATCAA CATCCGTAACGGGGGGGGCACGGTCGACGACATCGACCATCT GGGTAACCGCCGCGTCCGGTCCGTGGGGGAGATGGTGGAGA ATCAGTTCAGGCTCGGGCTGGTCCGGGTCGAACGGGCCGTGA AGGAGCGTCTGTCGCTGCCCGACGCCGATGGTCTGATGCCACA GGAGATCATCAACGCCAAACCGGTGGCCGCTTCCATCAAGGA ATTCTTCGGTTCGAGCCAGCTTTCGCGGTTCATGGACCAGAAT AACCCATTATCTGAGGTCACTCACAAGCGCCGTGTCTCGGCTCT GGGGCCGGGGGGGCTGGCGCGTGAGCGCGCCGGCTTCGAAG TGCGCGACGTGCATACCACCCACTACGGCCGTGTCTGTCCGAT CGAAACGCCCGAAGGTCCGAACATCGGCCTGATCAACTCGCTC GCGGTCTACTCGCGCACCAACGAATACGGCTTTCTGGAGACGC CGTATCGAAAGGTGATCGACGGCCGGGTGACCGATCAGATCG AGTACCTGTCGGCTATCGAGGAGGGCCAGTACTACATTGCTCA GGCCAGCGCCTCGGTCGATGAAAACGGCATGCTCAAGGATGA ACTGGTGTCGTGTCGCCACAAGGATGAATTCACCCTGGCGTCG CGGGAAAACATCAACTACATGGATGTGTCGTCCAAACAGATCG TGTCGGTCGCGGCCTCGCTGATCCCCTTCCTCGAACACGATGA TGCCAACCGCGCCCTGATGGGCTCGAACATGCAGCGGCAGGC CGTCCCGACGCTGCGTACGGAGAA (SEQ ID NO. 90) | 96% |
| gap gRNA5 | MCA25 98 | CGTCGTGC ATGAGTGC ACCG (SEQ ID NO. 91) | TTGACGGC TAGCTCAG TCCTAGGT ATAGTGCT AGCCGTCG TGCATGAG TGCACCGG TTTTAGAG CTAGAAAT AGCAAGTT AAAATAAG GCTAGTCC GTTATCAA CTTGAAAA | CCGGGACGGAACGCTTGCCAGGCCATCTGGATGTGGCGGGGA CCGGCGCCGTCGACGAACACGATCTCGAGGTCGTCGGCCACC GCCAGATAGAGCATGTTGCGAATGGGGACGAACAGTGGGTCG GGGCGCCGGCGGCCGAGCAGTACCCGGCTGAGGTTGTAGGTT GCGGCGCCGAGCAGGCGTGCCTCGCGTCGGAGTTCGCGCGAA CGATGGAAGGTTTCCTGCATGTGGATGGCGTCGCTTGCTGGGT CCCGGTTTAAGCTATCAGCCTTGGTGCGCGAAGGGCAAGAACT GGACGCTCGGCGCGGCGCTTTGCTATATTGGCCACGCTTTGTA TTGACAGATTCCCCGGAGAATGCCCGATTCTCCCTCGCCGAAG GCCCGCAGGCGTCCGGCCGGGACGGCCTCGACTGCTCTCCCCA CCCCACTCCGCCGGTCGCCAAGGGTGCGAGGGCTCTCGCGCAT GACCCCATCCTCACTTTATTTCAGCATTTCTGGAGCAGGGCAAT GACGATTAAGATTGCAATCAATGGATATGGGCGCATCGGCCG CAACATCCTGCGGGCGATTTACGAAACCGGGCGCAAGGATGT | 88% |

TABLE 3B-continued

| Plasmid | Gene Target | Targeting Sequence | Full sgRNA sequence | Donor sequence | Editing efficiency |
|---|---|---|---|---|---|
| | | | AGTGGCAC CGAGTCGG TGCTTTTTT T (SEQ ID NO. 92) | GGAGATCGTCGCCATCAATGACCTGGGGGATGCCCAGATCAA CGCCCATCTCACCCGCCATGACACCGTGCACGGGCCGTTCCGG GGGACCGTGGAGGTCGGCGAGGGCGAAATCATCGTCAACGG CGACCGCATCAGGGTTTTTTCCGAGAAGGATCCTTCCAAGCTG CCCTGGGGGGCTTTGGGCGTGGACGTCGTGCATGAGTGATAG CACCTGTTCCGCACCAAGGCCAAATGCCAGCCGCATCTCGATG CCGGCGCCAAGAAGGTGATCATTTCGGCCCCGGCCGACAAGA ACGAGTGCGACGCGACCATCGTCTACGGGGTCAATGAGCATA CGCTGAAAGCCGCCCACACCGTCATCTCGAATGCATCCTGCAC CACCAACTGCCTGGCGCCGCTGGTCAAGCCGCTGCTGGGAAA AATCGGGATCGTGTCCGGCCTCATGACCACCGTGCATTCCTAC ACCAACGACCAGGTGCTCACCGACGTTTATCACAAGGATCTGT ACCGGGCACGGGCGGCGGCGCTGAACATGATCCCGACCAAGA CCGGCGCGGCGCAGGCCGTGGGGCTGGTGCTGCCGGAGCTG GACGGCAAACTGTCCGGTTTCGCCATCCGGGTGCCGACCGCCA ATGTATCGGTCGTGGACCTGACCTTCATCGCGGCCCGGGAAAC CGACAAGGACGAGATCAACGCCATCCTCAAGGC (SEQ ID NO. 93) | |
| plK11 | MDH | CCCATCAC CTATCAGC ACAA (SEQ ID NO. 94) | TTGACGGC TAGCTCAG TCCTAGGT ATAGTGCT AGCCCCAT CACCTATC AGCACAAG TTTTAGAG CTAGAAAT AGCAAGTT AAAATAAG GCTAGTCC GTTATCAA CTTGAAAA AGTGGCAC CGAGTCGG TGCTTTTTT T (SEQ ID NO. 95) | AAGATCGATGACACCGTCAACTGGGTGAAAAAGGTCGATCTG AAGACCGGCCTGCCGATCCGCGATCCGGAGTACAGCACCCGC ATGGACCACAATGCCAAAGGCATCTGTCCCTCGGCCATGGGCT ATCACAACCAGGGCATCGAGTCCTACGATCCGGACAAGAAGCT GTTCTTCATGGGCGTGAACCACATCTGCATGGACTGGGAGCCG TTCATGCTGCCCTACCGCGCCGGCCAGTTCTTTGTGGGGGCGA CCCTCAACATGTATCCGGGACCCAAGGGGATGCTGGGTCAGG TCAAGGCGATGAACGCGGTCACCGGCAAGATGGAATGGGAA GTGCCGGAGAAGTTTGCGGTCTGGGGTGGCACCTTGGCGACC GCCGGCGACCTCGTGTTCTACGGTACCCTCGACGGCTTCATCA AGGCCCGCGACACCCGTACCGGCGAGCTGAAGTGGCAGTTCC AGTTGCCCTCCGGCGTGATCGGCCATCCCATCACGTACCAACA TAACGGCAAGCAATACATTGCCATCTACTCCGGCGTCGGCGGC TGGCCAGGAGTAGGGCTGGTATTCGACCTGAAGGACCCGACC GCAGGTCTGGGAGCTGTGGGTGCGTTCAGGGAACTGGCGCAT TACACCCAGATGGGTGGATCGGTGTTCGTGTTCTCGCTTTGAG TCGAAGGGGTGGAGGCGCTCCTGGGGGAGCGCCCCTATCCCA TGCTGTCGAAAGGATGAATCATGCGAATGAACCGTATTGCAGC CGCGGGGTTGGCCGCCTCCCTCGCGGTCGTGGGATGCGTGCA GGCAGCGACGAGCGTCGAACCGCTCAAGGTCTGCTCCGCGGA AAACGAGATGCCGTATTCGGACAAGGCCGGAGAGGGTTTCGA AAATAAGTTGGCTGAGCTCCTTGGAAAGGGATTGGGACGGCC AGTCGAGAACGTGTGGTGGACCGATGCCCGCTATTTCGTCCGG GATTATCTGGACAGGGGTTTGTGCGATGTGGTCATCGGCGTCG ATACCGGCGACCCGCGGATGCTCACCAGCAGTCCTTATTACCG GTCCGGCTACGTATTCGTCTACCGCAAGGACACGGGACTGAGC ATCCAAGATTGGAACAGCGCGGCACTGAAGACCGTGAAGCGG ATC (SEQ ID NO. 96) | 88% |

Example 9

Deletion of Portions of Genes

Portions of genes were deleted using AGE within specific genes such as the ppdK locus.

gRNA2 was designed to knock out ppdK function through gene deletion. Table 4A contains the gRNA and donor sequences used for creating the ppdK deletions.

TABLE 4A

| Plasmid | gRNA1 | Targeting Sequence | Full sgRNA sequence | Donor sequence | Editing efficiency |
|---|---|---|---|---|---|
| pSL178 | gRNA2 | TCAACCAC GATACACT CCAG (SEQ ID NO. 97) | TTGACGGCTAGCTCAGTCC TAGGTATAGTGCTAGCTCA ACCACGATACACTCCAGGT TTTAGAGCTAGAAATAGCA AGTTAAAATAAGGCTAGTC CGTTATCAACTTGAAAAAG TGGCACCGAGTCGGTGCTT TTTTT (SEQ ID NO. 98) | GTGTTCCCTGGAACACGCCATCA ATTTCGATCTCGTGCTCAACACC GACCATCTGCCAGCCGGTAACG CTCTGCCGACCGTACTCATGGCG GTACGGCAGTTCGGCTTCGAAAT CTTCGATCTCGGTCAGCGGGAA GCCTCGTGAGCCCGGCGGTGGG ACAGACCGCATCCCGTCTGCTAA CGGTCGAGATCGTCGACGTCTG | 72% |

TABLE 4A-continued

| Plasmid | gRNA1 | Targeting Sequence | Full sgRNA sequence | Donor sequence | Editing efficiency |
|---|---|---|---|---|---|
| | | | | CCGGGAGATATTTTCCGGGCGTT GTAGCCGGGTGGTCGCGCCAGC GGCAGACGGTGAGGTCGGCGTT CTGCCCCGTCATACGCCGTTCCT GACCCGGCTCCGGCCCGGCGAG ATAAGGC (SEQ ID NO. 99) | |

Additional targets were chosen for deletions within the ppdK gene. The deletion size of this second locus was 200 base pairs. Editing efficiency for the second locus was 88%. The gRNA and donor sequences are listed in Table 4B.

TABLE 4B

| Plasmid | Gene target | Targeting Sequence | Full sgRNA sequence | Donor sequence | Editing efficiency |
|---|---|---|---|---|---|
| pSL179 | ppdK | TCAACCAC GATACACT CCAG (SEQ ID NO. 100) | TTGACGGC TAGCTCAG TCCTAGGT ATAGTGCT AGCTCAAC CACGATAC ACTCCAGG TTTTAGAG CTAGAAAT AGCAAGTT AAAATAAG GCTAGTCC GTTATCAA CTTGAAAA AGTGGCAC CGAGTCGG TGCTTTTT T (SEQ ID NO. 101) | GTGTTCCCTGGAACACGCCATCAATTTCGATCTCGTGCTCAACACC GACCATCTGCCAGCCGGTAACGCTCTGCCGACCGTACTCATGGCGG TACGGCAGTTCGGCTTCGAAATCTTCGATCTCGGTCAGCGGGAAGC CTCGTGAGCCCGGCGGTGGGACAGACCGCATCCCGTCTGCTAACG GTCGAGATCGTCGACGTCTGCCGGGAGATATTTTCCGGGCGTTGT AGCCGGGTGGTCGCGCCAGCGGCAGACGGTGAGGTCGGCGTTCT GCCCCGTCATACGCCGTTCCTGACCCGGCTCCGGCCCGGCGAGATA AGGCTCAGGACCGAGGCAGGCGAAGACCAGTATTTCTACCTCTCC GGGGGCTACATGGAGGTGCAGCGCTGGGAGGTCAGCATCCTGGC CGACCAGGTGCTCCGCTCCCAAGAGATCGACCGGGAAGCGGCCCT GGCGGCCAAGCGCAACGCAGAGCGGATGCTCCGCGAGAACCGGA TTCCCGGCGAGCGTGACCGAGCCTATCTGGAATTGCTCAAGGCCCT GGCCCAGTTGCGCCTGCTGGAACGGCTGAATGCTCGAAAAATGGG CCGGAACCGGCTCTGATCCTGCAGTGACAAGCGGCGAACGCGACA GTTCGAGGAGACCATCATGACGATGAAAAAGCGTGTCTACGCCTT CTCCGAAGGCGACGGCAAGAACAAACGCCTGCTCGGCGGCAAGG GCGCCAACCTCTGCGAAATGACGCAGATCGGGCTCAACGTGCCGC CGGGTTTCGTTATTACCACGGAAGCCTGCCTCGAATACCTGGCAGA CAAGAAGCTGCCGGCCGGCTTGATGGACGAAGTCCGGGAGCACAT GGCCCGGCTCGAACGGGCTACCGGCAAGCGCTTCGGCGATCCCGC CAATCCACTCTTGGTTTCGGTGCGTTCCGGTTCGGCCCTGTCCATGC CGGGCATGATGGATACCATTCTCAACCTCGGCCTCAACCACGATAC ACTCTTTCCTCGCCGTCGTACGCCGCCATACCGGCAAGCCTTTCCCC GAGGACGTCTACGAGCAGCTCGAGATCGCGATCCGGGCGGTATTC GACTCCTGGATGGGAAAGCGCGCGGTGGATTACCGCCGCGAATTC CACATCACGCCCGACCAGGCCAACGGCACGGCGGTGAACGTGGTG ACCATGGTGTTCGGCAACATGGGCGACGACTCCGCCACCGGTGTC GGCTTCACCCGCAATCCGGGTACCGGTGAGAACGAGATGTTCGGC GAGTATCTGGTCAACGCCCAGGGTGAGGATGTGGTAGCCGGAATC CGCACGCCCAAGCCCGTGCACGAGATGGCAACCGAAATGCCGGCG CTTTACGCCCAACTGGTGGAACTGCGCGACAAGCTCGAAGCCCATT ACCACGAGGTGCAGGACTTCGAGTACACCATCGAGAAGGGGGTCT TGTACTGTCTGCAGACGCGCAACGGCAAGATGAACGCCCAGGCGA TGGTGCGCACCTCGGTCGAGATGTGCCGGGAAGGACTGATCACGC GGGATCAGGCCCTCTTGCGGGTCAACCCCGCCCATCTGGAACAGTT ACTCCATCCCTGCCTCGACACCTCGCACAACCCCACGCCGCTGGCG CAGGGGCTGCCTGCCTCGCCCGGCGCCGCCAGCGGCCGTTGCGTG TTCGATGCGGATCAGGCCGAACTGTTGGGACGGGCCGGTGAAAA GGTCATCCTGGTGCGTGAGGAGACCAAGCCGGAAGACATCCACGG CTTCTTCGCGGCCCAGGGAATCCTCACCAGTCGCGGCGGCAAGAC CTCGCATGCCGCCGTGGTCGCCCGCGGCATGGGCAAGGCCTGCGT GGCCGGGGCCGAAGGCATCAGGGTGGACAGCCGGGCGCGGCTG GCAACGGTGGGAGAGGTCACGTTGCACGAAGGTGACATCATCACC ATCGACGGCAGCACCGGCCGTGTCTATCTCGGCGCGATCCCGACG ATCGCGCCGACCTTCTCCGAACACCTCAGGACACTGCTGTC (SEQ ID NO. 102) | 88% |

Example 10

Insertion of Nucleotides

Nucleotides were inserted using AGE within the ppdK locus.

gRNA2 was designed to integrate gamma protein gene (417 bp) at ppdK locus. Table 5A indicates the gRNA and donor sequences used for creating the gamma protein gene integration.

TABLE 5A

| Plasmid | gRNA1 | Targeting Sequence | Full sgRNA sequence | Donor sequence | Editing efficiency |
|---|---|---|---|---|---|
| pSL162 | gRNA2 | TCAACCAC GATACACT CCAG (SEQ ID NO. 103) | TTGACGGCTAGCTCAGTCC TAGGTATAGTGCTAGCTCA ACCACGATACACTCCAGGT TTTAGAGCTAGAAATAGCA AGTTAAAATAAGGCTAGTC CGTTATCAACTTGAAAAAG TGGCACCGAGTCGGTGCTT TTTTT (SEQ ID NO. 104) | GTGACCGAGCCTATCTGGAATTG CTCAAGGCCCTGGCCCAGTTGCG CCTGCTGGAACGGCTGAATGCTC GAAAAATGGGCCGGAACCGGCT CTGATCCTGCAGTGACAAGCGG CGAACGCGACAGTTCGAGGAGA CCATCATGACGATGAAAAAGCG TGTCTACGCCTTCTCCGAAGGCG ACGGCAAGAACAAACGCCT (SEQ ID NO. 105) | 11% |

Additional targets were chosen for insertions within specific genes. The size of the fragments were relatively small, i.e., 34 and 39 bps. Editing efficiency for the second locus was 83% for both of these genes. The gRNA and donor sequences are listed in Table 5B.

TABLE 5B

| Plasmid | Gene target | Targeting Sequence sequence | Full sgRNA | Donor sequence | Editing efficiency |
|---|---|---|---|---|---|
| pSL154 | ppdK (attB site) | TCAACCAC GATACACT CCAG (SEQ ID NO. 106) | TTGACGGC TAGCTCAG TCCTAGGT ATAGTGCT AGCTCAAC CACGATAC ACTCCAGG TTTTAGAG CTAGAAAT AGCAAGTT AAAATAAG GCTAGTCC GTTATCAA CTTGAAAA AGTGGCAC CGAGTCGG TGCTTTTT T (SEQ ID NO. 107) | GTGACCGAGCCTATCTGGAATTGCTCAAGGCCCTGGCCCAGTTGCG CCTGCTGGAACGGCTGAATGCTCGAAAAATGGGCCGGAACCGGCT CTGATCCTGCAGTGACAAGCGGCGAACGCGACAGTTCGAGGAGAC CATCATGACGATGAAAAAGCGTGTCTACGCCTTCTCCGAAGGCGAC GGCAAGAACAAACGCCTGCTCGGCGGCAAGGGCGCCAACCTCTGC GAAATGACGCAGATCGGGCTCAACGTGCCGCCGGGTTTCGTTATT ACCACGGAAGCCTGCCTCGAATACCTGGCAGACAAGAAGCTGCCG GCCGGCTTGATGGACGAAGTCCGGGAGCACATGGCCCGGCTCGAA CGGGCTACCGGCAAGCGCTTCGGCGATCCCGCCAATCCACTCTTGG TTTCGGTGCGTTCCGGTTCGGCCCTGTCCATGCCGGGCATGATGGA TACCATTCTCAACCTCGGCCTCAACCACGATACACTCTAAGTGCCAG GGCGTGCCCTTGGGCTCCCCGGGCGCGGGGTTGATCCGGCAGACC GGCAACGAGCGCTTCGGTCACGATGCCTACCGGCGGTTCATCCAG TTGTTCGGCAAGGTTGCCCTCGGTGTTCCCGACGAGCTGTTCGACG CCGAATTCGAAGCCATCAAGCACCAGGCCGGGGTCGCCGCCGACA TCGGCCTGAGCGCCGTCCATCTCGCCGACATCGGCGAACGTTTCCT CGCCGTCGTACGCCGCCATACCGGCAAGCCTTTCCCCGAGGACGTC TACGAGCAGCTCGAGATCGCGATCCGGGCGGTATTCGACTCCTGG ATGGGAAAGCGCGCGGTGGATTACCGCCGCGAATTCCACATCACG CCCGACCAGGCCAACGGCACGGCGGTGAACGTGGTGACCATGGT GTTCGGCAACATGGGCGACGACTCCGCCACCGGTGTCGGCTTCAC CCGCAATCCGGGTACCGGTGAGAACGAGATGTTCGGCGAGTATCT GGTCAACGCCCAGGGTGAGGATGTGGTAGCCGGAATCCGCACGCC CAAGCCCGTGCACGAGATGGCAACCGAAATGC (SEQ ID NO. 108) | 83% |
| pSL175 | aacC (attP) site) | TACTACGG AGCAAGTT CCCG (SEQ ID NO. 109) | TTGACGGC TAGCTCAG TCCTAGGT ATAGTGCT AGCTACTA CGGAGCAA GTTCCCGG TTTTAGAG CTAGAAAT AGCAAGTT AAAATAAG GCTAGTCC GTTATCAA | GCCAGGACAGAAATGCCTCGACTTCGCTGCTGCCCAAGGTTGCCG GGTGACGCACACCGTGGAAACGGATGAAGGCACGAACCCAGTTG ACATAAGCCTGTTCGGTTCGTAAACTGTAATGCAAGTAGCGTATGC GCTCACGCAACTGGTCCAGAACCTTGACCGAACGCAGCGGTGGTA ACGGCGCAGTGGCGGTTTTCATGGCTTGTTATGACTGTTTTTTTGTA CAGTCTATGCCTCGGGCATCCAAGCAGCAAGCGCGTTACGCCGTG GGTCGATGTTTGATGTTATGGAGCAGCAACGATGTTACGCAGCAG CAACGATGTTACGCAGCAGGGCAGTCGCCCTAAAACAAAGTTAGG TGGCTCAAGTATGGGCATCATTCGCACATGTAGGCTCGGCCCTGAC CAAGTCAAATCCATGCGGGCTGCTCTTGATCTMCGGTCGTGAGT TCGGAGACGTAGCCACCTACTCCCAACATCAGCCGGACTCCGATTA GCTCCCCCAACTGAGAGAACTCAAAGGTTACCCCAGTTGGGGCGG GTAACTTGCTCCGTAGTAAGACATTCATCGCGCTTGCTGCCTTCGA | |

TABLE 5B-continued

| Plasmid | Gene target | Targeting Sequence sequence | Full sgRNA | Donor sequence | Editing efficiency |
|---|---|---|---|---|---|
| | | | CTTGAAAAAGTGGCACCGAGTCGGTGCTTTTTTT (SEQ ID NO. 110) | CCAAGAAGCGGTTGTTGGCGCTCTCGCGGCTTACGTTCTGCCCAGGTTTGAGCAGCCGCGTAGTGAGATCTATATCTATGATCTCGCAGTCTCCGGCGAGCACCGGAGGCAGGGCATTGCCACCGCGCTCATCAATCTCCTCAAGCATGAGGCCAACGCGCTTGGTGCTTATGTGATCTACGTGCAAGCAGATTACGGTGACGATCCCGCAGTGGCTCTCTATACAAAGTTGGGCATACGGGAAGAAGTGATGCACTTTGATATCGACCCAAGTACCGCCACCTAACAATTCGTTCAAGCCGAGATCGGCTTCATAACTTCGTATAGCATACATTATACGAAGTTATTGGCAGAGCATTACGCTGACTTGACCAGAGGCTGCATTTCCACCGCTGATTGCGATTCGGAAGGTGCAGGCCGGAGGGTCCGGACCGCCGCTCCACCCGTTGTTTTC(SEQ ID NO. 111) | |

Larger insertional targets were chosen. Targets with DNA insertion size of 684 bp and 1083 bp were chosen. Editing efficiency was lower for larger insertional size fragments, i.e., under 10% efficiency. The gRNA and donor sequences are listed in Table 5C.

TABLE 5C

| Plasmid | Gene target | Targeting Sequence | Full sgRNA sequence | Donor sequence | Editing efficiency |
|---|---|---|---|---|---|
| pSL163 | ppdK (mcherry) | TCAACCACGATACACTCCAG (SEQ ID NO. 112) | TTGACGGCTAGCTCAGTCCTAGGTATAGTGCTAGCTCAACCACGATACACTCCAGGTTTTAGAGCTAGAAATAGCAAGTTAAAATAAGGCTAGTCCGTTATCAACTTGAAAAAGTGGCACCGAGTCGGTGCTTTTTTT (SEQ ID NO. 113) | GTGACCGAGCCTATCTGGAATTGCTCAAGGCCCTGGCCCAGTTGCGCCTGCTGGAACGGCTGAATGCTCGAAAAATGGGCCGGAACCGGCTCTGATCCTGCAGTGACAAGCGGCGAACGCGACAGTTCGAGGAGACCATCATGACGATGAAAAAGCGTGTCTACGCCTTCTCCGAAGGCGACGGCAAGAACAAACGCCTGCTCGGCGGCAAGGGCGCCAACCTCTGCGAAATGACGCAGATCGGGCTCAACGTGCCGCCGGGTTTCGTTATTACCACGGAAGCCTGCCTCGAATACCTGGCAGACAAGAAGCTGCCGGCCGGCTTGATGGACGAAGTCCGGGAGCACATGGCCCGGCTCGAACGGGCTACCGGCAAGCGCTTCGGCGATCCCGCCAATCCACTCTTGGTTTCGGTGCGTTCCGGTTCGGCCCTGTCCATGCCGGGCATGATGGATACCATTCTCAACCTCGGCCTCAACCACGATACACTCTAATTGACGGCTAGCTCAGTCCTAGGTATAGTGCTAGCAAAAAGCTCAACGAGAGGAAGTTCCATGGCCATCATCAAGGAGTTCATGCGCTTCAAGGTGCACATGGAGGGCTCCGTGAACGGCCACGAGTTCGAGATCGAGGGCGAGGGCGAGGGCCGCCCCTACGAGGGCACCCAGACCGCCAAGCTGAAGGTGACCAAGGGTGGCCCCCTGCCCTTCGCCTGGGACATCCTGTCCCCTCAGTTCATGTACGGCTCCAAGGCCTACGTGAAGCACCCCGCCGACATCCCCGACTACTTGAAGCTGTCCTTCCCCGAGGGCTTCAAGTGGGAGCGCGTGATGAACTTCGAGGACGGCGGCGTGGTGACCGTGACCCAGGACTCCTCCCTCCAGGACGGCGAGTTCATCTACAAGGTGAAGCTGCGCGGCACCAACTTCCCCTCCGACGGCCCCGTAATGCAGAAGAAGACCATGGGCTGGGAGGCCTCCTCCGAGCGGATGTACCCCGAGGACGGCGCCCTGAAGGGCGAGATCAAGCAGAGGCTGAAGCTGAAGGACGGCGGCCACTACGACGCTGAGGTCAAGACCACCTACAAGGCCAAGAAGCCCGTGCAGCTGCCCGGCGCCTACAACGTCAACATCAAGTTGGACATCACCTCCCACAACGAGGACTACACCATCGTGGAACAGTACGAACGCGCCGAGGGCCGCCACTCCACCGGCGGCATGGACGAGCTGTACAAGTAAGGGTTGATCCGGCAGACCGGCAACGAGCGCTTCGGTCACGATGCCTACCGGCGGTTCATCCAGTTGTTCGGCAAGGTTGCCCTCGGTGTTCCCGACGAGCTGTTCGACGCCGAATTCGAAGCCATCAAGCACCAGGCCGGGGTCGCCGCCGACATCGGCCTGAGCGCCGTCCATCTCGCCGACATCGGCGAACGTTTCCTCGCCGTCGTACGCCGCCATACCGGCAAGCCTTTCCCCGAGGACGTCTACGAGCAGCTCGAGATCGCGATCCGGGCGGTATTCGACTCCTGGATGGGAAAGCGCGCGGTGGATTACCGCCGCGAATTCCACATCACGCCCGACCAGGCCAACGGCACGGCGGTGAACGTGGTGACCATGGTGTTCGGCAACATGGGCGACGACTCCGCCACCGGTGTCGGCTTCACCCGCAATCCGGGTACCGGTGAGAACGAGATGTTCGGCGAGTATCTGGTCAACGCCCAGGGTGAGGATGTGGTAGCCGGAATCCGCACGCCCAAGCCCGTGCACGAGATGGCAACCGAAATGC (SEQ ID NO. 114) | 6% |
| pSL165 | ppdK (adh) | TCAACCACGATACACTCCAG (SEQ ID NO. 115) | TTGACGGCTAGCTCAGTCCTAGGTATAGTGCTAGCTCAACCACGATACACTCCAGGTTTTAGAG | GTGACCGAGCCTATCTGGAATTGCTCAAGGCCCTGGCCCAGTTGCGCCTGCTGGAACGGCTGAATGCTCGAAAAATGGGCCGGAACCGGCTCTGATCCTGCAGTGACAAGCGGCGAACGCGACAGTTCGAGGAGACCATCATGACGATGAAAAAGCGTGTCTACGCCTTCTCCGAAGGCGACGGCAAGAACAAACGCCTGCTCGGCGGCAAGGGCGCCAACCTCTGCGAAATGACGCAGATCGGGCTCAACGTGCCGCCGGGTTTCGTTATTACCACGGAAGCCTGCCTCGAATACCTGGCAGACAAGAAGCTGCCGGCCGGCTTGATGGACGAAGTCCGGGAGCACATGGCCCGGCTCGAA | 5% |

TABLE 5C-continued

| Plasmid | Gene target | Targeting Sequence | Full sgRNA sequence | Donor sequence | Editing efficiency |
|---|---|---|---|---|---|
| | | | CTAGAAATAGCAAGTTAAAATAAGGCTAGTCCGTTATCAACTTGAAAAAGTGGCACCGAGTCGGTGCTTTTTTT (SEQ ID NO. 116) | CGGGCTACCGGCAAGCGCTTCGGCGATCCCGCCAATCCACTCTTGGTTTCGGTGCGTTCCGGTTCGGCCCTGTCCATGCCGGGCATGATGGATACCATTCTCAACCTCGGCCTCAACCACGATACACTCTAATTGACGGCTAGCTCAGTCCTAGGTATAGTGCTAGCAAAAAGCTCAACGAGAGGAAGTTCCATGAGCTATCCCGAGAAGTTCGAGGGGATCGCCATCCAGAGCCACGAGGACTGGAAGAACCCGAAAAAGACCAAGTATGATCCGAAGCCCTTCTACGATCACGACATCGACATCAAGATCGAGGCCTGCGGCGTCTGCGGCAGCGATATCCATTGTGCGGCTGGCCACTGGGGCAACATGAAGATGCCGTTGGTCGTCGGCCACGAGATCGTGGGCAAGGTCGTGAAGTTAGGCCCGAAAAGCAACAGCGGCTTGAAGGTGGGCCAGCGCGTGGGTGTGGGTGCGCAGGTCTTCAGCTGTCTGGAGTGCGACCGTTGCAAGAACGACAACGAACCGTACTGCACCAAGTTCGTCACCACCTACTCGCAGCCCTACGAGGACGGCTACGTCTCGCAGGGCGGTTACGCCAACTATGTCCGAGTCCACGAACACTTCGTGGTGCCCATCCCGGAAAATATCCCCAGCCATCTGGCGGCTCCCCTGCTGTGCGGTGGCTTGACCGTCTACAGCCCCCTCGTCCGCAATGGCTGCGGTCCCGGCAAGAAGGTGGGTATCGTGGGCCTCGGCGGTATAGGCTCTATGGGCACGCTGATCTCGAAAGCGATGGGCGCAGAAACGTACGTGATCTCGCGTTCCTCGCGCAAGCGCGAGGATGCGATGAAGATGGGTGCGGACCACTACATCGCCACGCTGGAGGAGGGTGACTGGGGTGAGAAGTACTTCGACACGTTCGACCTCATCGTGGTGTGCGCGAGTTCCCTGACGGACATCGACTTCAATATCATGCCCAAGGCGATGAAGGTCGGAGGGCGCATCGTCTCCATCTCGATCCCGGAGCAGCACGAAATGCTGTCGCTGAAGCCCTACGGCCTGAAAGCCGTCTCCATTAGCTACTCGGCGCTCGGTAGTATCAAGGAGCTCAACCAGCTGTTGAAGTTGGTTTCCGAAAAGGACATCAAGATCTGGGTGGAAACGCTCCCGGTGGGCGAAGCCGGTGTGCACGAGGCCTTTGAGCGGATGGAGAAGGGGGATGTCCGTTATCGGTTTACACTCGTCGGCTACGATAAAGAGTTCTCGGATTAAGGGTTGATCCGGCAGACCGGCAACGAGCGCTTCGGTCACGATGCCTACCGGCGGTTCATCCAGTTGTTCGGCAAGGTTGCCCTCGGTGTTCCCGACGAGCTGTTCGACGCCGAATTCGAAGCCATCAAGCACCAGGCCGGGGTCGCCGCCGACATCGGCCTGAGCGCCGTCCATCTCGCCGACATCGGCGAACGTTTCCTCGCCGTCGTACGCCGCCATACCGGCAAGCCTTTCCCCGAGGACGTCTACGAGCAGCTCGAGATCGCGATCCGGGCGGTATTCGACTCCTGGATGGGAAAGCGCGCGGTGGATTACCGCCGCGAATTCCACATCACGCCCGACCAGGCCAACGGCACGGCGGTGAACGTGGTGACCATGGTGTTCGGCAACATGGGCGACGACTCCGCCACCGGTGTCGGCTTCACCCGCAATCCGGGTACCGGTGAGAACGAGATGTTCGGCGAGTATCTGGTCAACGCCCAGGGTGAGGATGTGGTAGCCGGAATCCGCACGCCCAAGCCCGTGCACGAGATGGCAACCGAAATGC (SEQ ID NO. 117) | |

Example 11

Inhibition of Gene Expression Using AGEi-DCas9

Catalytically inactive Cas9 protein (dCas9) can form a complex with sgRNA and can bind to a target region to create a steric block interrupting transcript initiation or elongation by RNA polymerase. This can, if done correctly and in certain organisms, result in repression of a target gene, which is referred to as AGEi.

AGEi was performed in *Methylococcus capsulatus* using a two-plasmid based lacZ reporter assay (from Invitrogen lacZ assay kit): 1) OriV origin based plasmid carries pBAD_dCas9 and gRNA. 2) pBBR1 based plasmids carries Ptrc_lacZ. Five gRNA were designed to target different regions of lacZ. One gRNA that targets the promoter region of the reporter repressed lacZ expression consistently over a 72 hour time point. The relevant information related to the sequences is presented in Table 6A, Table 6B, and Table 6C below.

TABLE 6A

| SEQ ID NO. | NAME | SEQUENCE |
|---|---|---|
| 118 | dCas9 | ATGGACAAGAAGTATTCGATCGGCCTGGCCATCGGCACCAACAGCGTCGGCTGGGCGGTCATCACGGATGAGTACAAGGTGCCGTCGAAGAAGTTCAAGGTGCTGGGCAATACCGACCGCCATAGCATCAAGAAGAATCTCATCGGCGCACTGCTGTTCGACTCCGGCGAAACCGCCGAAGCGACCCGCCTCAAGCGCACGGCCCGGCGGCGCTATACGCGCCGGAAGAACCGCATCTGCTACCTCCAGGAAATCTTCTCCAACGAGATGGCCAAGGTGGATGACTCCTTCTTCCATCGCCTGGAAGAATCCTTCCTGGTCGAAGAAGATAAGAAACATGAGCGCCACCCCATCTTCGGCAATATCGTGGACGAGGTGGCGTATCACGAGAAATACCCGACCATCTATCACCTGCGGAAAAAGCTGGTGGACTCGACGGACAAAGCCGACCTGCGCCTCATCTATCTGGCCCTGGCCCACATGATCAAGTTCCGGGGCCATTTCCTGATCGAAGGCGACCTGAACCCCGATAACAGCGACGTGGACAAGCTCTTCATCCAGCTCGTCCAGACCTATAACCAGCTGTTCGAGGAGAACCCCATCAACGCCTCGGGCGTGGACGCCAAGGCCATCCTGAGCGCACGGCTCTCCAAGTCGCGCCGCCTGGAAAACCTGATCGCGCAGCTGCCGGGCGAAAAGAAAAACGGCCTGTTCGGCAACCTGATCGCCCTGTCCCTCGGCCTCACCCCGAACTTCAAGTCCAACTTCGACCTGGCCGAGGACGCGAAGCTCCAGCTGTCGAAAGACACCTACGATGACGACCTGGACAACCTCCTGGCGCAGATCGGCGACCAGTACGCCGACCTCTTCCTCGCGGCCAAGAATCTGTCGGACGCCATCCTGCTGTCGGATATCCTGCGGGTGAATACGGAGATCACGAAGGCCCCCCTCTCGGCCTCGATGATCAAGCGCTACGACGAG |

TABLE 6A-continued

| SEQ ID NO. | NAME | SEQUENCE |
|---|---|---|
| | | CACCATCAGGACCTGACGCTGCTCAAGGCCCTCGTCCGGCAGCAGCTGCCGGAGAAGTATAAAGAGATCTTCTTCG ACCAGTCCAAGAACGGCTACGCGGGCTACATCGACGGCGGCGCGTCGCAGGAGGAGTTCTATAAATTCATCAAGC CGATCCTGGAGAAAATGGACGGCACCGAAGAACTCCTCGTCAAGCTGAACCGGGAGGATCTGCTCCGCAAGCAGC GCACCTTCGACAATGGCTCCATCCCGCACCAGATCCATCTCGGCGAGCTGCACGCCATCCTGCGCCGCCAGGAGGA CTTCTACCCCTTCCTCAAAGACAACCGGGAGAAAATCGAGAAGATCCTGACGTTCCGCATCCCCTACTACGTGGGCC CCCTCGCCCGCGGCAACTCGCGGTTCGCGTGGATGACCCGGAAGAGCGAGGAGACGATCACCCCGTGGAATTTCG AGGAGGTCGTCGATAAAGGCGCGTCGGCGCAGTCGTTCATCGAGCGCATGACCAACTTCGATAAAAATCTGCCGA ACGAAAAAGTCCTGCCCAAGCATAGCCTGCTGTACGAGTACTTCACGGTCTACAACGAGCTGACGAAAGTGAAATA TGTCACGGAGGGCATGCGCAAACCGGCCTTCCTGTCCGGCGAGCAGAAAAAGGCCATCGTGGATCTGCTGTTCAA GACGAACCGGAAGGTCACCGTGAAACAGCTGAAGGAAGATTACTTCAAGAAAATCGAGTGCTTCGATTCCGTCGA AATCAGCGGCGTGGAGGACCGCTTCAATGCCTCGCTGGGCACCTATCACGATCTCCTCAAGATCATCAAGGACAAG GACTTCCTGGACAACGAAGAGAACGAGGACATCCTGGAAGACATCGTCCTCACCCTGACCCTGTTCGAGGACCGC GAAATGATCGAAGAGCGCCTGAAGACCTACGCCCACCTGTTCGACGACAAGGTCATGAAGCAGCTCAAGCGCCGC CGGTACACCGGCTGGGGCCGCCTGTCCCGGAAGCTGATCAACGGCATCCGCGATAAGCAGAGCGGCAAGACGATC CTGGACTTCCTCAAGAGCGACGGCTTCGCCAATCGGAATTTCATGCAGCTCATCCACGACGATAGCCTGACCTTCAA AGAGGATATCCAGAAGGCGCAGGTGTCCGGCCAGGGCGACAGCCTGCACGAACATATCGCCAACCTGGCGGGCT CCCCCGCGATCAAGAAAGGCATCCTCCAGACGGTCAAAGTCGTGGACGAGCTGGTCAAGGTGATGGGCCGCCACA AACCGGAGAATATCGTCATCGAGATGGCACGCGAGAACCAGACCACGCAGAAGGGCCAGAAGAACAGCCGGGAA CGCATGAAACGGATCGAAGAGGGCATCAAGGAACTGGGCTCGCAGATCCTGAAGGAGCACCCCGTCGAAAACAC GCAGCTCCAGAACGAGAAGCTGTATCTGTACTATCTCCAGAACGGCCGGGACATGTATGTCGATCAGGAACTGGAT ATCAACCGCCTCTCCGATTACGATGTGGACGCCATCGTGCCGCAGAGCTTCCTGAAAGACGACTCGATCGACAACA AGGTCCTGACCCGGTCGGACAAGAACCGCGGCAAGTCGGATAACGTGCCGTCGGAAGAAGTCGTGAAAAAGATG AAGAACTACTGGCGGCAGCTCCTGAACGCGAAGCTCATCACGCAGCGCAAGTTCGACAATCTGACCAAGGCCGAG CGCGGCGGCCTCTCGGAACTCGACAAGGCGGGCTTCATCAAACGGCAGCTCGTCGAGACGCGCCAGATCACCAAA CACGTGGCCCAGATCCTGGACAGCCGGATGAACACCAAATACGACGAAAACGACAAGCTGATCCGCGAAGTCAAG GTCATCACGCTGAAGAGCAAGCTGGTGTCGGATTTCCGCAAGGATTTCCAGTTCTACAAGGTGCGCGAGATCAACA ATTACCATCACGCGCACGATGCCTATCTCAATGCGGTCGTGGGCACCGCCCTGATCAAAAAGTACCCGAAACTGGA GTCCGAGTTCGTCTACGGCGACTATAAGGTCTATGATGTCCGCAAGATGATCGCCAAATCGGAGCAGGAGATCGG CAAGGCGACCGCGAAATATTTCTTCTACTCGAACATCATGAATTTCTTCAAGACCGAGATCACGCTGGCGAACGGC GAAATCCGCAAGCGGCCCCTGATCGAAACCAATGGCGAGACCGGCGAGATCGTGTGGGACAAAGGCCGGGATTT CGCCACCGTCCGCAAGGTCCTCTCGATGCCGCAGGTGAACATCGTCAAGAAGACGGAGGTCCAGACCGGCGGCTT CAGCAAAGAAAGCATCCTCCCCAAGCGGAATAGCGACAAACTGATCGCCCGGAAGAAGGACTGGGACCCGAAGA AGTATGGCGGCTTCGATAGCCCCACCGTCGCCTATTCCGTCCTGGTGGTGGCGAAGGTGGAGAAAGGCAAAAGCA AGAAACTGAAGAGCGTGAAGGAGCTGCTGGGCATCACCATCATGGAACGCAGCAGCTTCGAGAAGAACCCGATC GACTTCCTGGAAGCCAAAGGCTATAAGGAAGTGAAGAAGGACCTCATCATCAAACTCCCGAAGTATTCGCTGTTCG AGCTGGAAAATGGCCGCAAACGGATGCTCGCCTCCGCGGGCGAACTCCAGAAGGGCAACGAACTGGCGCTGCCG TCCAAATACGTCAACTTCCTCTATCTGGCCAGCCATTACGAAAAGCTGAAGGGCTCGCCCGAAGATAACGAGCAGA AACAGCTGTTCGTCGAGCAGCACAAGCACTACCTCGACGAGATCATCGAGCAGATCAGCGAGTTCTCCAAGCGGG TGATCCTCGCGGACGCCAACCTGGACAAGGTGCTGTCGGCGTACAACAAACATCGGGATAAGCCGATCCGCGAGC AGGCCGAAAATATCATCCACCTGTTCACCCTGACGAACCTCGGCGCCCCCGCCGCCTTCAAGTATTTCGATACCACC ATCGACCGGAAGCGCTATACCTCCACCAAAGAGGTCCTGGATGCCACCCTCATCCACCAGTCCATCACGGGCCTGT ACGAGACCCGCATCGACCTGTCGCAGCTGGGCGGCGACTAA (SEQ ID NO. 118) |

TABLE 6B

| Plasmid | gRNA name | Targeting Sequence | Full sgRNA sequence |
|---|---|---|---|
| oriv_ dCas9_ gRNA3 | gRNA3 | ATAATGTG TGGAATTG TGAG (SEQ ID NO. 119) | TTTATAGCTAGCTCAGCCCTTGGTACAATGCTAGCATAATGTGTGGAATTGTGAGGTTTTAGAGCTAG AAATAGCAAGTTAAAATAAGGCTAGTCCGTTATCAACTTGAAAAAGTGGCACCGAGTCGGTGCTTTT TTT (SEQ ID NO. 120) |

TABLE 6C

| Plasmid | Promoter | LacZ sequence |
|---|---|---|
| Ptrc_ laxZ | TTGACAAT TAATCATCC GGCTCGTA TAATGTGT GGAATTGT GAGCGGAT AACAATTA ACGAGAGG AAGTTCC (SEQ ID NO. 121) | ATGACCATGATTACGGATTCACTGGCCGTCGTTTTACAACGTCGTGACTGGGAAAACCCTGGCGTTACCCAACTT AATCGCCTTGCAGCACATCCCCCTTTCGCCAGCTGGCGTAATAGCGAAGAGGCCCGCACCGATCGCCCTTCCCAA CAGTTGCGCAGCCTGAATGGCGAATGGCGCTTTGCCTGGTTTCCGGCACCAGAAGCGGTGCCGGAAAGCTGGCT GGAGTGCGATCTTCCTGAGGCCGATACTGTCGTCGTCCCCTCAAACTGGCAGATGCACGGTTACGATGCGCCCAT CTACACCAACGTGACCTATCCCATTACGGTCAATCCGCCGTTTGTTCCCACGGAGAATCCGACGGGTTGTTACTC GCTCACATTTAATGTTGATGAAAGCTGGCTACAGGAAGGCCAGACGCGAATTATTTTTGATGGCGTTAACTCGGC GTTTCATCTGTGGTGCAACGGGCGCTGGGTCGGTTACGGCCAGGACAGTCGTTTGCCGTCTGAATTTGACCTGA GCGCATTTTTACGCGCCGGAGAAAACCGCCTCGCGGTGATGGTGCTGCGCTGGAGTGACGGCAGTTATCTGGAA GATCAGGATATGTGGCGGATGAGCGGCATTTTCCGTGACGTCTCGTTGCTGCATAAACCGACTACACAAATCAG CGATTTCCATGTTGCCACTCGCTTTAATGATGATTTCAGCCGCGCTGTACTGGAGGCTGAAGTTCAGATGTGCGG CGAGTTGCGTGACTACCTACGGGTAACAGTTTCTTTATGGCAGGGTGAAACGCAGGTCGCCAGCGGCACCGCGC |

TABLE 6C-continued

| Plasmid | Promoter | LacZ sequence |
|---|---|---|
| | | CTTTCGGCGGTGAAATTATCGATGAGCGTGGTGGTTATGCCGATCGCGTCACACTACGTCTGAACGTCGAAAAC |
| | | CCGAAACTGTGGAGCGCCGAAATCCCGAATCTCTATCGTGCGGTGGTTGAACTGCACACCGCCGACGGCACGCT |
| | | GATTGAAGCAGAAGCCTGCGATGTCGGTTTCCGCGAGGTGCGGATTGAAAATGGTCTGCTGCTGCTGAACGGC |
| | | AAGCCGTTGCTGATTCGAGGCGTTAACCGTCACGAGCATCATCCTCTGCATGGTCAGGTCATGGATGAGCAGAC |
| | | GATGGTGCAGGATATCCTGCTGATGAAGCAGAACAACTTTAACGCCGTGCGCTGTTCGCATTATCCGAACCATCC |
| | | GCTGTGGTACACGCTGTGCGACCGCTACGGCCTGTATGTGGTGGATGAAGCCAATATTGAAACCCACGGCATGG |
| | | TGCCAATGAATCGTCTGACCGATGATCCGCGCTGGCTACCGGCGATGAGCGAACGCGTAACGCGAATGGTGCA |
| | | GCGCGATCGTAATCACCCGAGTGTGATCATCTGGTCGCTGGGGAATGAATCAGGCCACGGCGCTAATCACGACG |
| | | CGCTGTATCGCTGGATCAAATCTGTCGATCCTTCCCGCCCGGTGCAGTATGAAGGCGGCGGAGCCGACACCACG |
| | | GCCACCGATATTATTTGCCCGATGTACGCCCGCGTGGATGAAGACCAGCCCTTCCCGGCTGTGCCGAAATGGTCC |
| | | ATCAAAAAATGGCTTTCGCTACCTGGAGAGACGCGCCCGCTGATCCTTTGCGAATACGCCCACGCGATGGGTAA |
| | | CAGTCTTGGCGGTTTCGCTAAATACTGGCAGGCGTTTCGTCAGTATCCCCGTTTACAGGGCGGCTTCGTCTGGGA |
| | | CTGGGTGGATCAGTCGCTGATTAAATATGATGAAAACGGCAACCCGTGGTCGGCTTACGGCGGTGATTTTGGCG |
| | | ATACGCCGAACGATCGCCAGTTCTGTATGAACGGTCTGGTCTTTGCCGACCGCACGCCGCATCCAGCGCTGACG |
| | | GAAGCAAAACACCAGCAGCAGTTTTTCCAGTTCCGTTTATCCGGGCAAACCATCGAAGTGACCAGCGAATACCT |
| | | GTTCCGTCATAGCGATAACGAGCTCCTGCACTGGATGGTGGCGCTGGATGGTAAGCCGCTGGCAAGCGGTGAA |
| | | GTGCCTCTGGATGTCGCTCCACAAGGTAAACAGTTGATTGAACTGCCTGAACTACCGCAGCCGGAGAGCGCCGG |
| | | GCAACTCTGGCTCACAGTACGCGTAGTGCAACCGAACGCGACCGCATGGTCAGAAGCCGGGCACATCAGCGCCT |
| | | GGCAGCAGTGGCGTCTGGCGGAAAACCTCAGTGTGACGCTCCCCGCCGCGTCCCACGCCATCCCGCATCTGACC |
| | | ACCAGCGAAATGGATTTTTGCATCGAGCTGGGTAATAAGCGTTGGCAATTTAACCGCCAGTCAGGCTTTCTTTCA |
| | | CAGATGTGGATTGGCGATAAAAAACAACTGCTGACGCCGCTGCGCGATCAGTTCACCCGTGCACCGCTGGATAA |
| | | CGACATTGGCGTAAGTGAAGCGACCCGCATTGACCCTAACGCCTGGGTCGAACGCTGGAAGGCGGCGGGCCAT |
| | | TACCAGGCCGAAGCAGCGTTGTTGCAGTGCACGGCAGATACACTTGCTGATGCGGTGCTGATTACGACCGCTCA |
| | | CGCGTGGCAGCATCAGGGGAAAACCTTATTTATCAGCCGGAAAACCTACCGGATTGATGGTAGTGGTCAAATGG |
| | | CGATTACCGTTGATGTTGAAGTGGCGAGCGATACACCGCATCCGGCGCGGATTGGCCTGAACTGCCAGCTGGCG |
| | | CAGGTAGCAGAGCGGGTAAACTGGCTCGGATTAGGGCCGCAAGAAAACTATCCCGACCGCCTTACTGCCGCCTG |
| | | TTTTGACCGCTGGGATCTGCCATTGTCAGACATGTATACCCCGTACGTCTTCCCGAGCGAAAACGGTCTGCGCTG |
| | | CGGGACGCGCGAATTGAATTATGGCCCACACCAGTGGCGCGGCGACTTCCAGTTCAACATCAGCCGCTACAGTC |
| | | AACAGCAACTGATGGAAACCAGCCATCGCCATCTGCTGCACGCGGAAGAAGGCACATGGCTGAATATCGACGG |
| | | TTTCCATATGGGGATTGGTGGCGACGACTCCTGGAGCCCGTCAGTATCGGCGGAATTCCAGCTGAGCGCCGGTC |
| | | GCTACCATTACCAGTTGGTCTGGTGTCAAAAATAA (SEQ ID NO. 122) |

What is claimed is:

1. A genetically-modified microorganism capable of converting a methane to a multicarbon product, wherein the genetically-modified microorganism is a *Methylococcus capsulatus* and comprises a polynucleotide encoding a heterologous CRISPR-associated protein, the polynucleotide operably linked to a weak promoter.

2. The genetically modified microorganism of claim 1, wherein the CRISPR-associated protein is a *Streptococcus pyogenes* CRISPR-associated protein 9 (Cas9).

3. The genetically-modified microorganism of claim 1, wherein the heterologous CRISPR-associated protein is expressed within by way of a plasmid that comprises a weak promoter.

4. The genetically-modified microorganism of claim 1, further comprising a polynucleotide encoding a gRNA.

5. The genetically-modified microorganism of claim 4, wherein the polynucleotide encoding a gRNA comprises a 10 nucleotide sequence that is identical to a 10 nucleotide sequence portion of a promoter, intron, or coding sequence of an rpoB gene or a gene within a pathway for the production of 2,3-butanediol (2,3-BDO), 1,4-butanediol (1,4-BDO), isobutyraldehyde, or isobutanol.

6. The genetically-modified microorganism of claim 1, wherein the genetically-modified microorganism comprises: a point mutation compared to a wild-type microorganism of the same species; or a point mutation, deletion, or addition of one or more nucleotides within a promoter, intron, or coding sequence of an rpoB gene or a gene within a pathway for the production of 2,3-butanediol (2,3-BDO), 1,4-butanediol (1,4-BDO), isobutyraldehyde, or isobutanol.

7. The genetically-modified microorganism of claim 1, further comprising a donor polynucleotide.

8. The genetically-modified microorganism of claim 7, wherein the donor polynucleotide comprises fewer than 1000 bases.

9. The genetically-modified microorganism of claim 1, wherein the weak promoter is pBAD, J23110, lacO, J23116, J23106, J23105, J23108, J23107, J23115, J23114, or a mutant pMxaF.

10. The genetically-modified microorganism of claim 1, wherein the weak promoter is a mutant pMxaF comprising the sequence SEQ ID NO: 78.

11. The genetically-modified microorganism of claim 2, wherein the weak promoter is a mutant pMxaF comprising the sequence SEQ ID NO: 78.

12. The genetically-modified microorganism of claim 4, wherein the polynucleotide encoding the gRNA is operably linked to a strong promoter.

13. The genetically-modified microorganism of claim 12, wherein the strong promoter is pMxaF, J2311, J12100, or J23102.

14. The genetically-modified microorganism of claim 4, wherein the genetically-modified microorganism is prepared by transforming a microorganism with the polynucleotide encoding a gRNA before the microorganism is transformed with the polynucleotide encoding a heterologous CRISPR-associated protein.

15. The genetically-modified microorganism of claim 7, wherein the genetically-modified microorganism is prepared by transforming a microorganism with the polynucleotide expressing a donor DNA before the microorganism is transformed with the polynucleotide encoding a heterologous CRISPR-associated protein.

16. The genetically-modified microorganism of claim 1, wherein the genetically-modified microorganism is prepared by transforming a microorganism with a polynucleotide encoding a gRNA and expressing a donor DNA before the microorganism is transformed with the polynucleotide encoding a heterologous CRISPR-associated protein.

17. The genetically-modified microorganism of claim 16, wherein the CRISPR-associated protein is operably linked to a weak promoter that is pBAD, J23110, lacO, J23116, J23106, J23105, J23108, J23107, J23115, J23114, or a mutant pMxaF.

18. The genetically-modified microorganism of claim 16, wherein the CRISPR-associated protein is Cas9.

19. The genetically-modified microorganism of claim 18, wherein the CRISPR-associated protein is operably linked to a mutant pMxaF comprising the sequence SEQ ID NO: 78.

* * * * *